United States Patent
Kim et al.

(10) Patent No.: US 9,741,939 B2
(45) Date of Patent: Aug. 22, 2017

(54) CONDENSED CYCLIC COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Youngkook Kim, Yongin (KR); Kwanghyun Kim, Yongin (KR); Jongwoo Kim, Yongin (KR); Mieun Jun, Yongin (KR); Seokhwan Hwang, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 281 days.

(21) Appl. No.: 14/695,021

(22) Filed: Apr. 23, 2015

(65) Prior Publication Data

US 2016/0118593 A1  Apr. 28, 2016

(30) Foreign Application Priority Data

Oct. 23, 2014  (KR) .......................... 10-2014-0144276

(51) Int. Cl.
    *H01L 51/00*  (2006.01)
    *C07D 311/78*  (2006.01)
    (Continued)

(52) U.S. Cl.
    CPC ........ *H01L 51/0061* (2013.01); *C07D 311/78* (2013.01); *C07D 335/04* (2013.01);
    (Continued)

(58) Field of Classification Search
    CPC .. C07D 311/78; C07D 445/04; C07D 405/14; C07D 407/12; C07D 407/14;
    (Continued)

(56) References Cited

U.S. PATENT DOCUMENTS

| 7,053,255 B2 | 5/2006 | Ikeda et al. |
| 7,233,019 B2 | 6/2007 | Ionkin et al. |
| | (Continued) | |

FOREIGN PATENT DOCUMENTS

| KR | 10-2006-0006760 A | 1/2006 |
| KR | 10-2009-0033493 A | 4/2009 |
| | (Continued) | |

OTHER PUBLICATIONS

STN search (Mar. 20, 2017).*
(Continued)

*Primary Examiner* — Vu A Nguyen
(74) *Attorney, Agent, or Firm* — Lewis Roca Rothgerber Christie LLP

(57) ABSTRACT

A condensed cyclic compound represented by Formula 1:

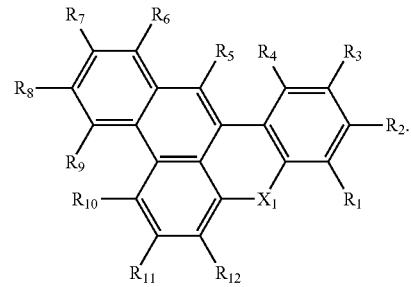

Formula 1

An organic light-emitting device including a first electrode; a second electrode facing the first electrode; and an organic layer between the first electrode and the second electrode,
(Continued)

10

| 190 |
|---|
| 150 |
| 110 | the organic layer including an emission layer, and further including at least one of the condensed cyclic compounds of Formula 1.

20 Claims, 4 Drawing Sheets

(51) Int. Cl.
| | |
|---|---|
| C07D 405/14 | (2006.01) |
| C07F 7/08 | (2006.01) |
| C07D 407/14 | (2006.01) |
| C07D 409/14 | (2006.01) |
| C07D 409/12 | (2006.01) |
| C07D 407/12 | (2006.01) |
| C07D 335/04 | (2006.01) |
| H05B 33/22 | (2006.01) |
| C09K 11/06 | (2006.01) |
| H01L 51/50 | (2006.01) |

(52) U.S. Cl.
CPC ......... *C07D 405/14* (2013.01); *C07D 407/12* (2013.01); *C07D 407/14* (2013.01); *C07D 409/12* (2013.01); *C07D 409/14* (2013.01); *C07F 7/0812* (2013.01); *H01L 51/006* (2013.01); *H01L 51/0067* (2013.01); *H01L 51/0073* (2013.01); *H01L 51/0074* (2013.01); *H01L 51/0094* (2013.01); *H05B 33/22* (2013.01); *C09K 11/06* (2013.01); *H01L 51/0081* (2013.01); *H01L 51/5016* (2013.01); *H01L 51/5056* (2013.01)

(58) Field of Classification Search
CPC ... C07D 409/12; C07D 409/14; H01L 51/006; H01L 51/0061; H01L 51/0067; H01L 51/0073; H01L 51/0074; H01L 51/0094; H05B 33/22; C07F 7/0812
See application file for complete search history.

(56) References Cited

U.S. PATENT DOCUMENTS

| | | |
|---|---|---|
| 2005/0156164 A1 | 7/2005 | Sotoyama |
| 2007/0237984 A1 | 10/2007 | Matsuura et al. |
| 2010/0013381 A1 | 1/2010 | Stoessel et al. |
| 2010/0032658 A1 | 2/2010 | Lee et al. |
| 2011/0006289 A1 | 1/2011 | Mizuki et al. |
| 2013/0306958 A1 | 11/2013 | Ito et al. |
| 2014/0361266 A1* | 12/2014 | Jung .................. H01L 51/0094 257/40 |
| 2015/0171337 A1* | 6/2015 | Jung .................. H01L 51/0058 257/40 |

FOREIGN PATENT DOCUMENTS

| | | |
|---|---|---|
| KR | 10-2009-0111355 A | 10/2009 |
| KR | 10-2010-0007780 A | 1/2010 |
| KR | 10-2010-0097182 A | 9/2010 |
| WO | WO 2012/070226 A1 | 5/2012 |

OTHER PUBLICATIONS

Katritzky, Alan R. et al., "Polycyclic Fused Phenanthridines: An Alternative Approach from Benzotriazoles", pp. 1-27, Center for Heterocyclic Compounds, Department of Chemistry, University of Florida, Gainesville, Florida, USA.

* cited by examiner

| 190 |
|---|
| 150 |
| 110 |

| 190 |
|---|
| 150 |
| 110 |
| 210 |

| 220 |
|---|
| 190 |
| 150 |
| 110 |

| 220 |
|---|
| 190 |
| 150 |
| 110 |
| 210 |

CONDENSED CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2014-0144276, filed on Oct. 23, 2014, in the Korean Intellectual Property Office, the disclosure of which is incorporated herein in its entirety by reference.

BACKGROUND

1. Field

One or more aspects of embodiments of the present invention relate to a condensed cyclic compound and an organic light-emitting device including the same.

2. Description of the Related Art

Organic light emitting devices are self-emission devices that have wide viewing angles, high contrast ratios, short response times, low driving voltage, and excellent brightness and response speed characteristics, and can produce full-color images.

The organic light-emitting device may include a first electrode disposed on a substrate, and a hole transport region, an emission layer, an electron transport region, and a second electrode sequentially disposed on the first electrode. Holes provided from the first electrode may move toward the emission layer through the hole transport region, and electrons provided from the second electrode may move toward the emission layer through the electron transport region. Carriers (e.g., holes and electrons), are recombined in the emission layer to produce excitons. When these excitons change from an excited state to a ground state, light is generated.

SUMMARY

One or more aspects of embodiments of the present invention relate to a novel condensed cyclic compound and an organic light-emitting device including the same.

Additional aspects will be set forth in part in the description which follows and, in part, will be apparent from the description, or may be learned by practice of the presented embodiments.

An embodiment provides a condensed cyclic compound represented by Formula 1, where $R_1$ to $R_{12}$ may be each independently a group represented by Formula 2:

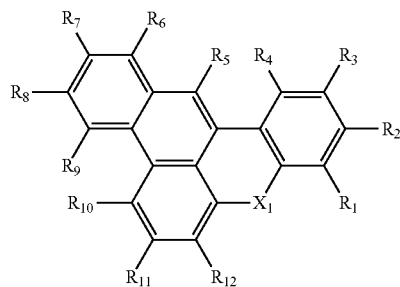

Formula 1

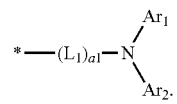

Formula 2

In Formulae 1 and 2, $X_1$ may be O or S;

$L_1$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 is selected from 0, 1, 2, and 3, and when a1 is two or more, a plurality of $L_1$ may be identical to or different from each other;

$Ar_1$ and $Ar_2$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

$R_1$ to $R_{12}$ may be each independently selected from a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), and —B($Q_4$)($Q_5$);

at least two selected from $R_1$ to $R_{12}$ may be each independently the group represented by Formula 2;

at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), and —B($Q_{14}$)($Q_{15}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, —Si($Q_{21}$)($Q_{22}$)($Q_{23}$), and —B($Q_{24}$)($Q_{25}$); and —Si($Q_{31}$)($Q_{32}$)($Q_{33}$) and —B($Q_{34}$)($Q_{35}$), where $Q_1$ to $Q_5$, $Q_{11}$ to $Q_{15}$, $Q_{21}$ to $Q_{25}$, and $Q_{31}$ to $Q_{35}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

An embodiment provides an organic light-emitting device that includes: a first electrode; a second electrode facing the first electrode; and an organic layer between the first electrode and the second electrode and including an emission layer, where the organic layer includes at least one of the condensed cyclic compounds of Formula 1.

BRIEF DESCRIPTION OF THE DRAWINGS

These and/or other aspects will become apparent and more readily appreciated from the following description of the exemplary embodiments, taken in conjunction with the accompanying drawings in which:

FIG. 1 is a schematic view of an organic light-emitting device according to some embodiments of the present invention;

FIG. 2 is a schematic view of an organic light-emitting device according to some embodiments of the present invention;

FIG. 3 is a schematic view of an organic light-emitting device according to some embodiments of the present invention; and FIG. 4 is a schematic view of an organic light-emitting device according to some embodiments of the present invention.

DETAILED DESCRIPTION

Reference will now be made in detail to embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list. Further, the use of "may" when describing embodiments of the present invention refers to "one or more embodiments of the present invention." In addition, as used herein, the terms "use," "using," and "used" may be considered synonymous with the terms "utilize," "utilizing," and "utilized," respectively. Also, the term "exemplary" is intended to refer to an example or illustration.

A condensed cyclic compound according to some embodiments is represented by Formula 1 below:

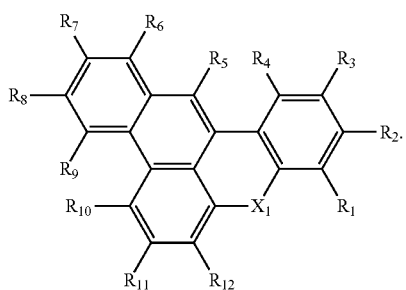

Formula 1

$X_1$ in Formula 1 may be O or S. According to some embodiments, $X_1$ in Formula 1 may be O, but is not limited thereto.

$R_1$ to $R_{12}$ in Formula 1 may be each independently selected from a group represented by Formula 2 below, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), and —B($Q_4$)($Q_6$).

In some embodiments, at least two selected from $R_1$ to $R_{12}$ in Formula 1 may be each independently a group represented by Formula 2 below:

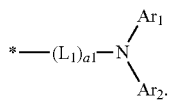

Formula 2

$L_1$ in Formula 2 may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_r$-$C_{60}$ heteroarylene group, a substituted or unsubstituted divalent non-aromatic condensed polycyclic group, and a substituted or unsubstituted divalent non-aromatic condensed heteropolycyclic group.

In some embodiments, $L_1$ in Formula 2 may be selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group (e.g., thiophenylene), a furanylene group, an imidazolylene group, a pyrazolylene group, a thiazolylene group, an isothiazolylene group, an oxazolylene group, a isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, ovalenylene group, a pyrrolylene group, a thiophenylene group, a furanylene group, an imidazolylene group, a pyrazolylene group, a thiazolylene group, an isothiazolylene group, an oxazolylene group, a isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

In some embodiments, $L_1$ in Formula 2 may be selected from a group represented by any one of Formulae 3-1 to 3-35 illustrated below:

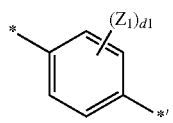

Formula 3-1

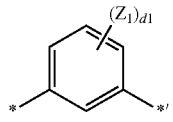

Formula 3-2

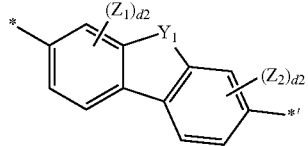

Formula 3-3

-continued

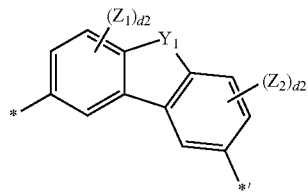

Formula 3-4

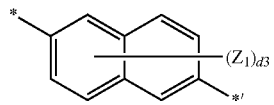

Formula 3-5

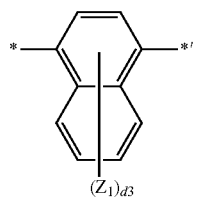

Formula 3-6

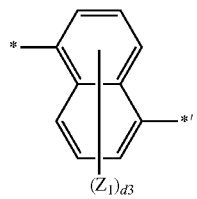

Formula 3-7

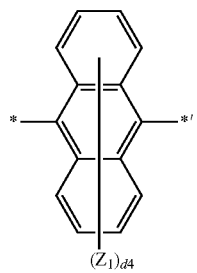

Formula 3-8

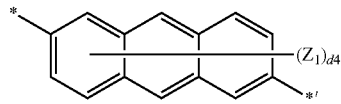

Formula 3-9

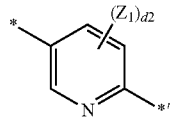

Formula 3-10

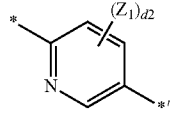

Formula 3-11

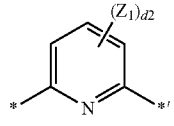

Formula 3-12

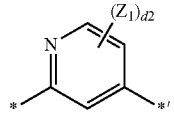

Formula 3-13

Formula 3-14
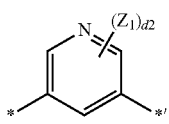
Formula 3-15
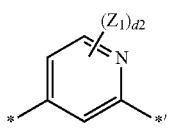
Formula 3-16
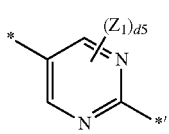
Formula 3-17
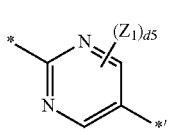
Formula 3-18
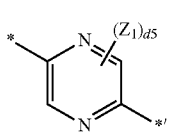
Formula 3-19
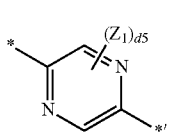
Formula 3-20
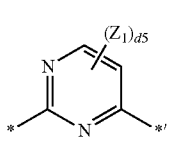
Formula 3-21
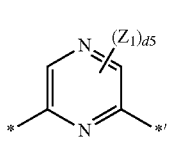
Formula 3-22
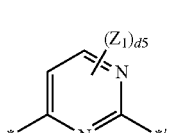
Formula 3-23
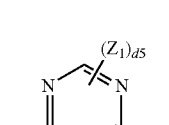
Formula 3-24
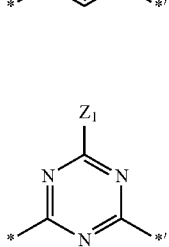
Formula 3-25
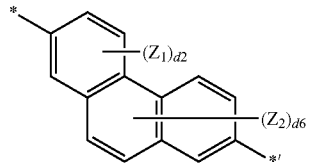
Formula 3-26
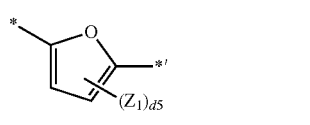
Formula 3-27
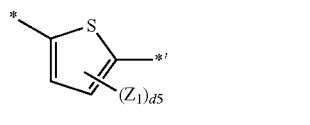
Formula 3-28
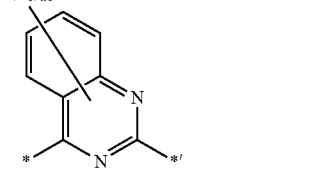
Formula 3-29
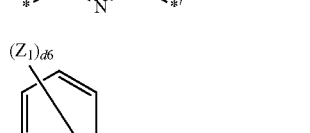
Formula 3-30
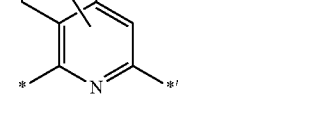
Formula 3-31
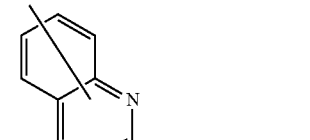
Formula 3-32
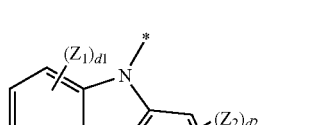
Formula 3-33
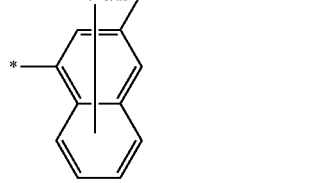

Formula 3-34

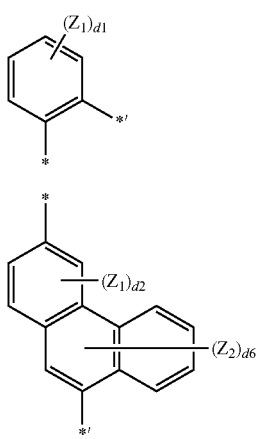

Formula 3-35

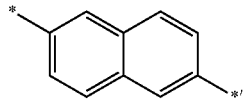

In Formulae 3-1 to 3-35, $Y_1$ may be O, S, $C(Z_3)(Z_4)$, $N(Z_5)$, or $Si(Z_6)(Z_7)$;

- $Z_1$ to $Z_7$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group,
- d1 is an integer selected from 1, 2, 3, and 4, d2 is an integer selected from 1, 2, and 3, d3 is an integer selected from 1, 2, 3, 4, 5, and 6, d4 is an integer selected from 1, 2, 3, 4, 5, 6, 7, and 8, d5 is 1 or 2, and d6 is an integer selected from 1, 2, 3, 4, and 5, and * and *' each indicate a binding site to a neighboring atom.

In some embodiments, $L_1$ in Formula 2 may be selected from:

a phenylene group, a naphthylene group, a pyridinylene group, a dibenzofuranylene group, and a dibenzothiophenylene group; and a phenylene group, a naphthylene group, a pyridinylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a phenyl group, a naphthyl group, a pyridinyl group, a pyrimidinyl group, and a triazinyl group. However, embodiments of the present invention are not limited thereto.

In some embodiments, $L_1$ in Formula 2 may be selected from a group represented by any one of Formulae 4-1 to Formula 4-28. However, embodiments of the present invention are not limited thereto.

Formula 4-1

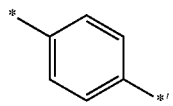

Formula 4-2

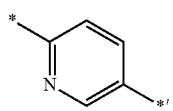

Formula 4-3

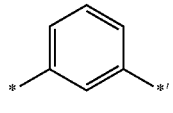

Formula 4-4

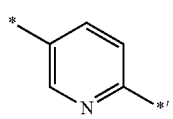

Formula 4-5

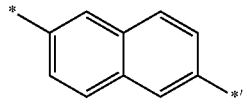

Formula 4-6

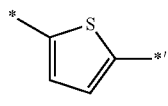

Formula 4-7

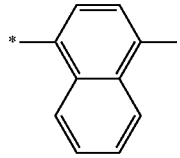

Formula 4-8

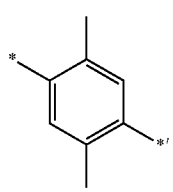

Formula 4-9

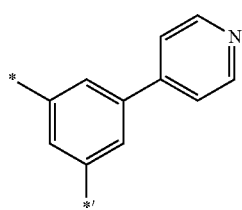

Formula 4-10

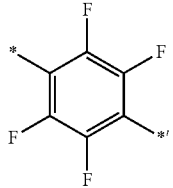

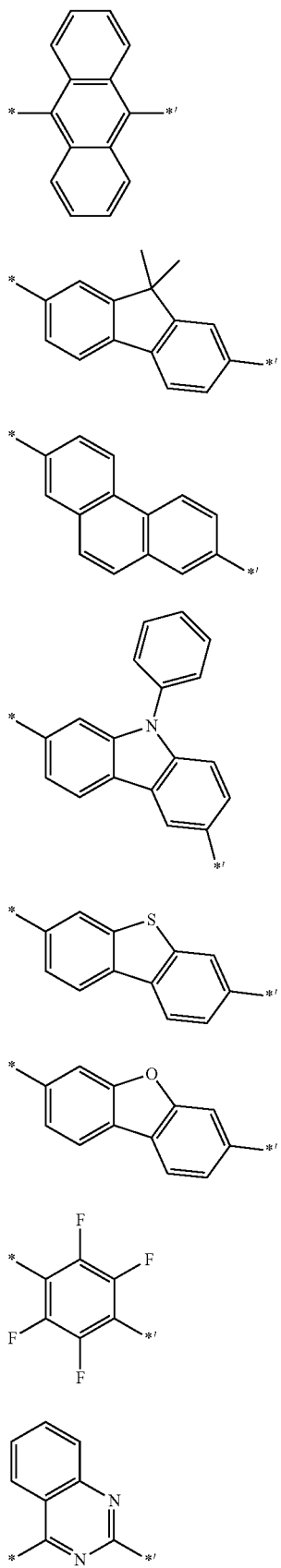
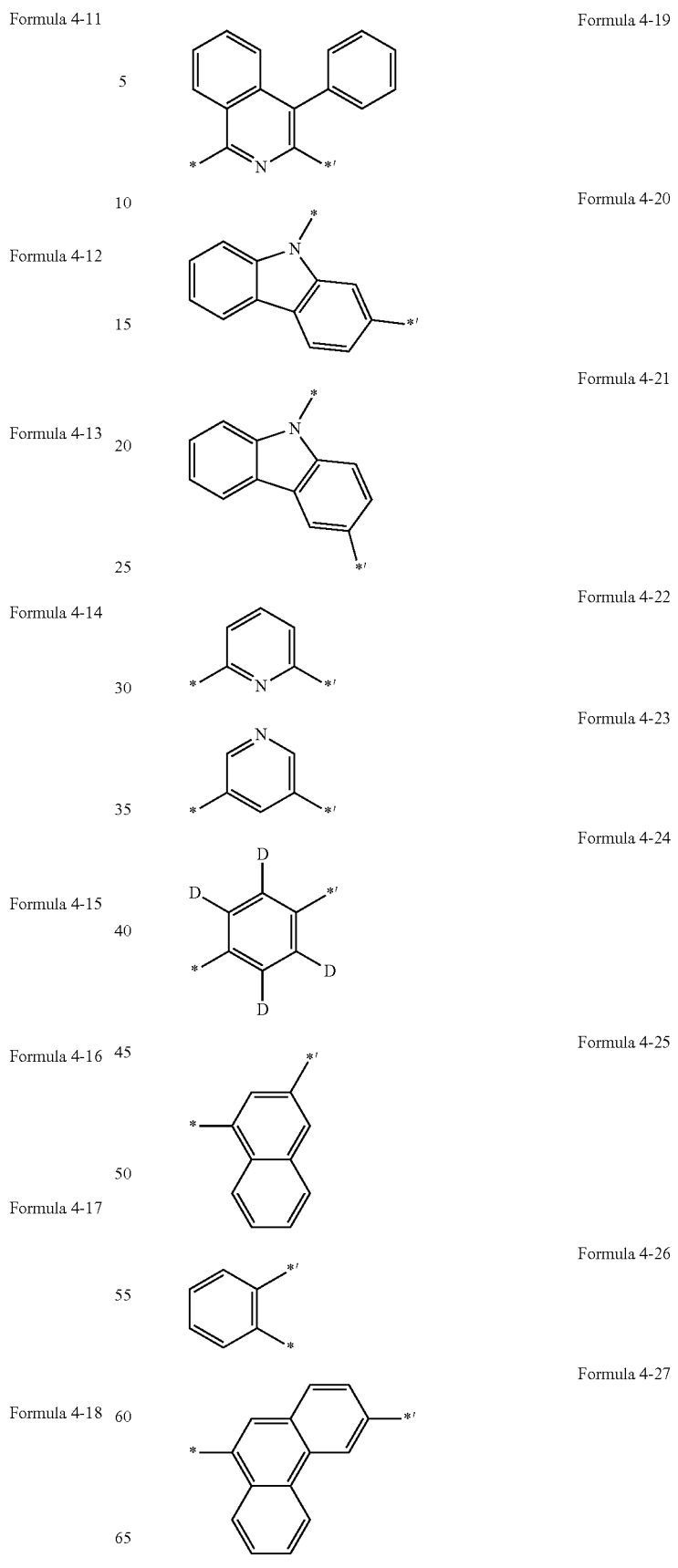
Formula 4-11
Formula 4-12
Formula 4-13
Formula 4-14
Formula 4-15
Formula 4-16
Formula 4-17
Formula 4-18
Formula 4-19
Formula 4-20
Formula 4-21
Formula 4-22
Formula 4-23
Formula 4-24
Formula 4-25
Formula 4-26
Formula 4-27

-continued

Formula 4-28

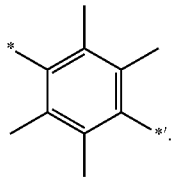

* and *' in Formulae 4-1 to 4-28 each indicate a binding site to a neighboring atom.

Referring to Formula 2, a1 indicates the number of $L_1$ and may be selected from 0, 1, 2, and 3. When a1 is 2 or greater, a plurality of $L_1$(s) may be identical to or different from each other. When a1 is 0, $-(L_1)_{a1}-$ is a single bond. In some embodiments, a1 may be 0, 1, or 2. In some embodiments, a1 may be 0 or 1.

$Ar_1$ and $Ar_2$ in Formula 2 may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, $Ar_1$ and $Ar_2$ in Formula 2 may be each independently selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$); and $Q_{31}$ to $Q_{33}$ may be each independently selected from a $C_1$-$C_{10}$ alkyl group, a $C_1$-$C_{10}$ alkoxy group, a phenyl group, a naphthyl group, a fluorenyl group, a spirofluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzooxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group.

In some embodiments, $Ar_1$ and $Ar_2$ in Formula 2 may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$), and $Q_{31}$ to $Q_{33}$ may be each independently selected from a $C_1$-$C_{10}$ alkyl group, a $C_1$-$C_{10}$ alkoxy group, a phenyl group, and a naphthyl group. However, embodiments of the present Invention are not limited thereto.

In some embodiments, $Ar_1$ and $Ar_2$ in Formula 2 may be each Independently selected from:

a phenyl group, a naphthyl group, a fluorenyl group, a phenanthrenyl group, a pyridinyl group, a pyrimidinyl group, a triazinyl group, a dibenzofuranyl group, and a dibenzothiophenyl group; and a phenyl group, a naphthyl group, a fluorenyl group, a phenanthrenyl group, a pyridinyl group, a pyrimidinyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a phenanthrenyl group, a pyridinyl group, a pyrimidinyl group, a triazinyl group, a dibenzofuranyl group, a dibenzothiophenyl group, and —Si($Q_{31}$)($Q_{32}$)($Q_{33}$), and $Q_{31}$ to $Q_{33}$ may be each independently selected from a $C_1$-$C_{10}$ alkyl group, a $C_1$-$C_{10}$ alkoxy group, a phenyl group, and a naphthyl group.

$R_1$ to $R_{12}$ in Formula 1 may be each independently selected from:

a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an Isobenzooxazolyl group, an oxadiazolyl group, a triazinyl group, a dibenzofuranyl group, a dibenzothiophenyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$); and —Si($Q_1$)($Q_2$)($Q_3$), where $Q_1$ to $Q_3$ and $Q_3$ to $Q_3$ may be each independently selected from a $C_1$-$C_{10}$ alkyl group, a $C_1$-$C_{10}$ alkoxy group, a phenyl group, and a naphthyl group.

For example, $R_1$ to $R_{12}$ in Formula 1 may be each independently selected from:

a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, and a $C_1$-$C_{10}$ alkoxy group;

a phenyl group, a naphthyl group, a pyrimidinyl group, and a triazinyl group;

a phenyl group, a naphthyl group, a pyridinyl group, a pyrimidinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{31}$)($Q_{32}$)($Q_{33}$); and —Si($Q_1$)($Q_2$)($Q_3$), where $Q_1$ to $Q_3$ and $Q_{31}$ to $Q_{33}$ may be each independently selected from a $C_1$-$C_{10}$ alkyl group, a $C_1$-$C_{10}$ alkoxy group, a phenyl group, and a naphthyl group. However, embodiments of the present invention are not limited thereto.

In some embodiments, in Formulae 1 and 2, $Ar_1$ and $Ar_2$ may be each Independently selected from a group represented by any one of Formula 5-1 to Formula 5-42, $R_1$ to $R_{12}$ may be each independently selected from a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid and a salt thereof, a $C_1$-$C_{20}$ alkyl group, a $C_1$-$C_{20}$ alkoxyl group, and a group represented by any one of Formula 5-1 to Formula 5-42:

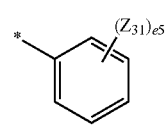

Formula 5-1

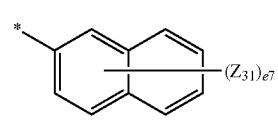

Formula 5-2

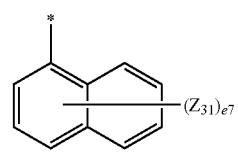

Formula 5-3

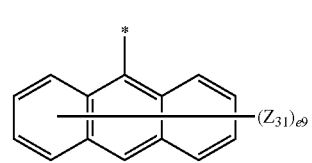

Formula 5-4

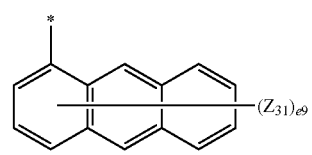

Formula 5-5

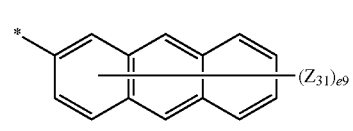

Formula 5-6

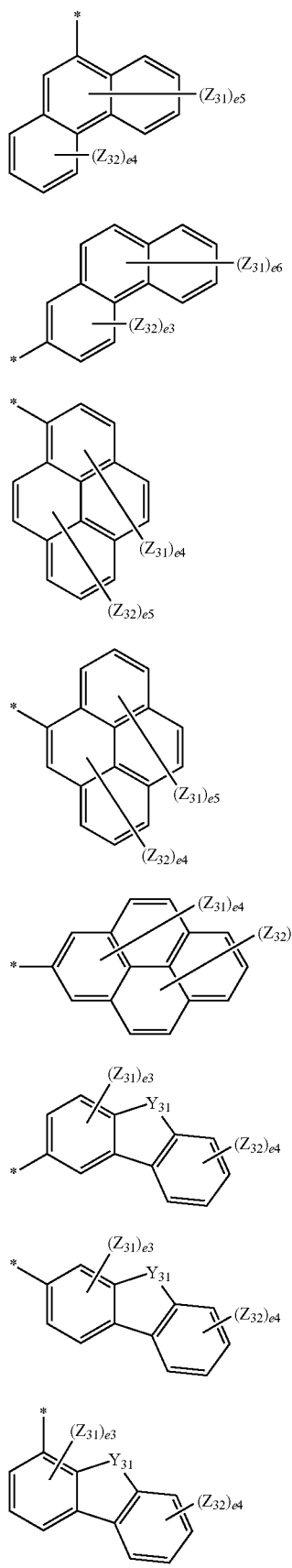
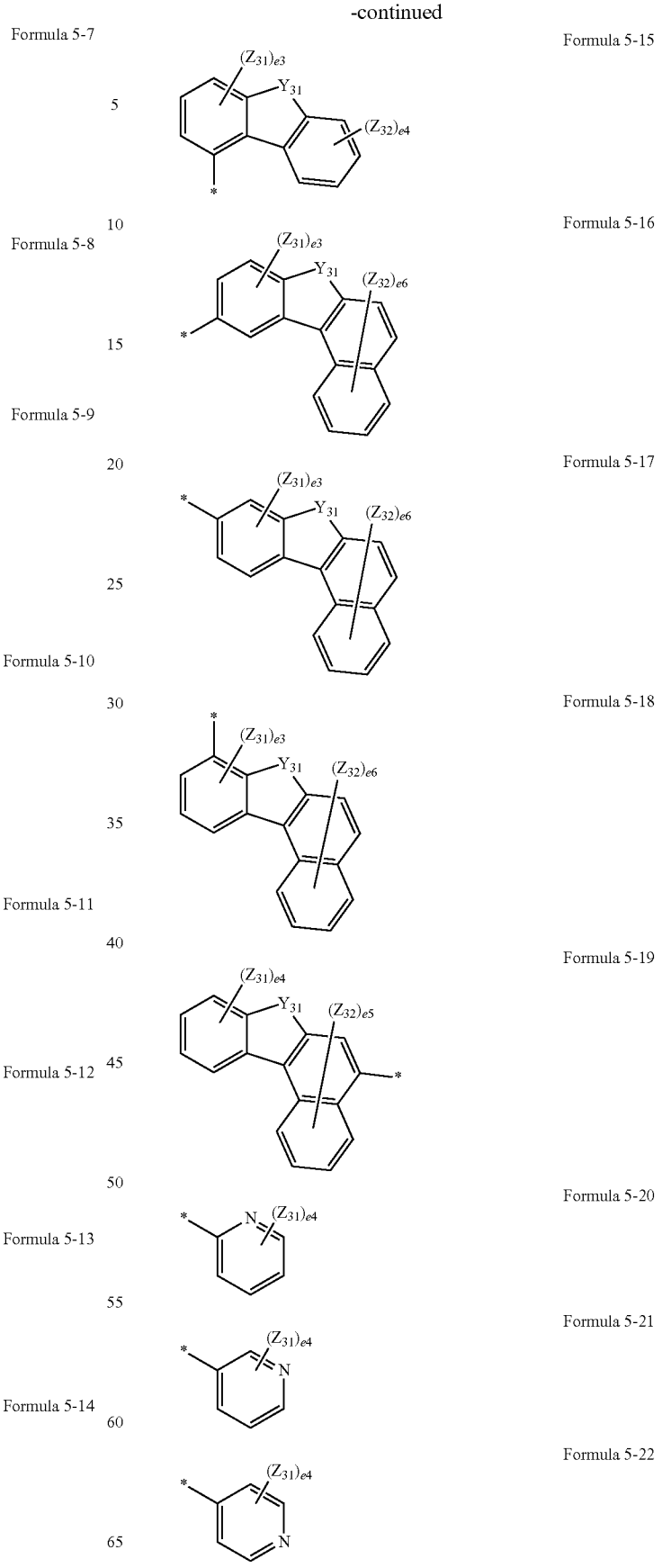

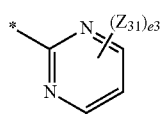

Formula 5-23

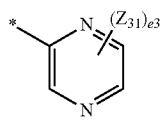

Formula 5-24

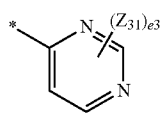

Formula 5-25

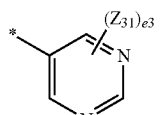

Formula 5-26

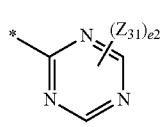

Formula 5-27

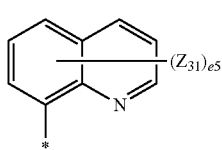

Formula 5-28

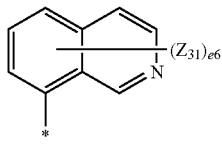

Formula 5-29

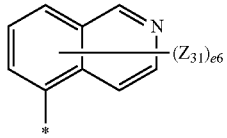

Formula 5-30

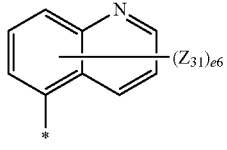

Formula 5-31

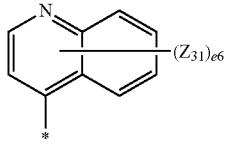

Formula 5-32

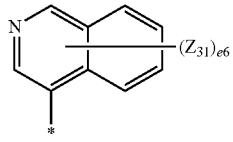

Formula 5-33

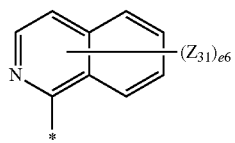

Formula 5-34

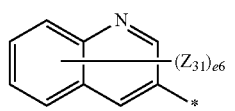

Formula 5-35

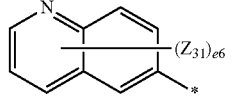

Formula 5-36

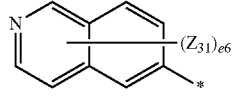

Formula 5-37

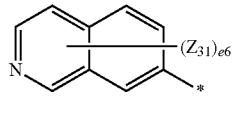

Formula 5-38

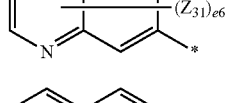

Formula 5-39

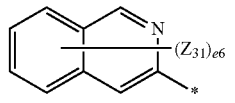

Formula 5-40

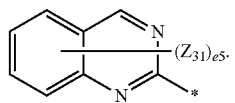

Formula 5-41

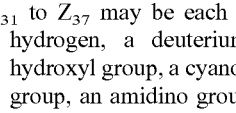

Formula 5-42

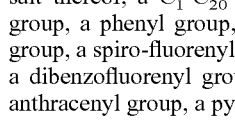

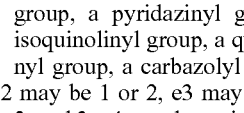

In Formulae 5-1 to 5-42, $Y_{31}$ may be O, S, $C(Z_{33})(Z_{34})$, $N(Z_{35})$, or $Si(Z_{36})(Z_{37})$;

$Z_{31}$ to $Z_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, e2 may be 1 or 2, e3 may be an integer selected from 1, 2, and 3, e4 may be an integer selected from 1, 2, 3, and 4, e5 may be an integer selected from 1, 2, 3, 4, and 5, e6 may be an integer selected from 1, 2, 3, 4, 5, and 6, e7 may be an integer selected from 1, 2, 3, 4, 5, 6, and 7, e9 may be an integer selected from 1, 2, 3, 4, 5, 6, 7, 8, and 9, and * indicates a binding site to a neighboring atom.

In some embodiments, in Formulae 1 and 2,

Ar$_1$ and Ar$_2$ may be each independently selected from a group represented by any one of Formula 6-1 to Formula 6-29 illustrated below, R$_1$ to R$_{12}$ may be each independently selected from a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid and a salt thereof, a C$_1$-C$_{20}$ alkyl group, a C$_1$-C$_{20}$ alkoxyl group, a phenyl group, a naphthyl group, a pyridinyl group, a pyrimidinyl group and a triazinyl group, but embodiments of the present invention are not limited thereto:

Formula 6-1
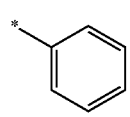

Formula 6-2
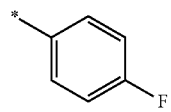

Formula 6-3
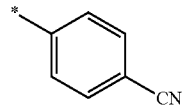

Formula 6-4
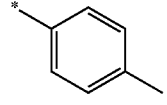

Formula 6-5
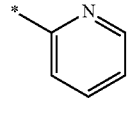

Formula 6-6
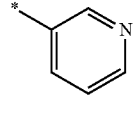

Formula 6-7
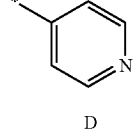

Formula 6-8
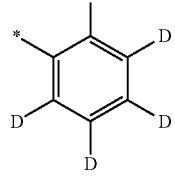

Formula 6-9
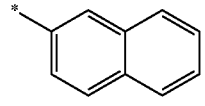

-continued

Formula 6-10
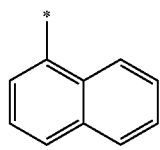

Formula 6-11
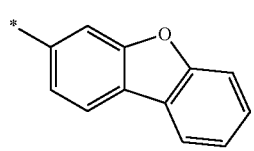

Formula 6-12
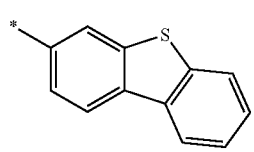

Formula 6-13
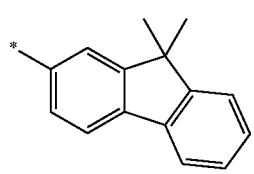

Formula 6-14
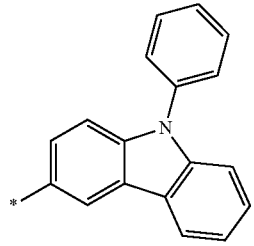

Formula 6-15
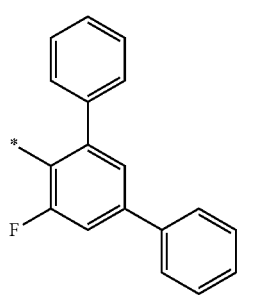

Formula 6-16
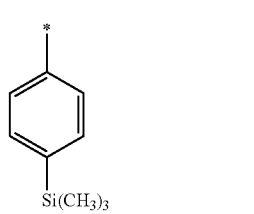

Formula 6-17
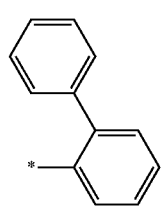

Formula 6-18
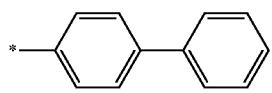

Formula 6-19
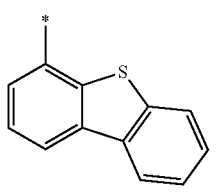

Formula 6-20
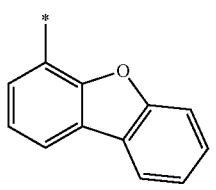

Formula 6-21
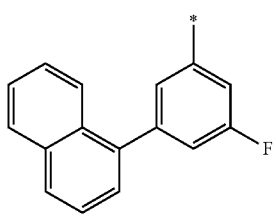

Formula 6-22
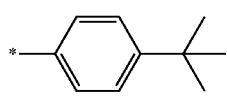

Formula 6-23
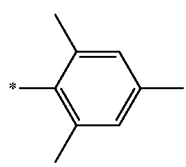

Formula 6-24
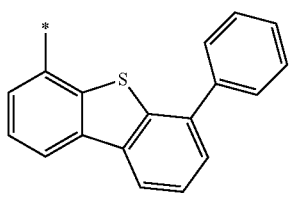

Formula 6-25
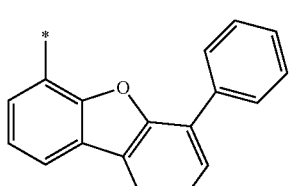

Formula 6-26
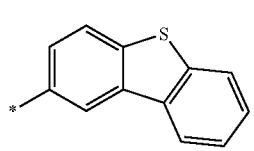

Formula 6-27
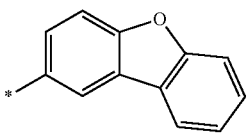

Formula 6-28
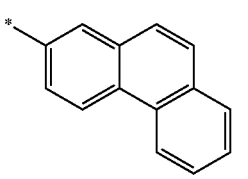

Formula 6-29
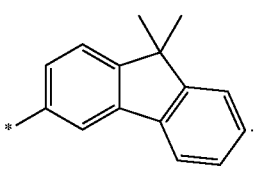

\* in Formulae 6-1 to 6-29 indicates a binding site to a neighboring atom.

Referring to Formula 1, $R_5$ in Formula 1 may not be a hydrogen.

In some embodiments, $R_5$ may be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid and a salt thereof, a $C_1$-$C_{20}$ alkyl group, a $C_1$-$C_{20}$ alkoxyl group, a phenyl group, a naphthyl group, a pyridinyl group, a pyrimidinyl group and a triazinyl group.

Any two substituents selected from $R_1$ to $R_{12}$ in Formula 1 may be each Independently a group represented by Formula 2.

For example, the condensed cyclic compound represented by Formula 1 may be represented by one of Formulae 1-1 to 1-4 below:

Formula 1-1

Formula 1-2

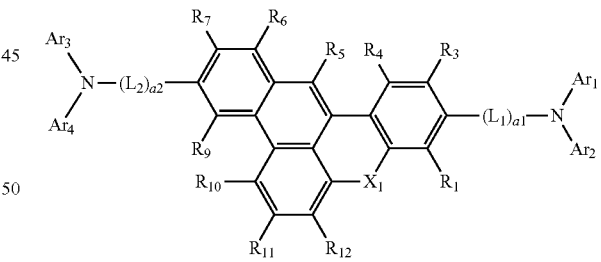

Formula 1-3

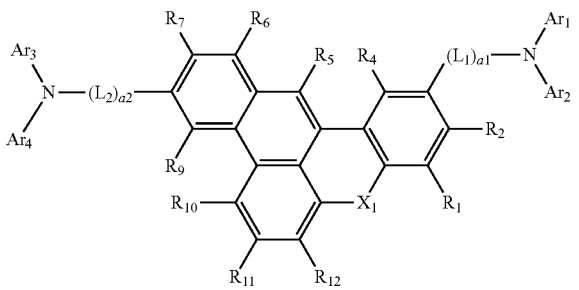

Formula 1-4

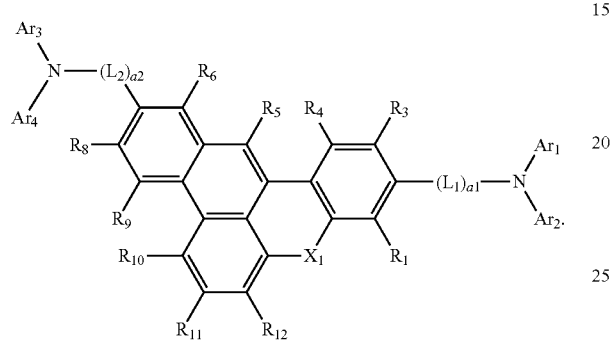

Regarding Formulae 1-1 to 1-4, descriptions of $X_1$, $L_1$, a1, $Ar_1$, $Ar_2$, and $R_1$ to $R_{12}$ are as provided above, and descriptions of $L_2$, a2, $Ar_3$, and $Ar_4$ are the same as the descriptions presented in connection with $L_1$, a1, $Ar_1$, and $Ar_2$, respectively.

In some embodiments, in Formulae 1-1 and 1-4,
a1 is 0 and a2 is 0;
a1 is 0 and a2 is 1 or 2;
a1 is 1 or 2 and a2 is 0;
a1 is 1 and a2 is 1;
a1 is 1 and a2 is 2;
a1 is 2 and a2 is 1; or
a1 is 2 and a2 is 2.

In some embodiments, in Formulae 1-1 and 1-4,
a1 is 0 and a2 is 0;
a1 is 0 and a2 is 1;
a1 is 1 and a2 is 0; or
a1 is 1 and a2 is 1. However, embodiments of the present Invention are not limited thereto.

In Formulae 1-1 to 1-4,
$Ar_1$, $Ar_2$, $Ar_3$ and $Ar_4$ may be the same ($Ar_1=Ar_2=Ar_3=Ar_4$);
$Ar_1$ may be the same as $Ar_3$, and $Ar_2$ may be the same as $Ar_4$, but $Ar_2$ may be different from $Ar_3$ ($Ar_1=Ar_3$ and $Ar_2=Ar_4$, but $Ar_2 \neq Ar_3$);
$Ar_1$ may be the same as $Ar_3$, but $Ar_2$ may be different from $Ar_4$ and $Ar_2$ may be different from $Ar_3$ ($Ar_1=Ar_3$ and, $Ar_2=Ar_4$ and, $Ar_2 \neq Ar_3$); or
$Ar_1$, $Ar_2$, $Ar_3$ and $Ar_4$ may be all different from each other ($Ar_1 \neq Ar_2 \neq Ar_3 \neq Ar_4$).

In some embodiments, in Formulae 1-1 and 1-4,
$R_1$ to $R_{12}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group, $L_1$ and $L_2$ may be each independently selected from a group represented by any one of Formula 3-1 to Formula 3-35, a1 and a2 may be each independently 0, 1, or 2;

$Ar_1$ to $Ar_4$ may be each independently selected from a group represented by any one of Formula 5-1 to Formula 5-24.

In some embodiments, in Formulae 1-1 and 1-4,
$R_1$ to $R_4$, and $R_6$ to $R_{12}$ may each be a hydrogen,
$R_5$ may be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group, $L_1$ and $L_2$ may be each Independently selected from a group represented by any one of Formula 4-1 to Formula 4-28, a1 and a2 may be each independently 0 or 1, $Ar_1$ to $Ar_4$ may be each Independently selected from a group represented by any one of Formula 6-1 to Formula 6-29. However, embodiments of the present Invention are not limited thereto.

In some embodiments, the condensed cyclic compound represented by Formula 1 may be represented by one of Formulae 1-1(1) to 1-1(4) below, but embodiments of the present invention are not limited thereto:

Formula 1-1(1)

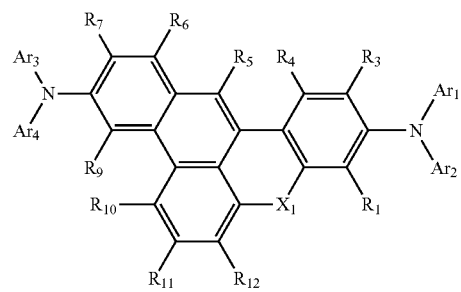

Formula 1-1(2)

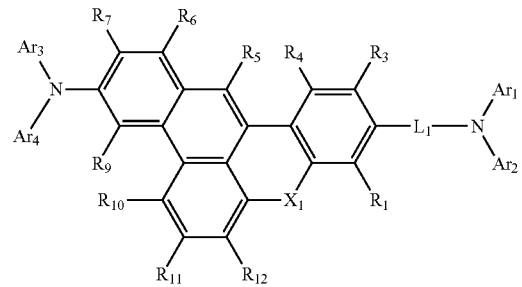

Formula 1-1(3)

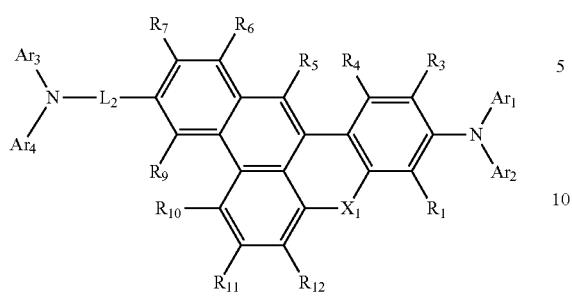

Formula 1-1(4)

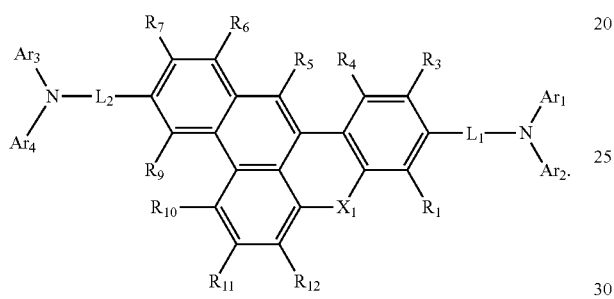

Regarding Formulae 1-1(1) to 1-1(4), descriptions of $X_1$, $L_1$, a1, $Ar_1$, $Ar_2$, $R_1$, $R_3$ to $R_7$, and $R_9$ to $R_{12}$ are the same as those provided above, and descriptions of $L_2$, a2, $Ar_3$, and $Ar_4$ are the same as the description presented in connection with $L_1$, a1, $Ar_1$, and $Ar_2$, respectively.

For example, the condensed cyclic compound represented by Formula 1 may be one selected from Compounds 1 to 189 and 1A to 164A below, but is not limited thereto:

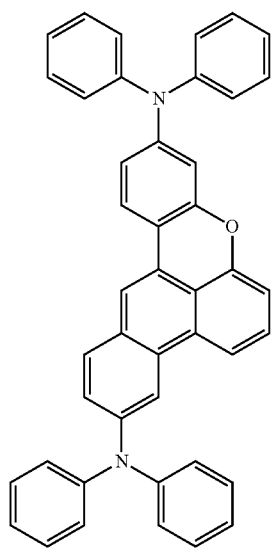

1

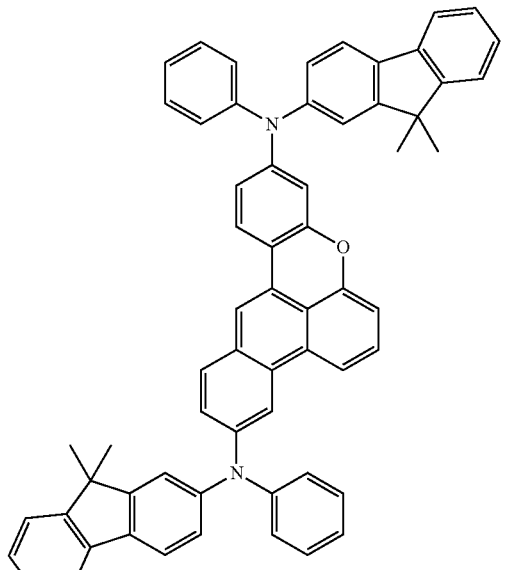

2

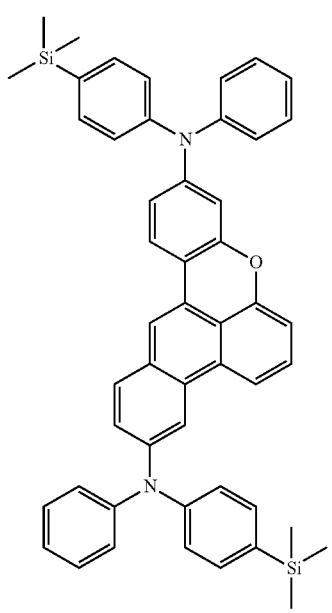

3

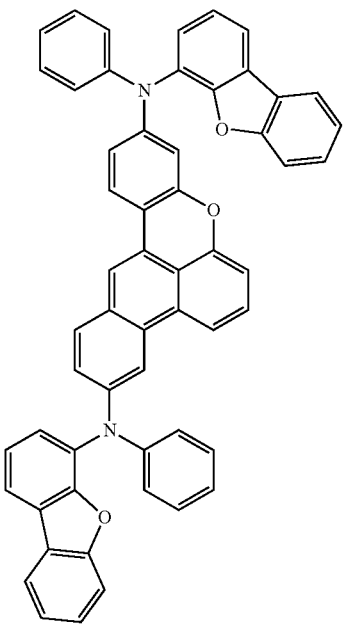
4
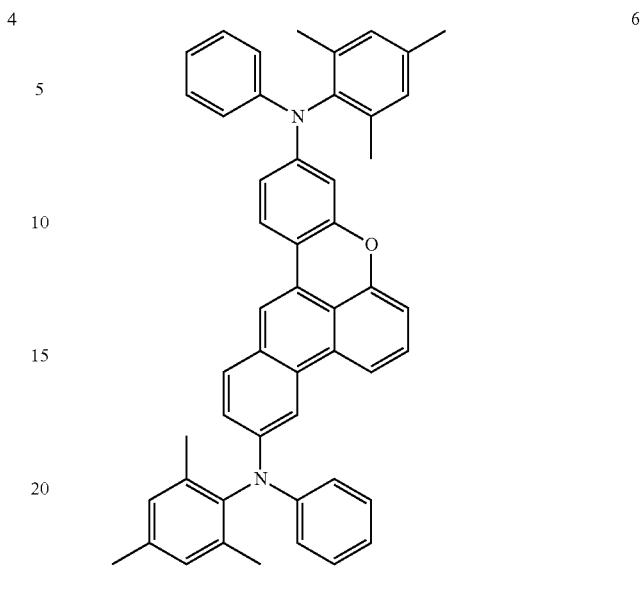
5
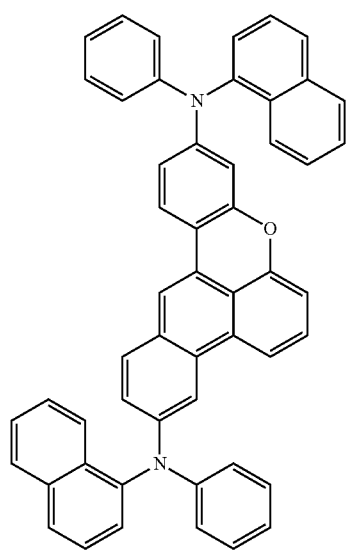
6
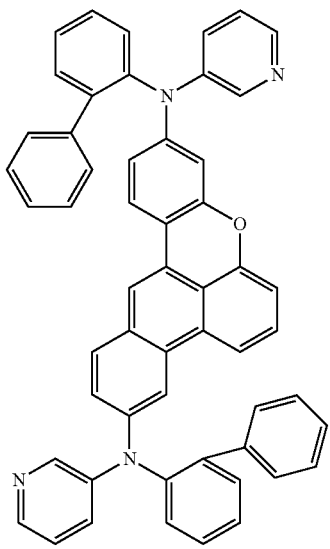
7

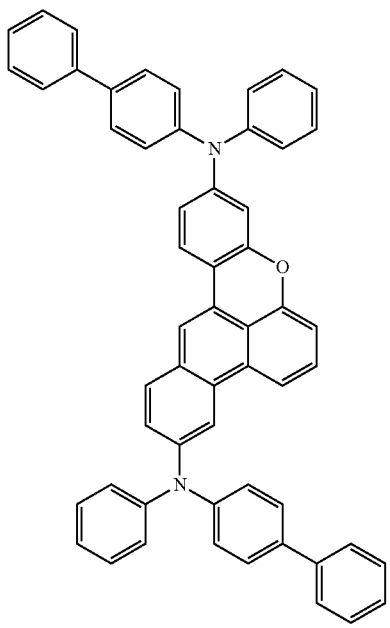
8
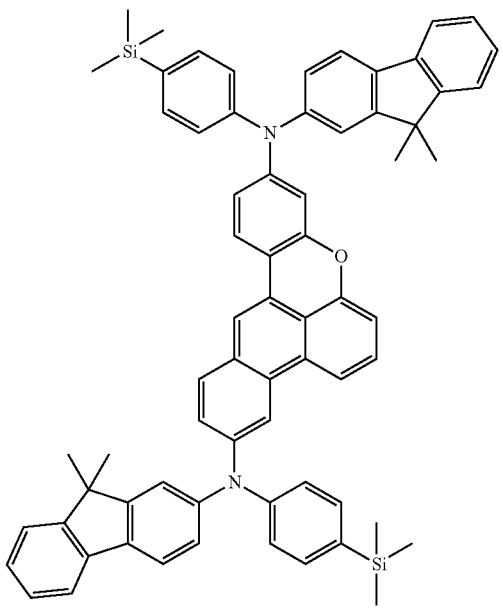
10
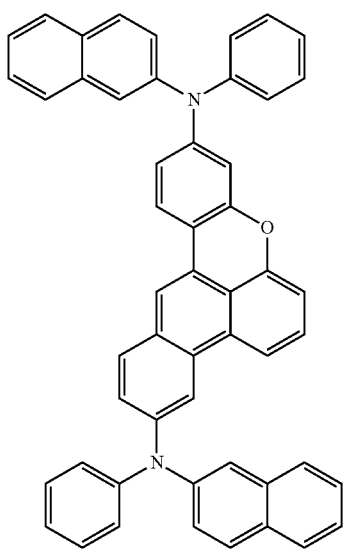
9
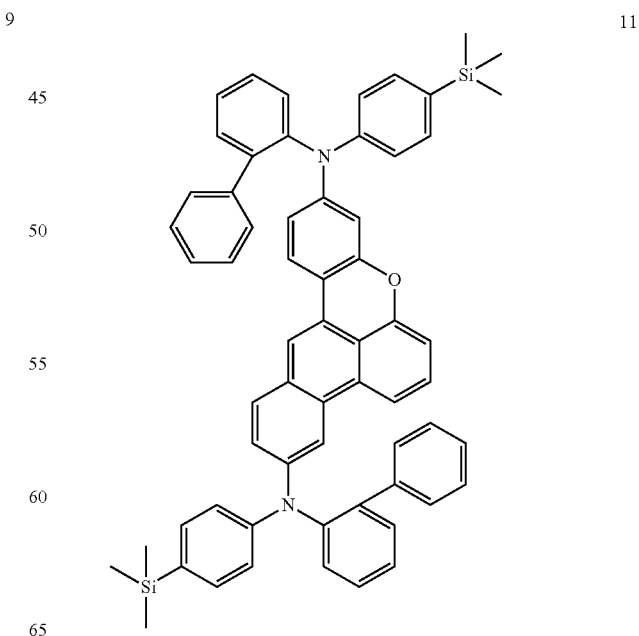
11

-continued
12
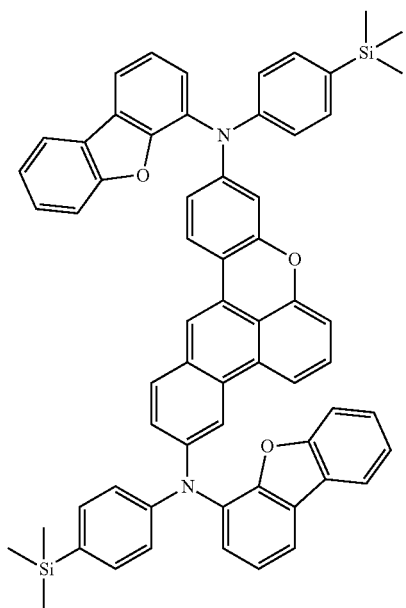
-continued
14
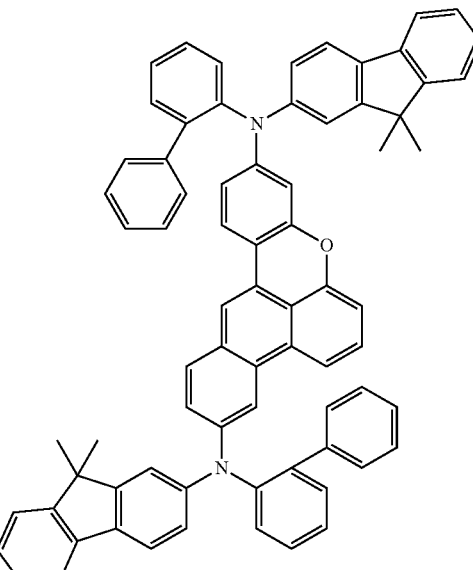
13
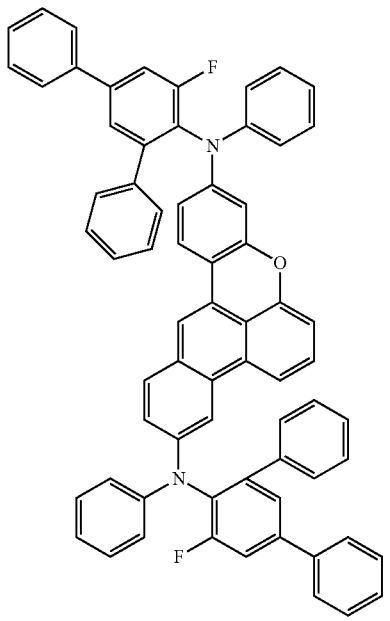
15

16
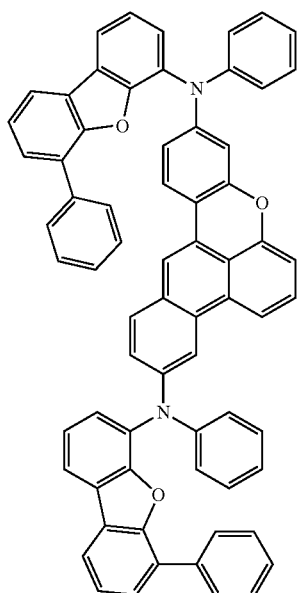
17
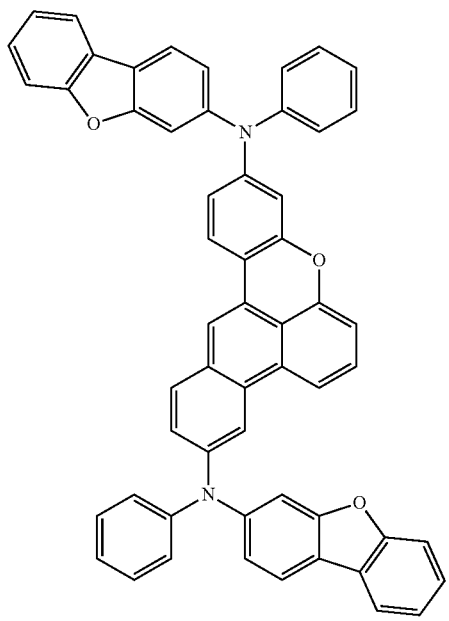
18
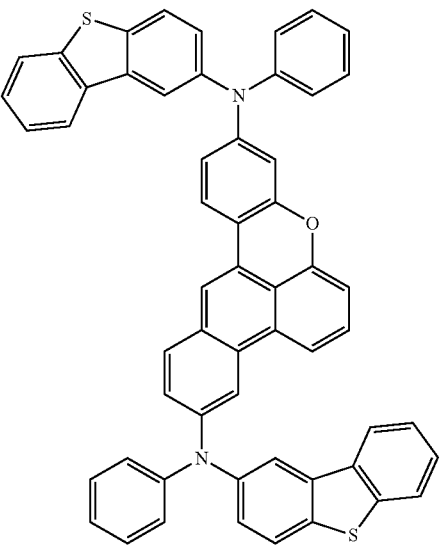
19

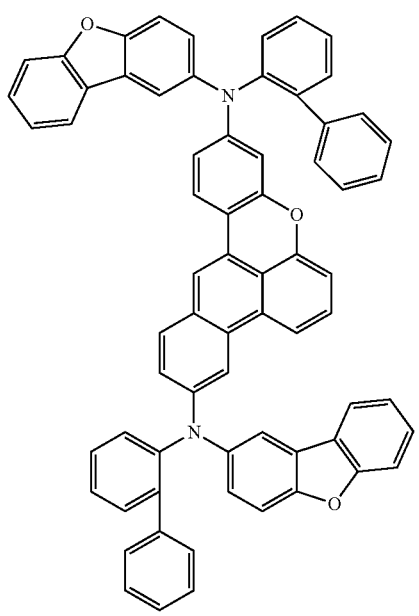
20
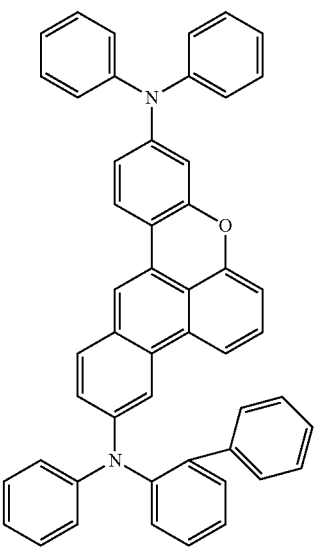
22
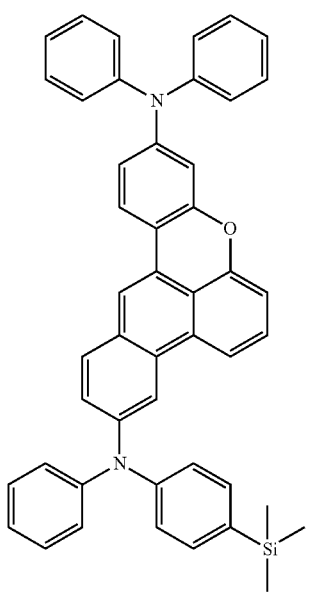
21
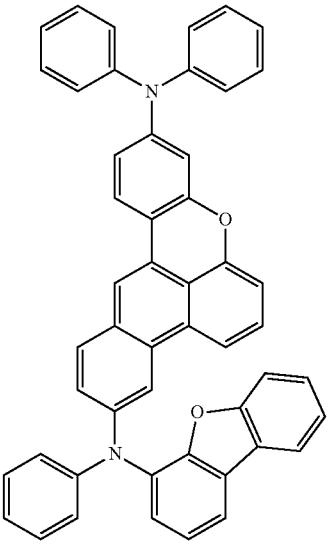
23

24
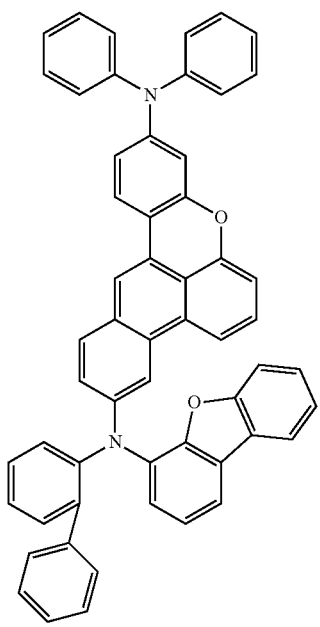
26
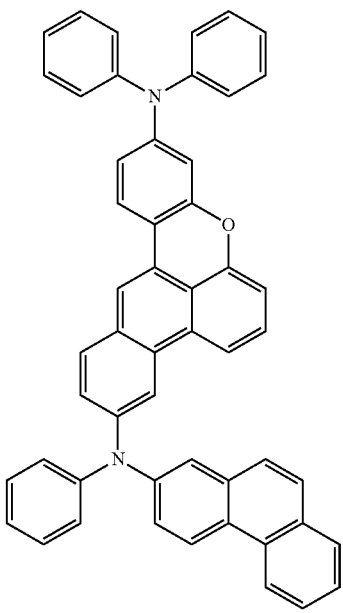
25
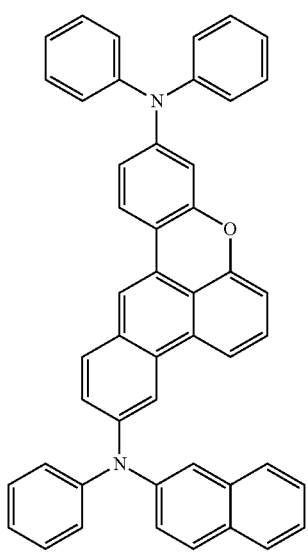
27
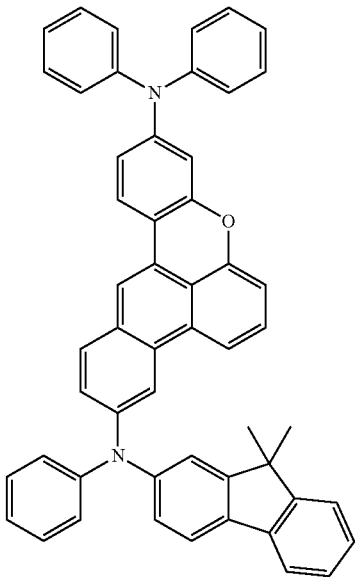

28
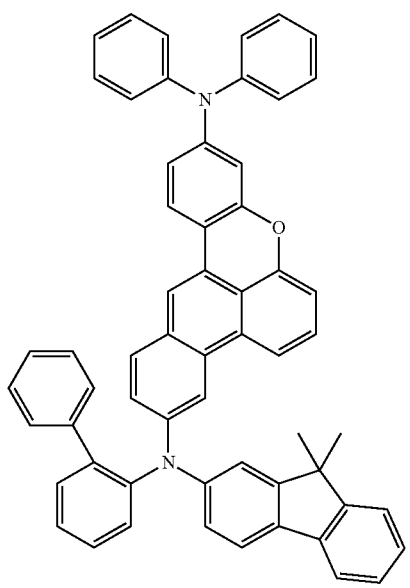
29
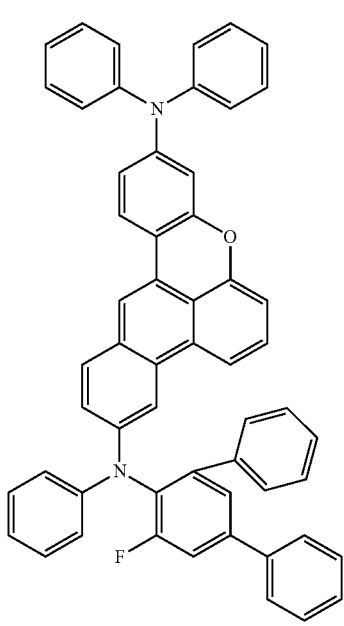
30
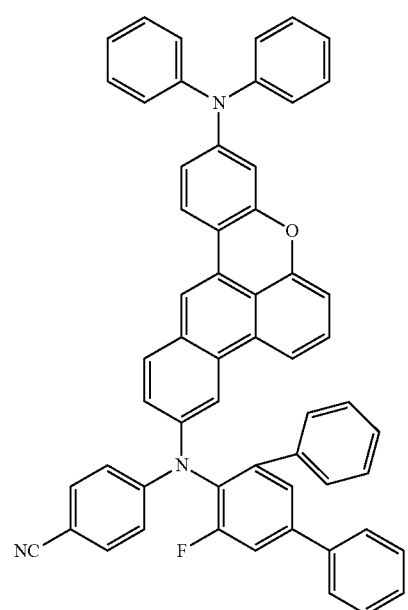
31
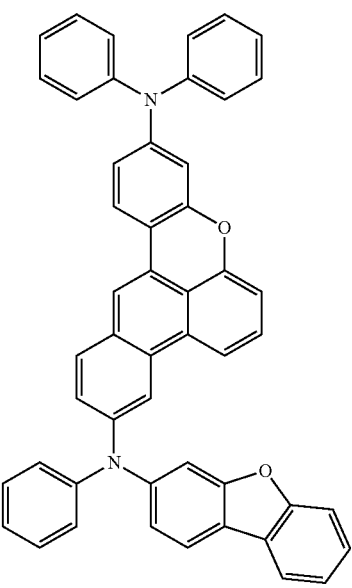

32
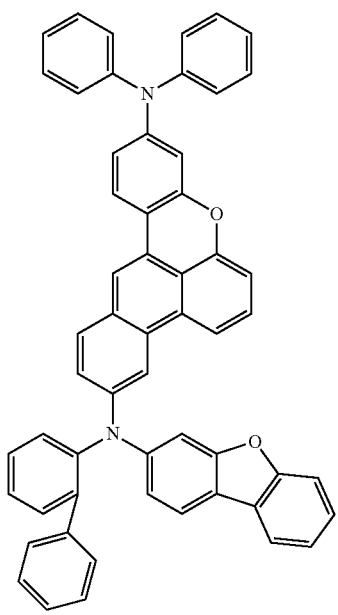
34
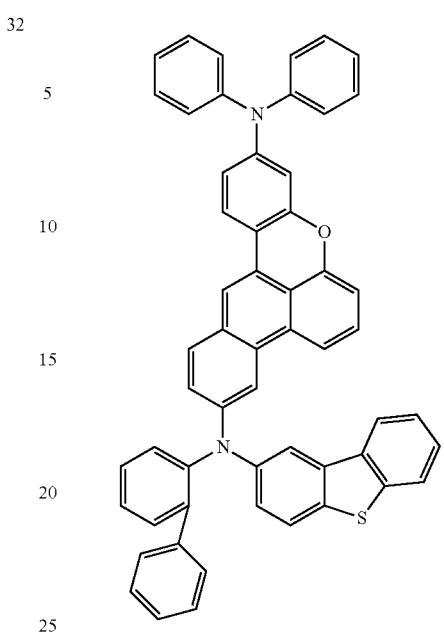
33
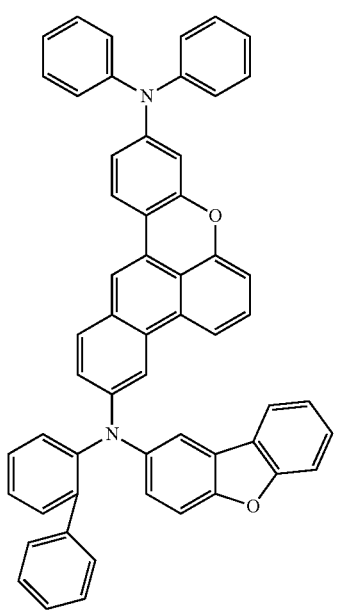
35
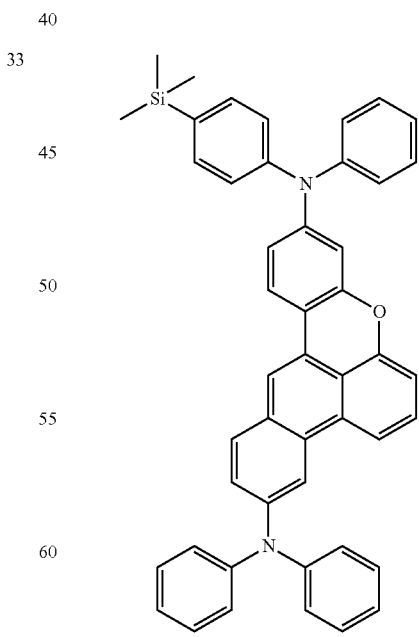

36
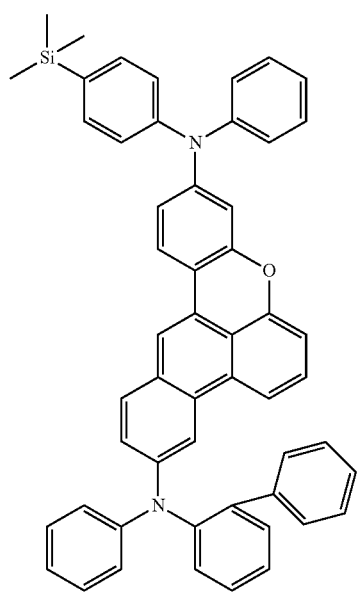
38
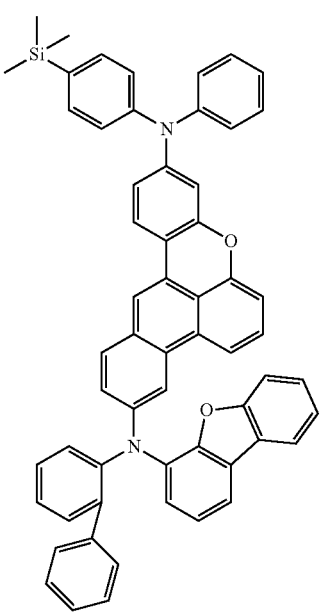
37
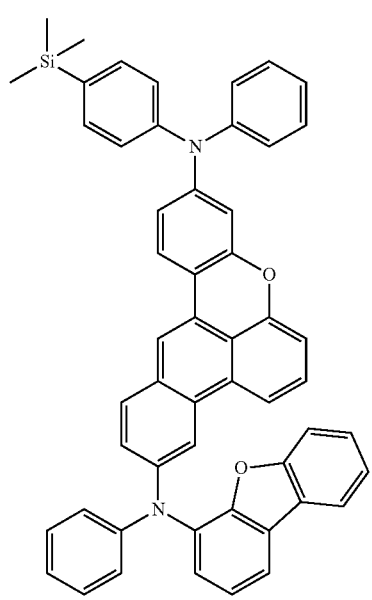
39
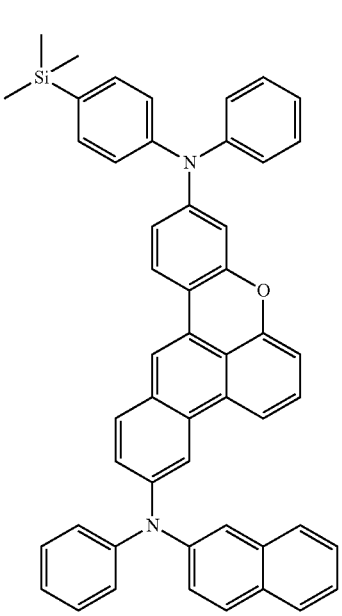

51
-continued
40
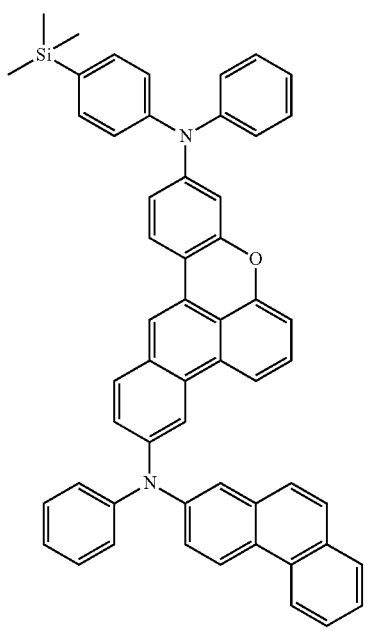
52
-continued
42
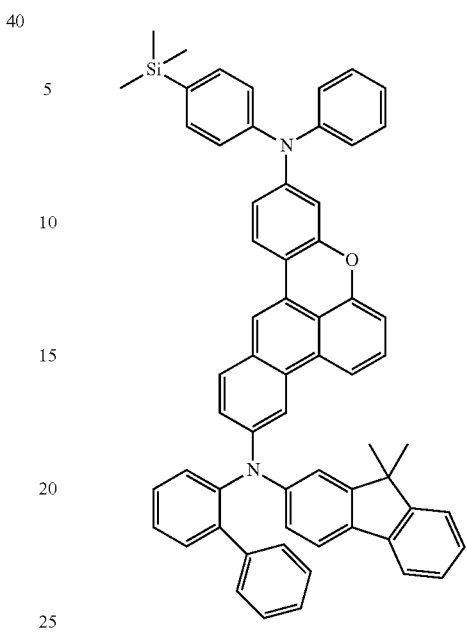
41
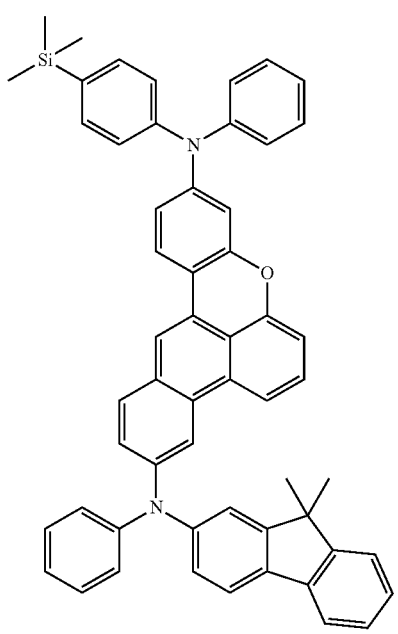
43
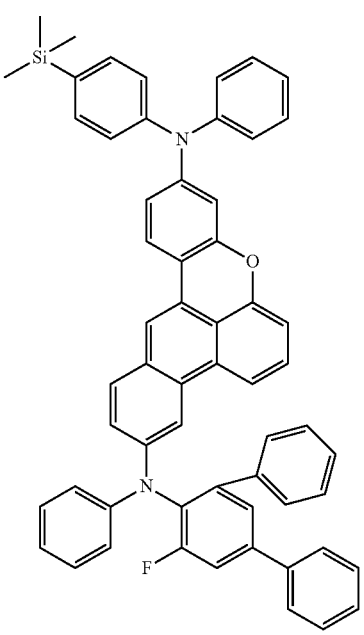

44
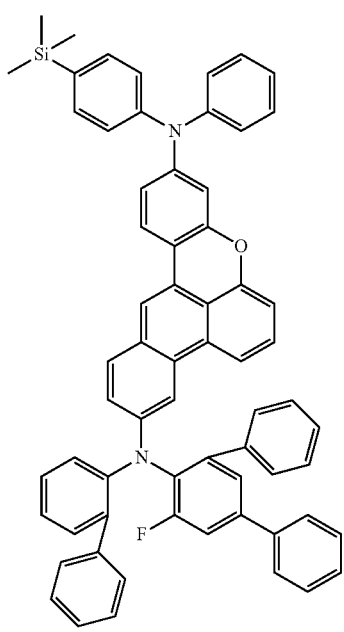
46
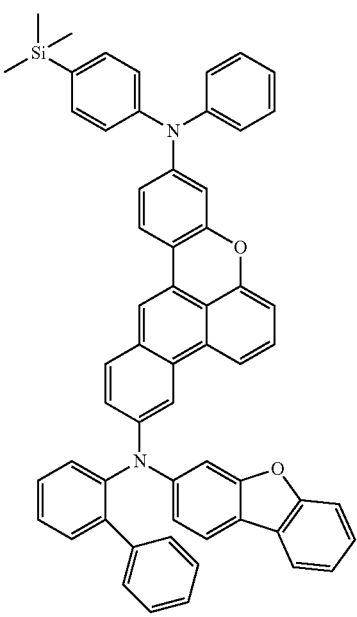
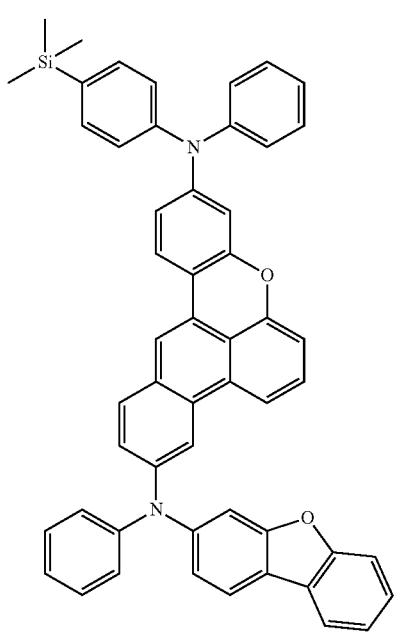
47
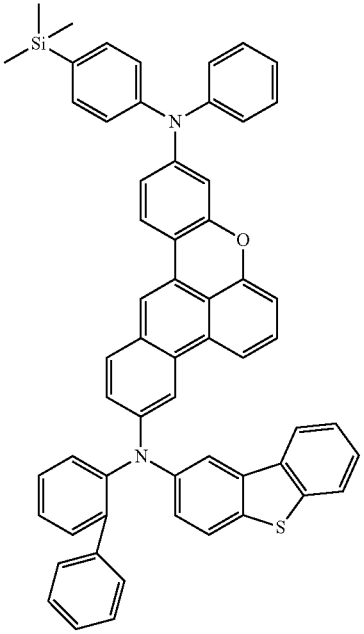

48
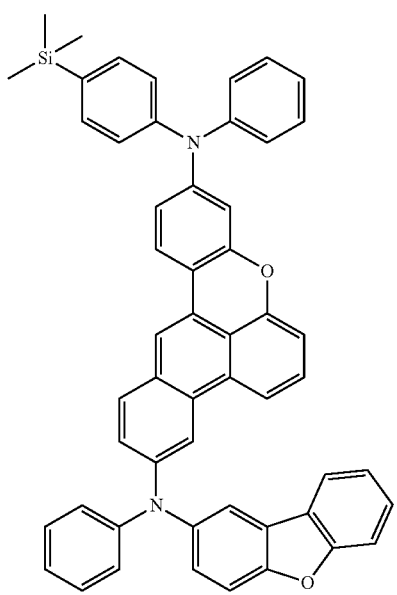
49
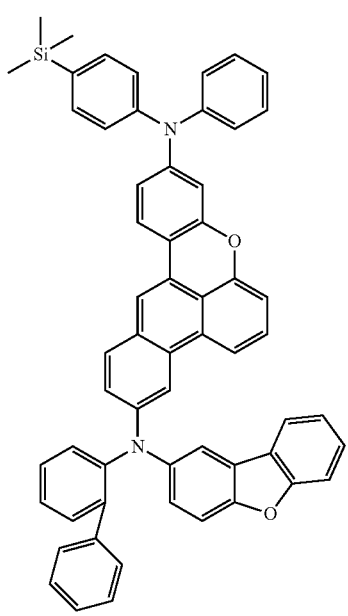
50
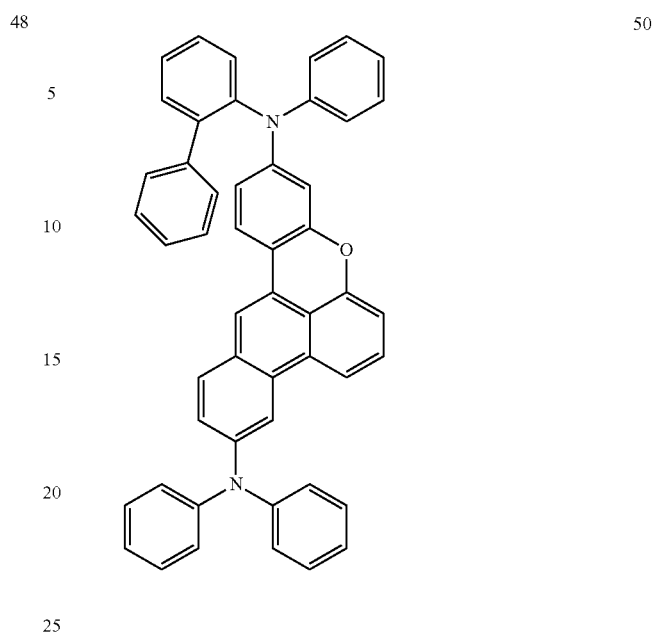
51
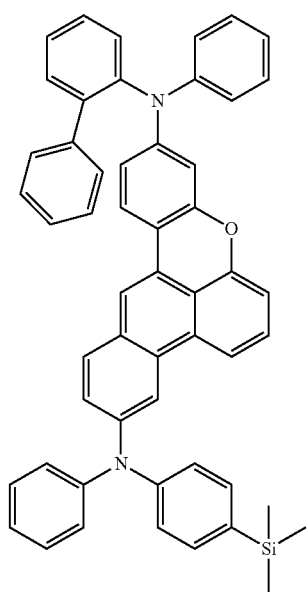

-continued
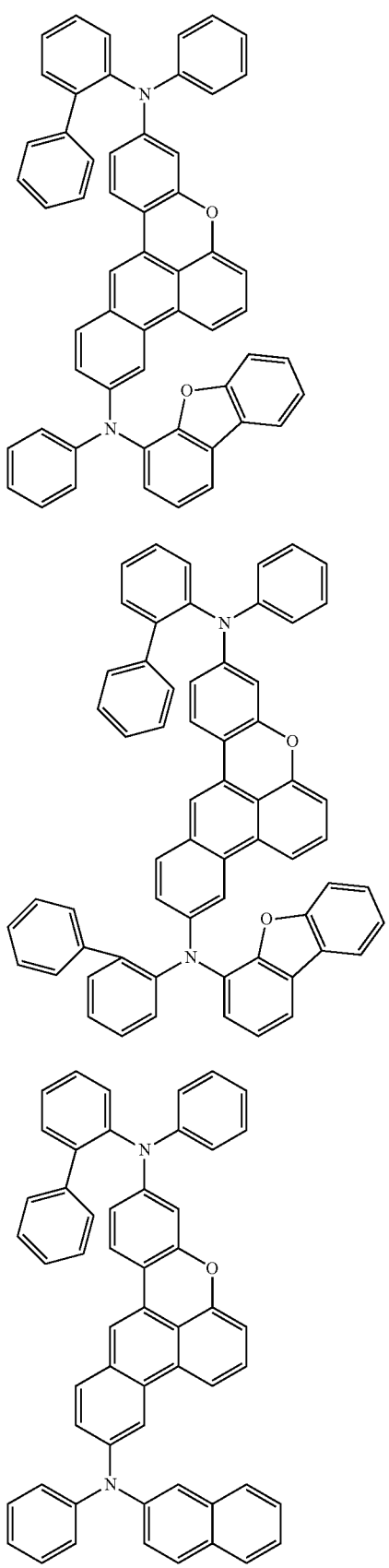
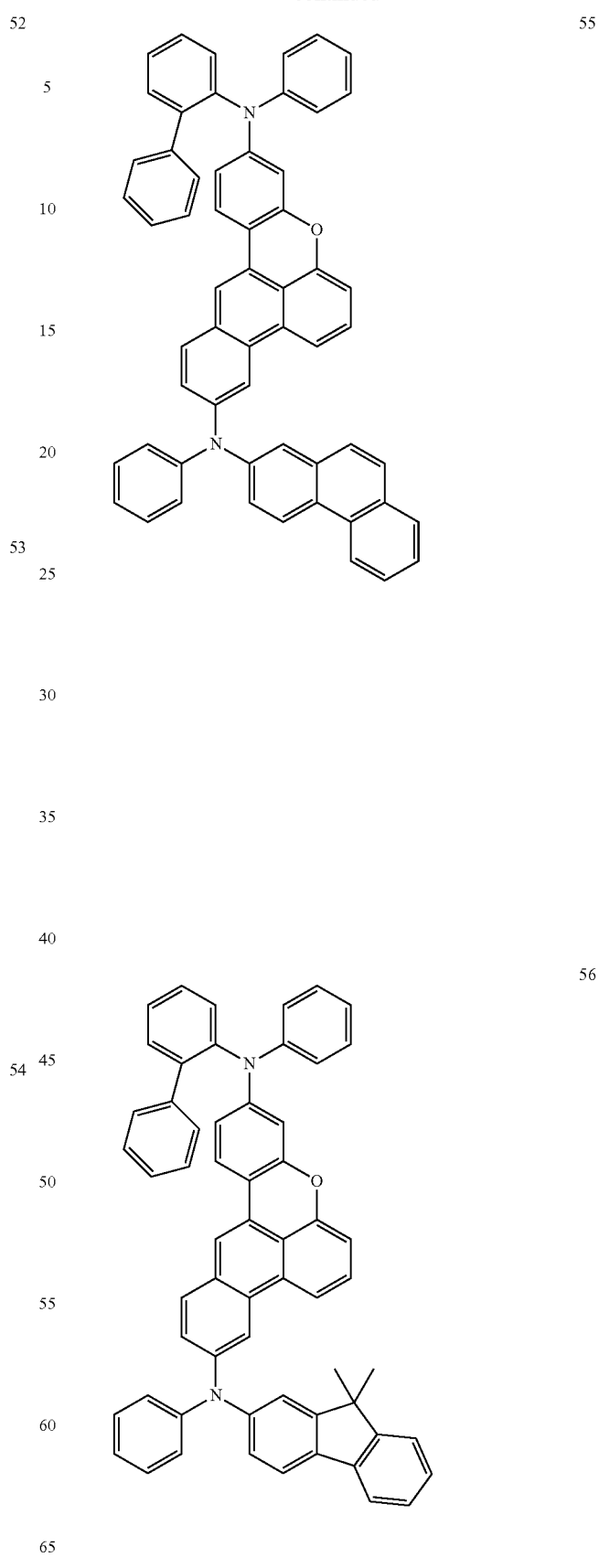

57
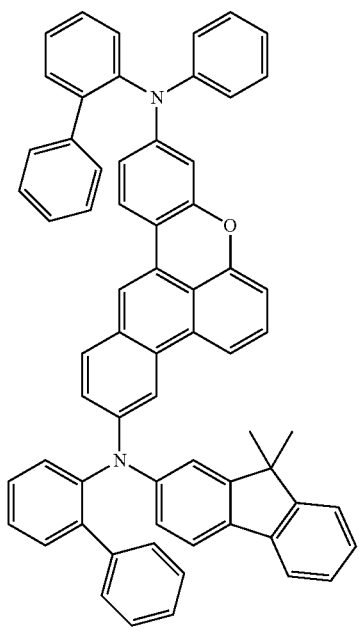
58
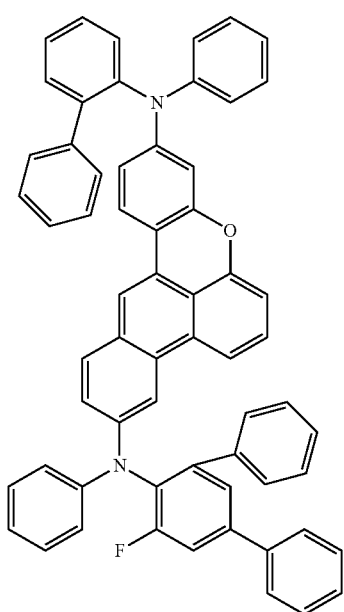
59
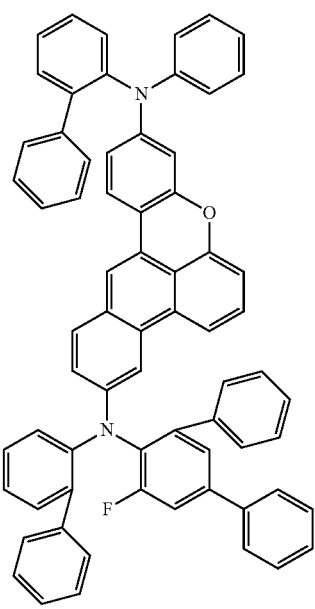
60
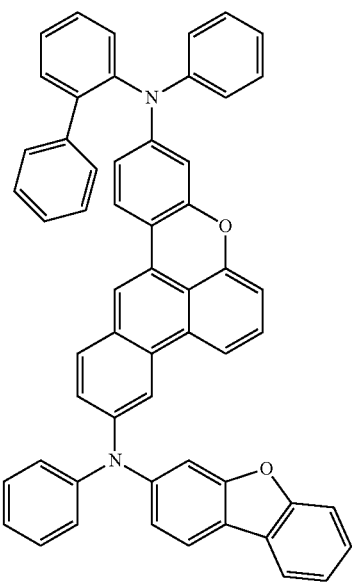

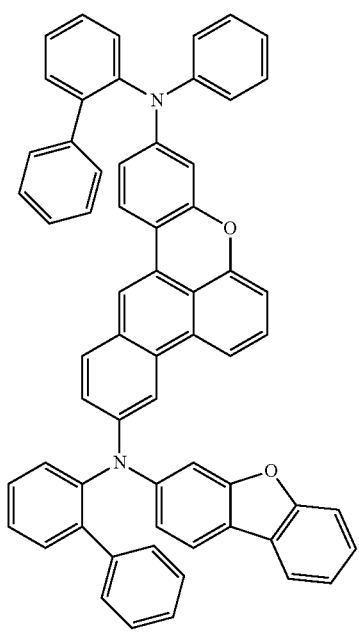
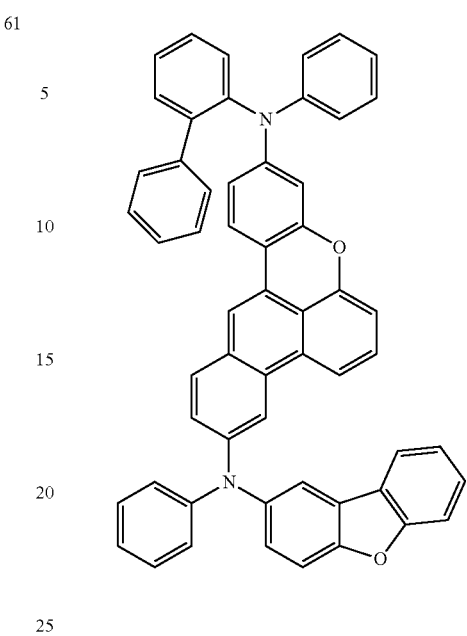
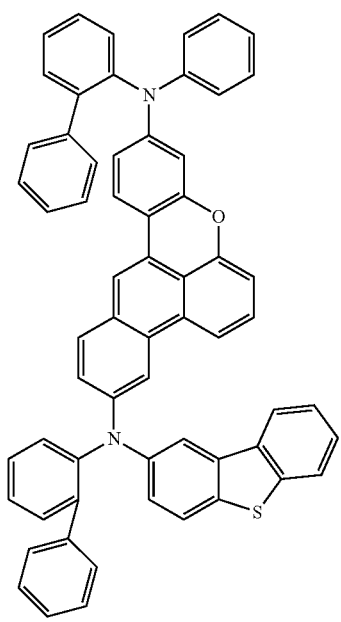
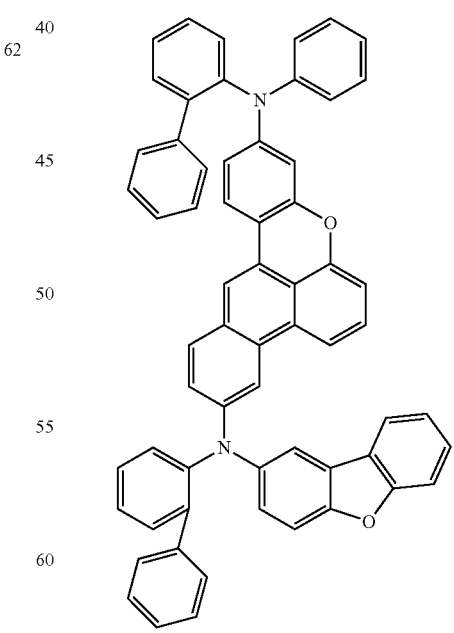

63
-continued
65
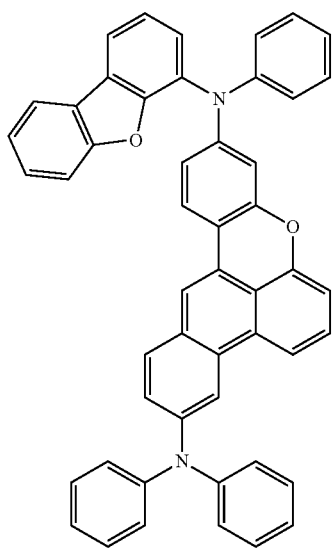
66
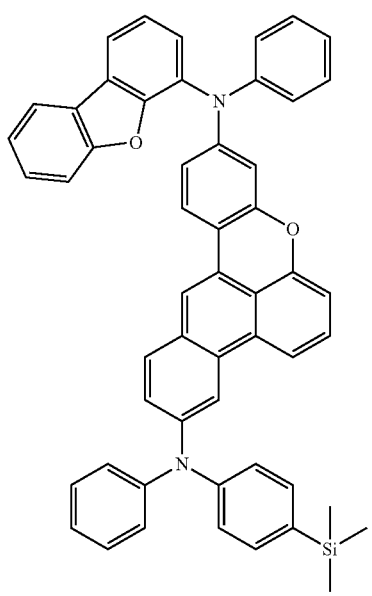
64
-continued
67
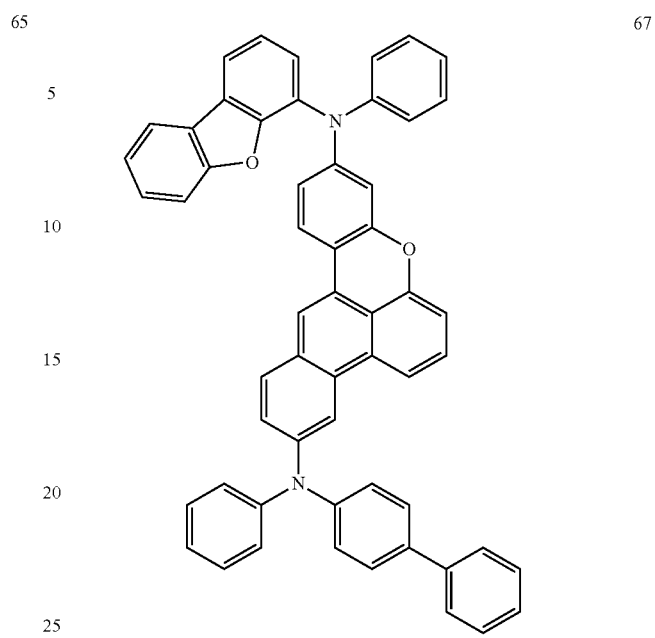
68

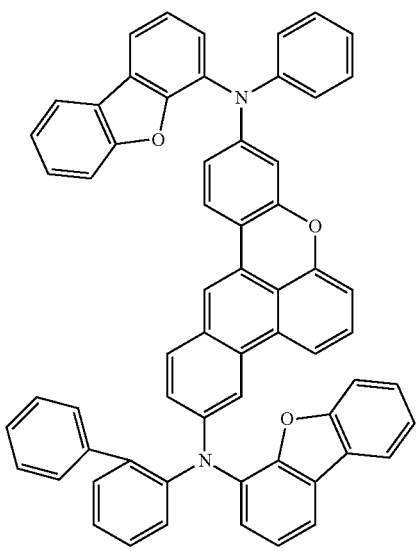
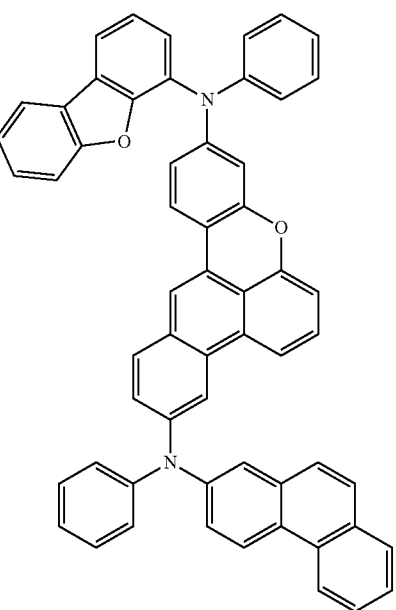
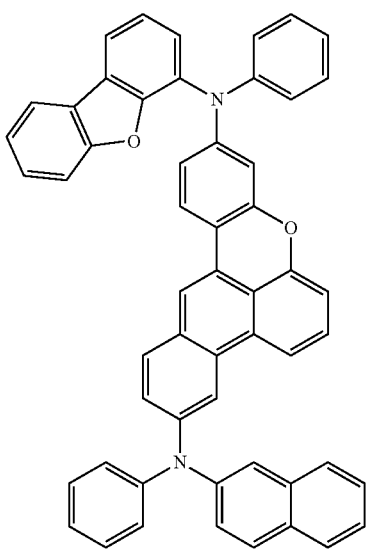
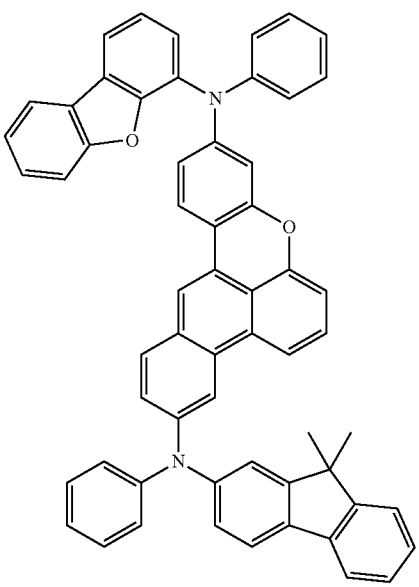

73
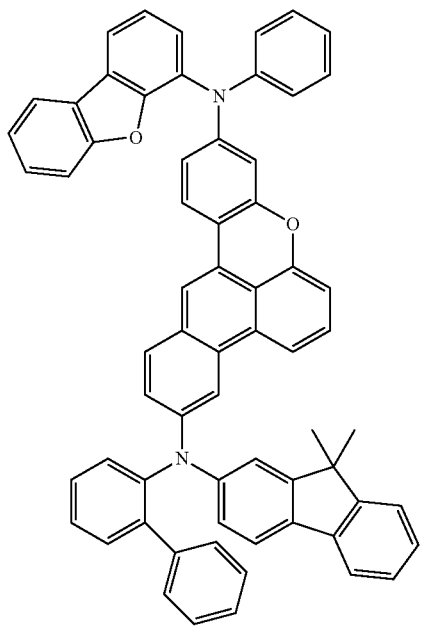
74
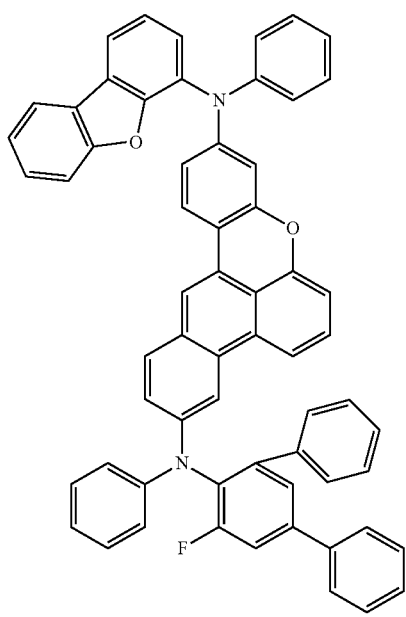
75
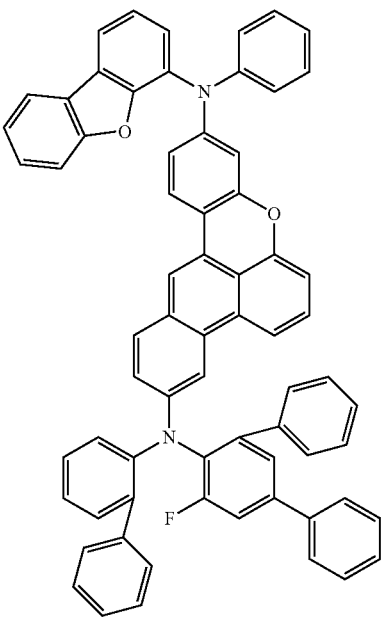
76
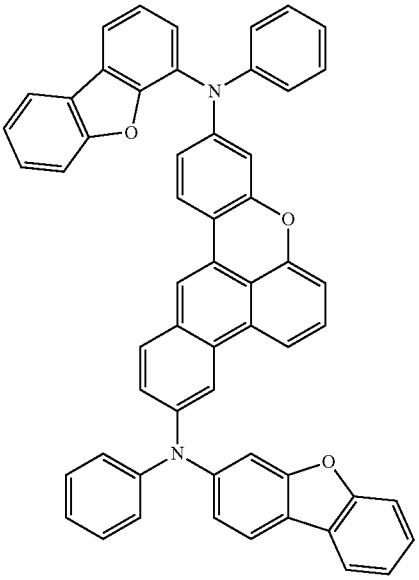

-continued
77
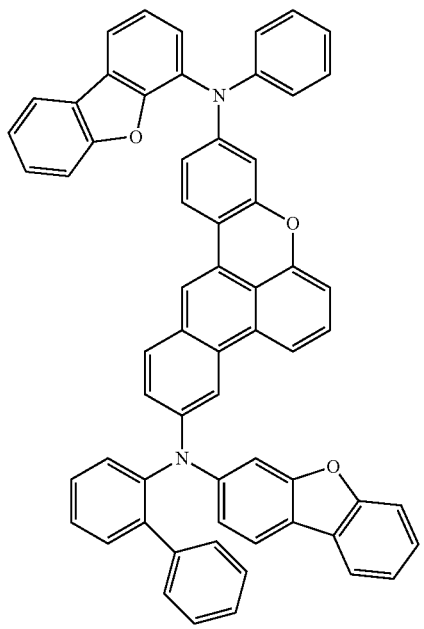
-continued
79
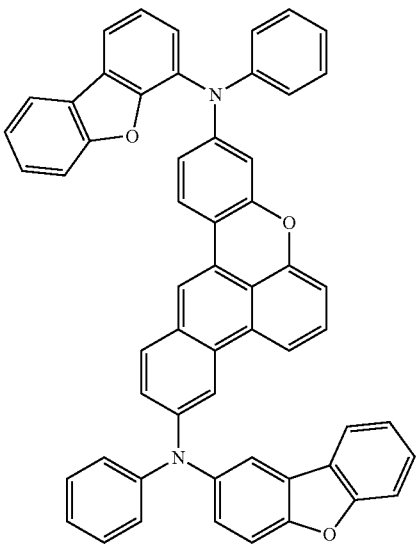
78
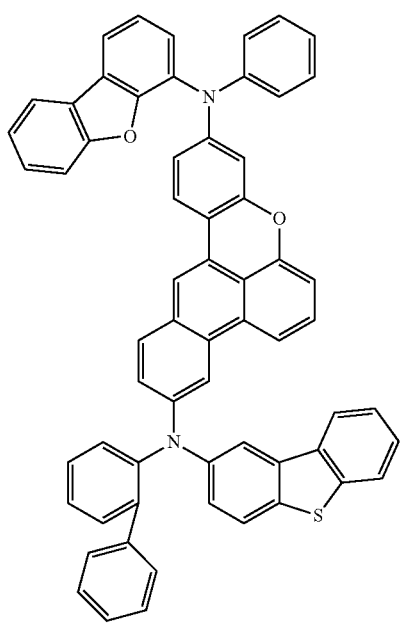
80
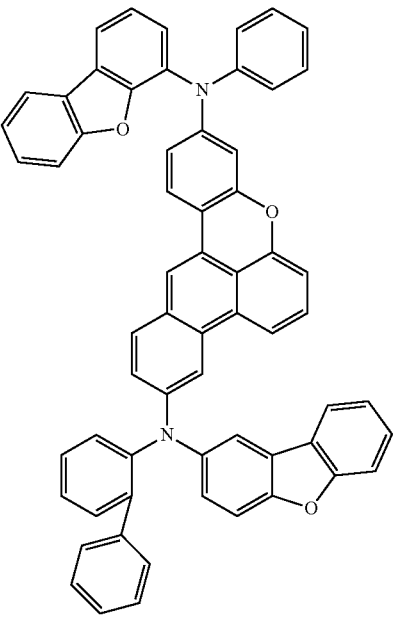

81
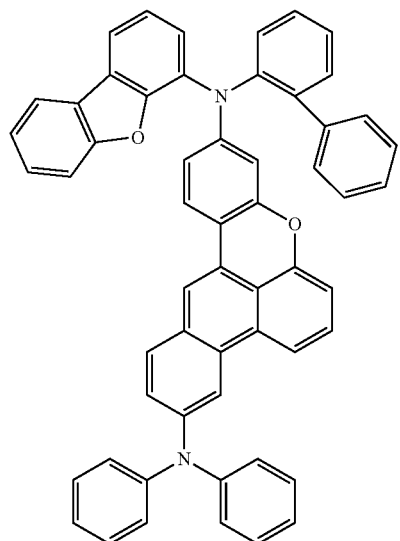
83
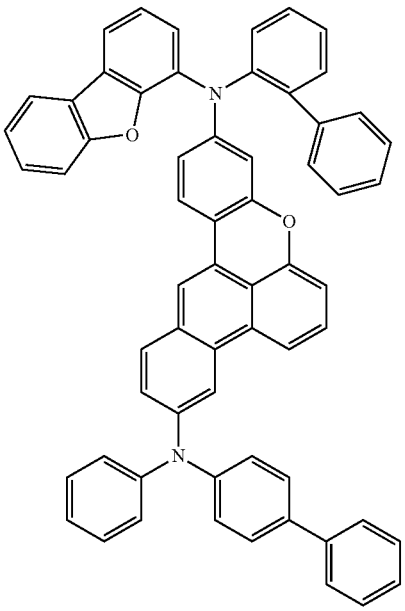
82
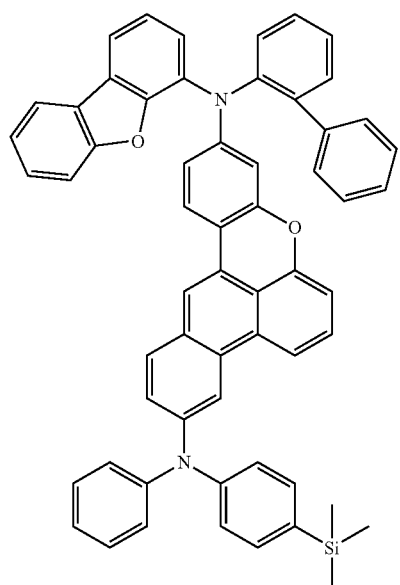
84
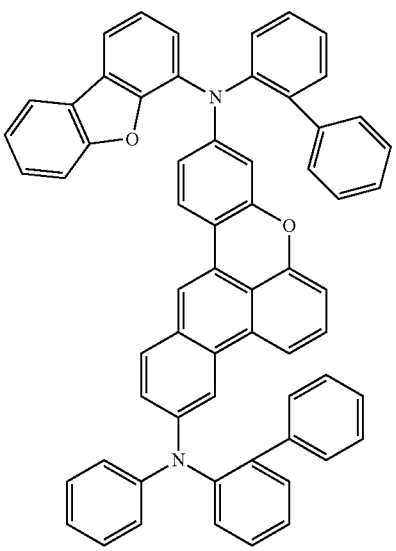

85
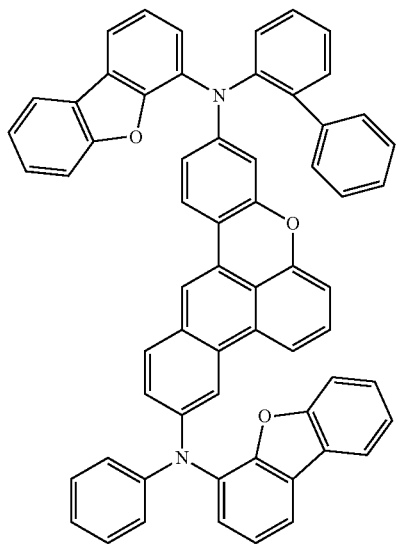
87
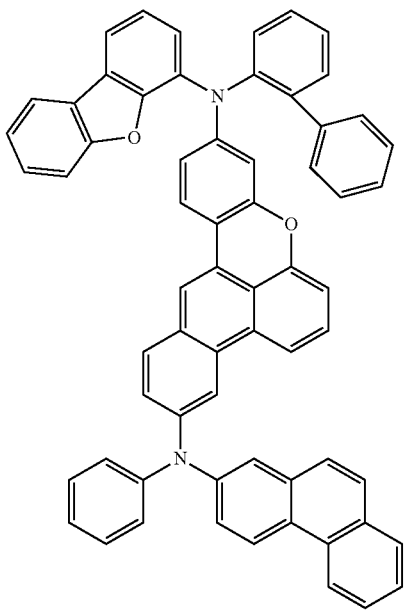
86
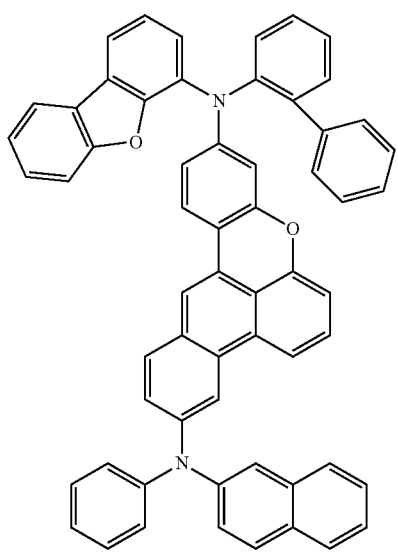
88
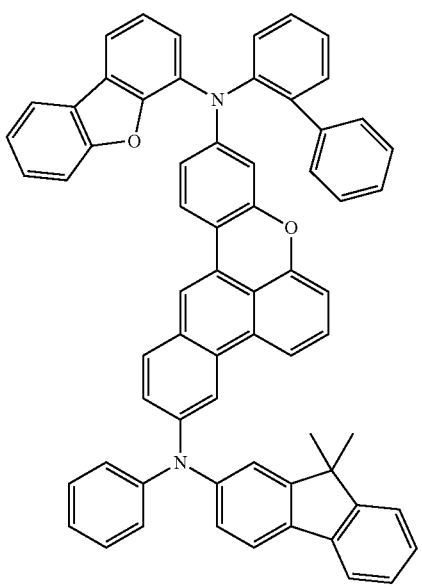

89
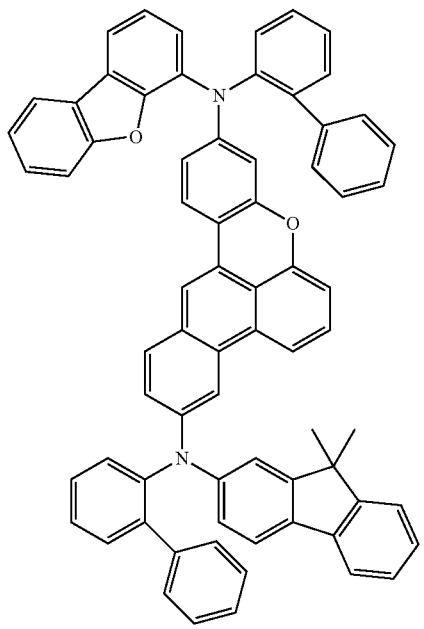
90
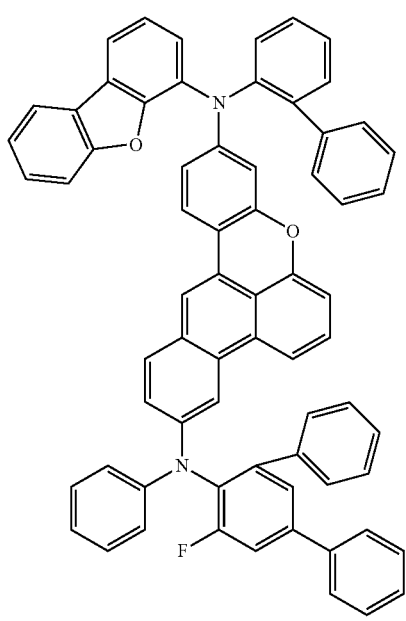
91
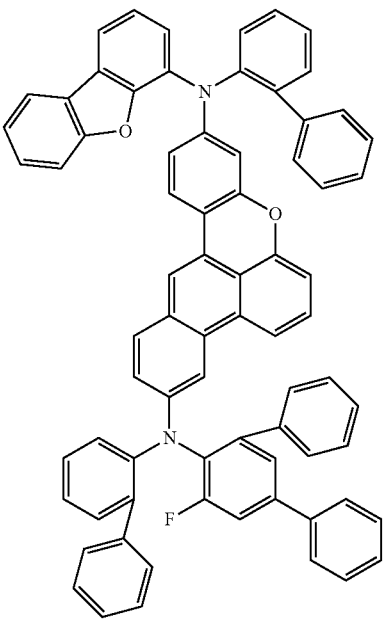
92
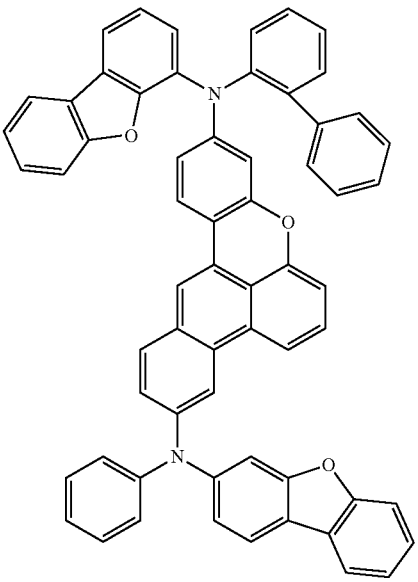

93
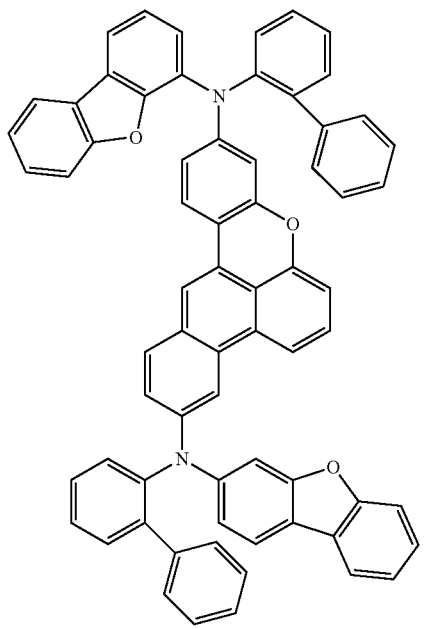
94
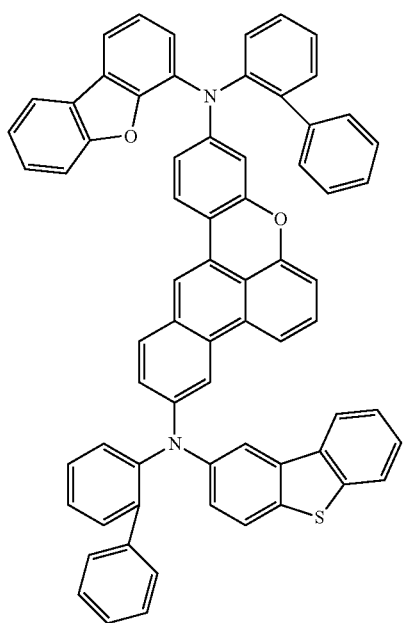
95
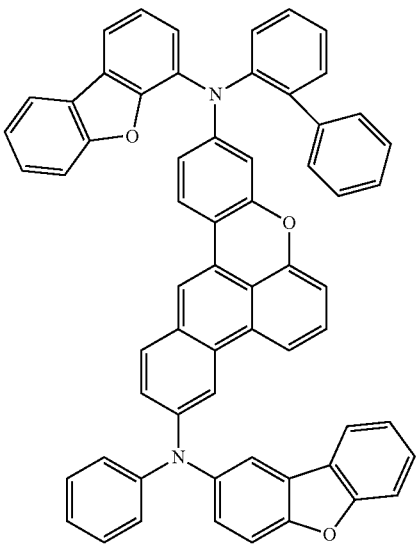
96
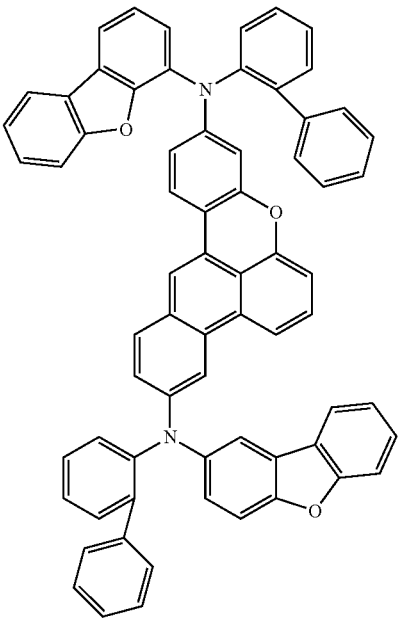

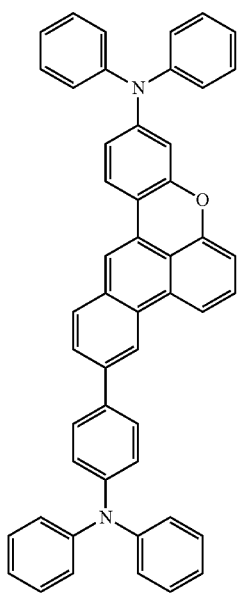
97
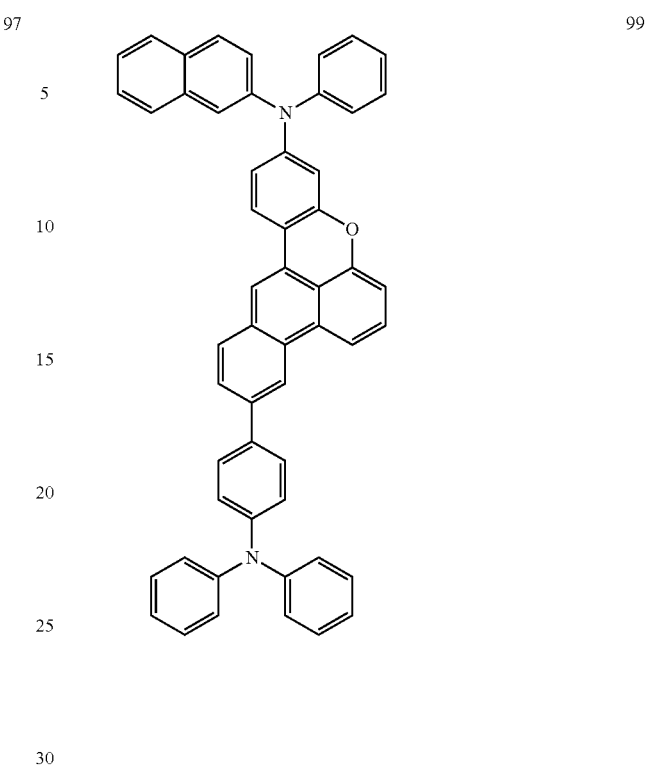
99
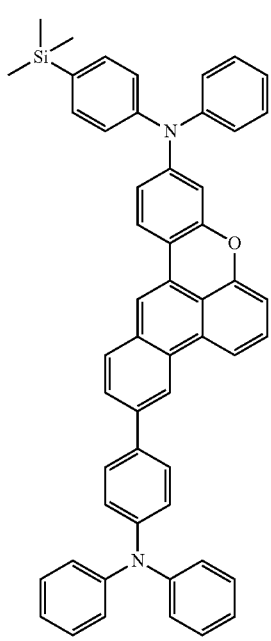
98
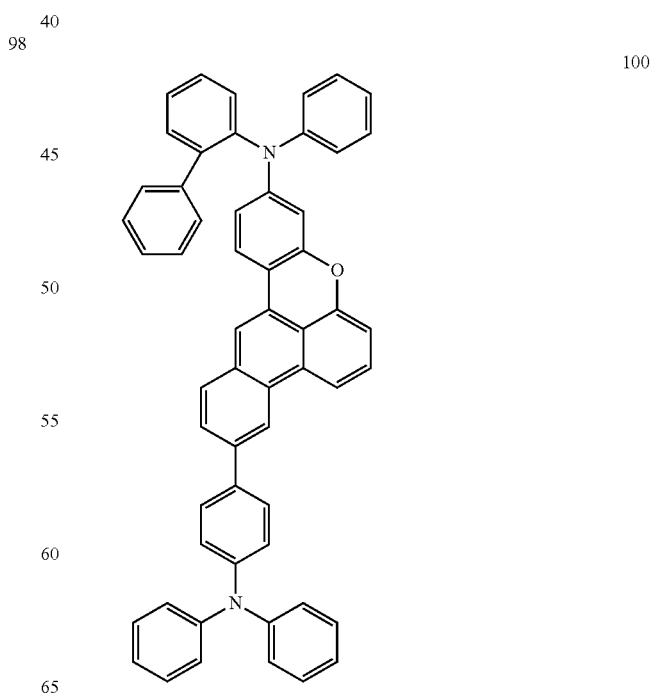
100

81
-continued
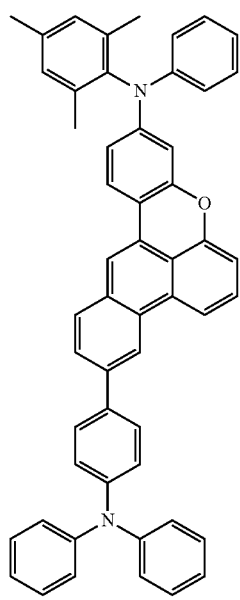
101
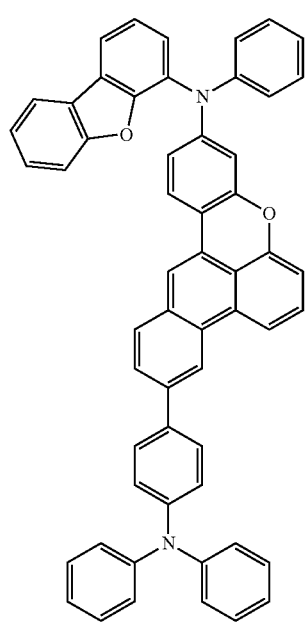
102
82
-continued
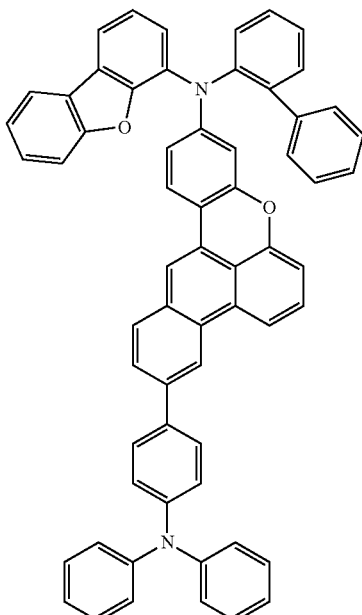
103
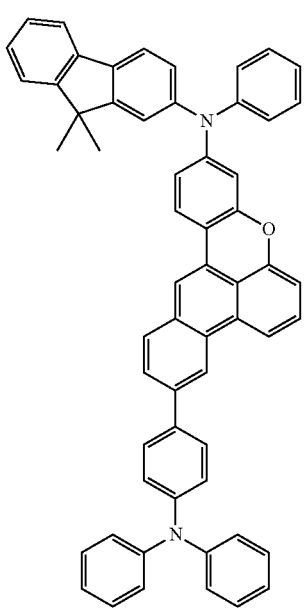
104

105
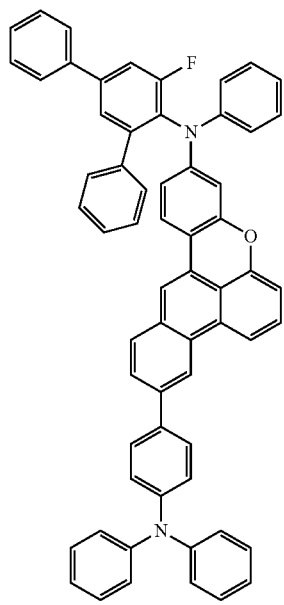
106
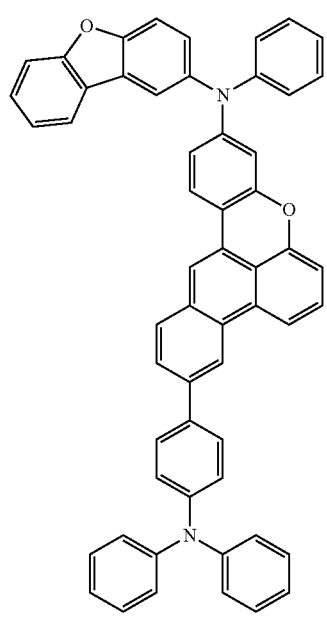
107
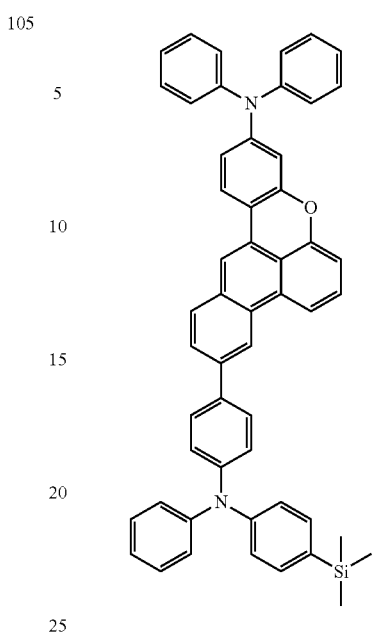
108
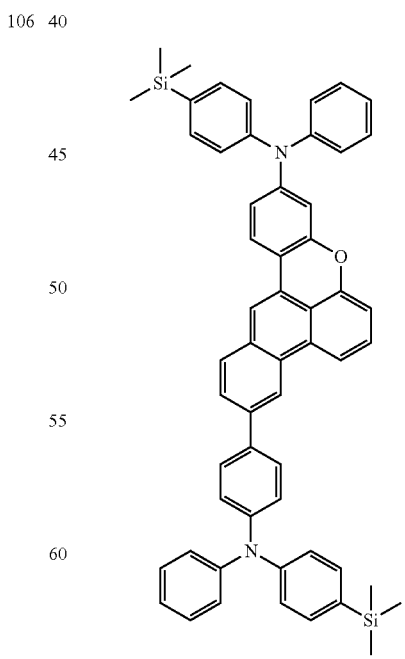

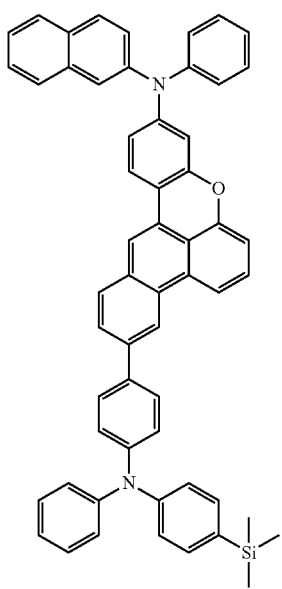
109
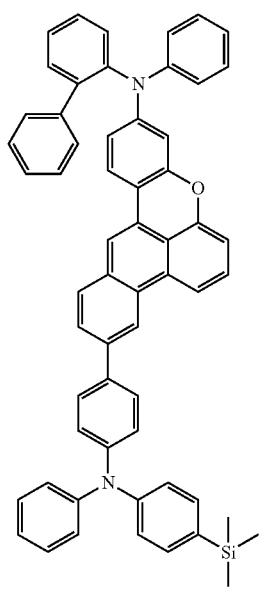
110
111
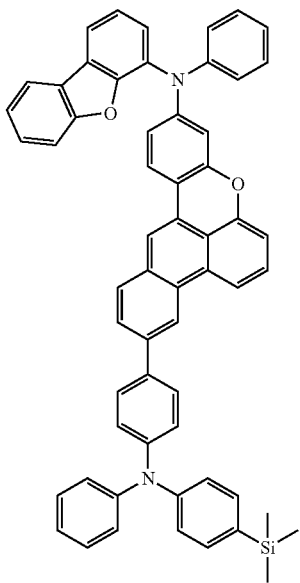
112

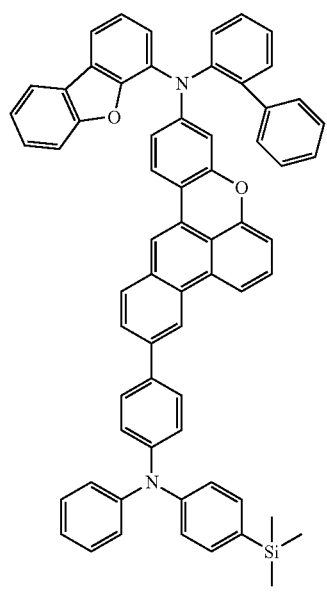
113
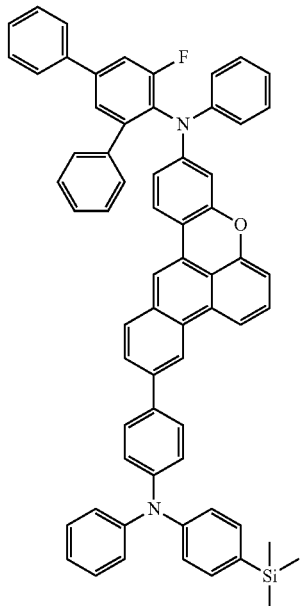
115
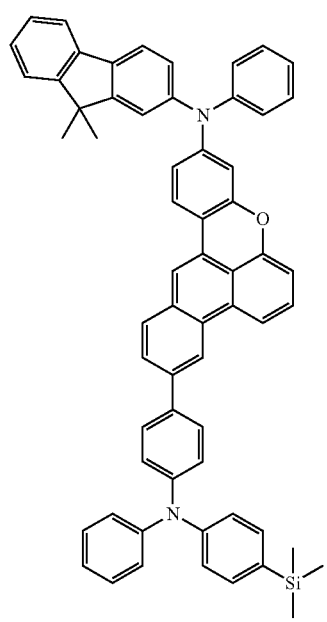
114
116

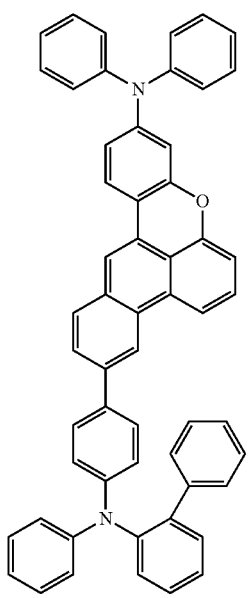
117
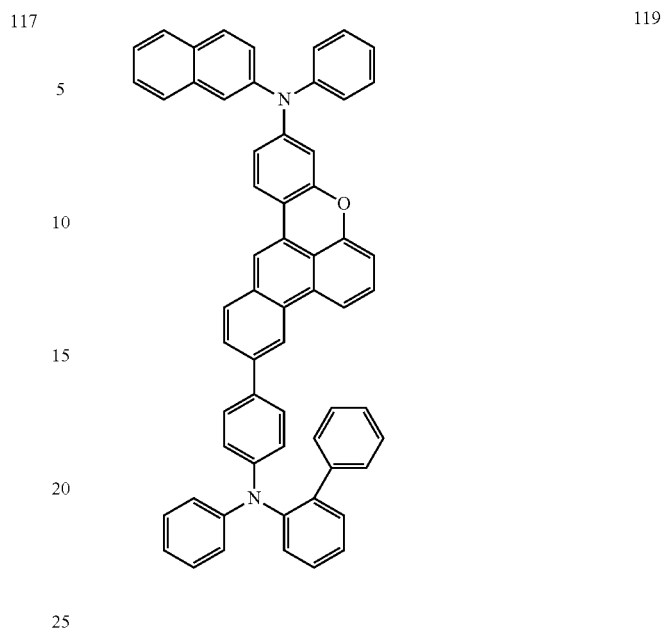
119
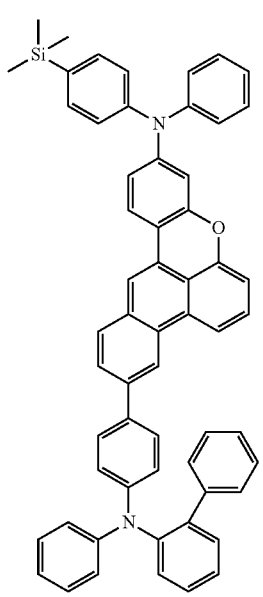
118
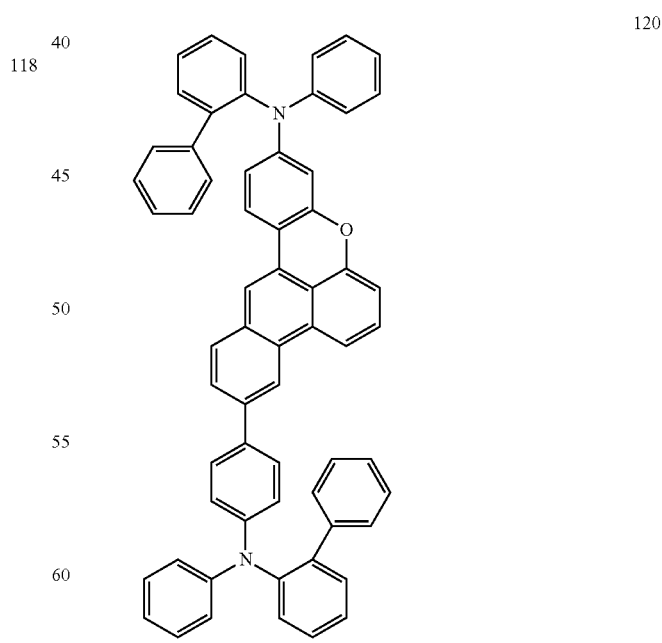
120

91
92
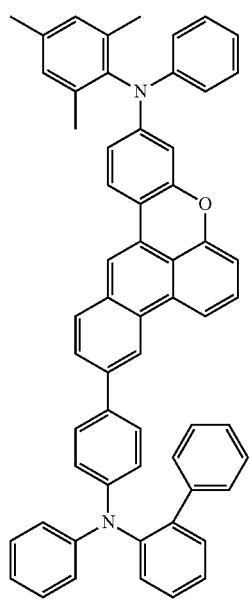
121
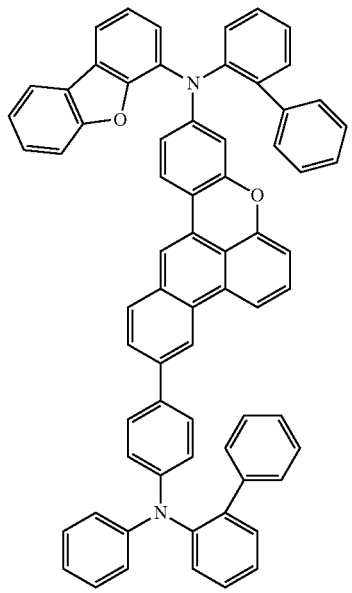
123
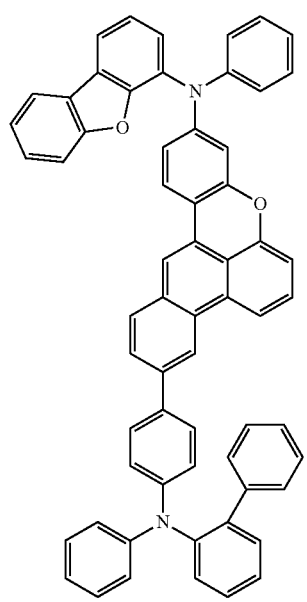
122
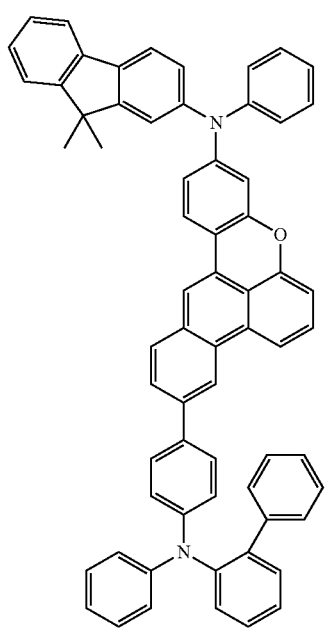
124

93
-continued
125
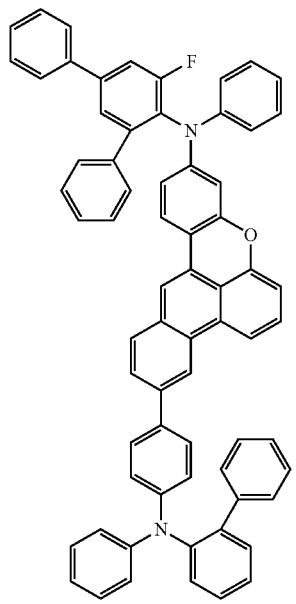
126
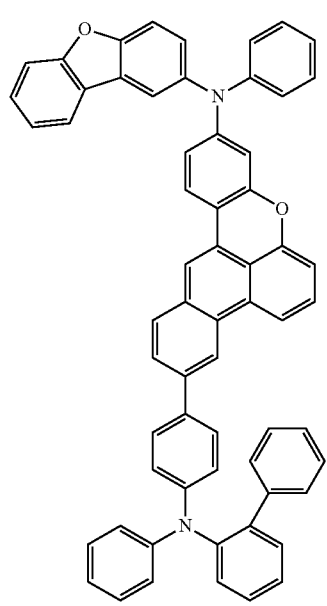
94
-continued
127
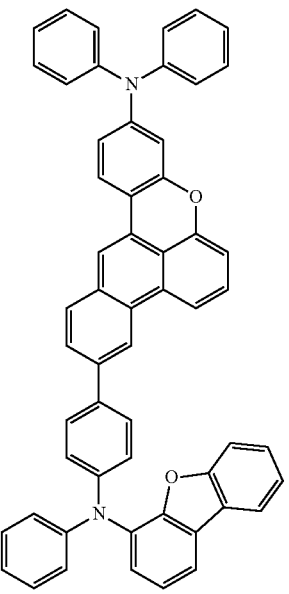
128
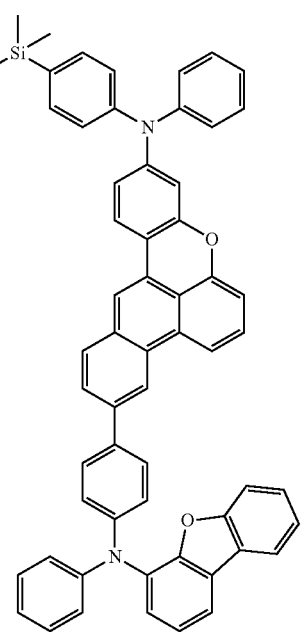

129
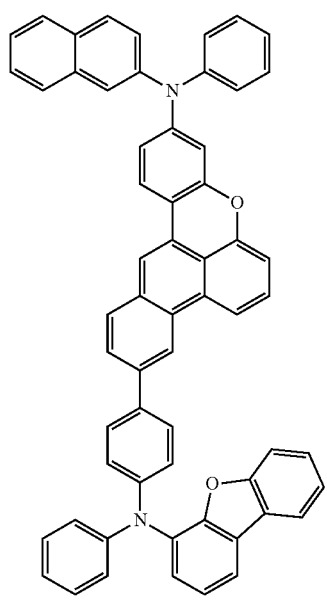
130
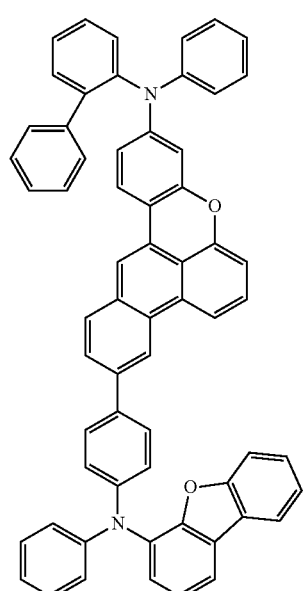
131
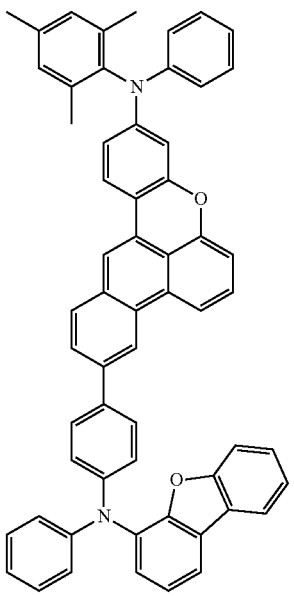
132
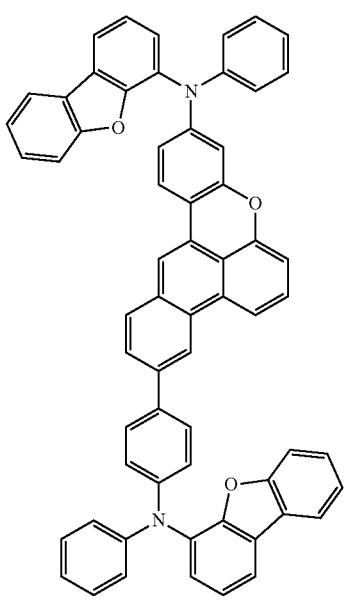

97
-continued
133
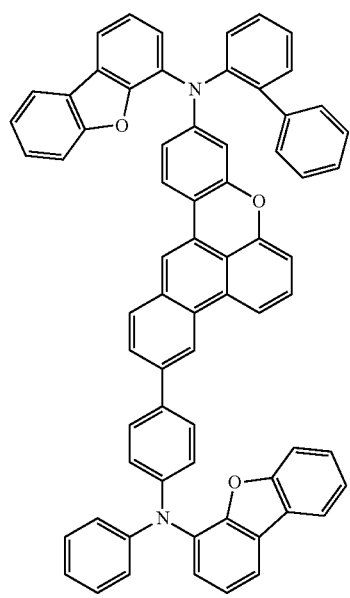
134
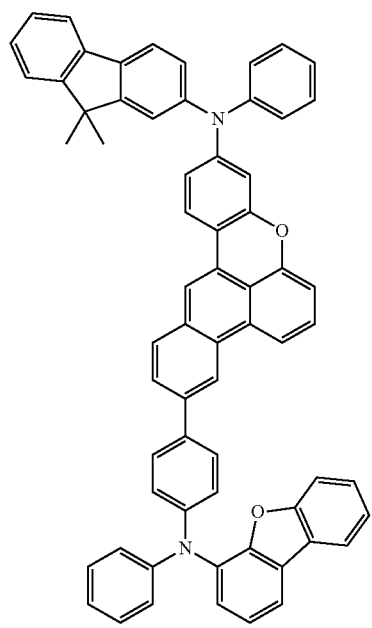
98
-continued
135
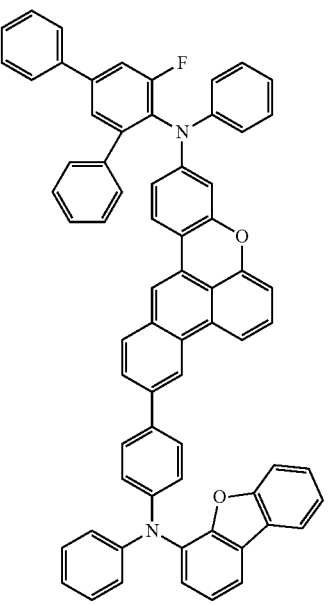
136
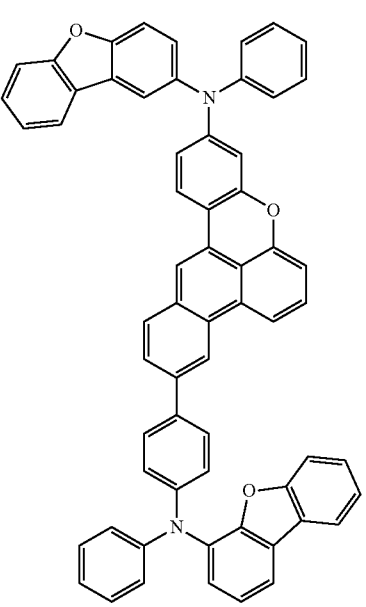

99
-continued
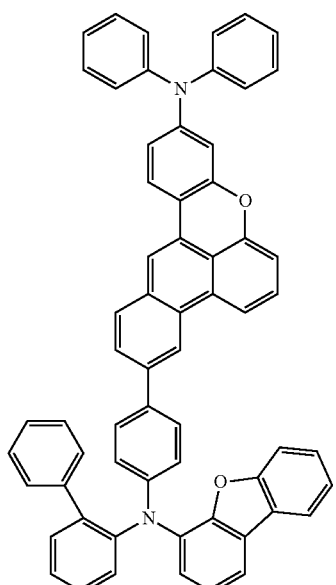
137
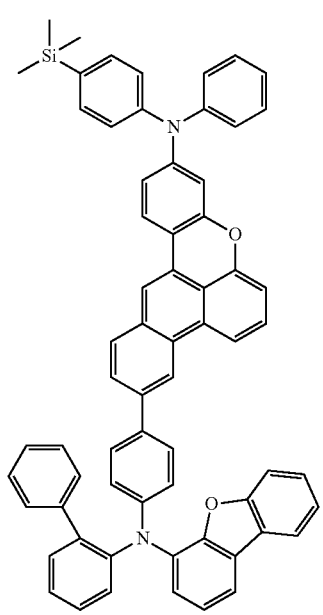
138
100
-continued
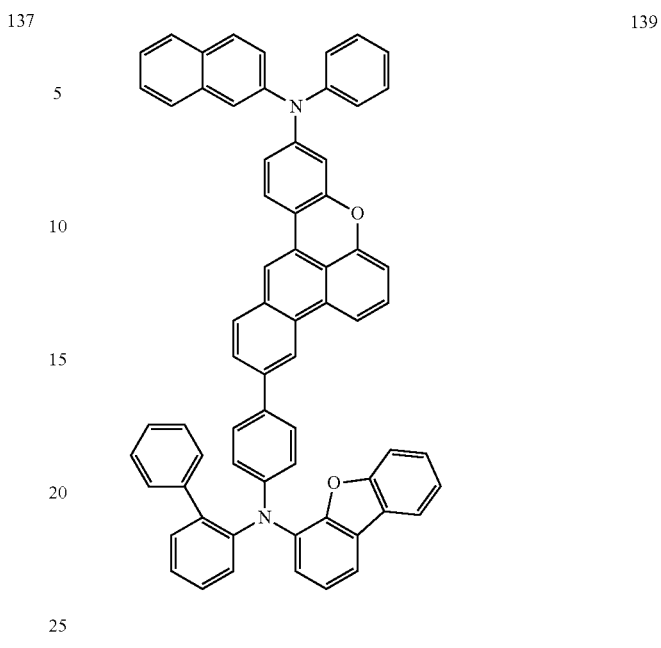
139
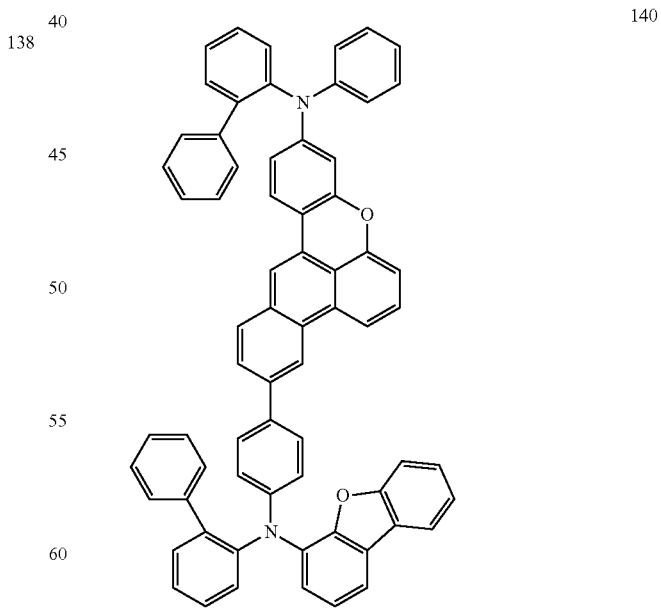
140

141
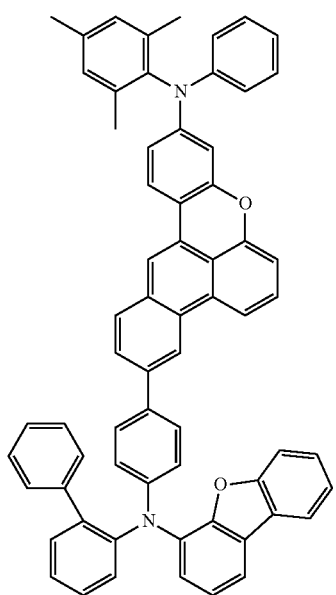
142
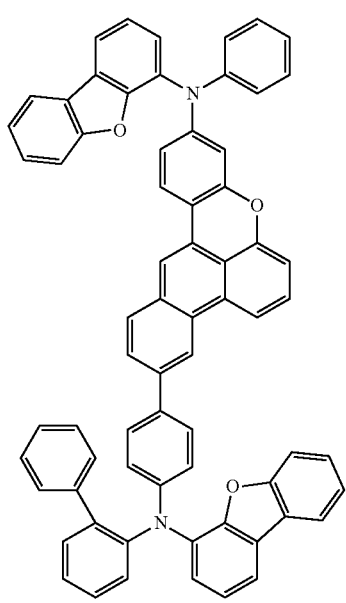
143
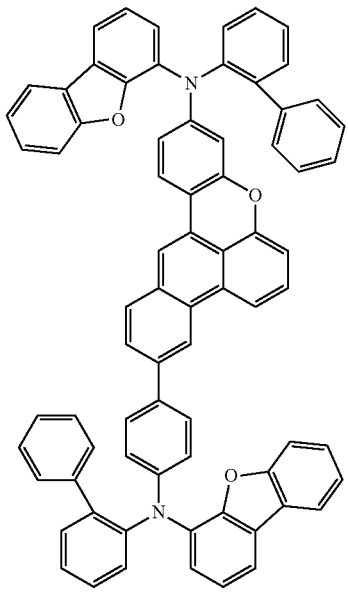
144
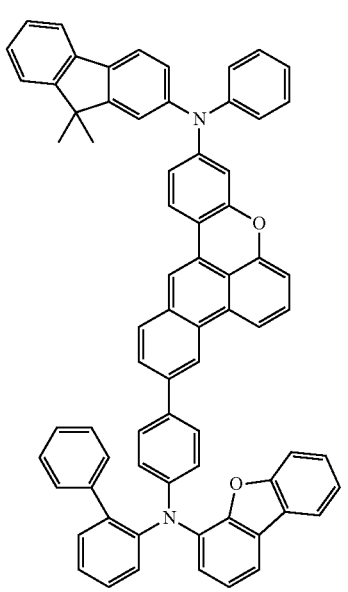

-continued
145
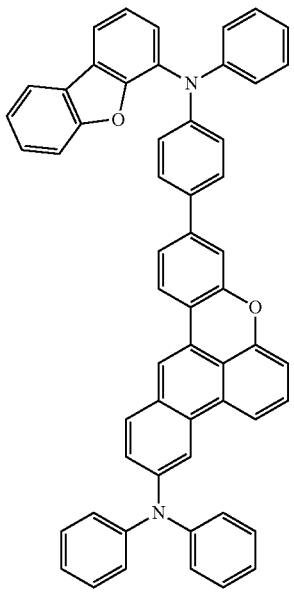
147
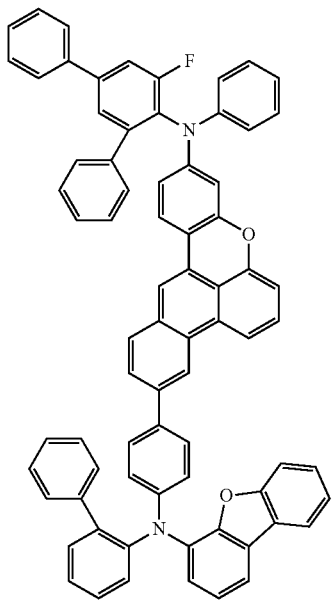
146
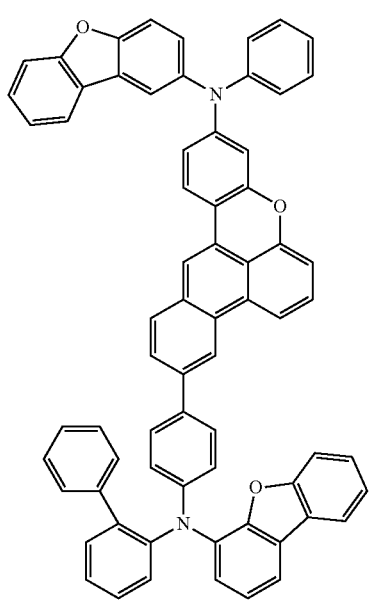
148
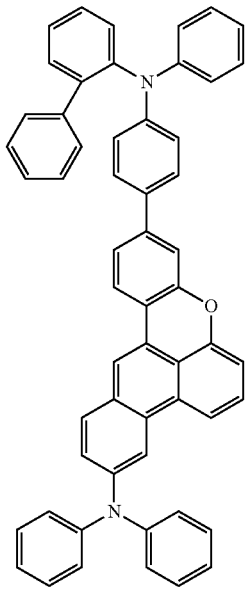

149
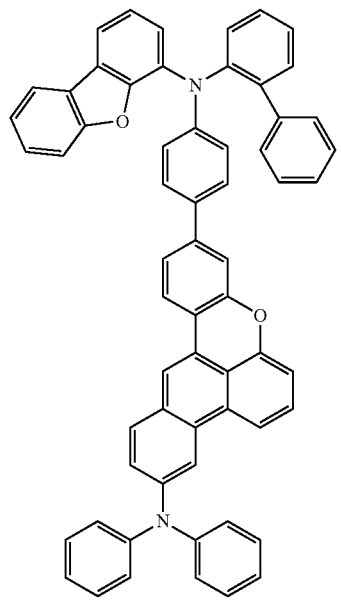
151
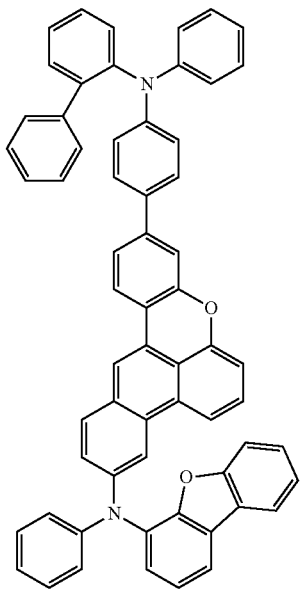
150
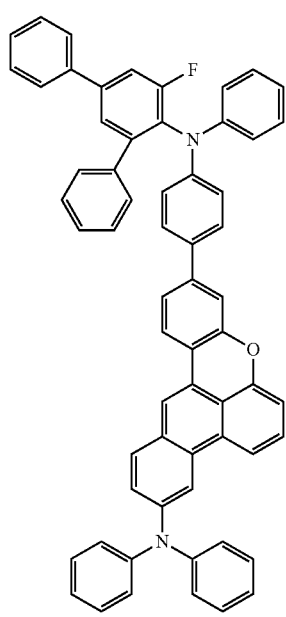
152
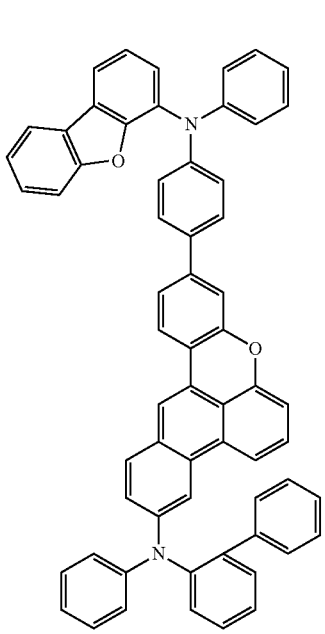

153
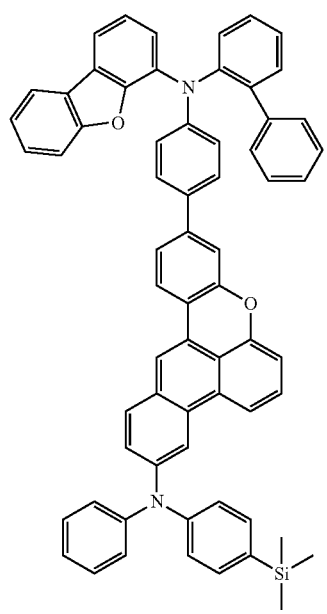
155
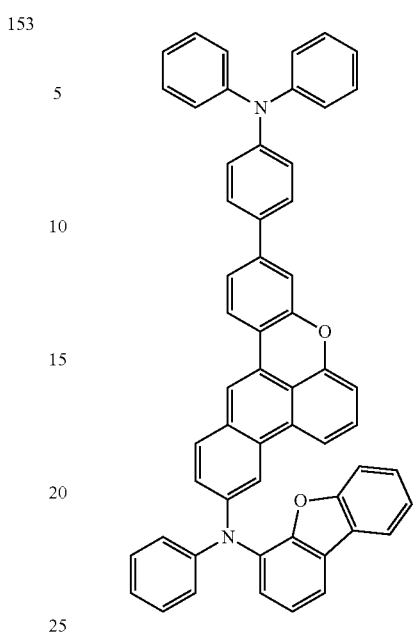
154
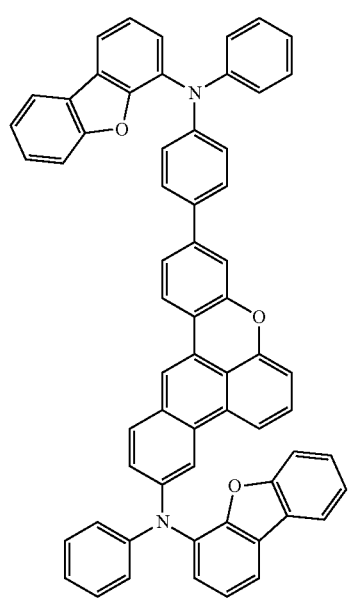
156
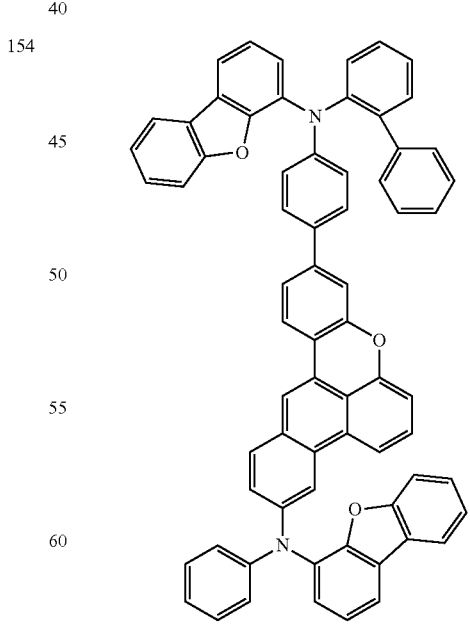

157 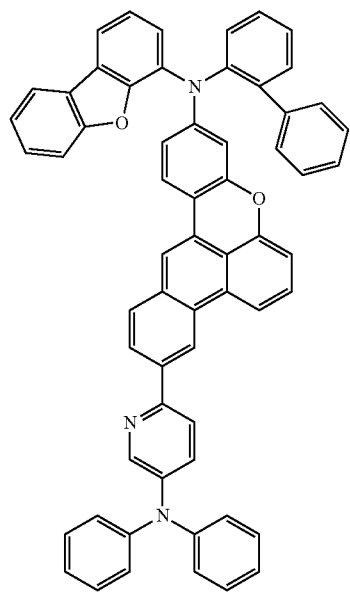
158 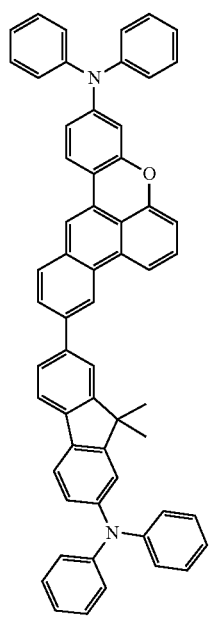
159 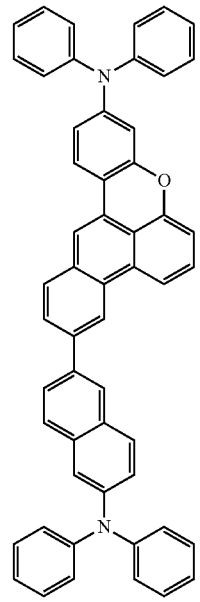
160 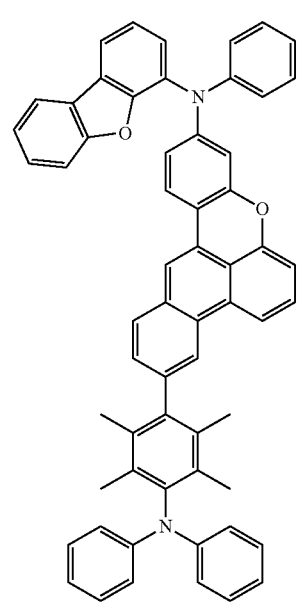

111
-continued
112
-continued
161
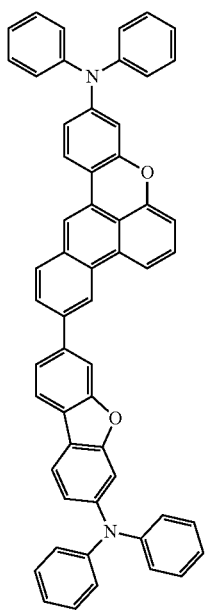
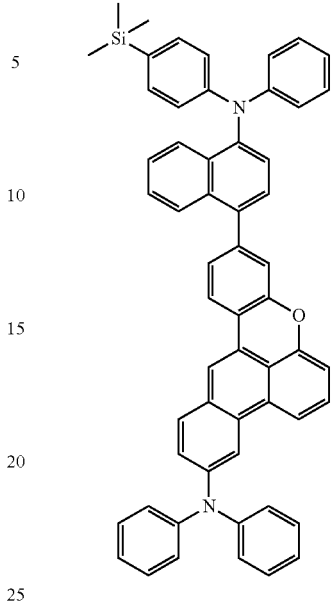
162
163
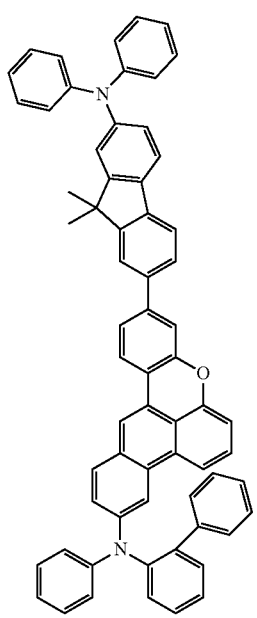
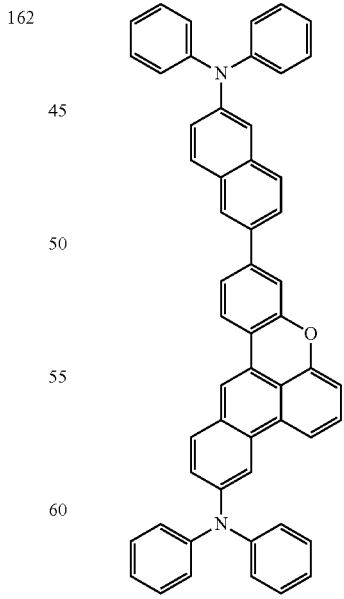
164

113
-continued
165
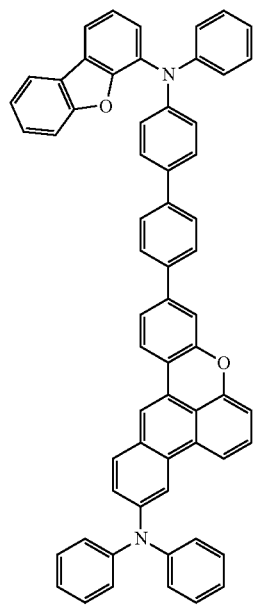
166
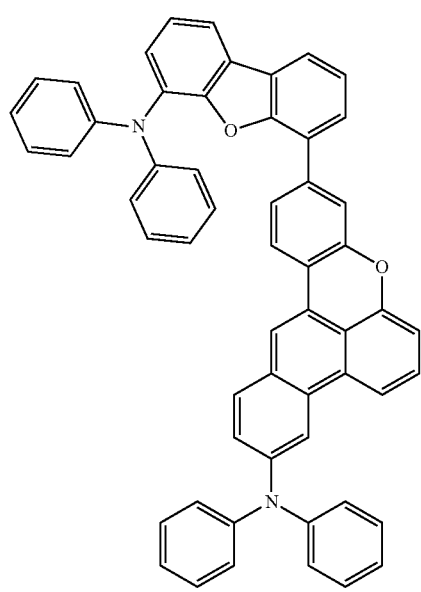
114
-continued
167
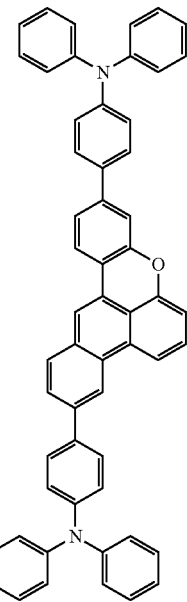
168
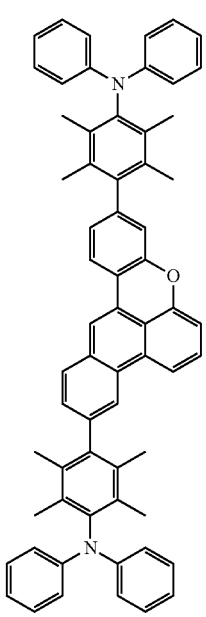

115
-continued
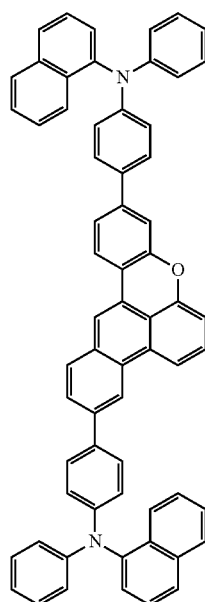
169
116
-continued
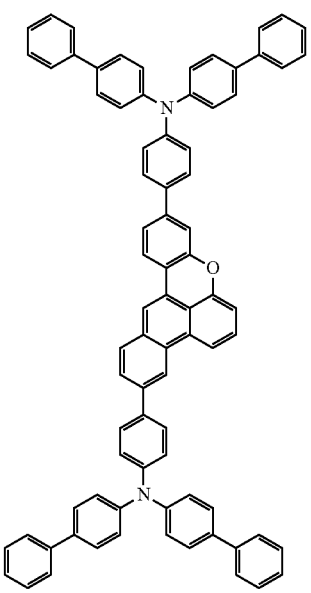
171
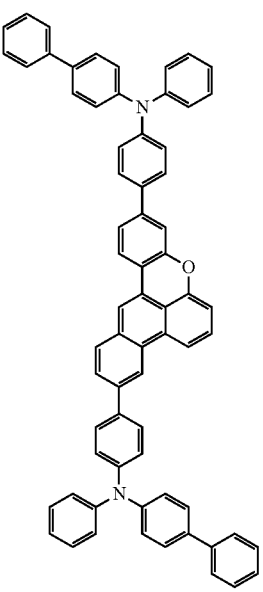
170
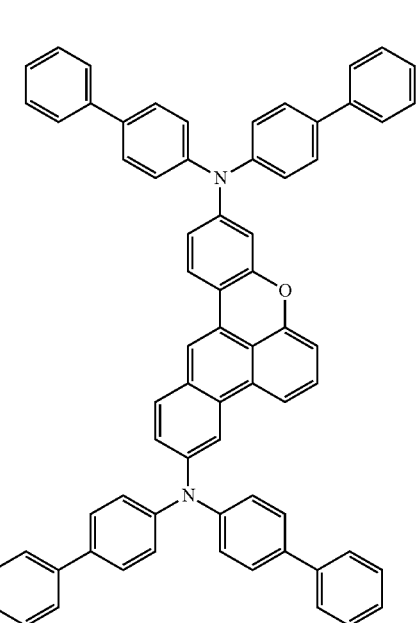
172

117
-continued
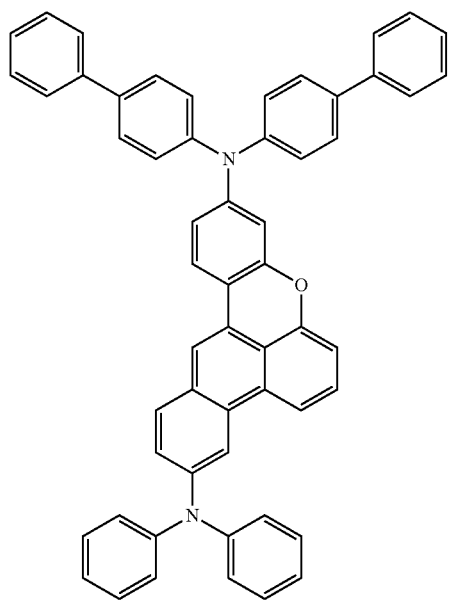
173
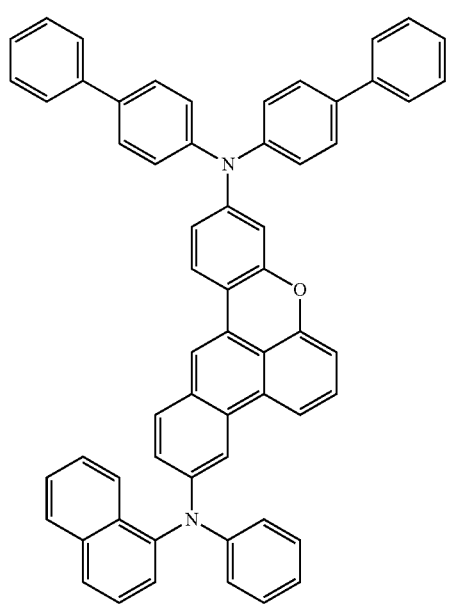
174
118
-continued
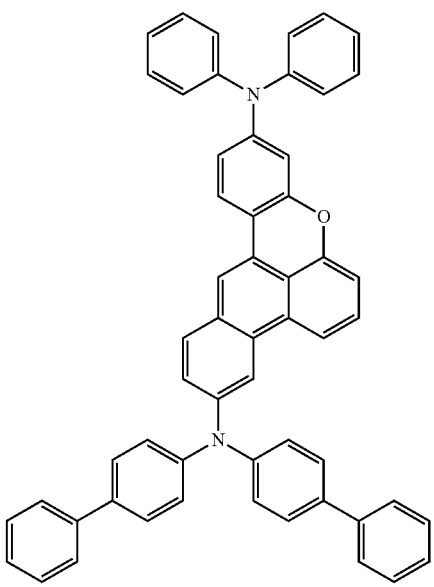
175
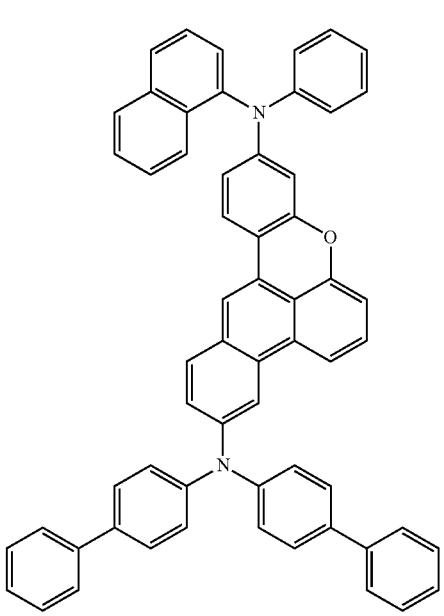
176

119
-continued
120
-continued
177
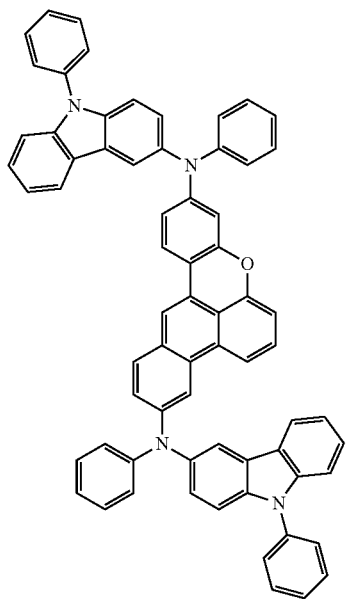
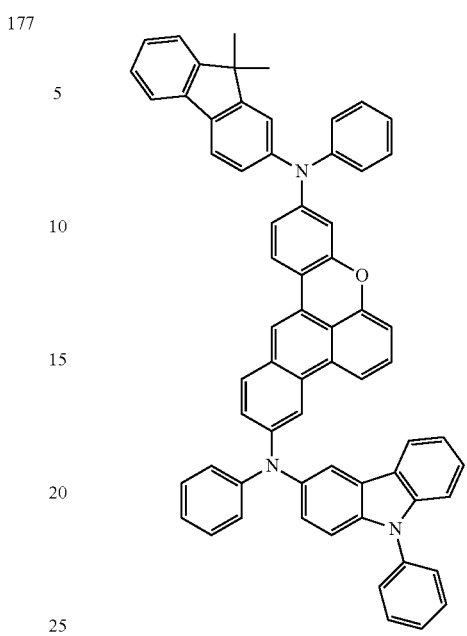
179
178
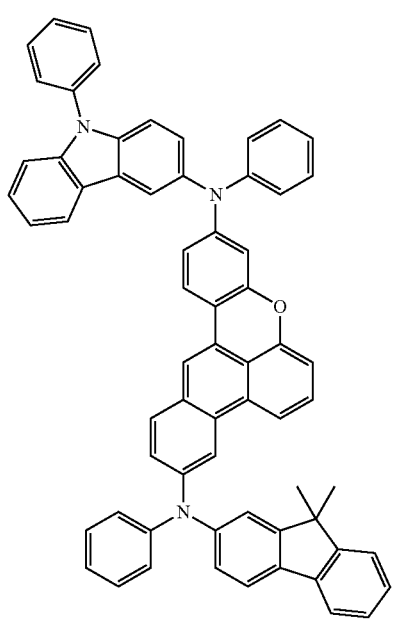
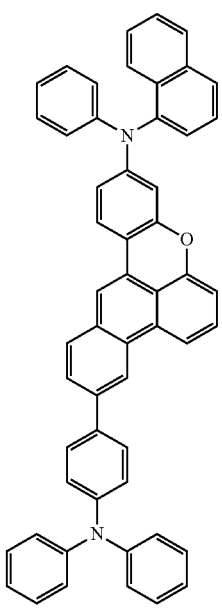
180

121
-continued
182
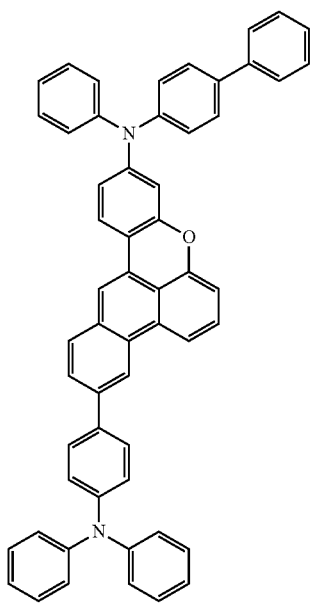
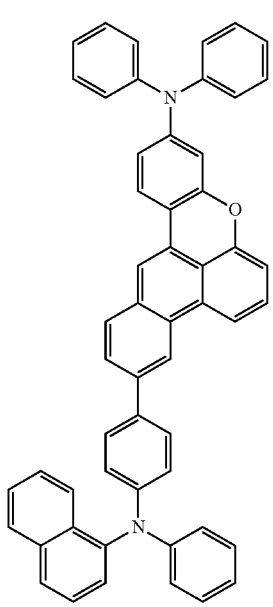
122
-continued
181
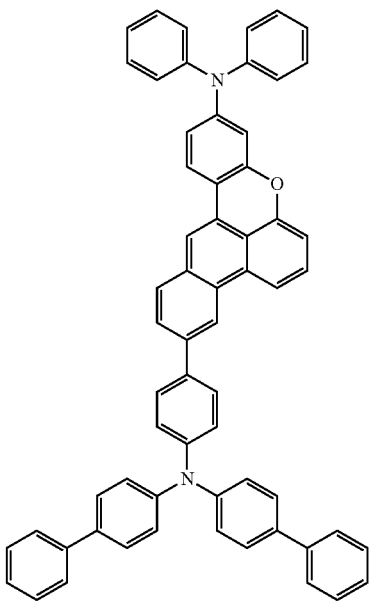
183
184
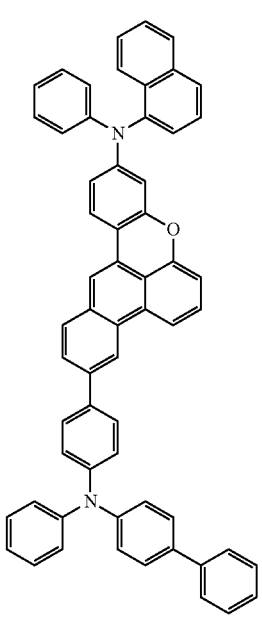

123
-continued
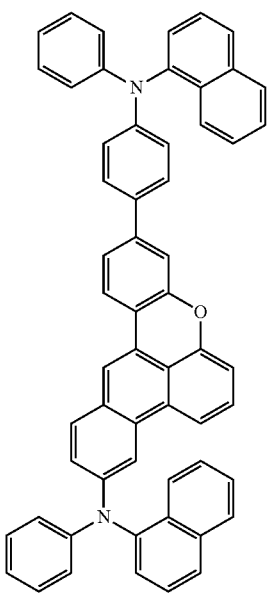
185
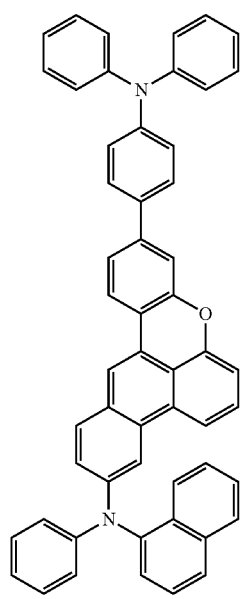
186
124
-continued
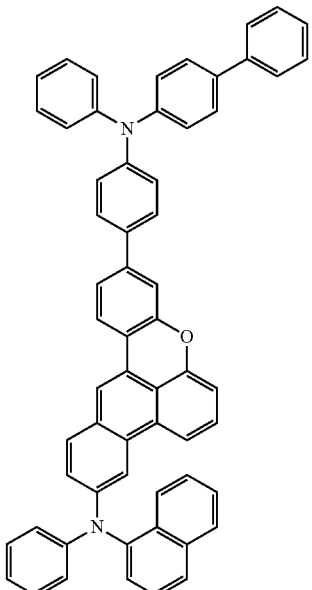
187
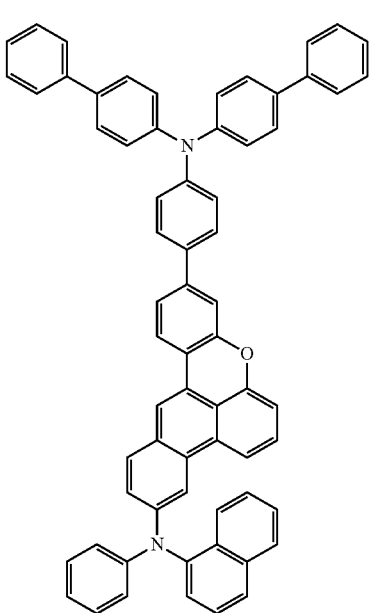
188

125
-continued
126
-continued
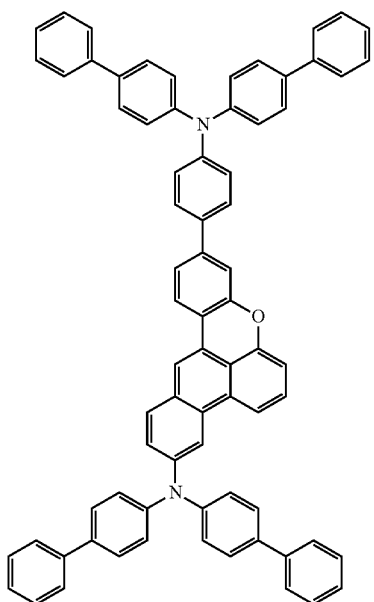
189
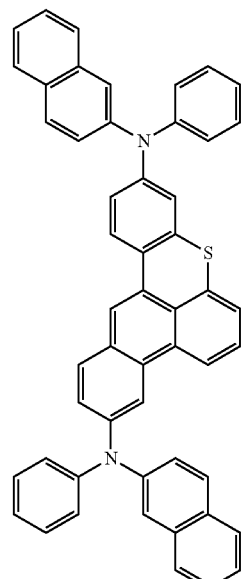
2A
1A
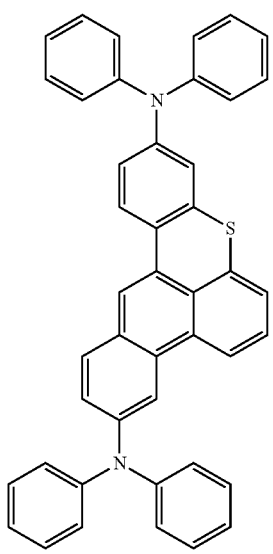
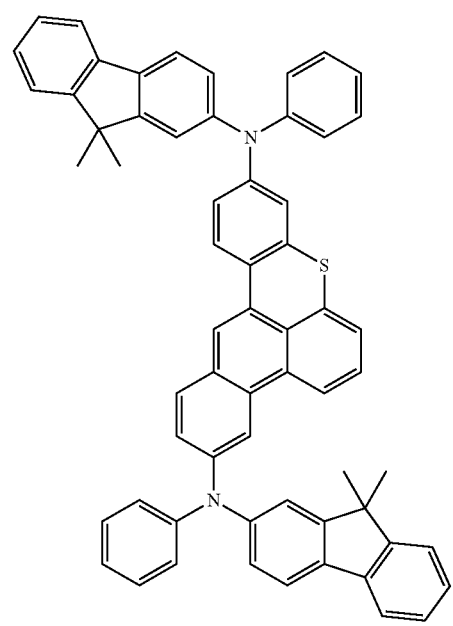
3A

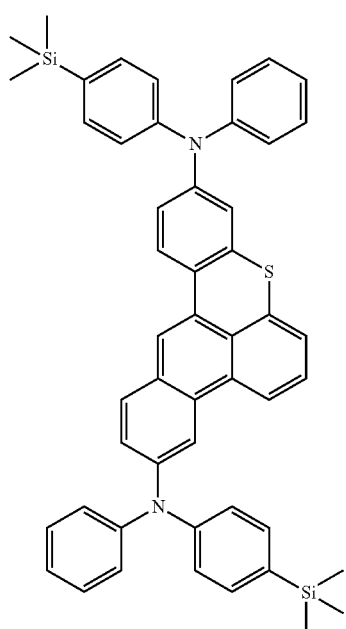
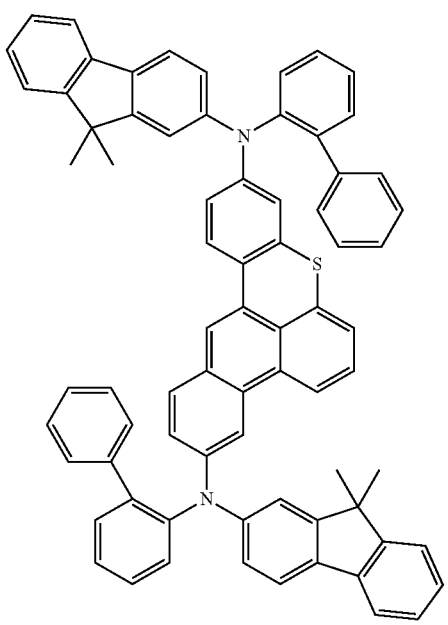
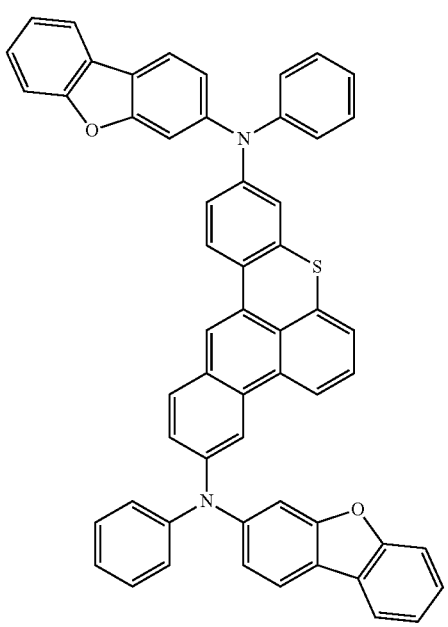

129
-continued
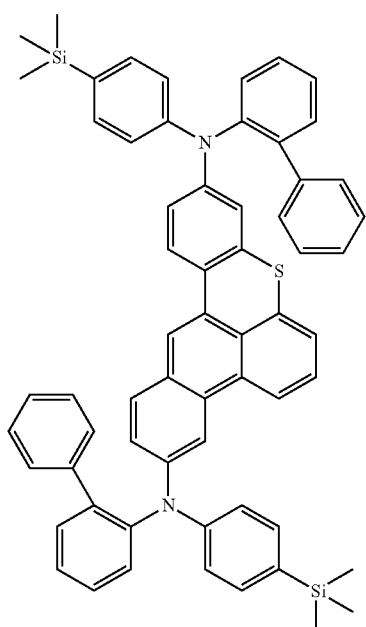
130
-continued
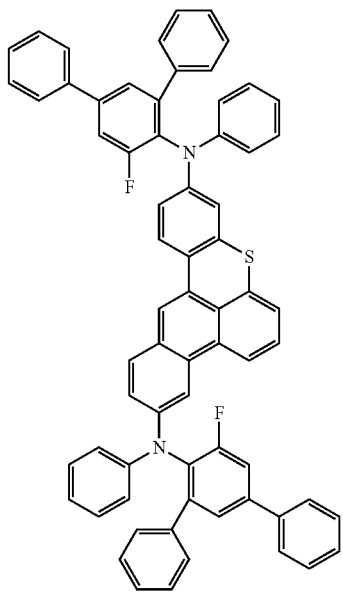
8A
9A
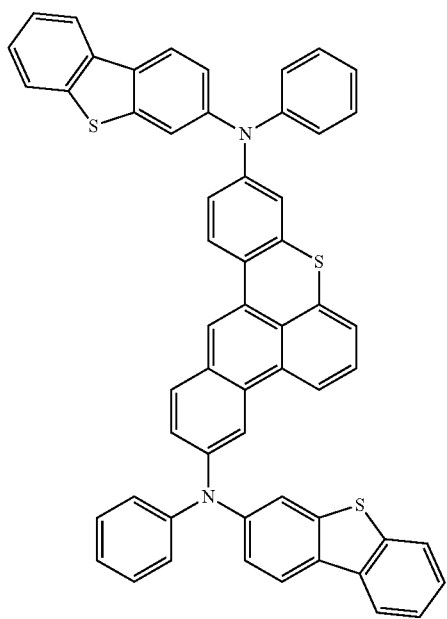
10A
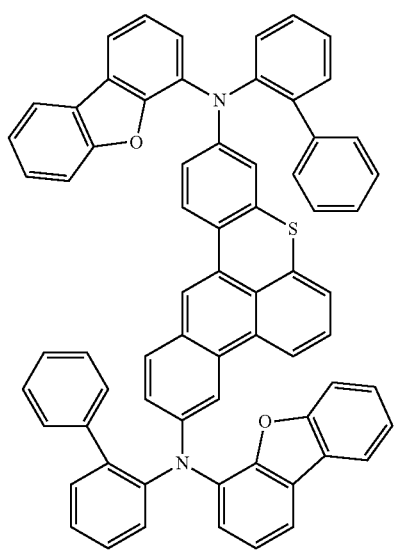
11A 131
-continued
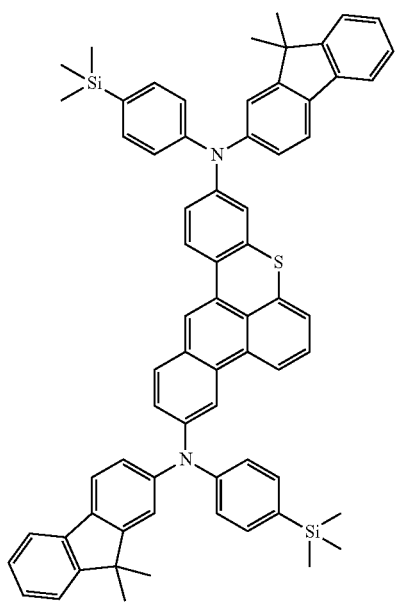
12A
132
-continued
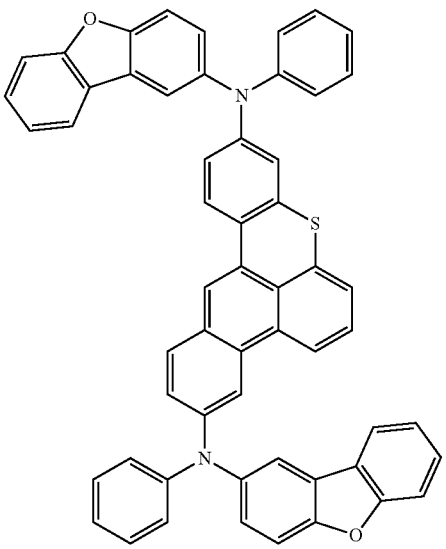
14A
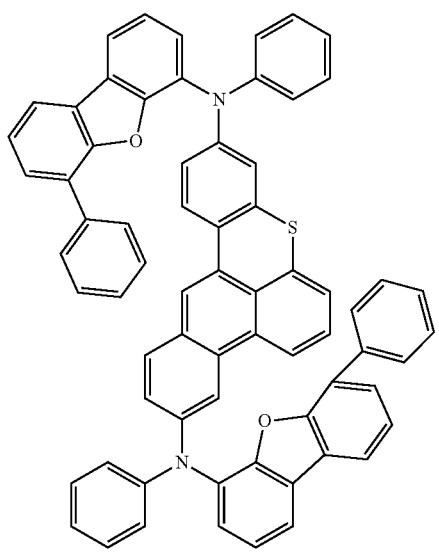
13A
15A 133
-continued
134
-continued
16A
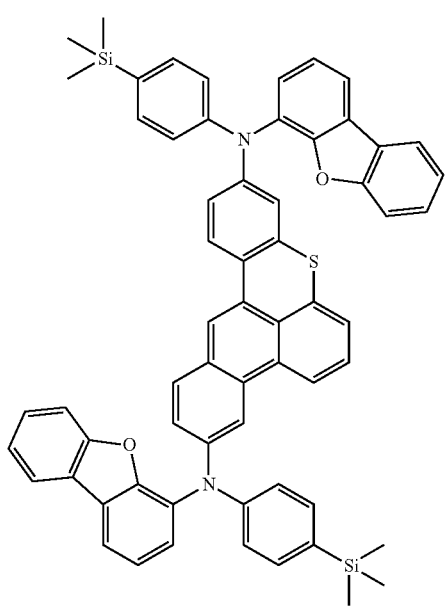
18A
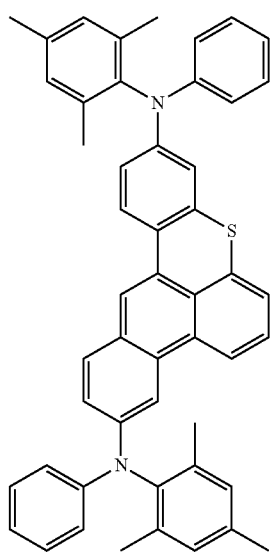
17A
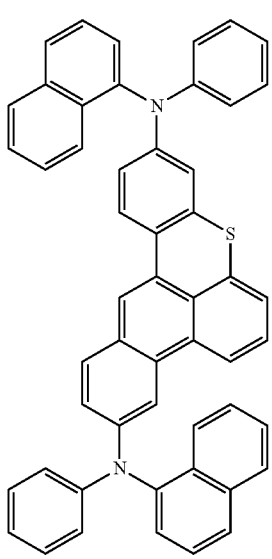
19A
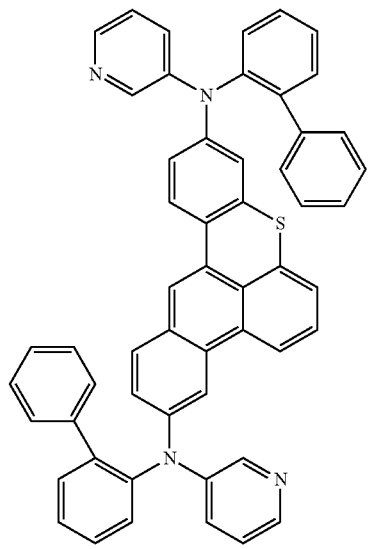

135
-continued
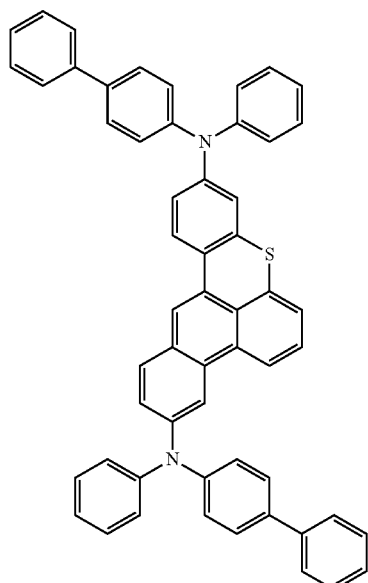
136
-continued
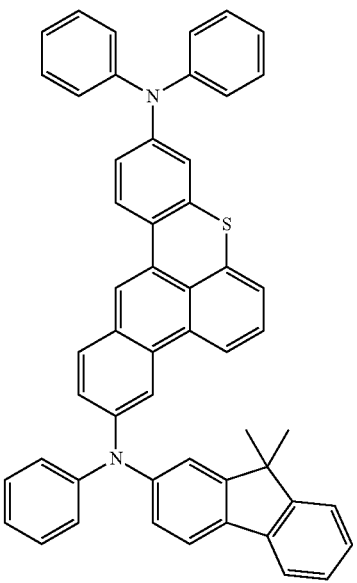
20A
21A
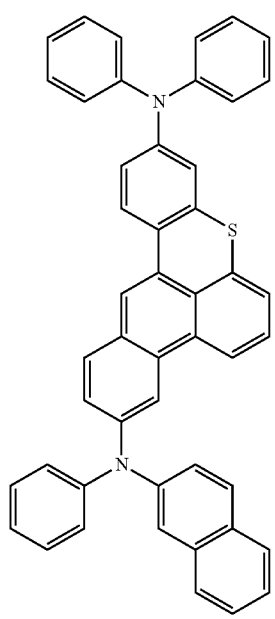
22A
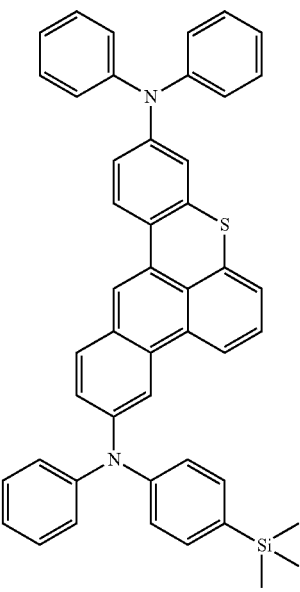
23A 137
-continued
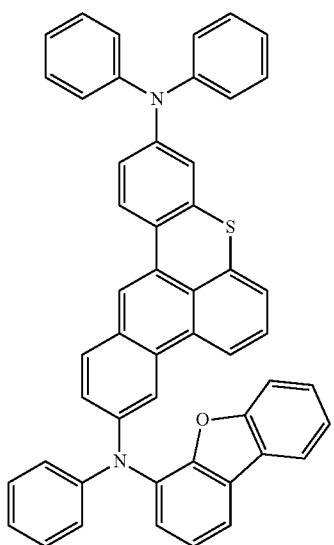
24A
138
-continued
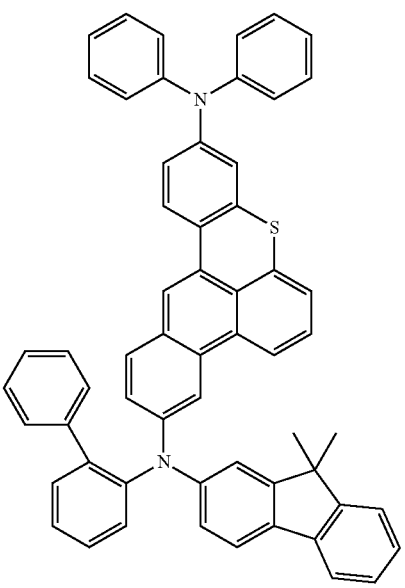
26A
25A
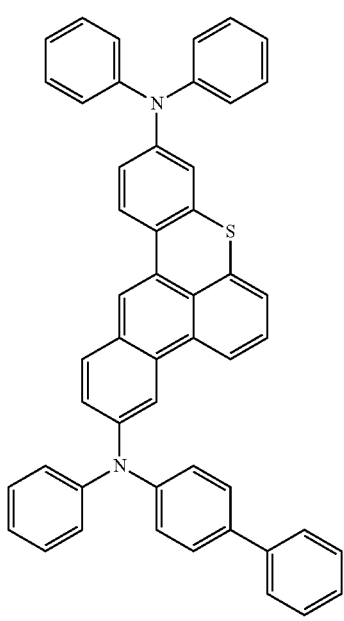
27A
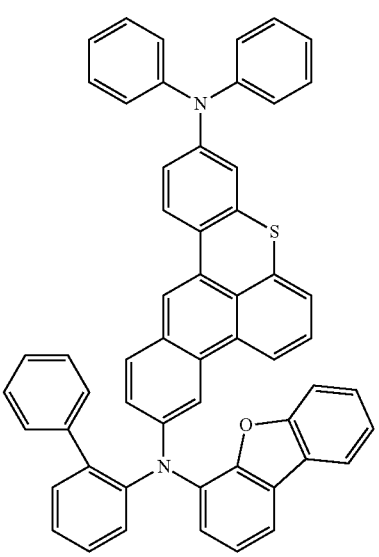

139
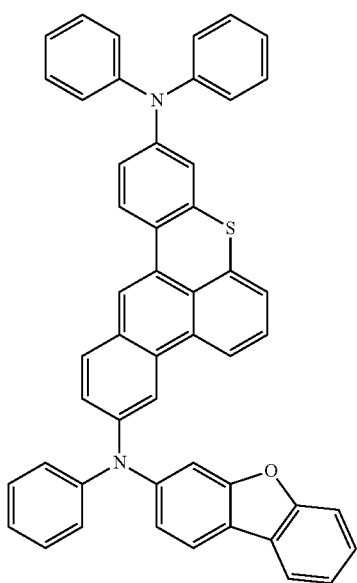
28A
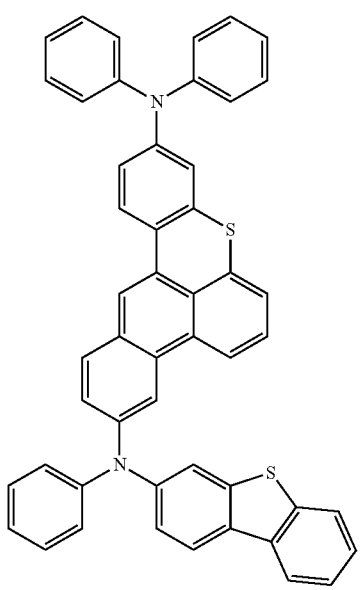
29A
140
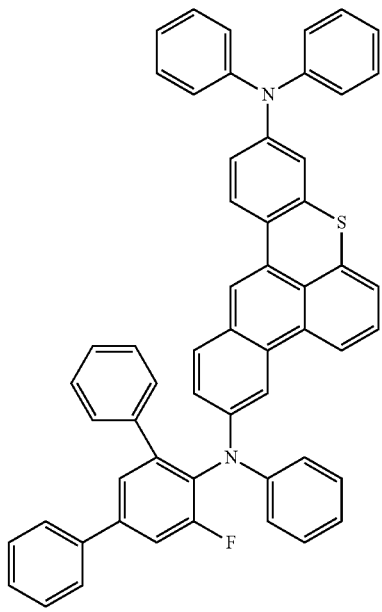
30A
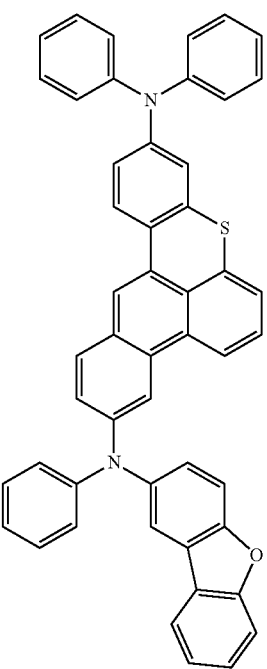
31A

141
-continued
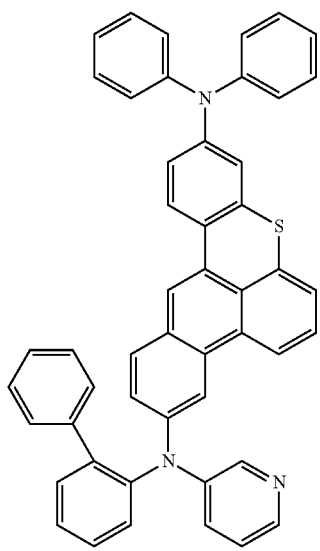
142
-continued
32A
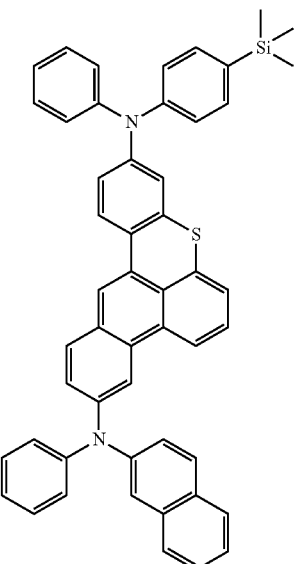
34A
33A
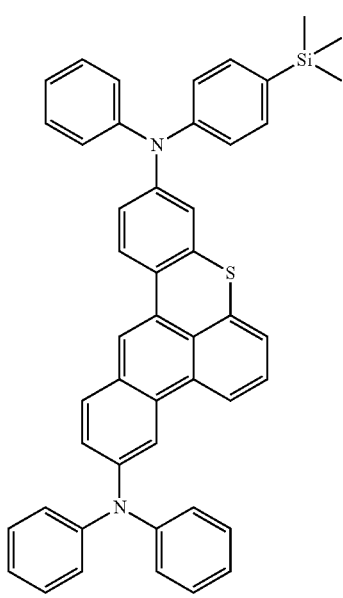
35A 143
-continued
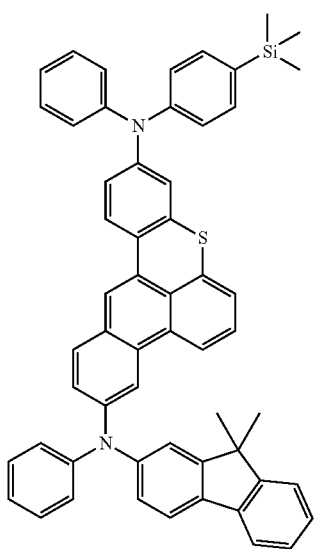
36A
144
-continued
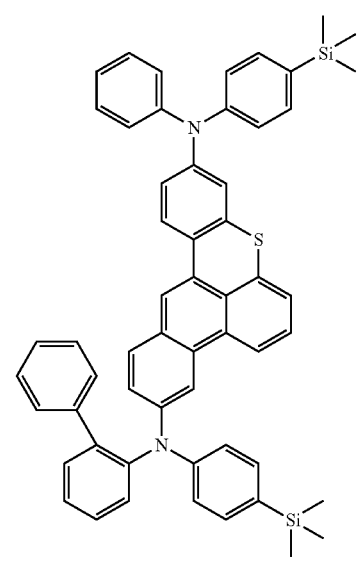
38A
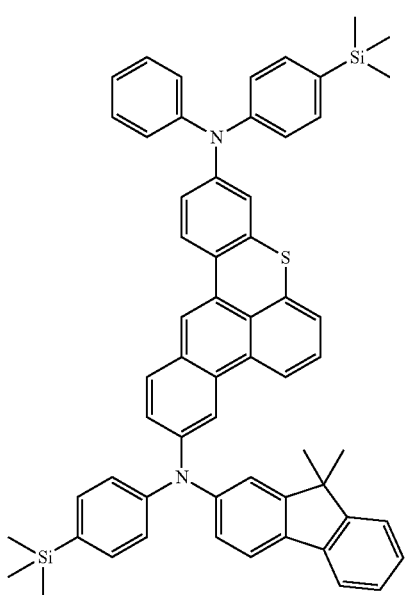
37A
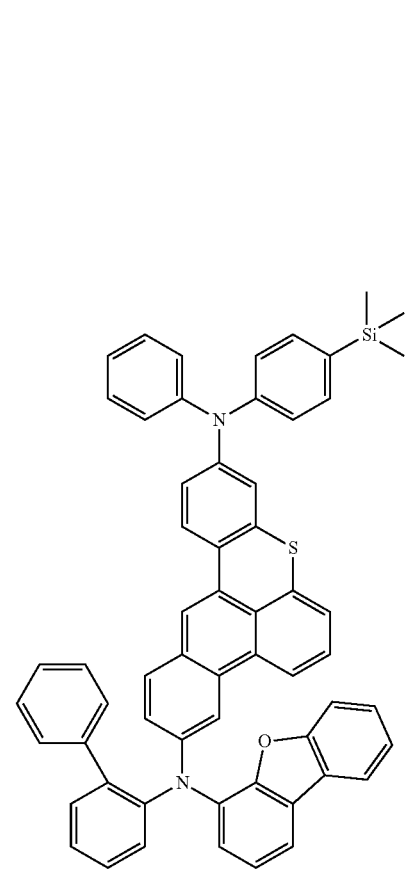
39A 145
-continued
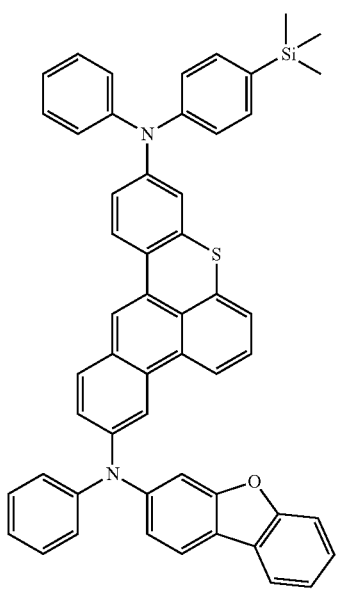
40A
146
-continued
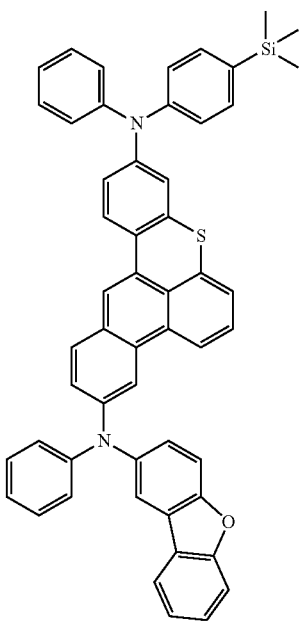
42A
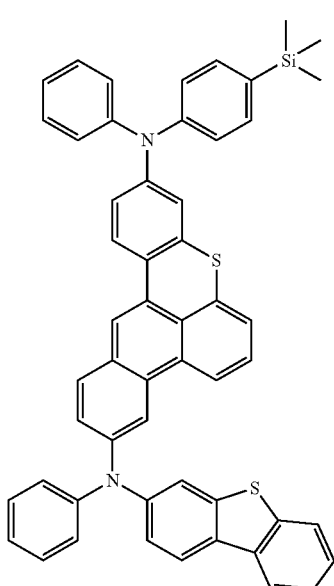
41A
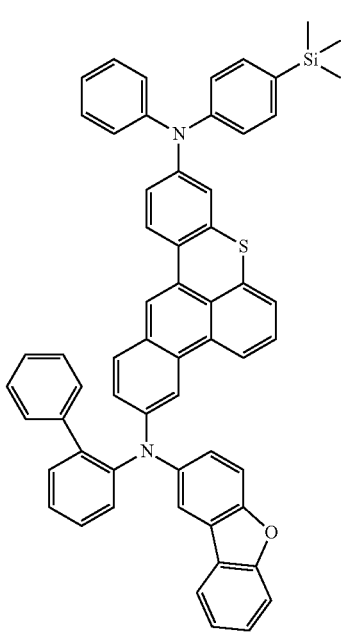
43A 44A
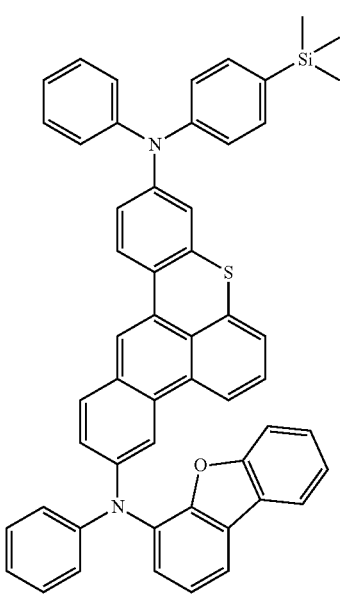
46A
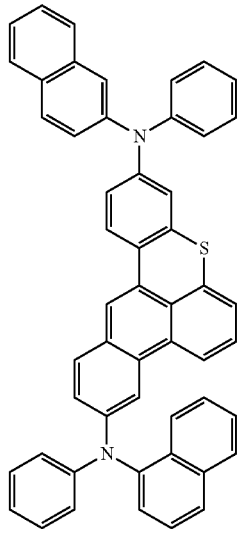
45A
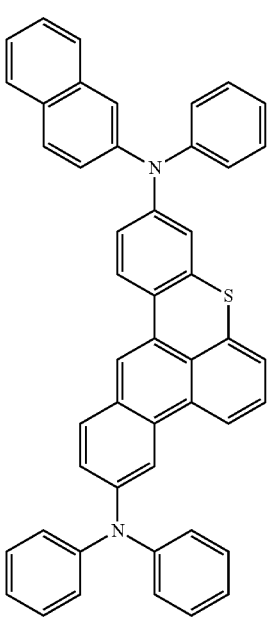
47A
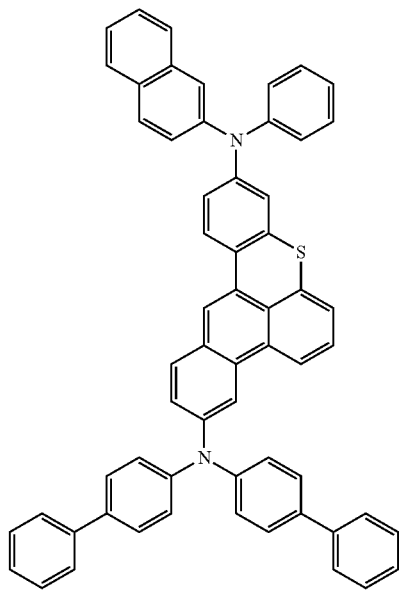

149
-continued
150
-continued
48A
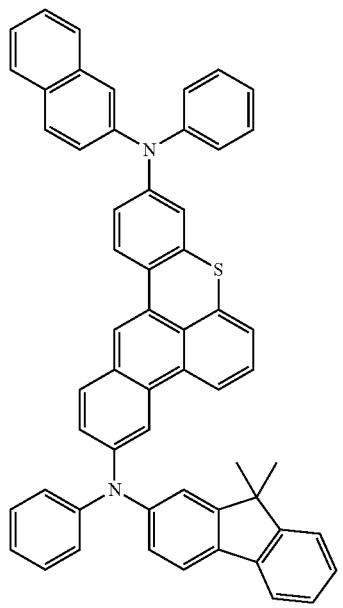
50A
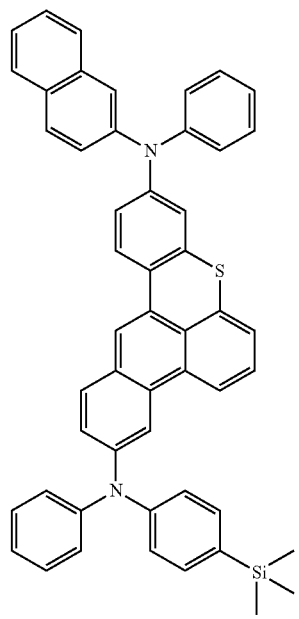
49A
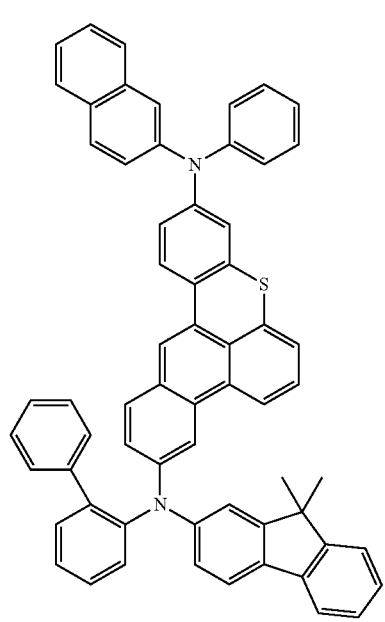
51A
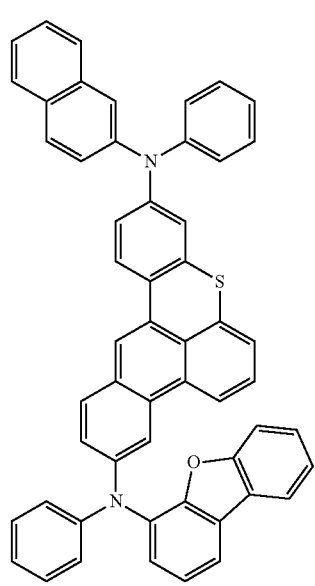

151
-continued
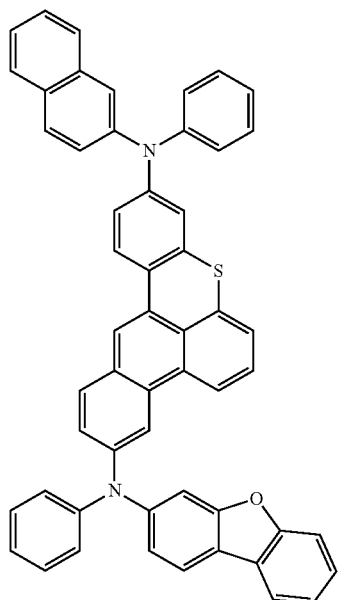
152
-continued
52A
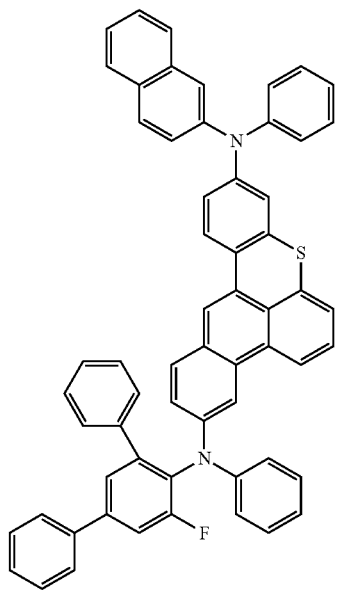
53A
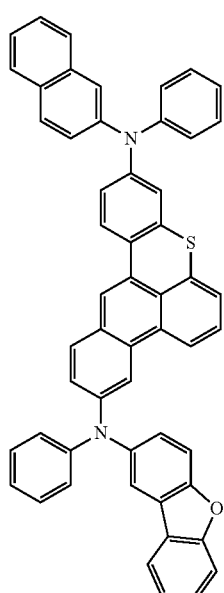
54A
55A
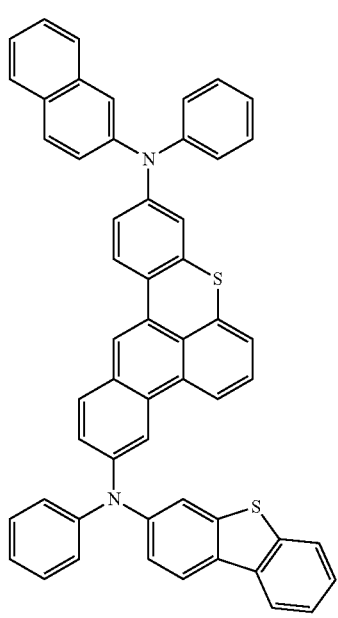

153
-continued
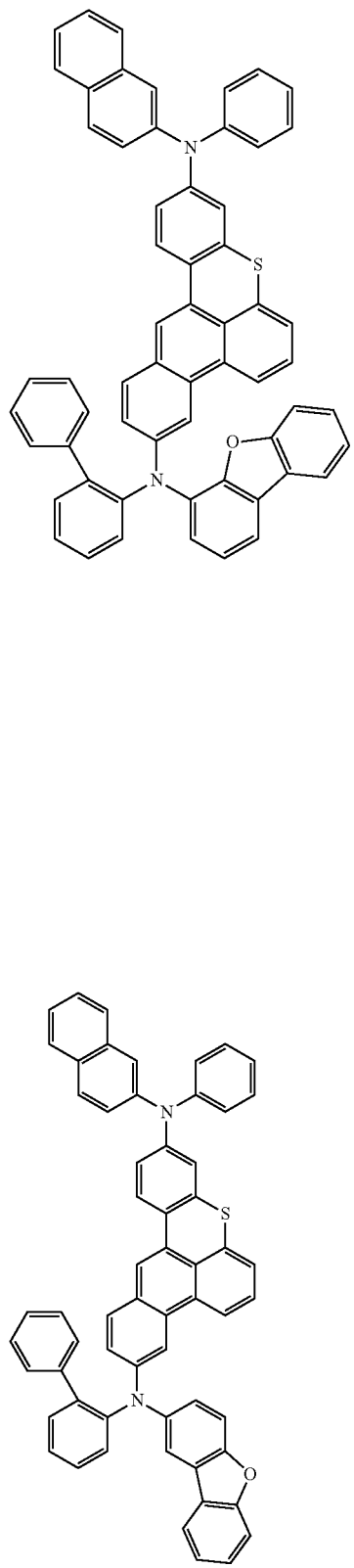
154
-continued
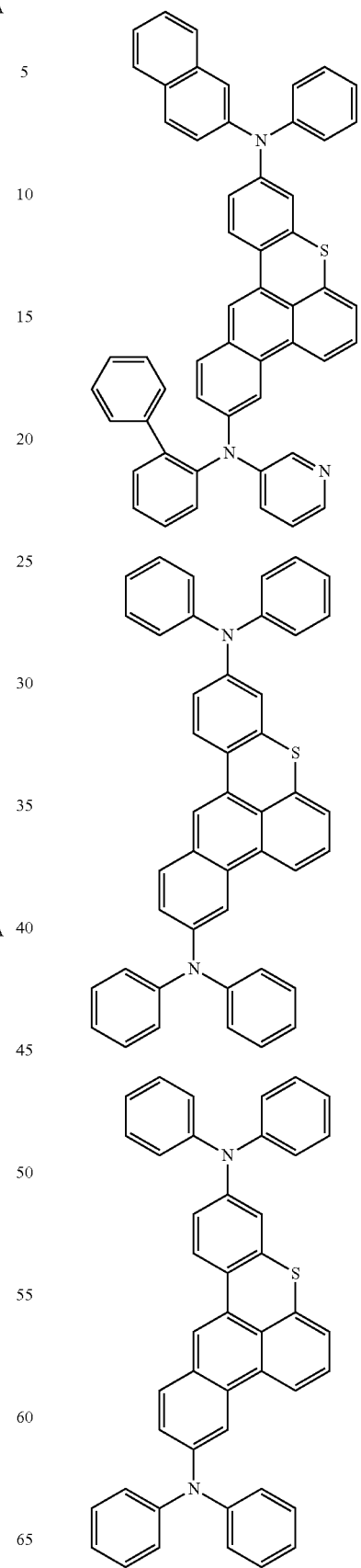
56A
57A
58A
59A
60A

155
-continued
156
-continued
61A
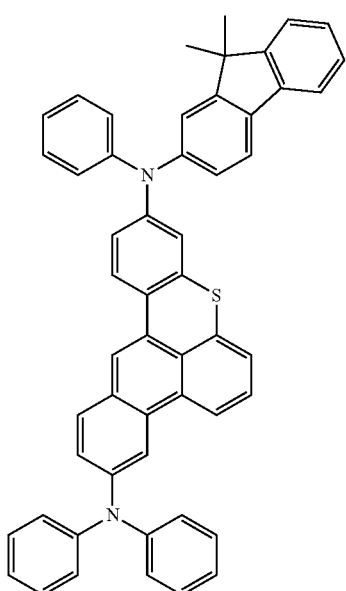
63A
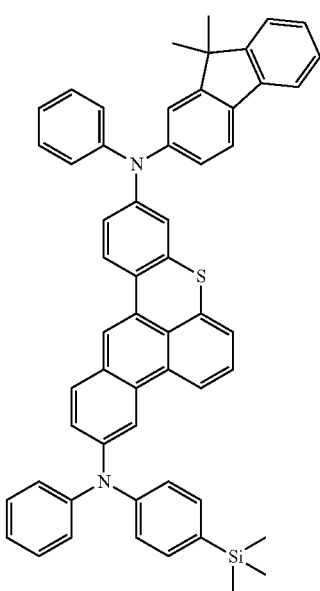
62A
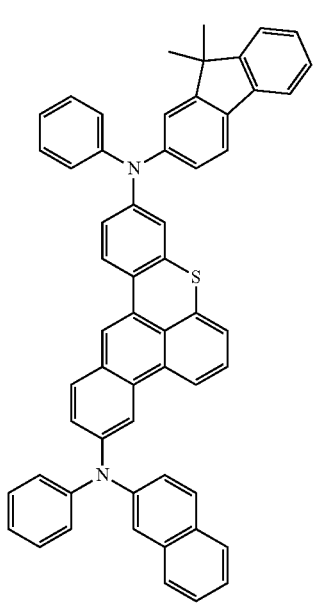
64A
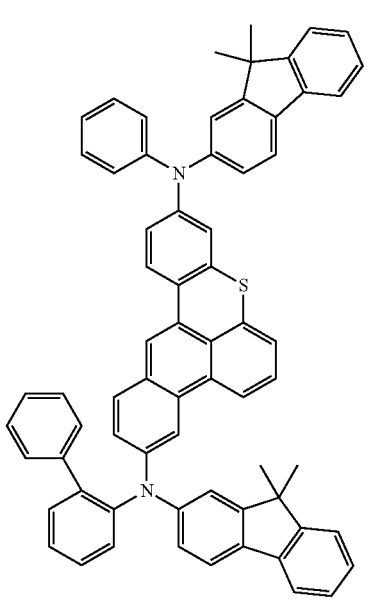

157
-continued
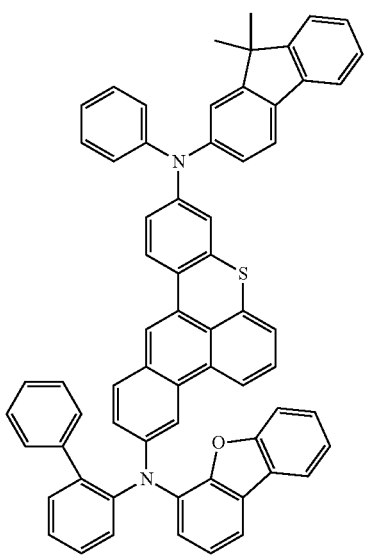
65A
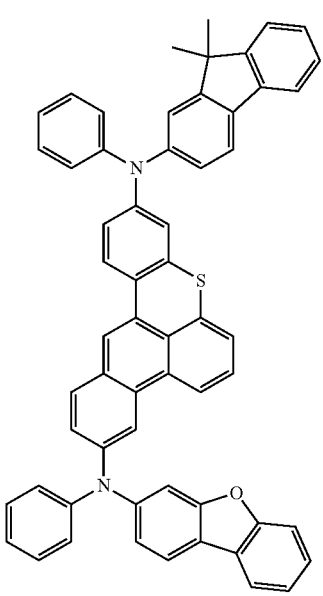
66A
158
-continued
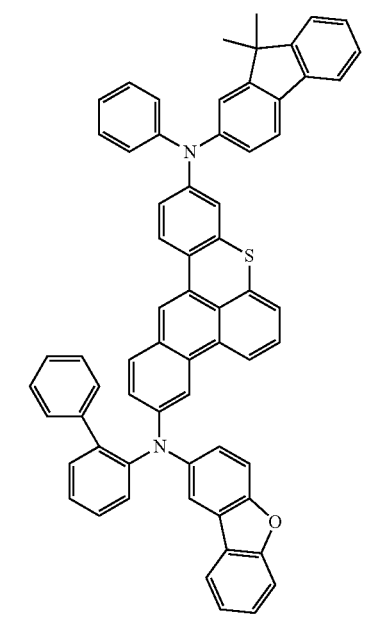
67A
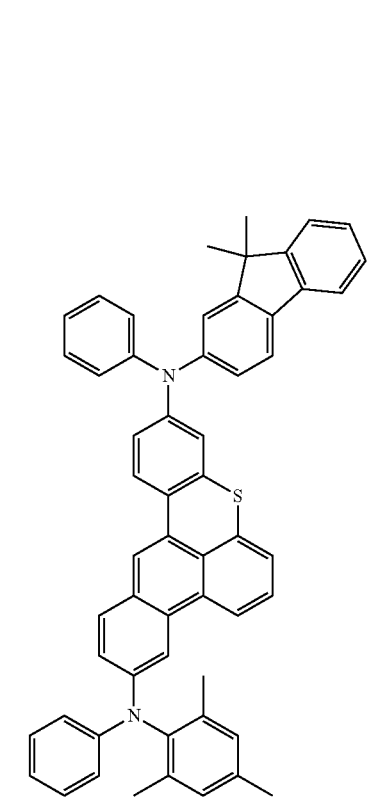
68A 159
-continued
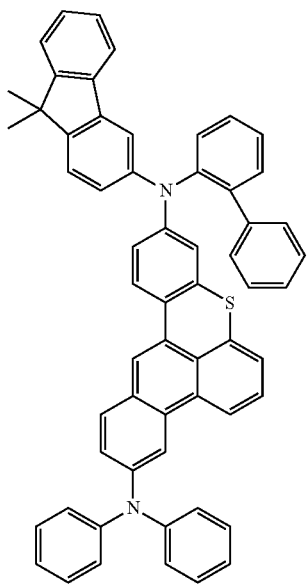
69A
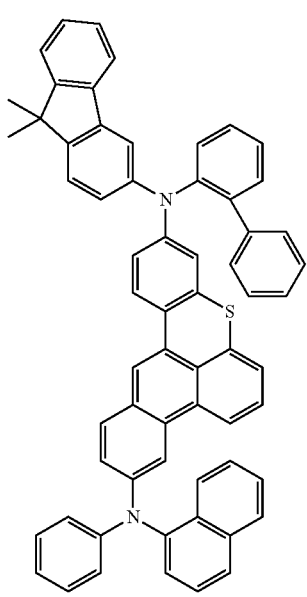
70A
160
-continued
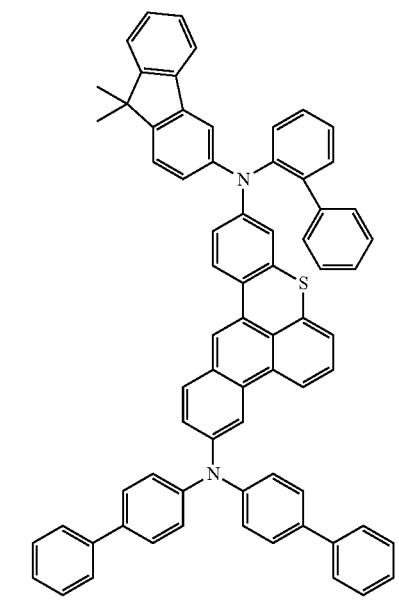
71A
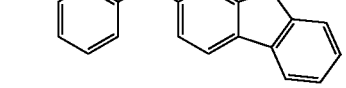
72A 161
-continued
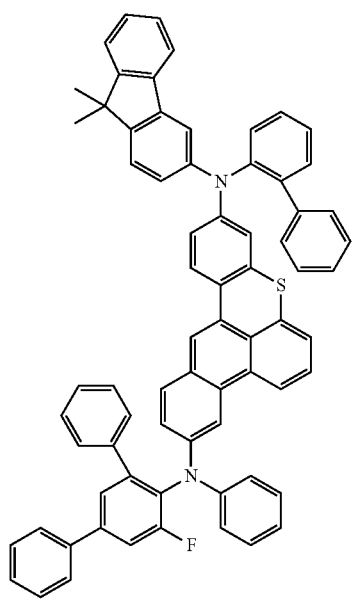
73A
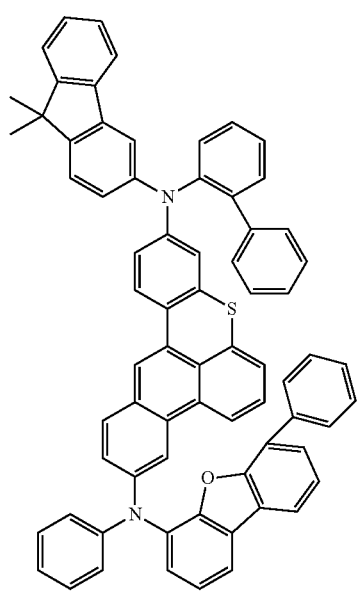
74A
162
-continued
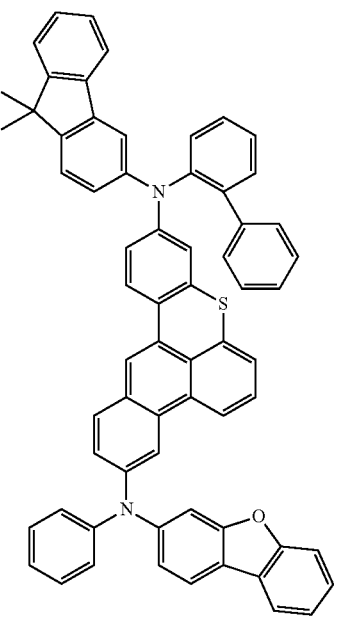
75A
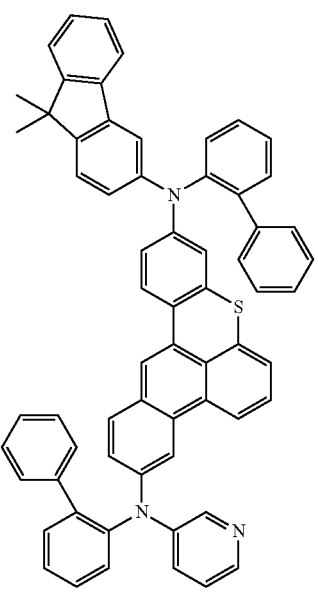
76A -continued
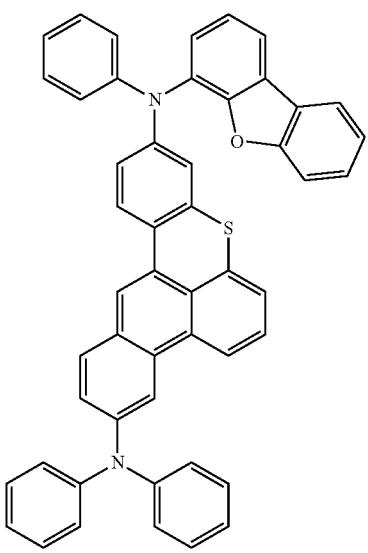
77A
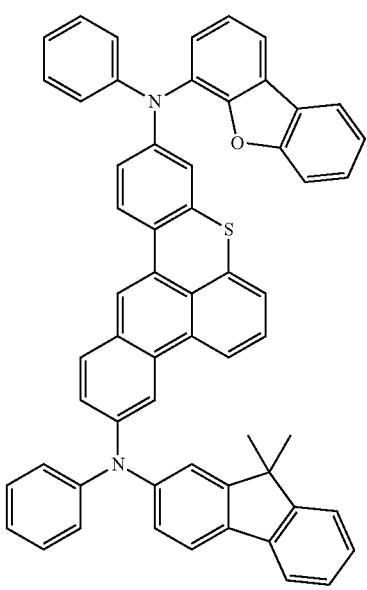
79A
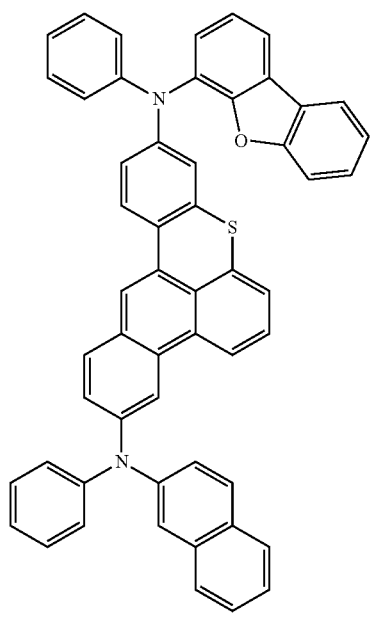
78A
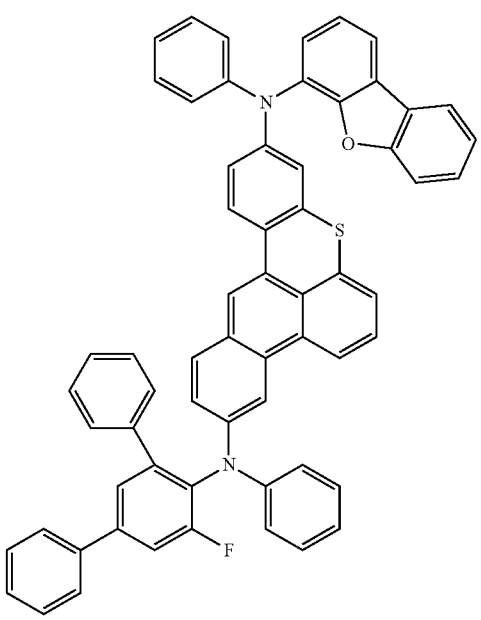
80A 165
-continued
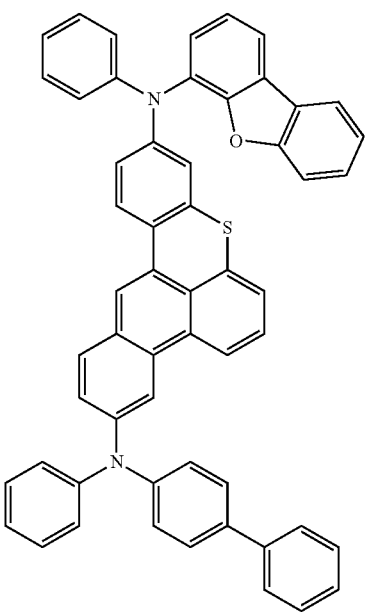
81A
166
-continued
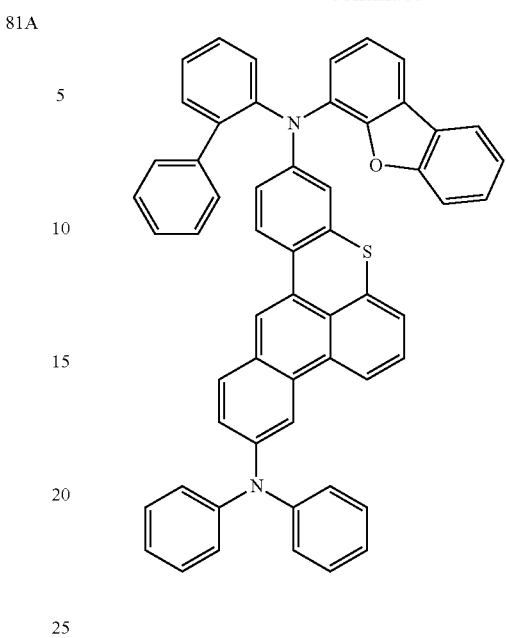
83A
82A
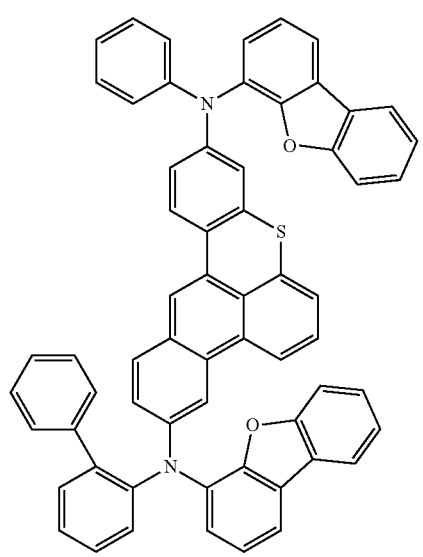
84A
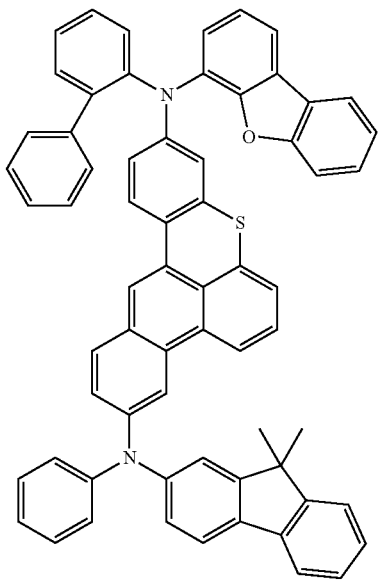

167
-continued
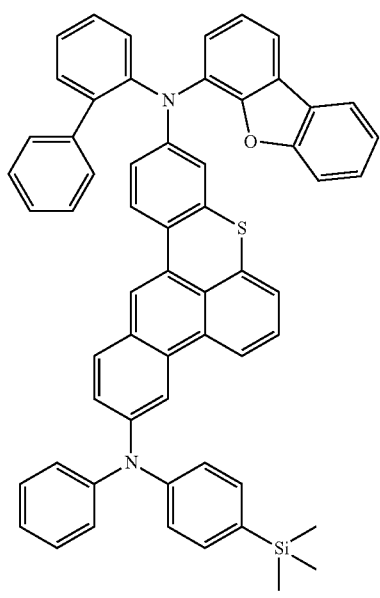
85A
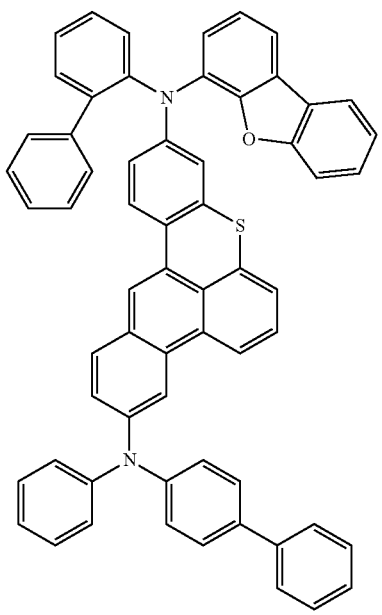
168
-continued
87A
86A
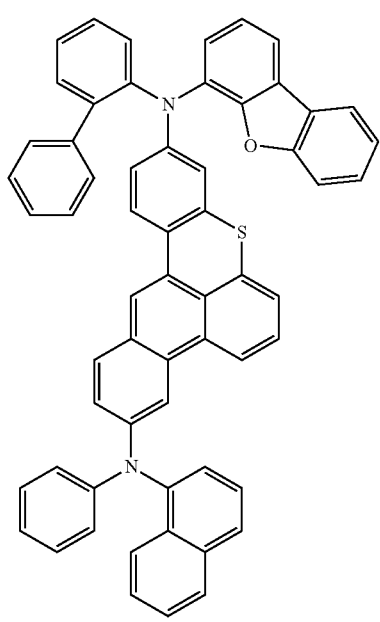
88A
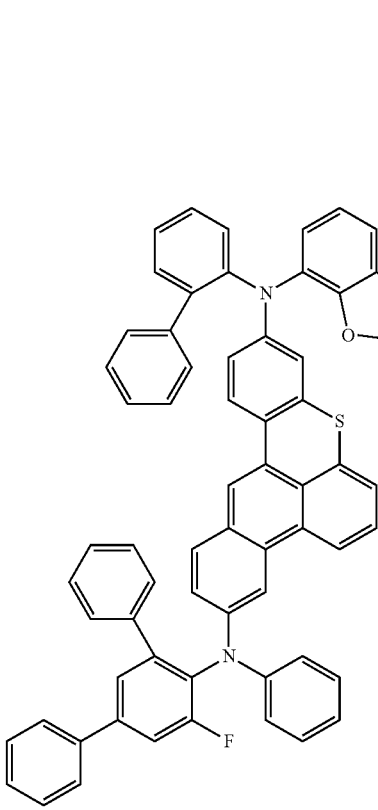

169
-continued
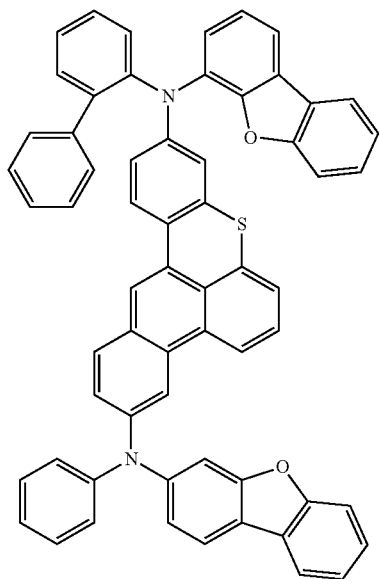
89A
170
-continued
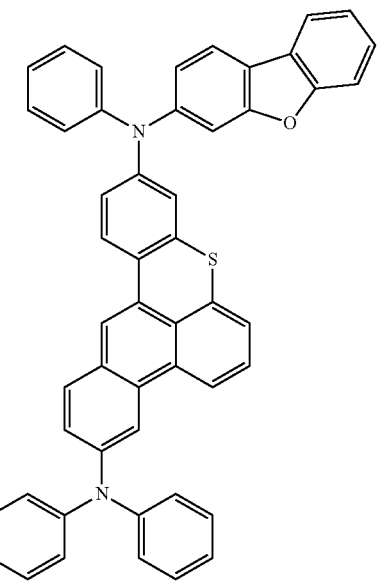
91A
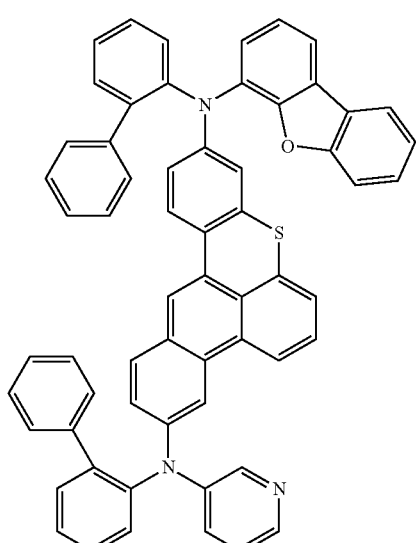
90A
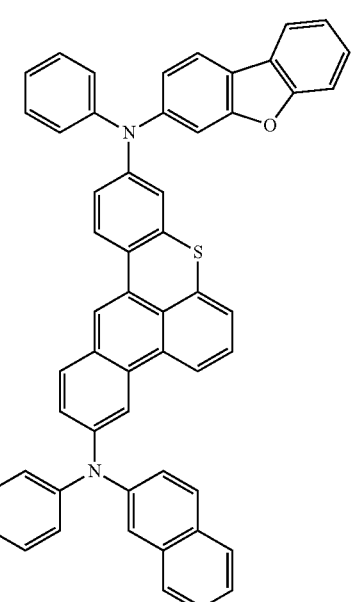
92A 171
-continued
93A
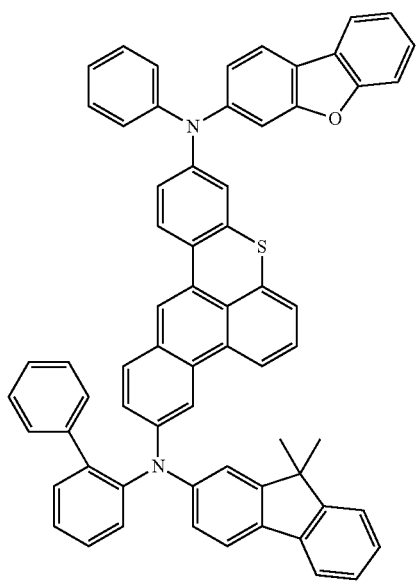
94A
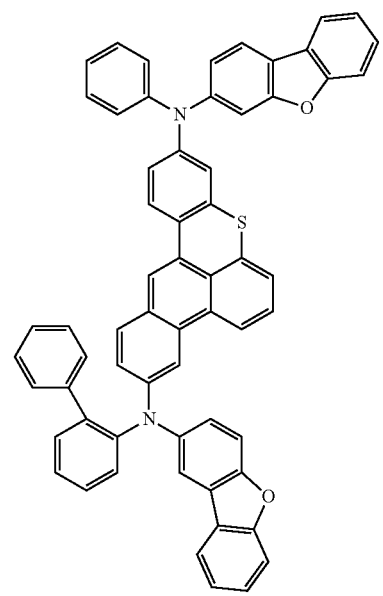
172
-continued
95A
96A -continued
97A
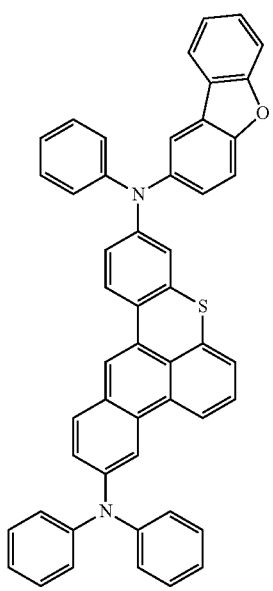
98A
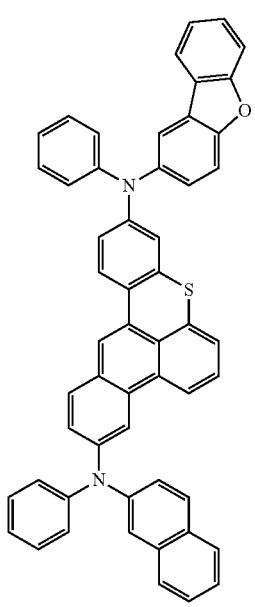
-continued
99A
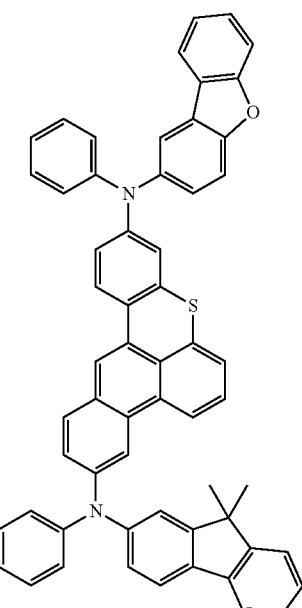
100A
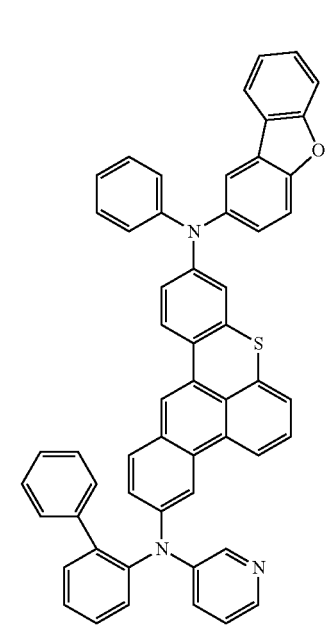

-continued
101A
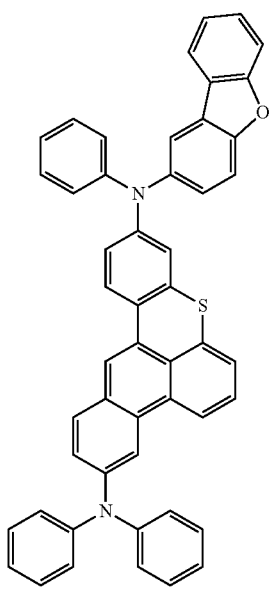
102A
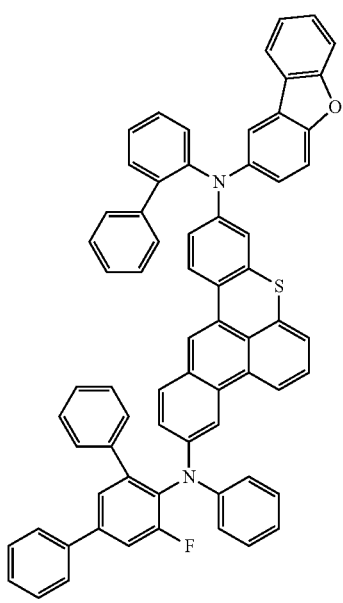
-continued
103A
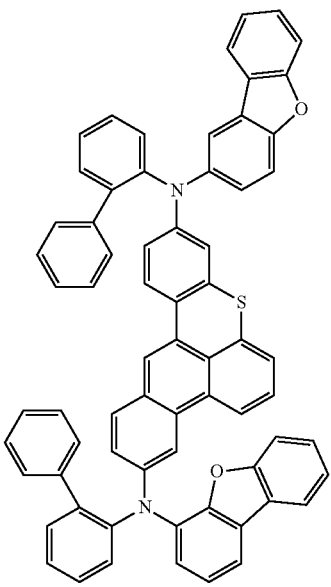
104A
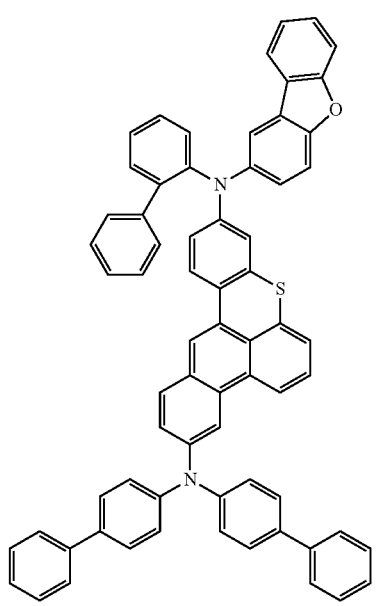

177
-continued
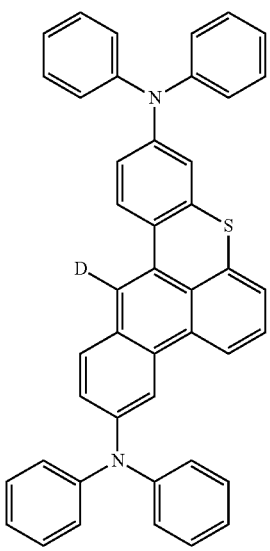
178
-continued
105A
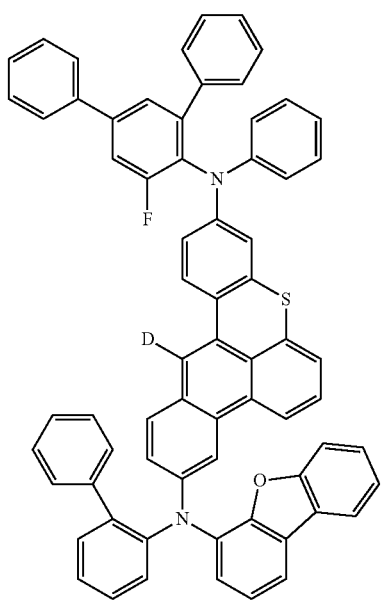
107A
106A
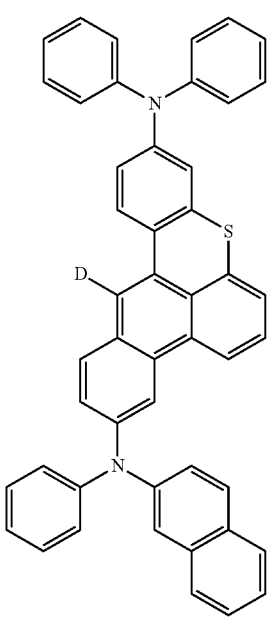
108A
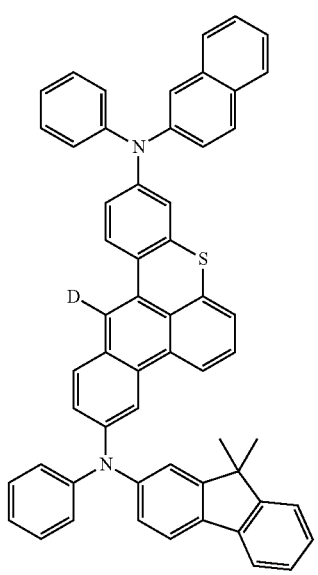

179
-continued
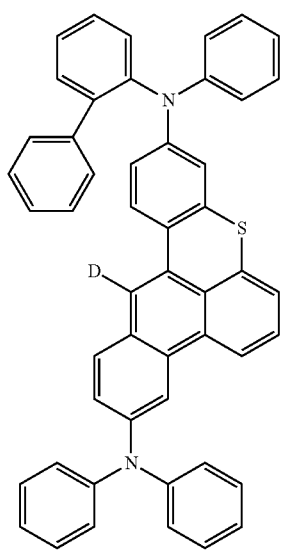
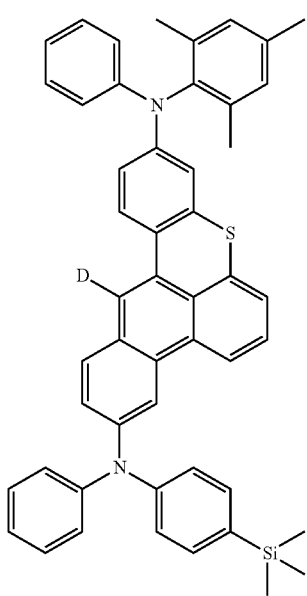
180
-continued
109A
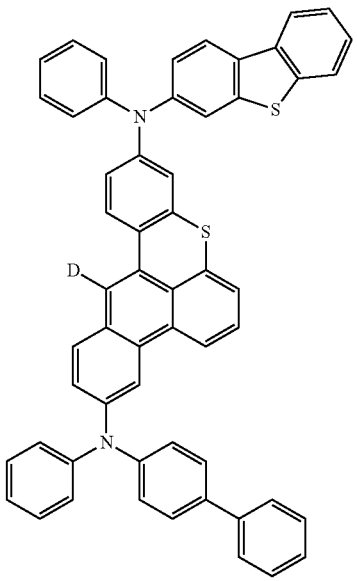
110A
111A
112A
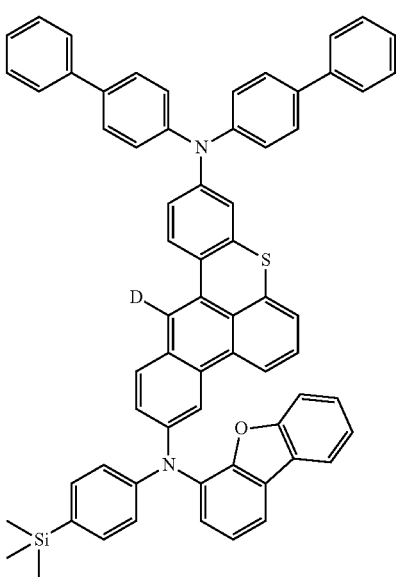

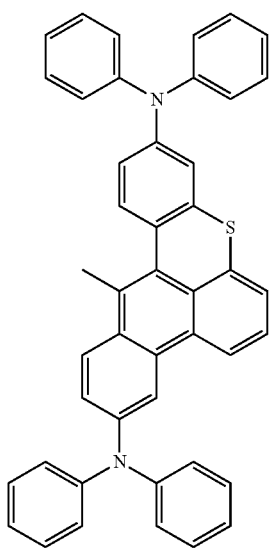
113A
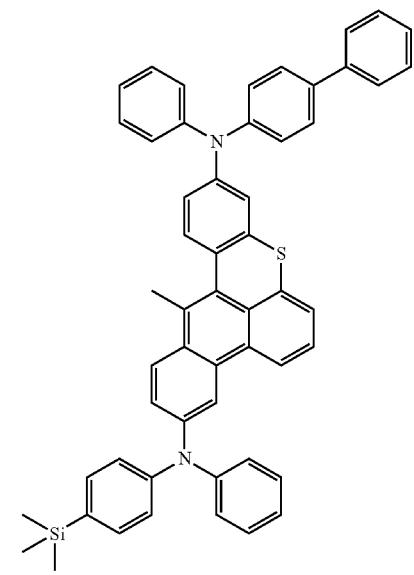
115A
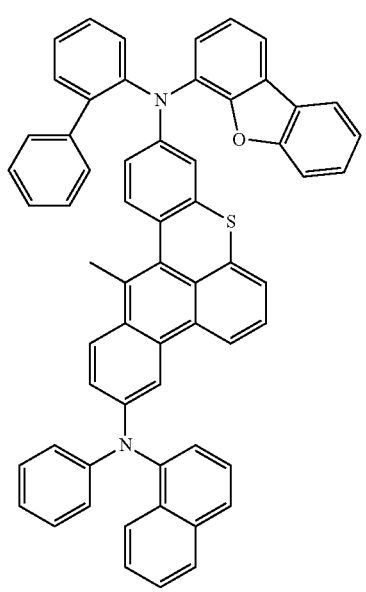
114A
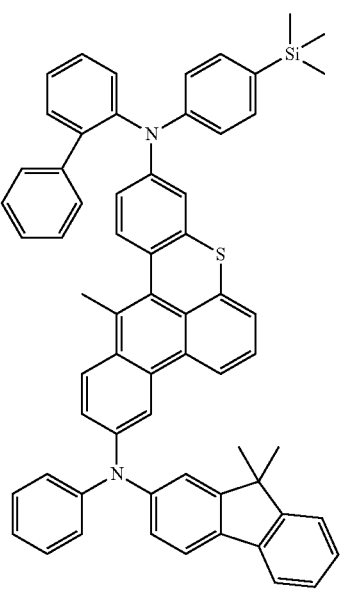
116A

183
-continued
117A
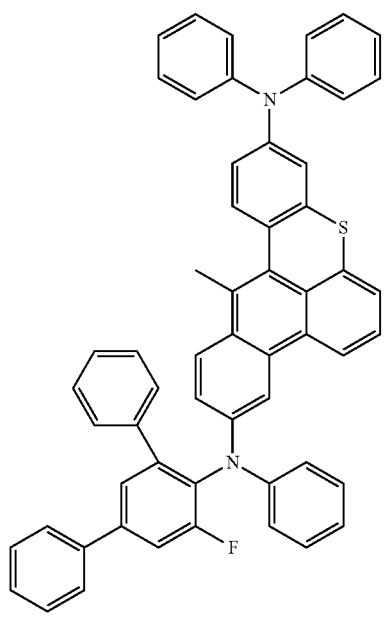
118A
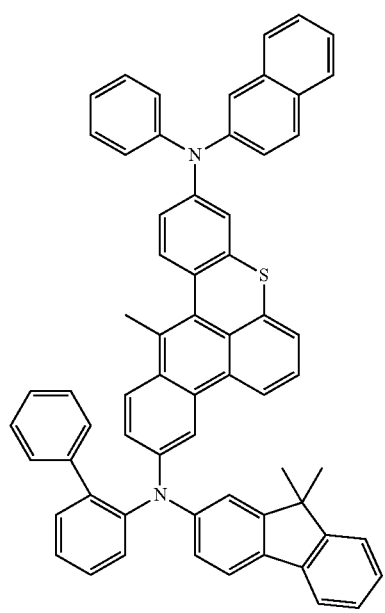
184
-continued
119A
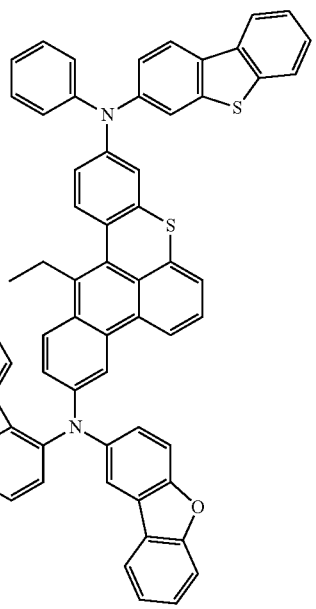
120A
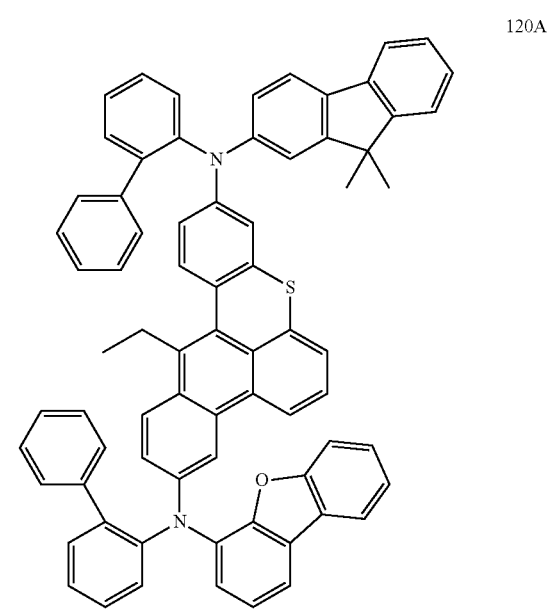

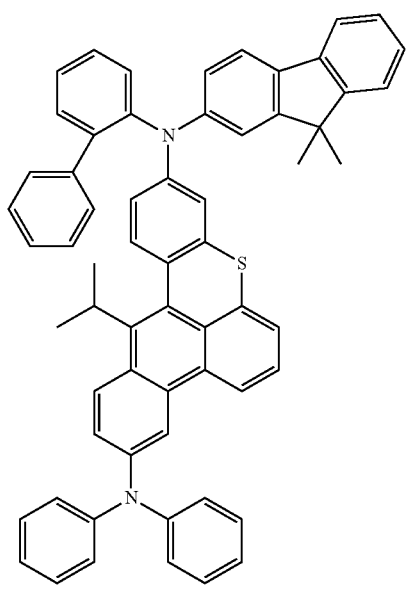
121A
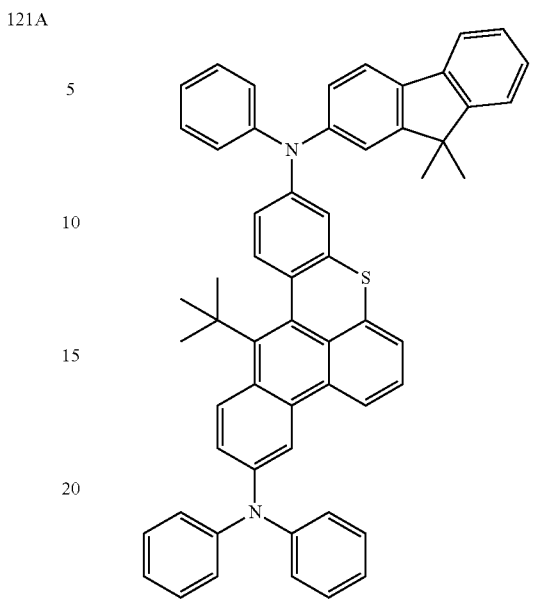
123A
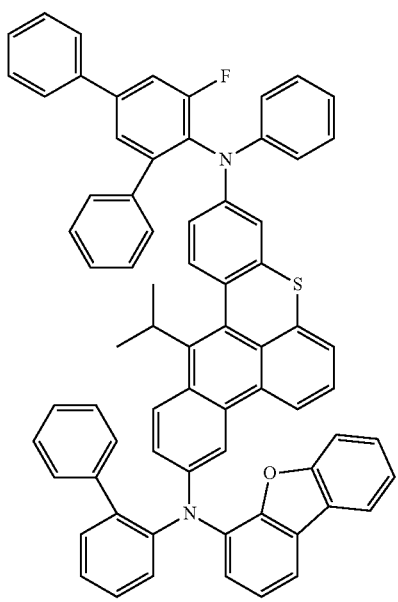
122A
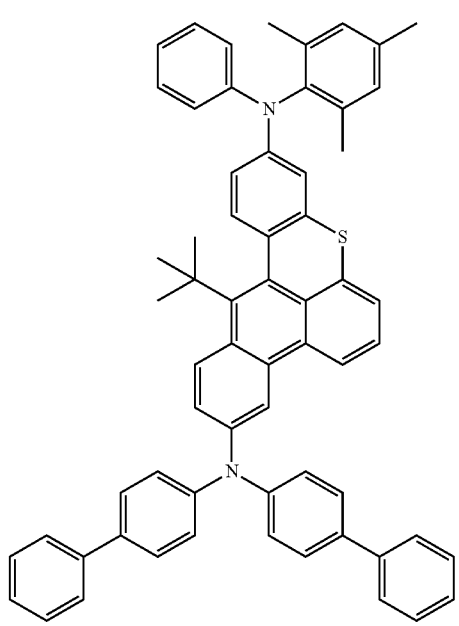
124A 187
125A
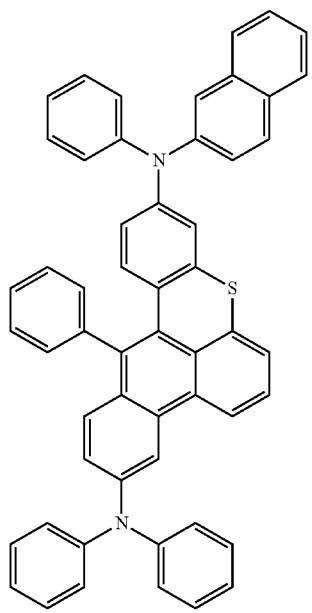
126A
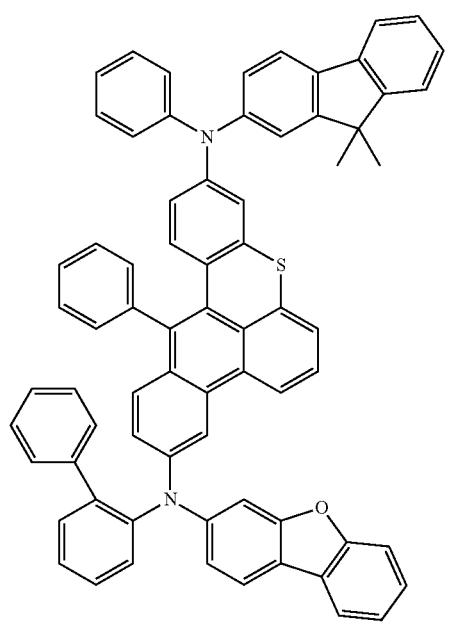
188
127A
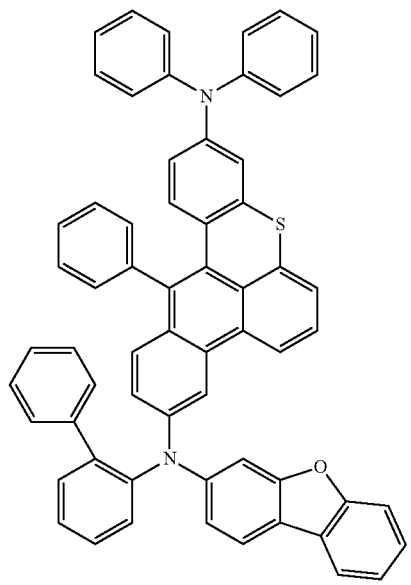
128A
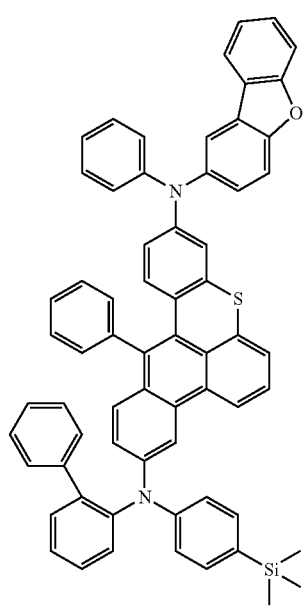

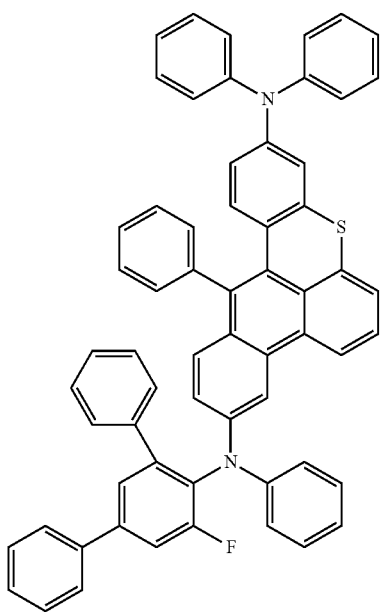
129A
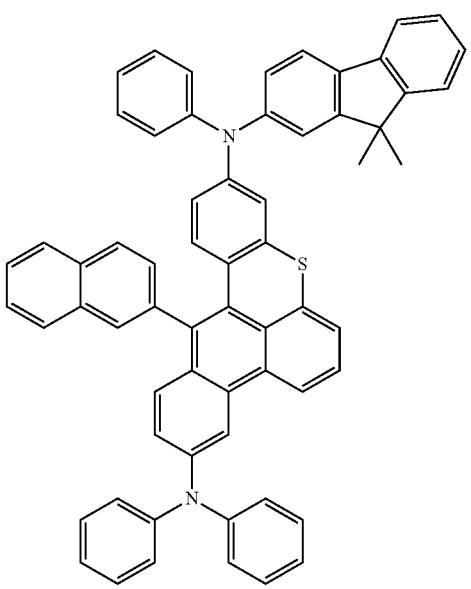
131A
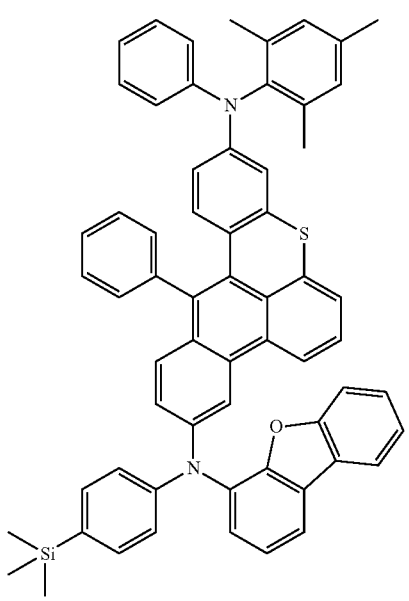
130A
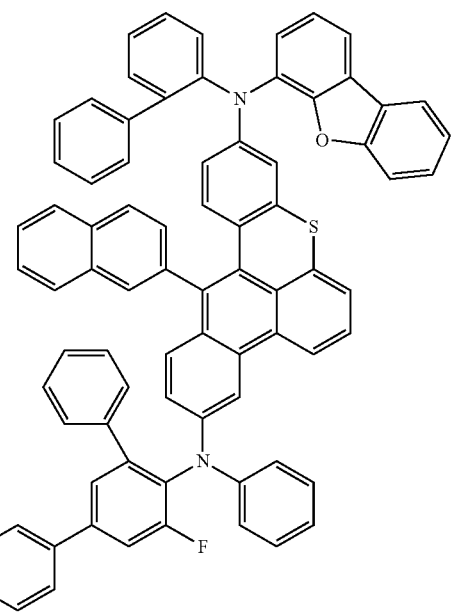
132A

191
-continued
133A
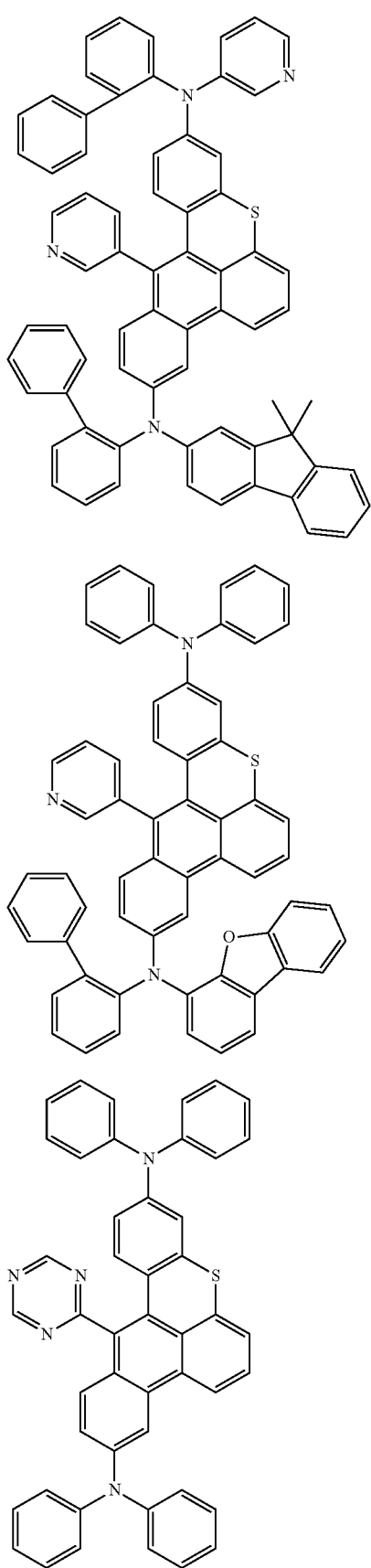
134A
135A
192
-continued
136A
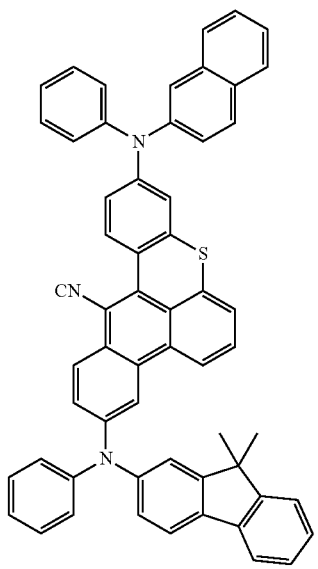
137A
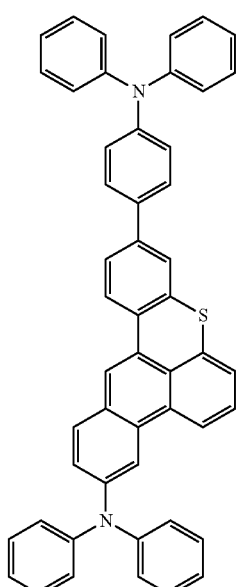

193
-continued
194
-continued
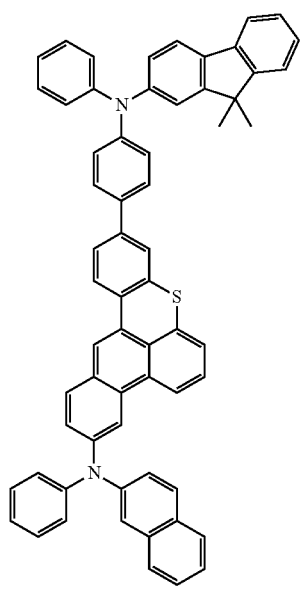
138A
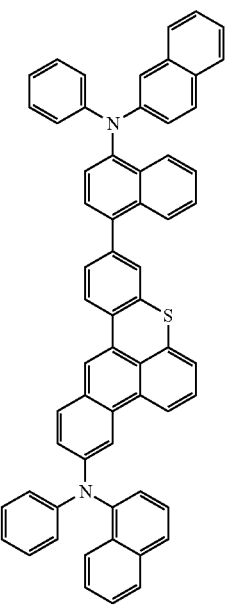
140A
139A
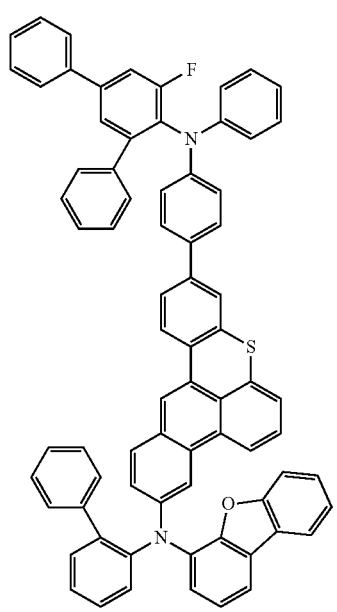
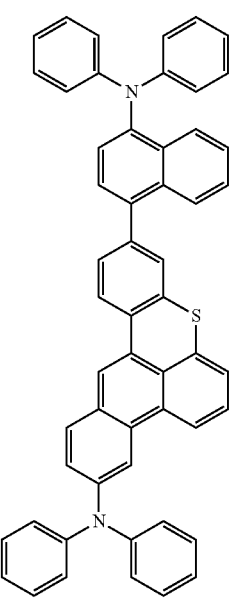
141A 195
-continued
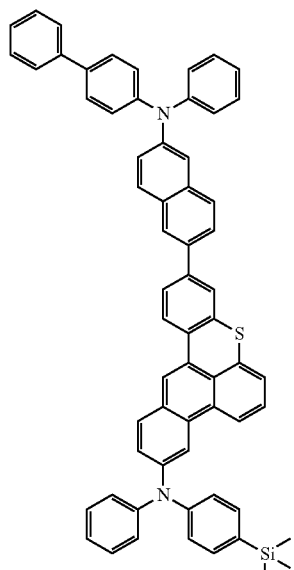
143A
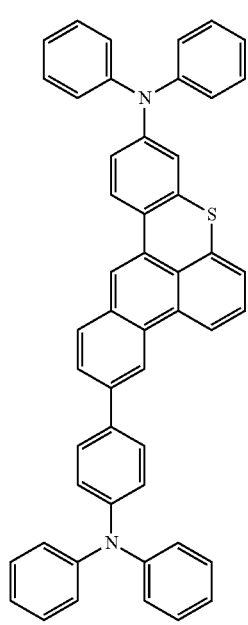
196
-continued
142A
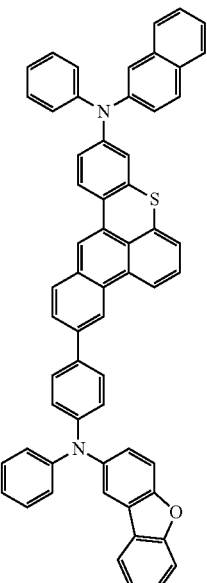
144A
145A
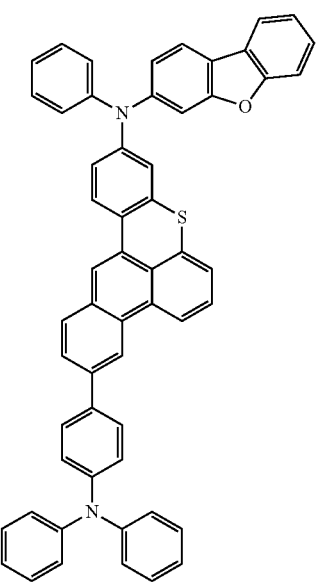

197
-continued
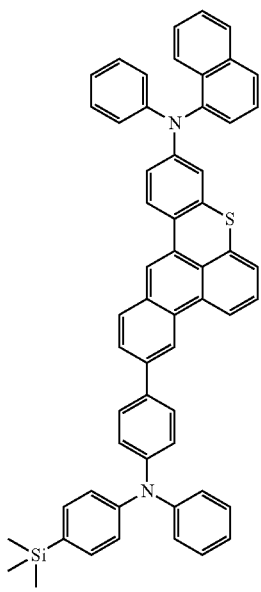
146A
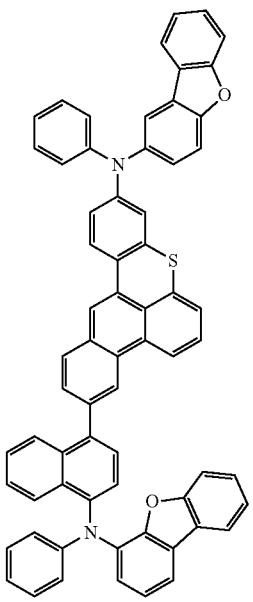
198
-continued
148A
147A
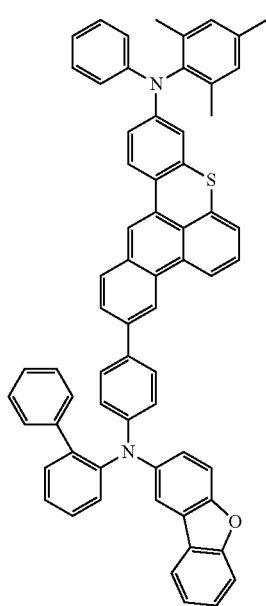
149A
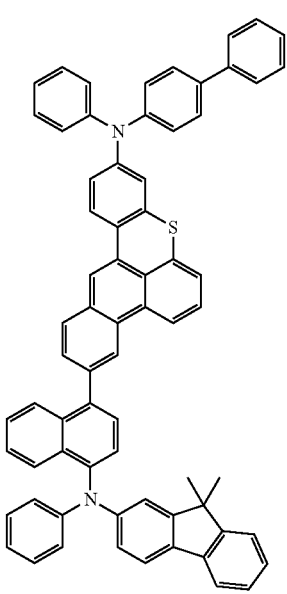

199
-continued
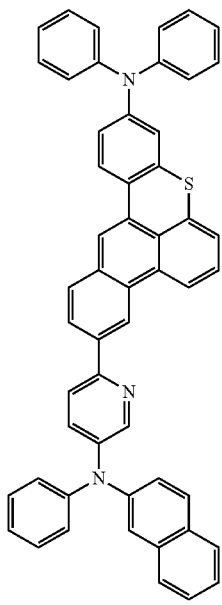
200
-continued
150A
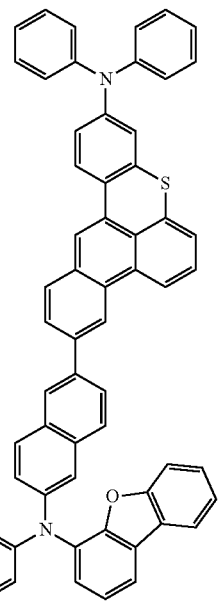
151A
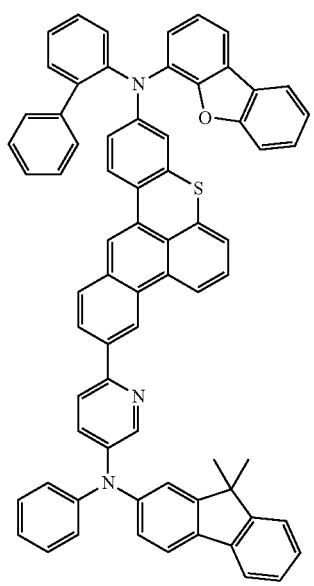
152A
153A
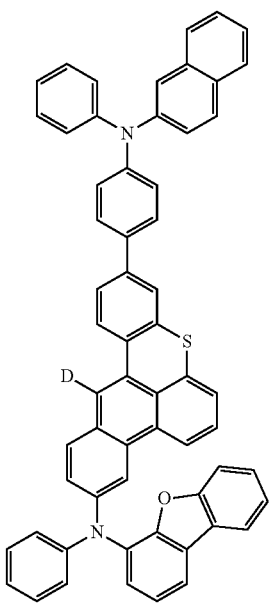

154A
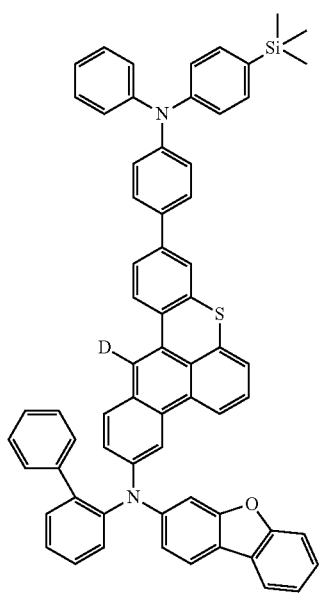
155A
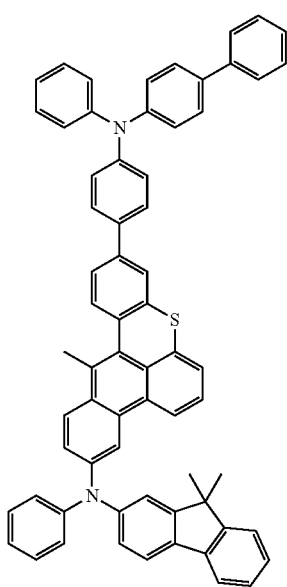
156A
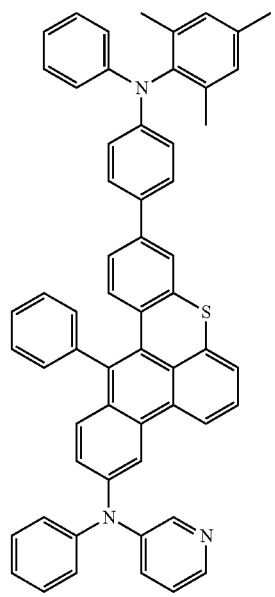
157A
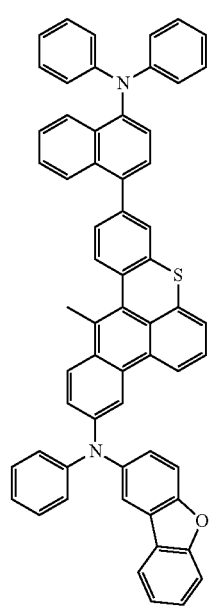

203
-continued
158A
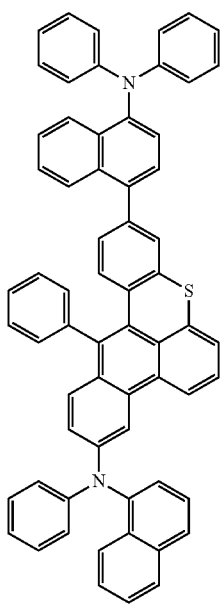
159A
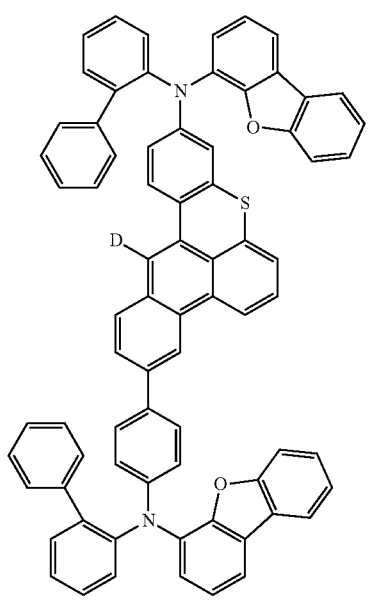
204
-continued
160A
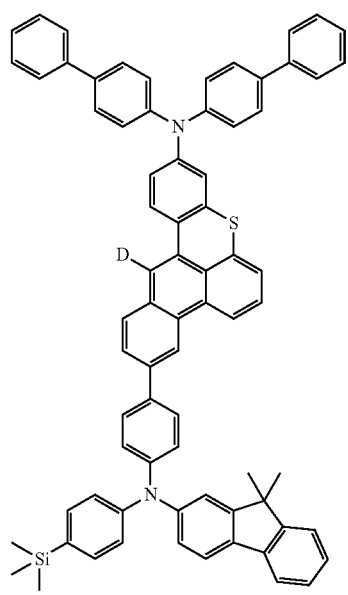
161A
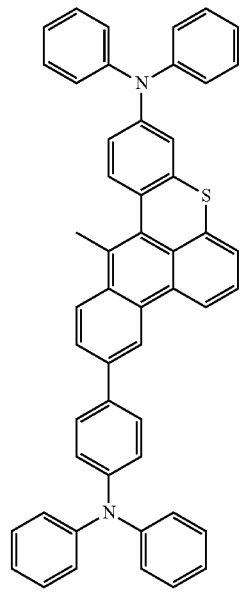

162A 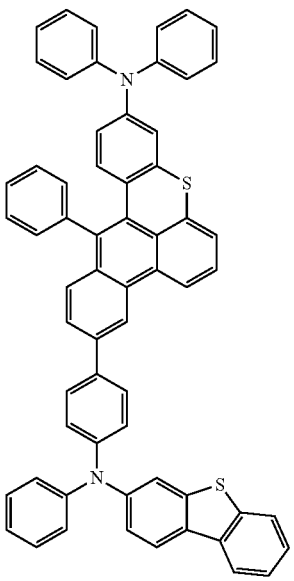

164A 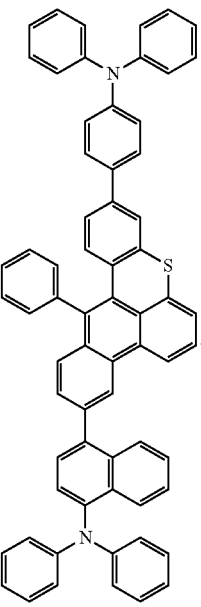

163A 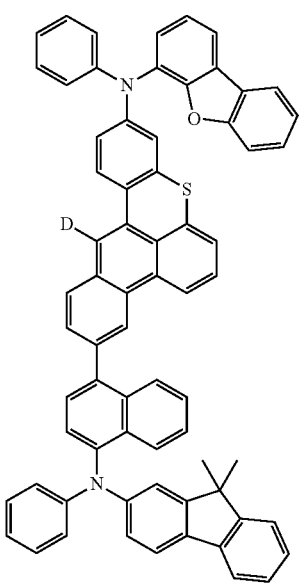

The condensed cyclic compound represented by Formula 1 has a core that has a phenanthrene moiety fused to a benzene moiety, each of which is enriched with π-electrons, with $X_1$ (O or S) therebetween, and at least two substituents selected from a group represented by Formula 2. Accordingly, radical cations or anions generated by the group represented by Formula 2 may be effectively delocalized and stabilized in the condensed cyclic compound represented by Formula 1. Accordingly, p-p* (pi to pi star) or n-p* (n to pi star) electron transition may be highly likely to occur in the molecule of the condensed cyclic compound represented by Formula 1, and thus the condensed cyclic compound represented by Formula 1 may provide high-efficient emission. Also, since the core of the condensed cyclic compound represented by Formula 1 has a relatively short conjugation length, relatively deep blue light emission may be achieved. Accordingly, an organic light-emitting device using the condensed cyclic compound represented by Formula 1 may have high efficiency and long lifespan.

The condensed cyclic compound represented by Formula 1 may be synthesized using one or more suitable organic synthesis methods known to those of ordinary skill in the art. Suitable synthesis method of the condensed cyclic compound should be apparent to those of ordinary skill in the art in view of the following embodiments.

At least one condensed cyclic compound of Formula 1 may be positioned between a pair of electrodes of an organic light-emitting device. In some embodiments, the condensed cyclic compound may be included in a hole transport region, for example, in a hole transport layer. In some embodiments, the condensed cyclic compound may be included in an emission layer. In some embodiments, the condensed cyclic compound of Formula 1 may be used as a material for a capping layer located outside a pair of electrodes of an organic light-emitting device.

An organic light-emitting device according to some embodiments includes: a first electrode; a second electrode facing the first electrode; and an organic layer between the first electrode and the second electrode, the organic layer including an emission layer, where the organic layer includes at least one of the condensed cyclic compounds represented by Formula 1.

The expression "a layer includes at least one condensed cyclic compound of Formula 1" as used herein may refer to embodiments in which a layer includes one or more of the same condensed cyclic compounds represented by Formula 1 and embodiments in which a layer includes two or more different condensed cyclic compounds represented by Formula 1.

For example, the organic layer may include, as the condensed cyclic compound, only Compound 1. In this regard, Compound 1 may be in a hole transport layer of the organic light-emitting device. In some embodiments, the organic layer may include, as the condensed cyclic compound, Compound 1 and Compound 2. In this regard, Compound 1 and Compound 2 may both be in the same layer (for example, Compound 1 and Compound 2 may both be in an emission layer), or in different layers (for example, Compound 1 may be in a hole transport layer and Compound 2 may be in an emission layer).

In some embodiments, the organic layer further includes i) a hole transport region between the first electrode (anode) and the emission layer, the hole transport region including at least one of a hole injection layer, a hole transport layer, a buffer layer, and an electron blocking layer, and ii) an electron transport region between the emission layer and the second electrode (cathode), the electron transport region including at least one selected from a hole blocking layer, an electron transport layer, and an electron injection layer. At least one of the hole transport region and the emission layer may include at least one condensed cyclic compound represented by Formula 1. For example, the hole transport region may include the hole transport layer, and the hole transport layer may include at least one condensed cyclic compound represented by Formula 1.

In some embodiments, in the organic layer of the organic light-emitting device, the emission layer may include the condensed cyclic compound represented by Formula 1. In the emission layer, the condensed cyclic compound represented by Formula 1 may act as a dopant, and the emission layer may further include a host.

In some embodiments, each of the hole transport region (for example, a hole transport layer in the hole transport region) and the emission layer may include the condensed cyclic compound of Formula 1, and the condensed cyclic compound included in the hole transport region (for example, in the hole transport layer of the hole transport region) may be different from the condensed cyclic compound Included in the emission layer.

The organic light-emitting device may further include at least one selected from a first capping layer positioned in a pathway along which the light generated in the emission layer proceeds toward the outside through the first electrode and a second capping layer positioned in a pathway along which the light generated in the emission layer proceeds toward the outside through the second electrode, and the at least one selected from the first capping layer and the second capping layer may include at least one condensed cyclic compound of Formula 1.

For example, the organic light-emitting device may have i) a stack structure including a first electrode, an organic layer, a second electrode, and a second capping layer which are sequentially stacked in this stated order, ii) a stack structure including a first capping layer, a first electrode, an organic layer, and a second electrode which are sequentially stacked in this stated order, or iii) a stack structure including a first capping layer, a first electrode, an organic layer, a second electrode, and a second capping layer which are sequentially stacked in this stated order, and at least one selected from the first capping layer and the second capping layer may include the condensed cyclic compound.

The term "organic layer" as used herein refers to a single layer and/or a plurality of layers disposed between the first electrode and the second electrode of an organic light-emitting device. A material included in the "organic layer" is not limited to an organic material.

Figure 1:
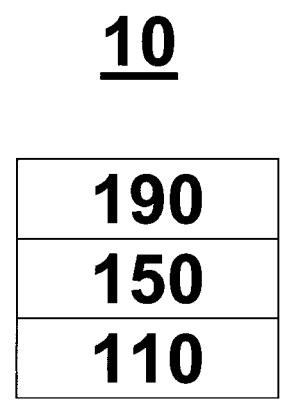

FIG. 1 is a schematic view of an organic light-emitting device 10 according to an embodiment. The organic light-emitting device 10 includes a first electrode 110, an organic layer 150, and a second electrode 190.

Hereinafter, the structure of an organic light-emitting device and a method of manufacturing an organic light-emitting device according to some embodiments will be described in connection with FIG. 1.

In FIG. 1, a substrate may be additionally positioned under the first electrode 110 or above the second electrode 190. The substrate may be a glass substrate or transparent plastic substrate, each having excellent mechanical strength, thermal stability, transparency, surface smoothness, ease of handling, and being waterproof.

The first electrode 110 may be formed by depositing and/or sputtering a material for forming the first electrode on the substrate. When the first electrode 110 is an anode, the material for the first electrode may be selected from materials with a high work function such that the holes may be easily injected. The first electrode 110 may be a reflective electrode or a transmissive electrode. The material for the first electrode may be a transparent and highly conductive material, and non-limiting examples of such a material include indium tin oxide (ITO), Indium zinc oxide (IZO), tin oxide ($SnO_2$), and zinc oxide (ZnO). When the first electrode 110 is a semi-transmissive electrode or a reflective electrode, as a material for forming the first electrode, at least one of magnesium (Mg), aluminum (Al), aluminum-lithium (Al—Li), calcium (Ca), magnesium-indium (Mg—In), and magnesium-silver (Mg—Ag) may be used.

The first electrode 110 may have a single-layer structure, or a multi-layer structure including two or more layers. For example, the first electrode 110 may have a three-layered structure of ITO/Ag/ITO, but the structure of the first electrode 110 is not limited thereto.

The organic layer 150 is positioned on the first electrode 110. The organic layer 150 may include an emission layer.

The organic layer 150 may further include a hole transport region between the first electrode and the emission layer, and an electron transport region between the emission layer and the second electrode.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron Injection layer (EIL), but embodiments of the present invention are not limited thereto.

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, where the layers of each structure are sequentially stacked on the first electrode 110 in this stated order, but the structure of the hole transport region is not limited thereto.

When the hole transport region includes a hole injection layer, the hole injection layer may be formed on the first electrode 110 using one or more suitable methods, such as vacuum deposition, spin coating casting, a Langmuir-Blodgett (LB) method, Ink-jet printing, laser-printing, and/or laser-Induced thermal Imaging.

When the hole injection layer is formed by vacuum deposition, for example, the vacuum deposition may be performed at a deposition temperature of about 100 to about 500° C., at a vacuum degree of about $10^{-8}$ to about $10^{-3}$ torr, and at a deposition rate of about 0.01 to about 100 Å/sec, depending on a compound for forming the hole injection layer, and the structure of the hole injection layer to be formed.

When the hole injection layer is formed by spin coating, the spin coating may be performed at a coating rate of about 2000 rpm to about 5000 rpm, and at a temperature of about 80° C. to 200° C., depending on a compound for forming the hole injection layer, and the structure of the hole injection layer to be formed.

When the hole transport region Includes a hole transport layer, the hole transport layer may be formed on the first electrode 110 or the hole injection layer using one or more suitable methods, such as vacuum deposition, spin coating, casting, a LB method, ink-jet printing, laser-printing, and/or laser-induced thermal imaging. When the hole transport layer is formed by vacuum deposition and/or spin coating, deposition and coating conditions for the hole transport layer may be similar to the deposition and coating conditions for the hole injection layer.

The hole transport region may include the condensed cyclic compound represented by Formula 1. For example, the hole transport region may include the hole transport layer, and the hole transport layer may include the condensed cyclic compound represented by Formula 1.

In some embodiments, the hole transport region may include at least one selected from m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), (polyaniline)/poly(4-styrenesulfonate) (PANI/PSS), a compound represented by Formula 201 below, and a compound represented by Formula 202 below:

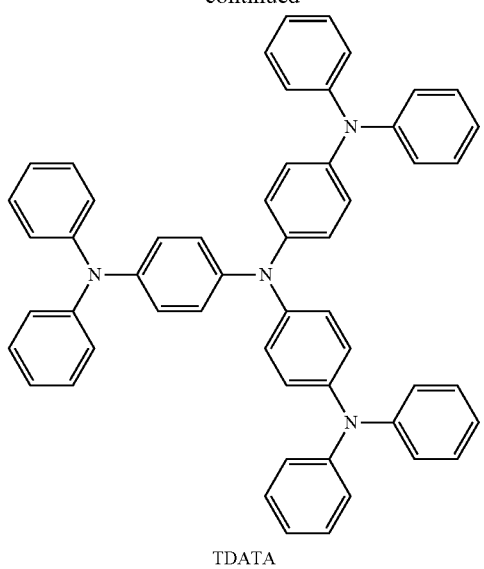

TDATA

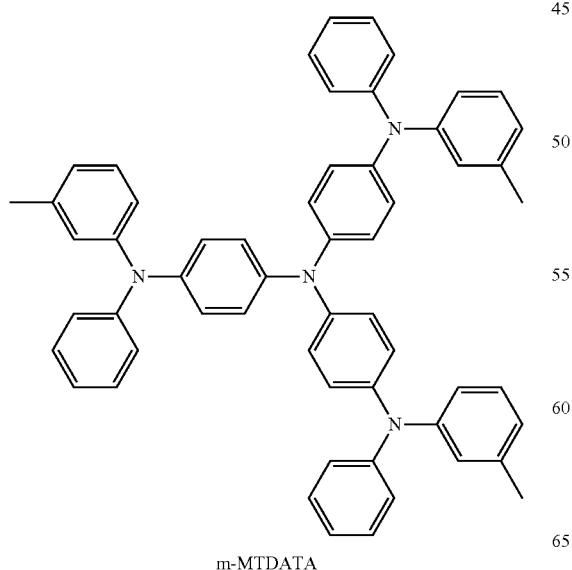

m-MTDATA

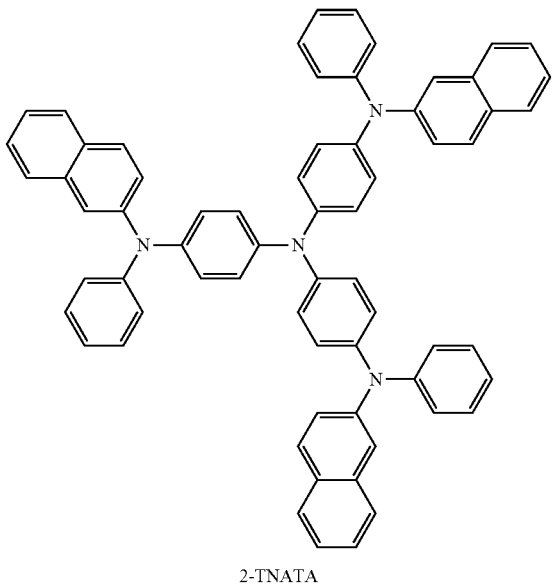

2-TNATA

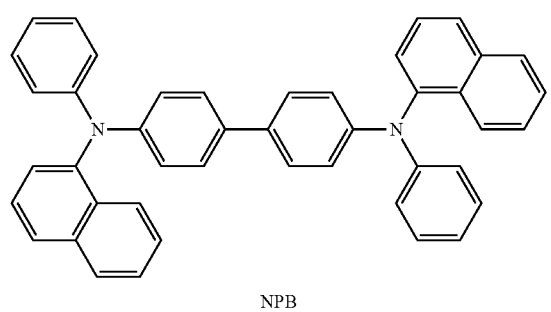

NPB

-continued

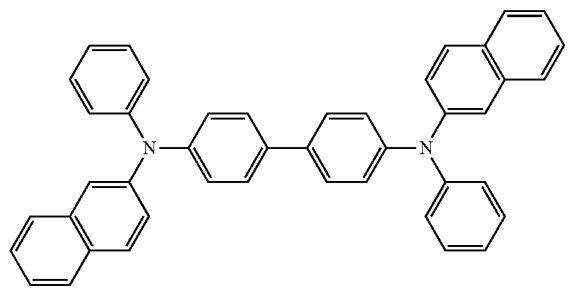

β-NPB

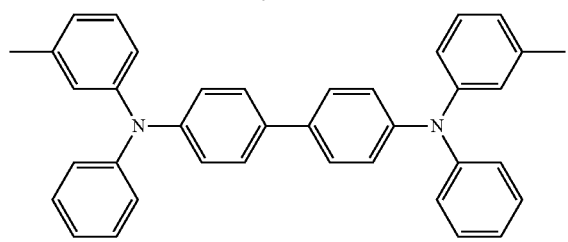

TPD

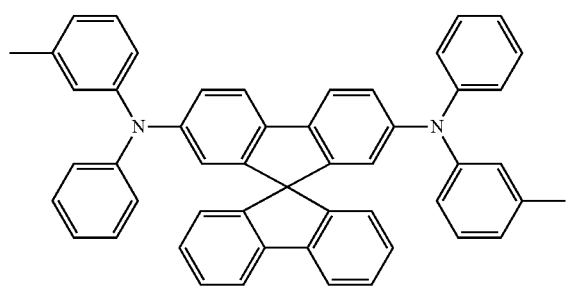

Spiro-TPD

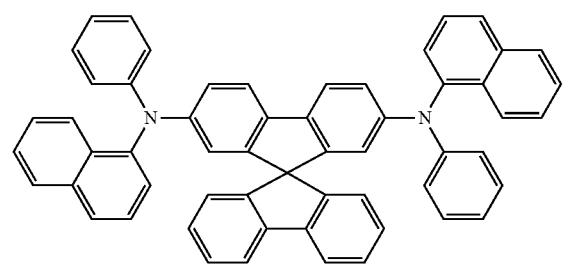

Spiro-NPB

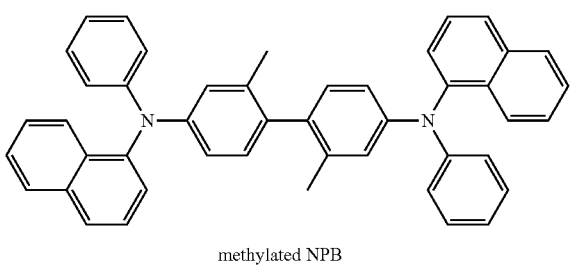

methylated NPB

-continued

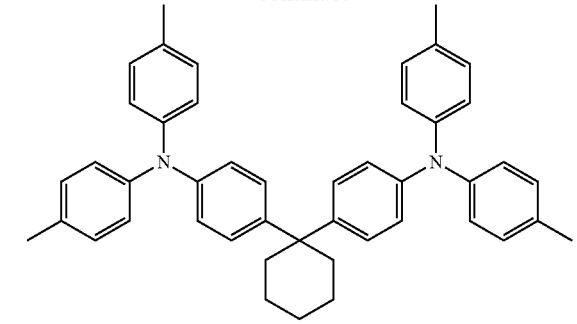

TAPC

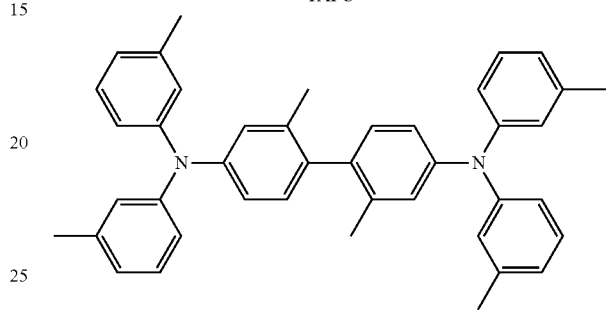

HMTPD

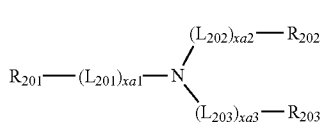

Formula 201

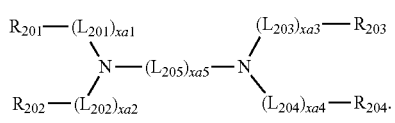

Formula 202

In Formulae 201 and 202, $L_{201}$ to $L_{205}$ may each independently be the same as described in connection with $L_1$;

xa1 to xa4 may be each independently selected from 0, 1, 2, and 3;

xa5 may be selected from 1, 2, 3, 4, and 5; and $R_{201}$ to $R_{204}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formulae 201 and 202, $L_{201}$ to $L_{205}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently 0, 1, or 2;

xa5 may be 1, 2, or 3;

$R_{201}$ to $R_{204}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present Invention are not limited thereto.

The compound represented by Formula 201 may be represented by Formula 201A:

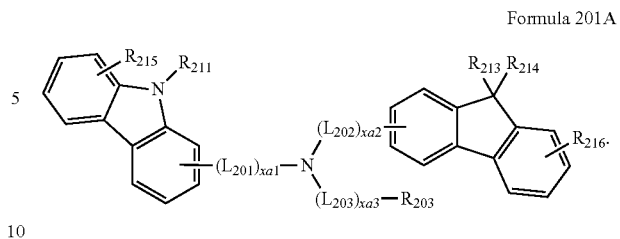

Formula 201A

For example, the compound represented by Formula 201 may be represented by Formula 201A-1 below, but is not limited thereto:

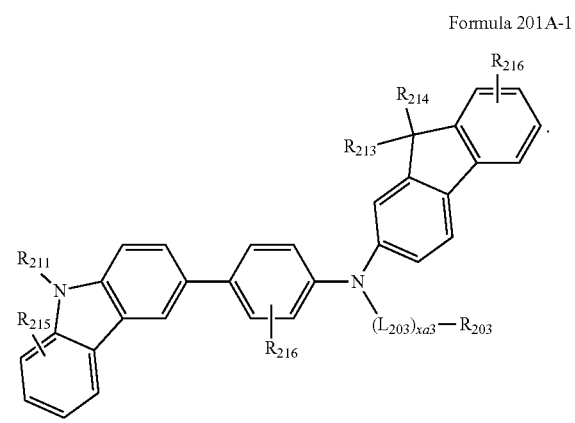

Formula 201A-1

For example, the compound represented by Formula 202 may be represented by Formula 202A below, but is not limited thereto:

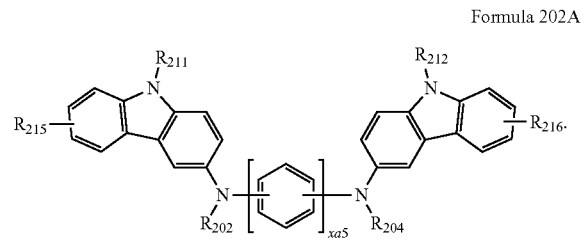

Formula 202A

Regarding Formulae 201A, 201A-1, and 202A, descriptions of $L_{201}$ to $L_{203}$, xa1 to xa3, xa5, and $R_{202}$ to $R_{204}$ are the same as provided above, descriptions of $R_{211}$ and $R_{212}$ are the same as the description of $R_{203}$, and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

The compound represented by Formula 201, and the compound represented by Formula 202 may each include compounds HT1 to HT20 illustrated below, but are not limited thereto.
HT1
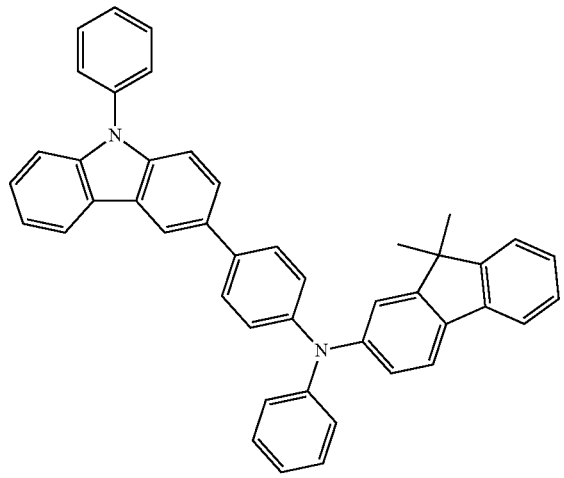
HT2
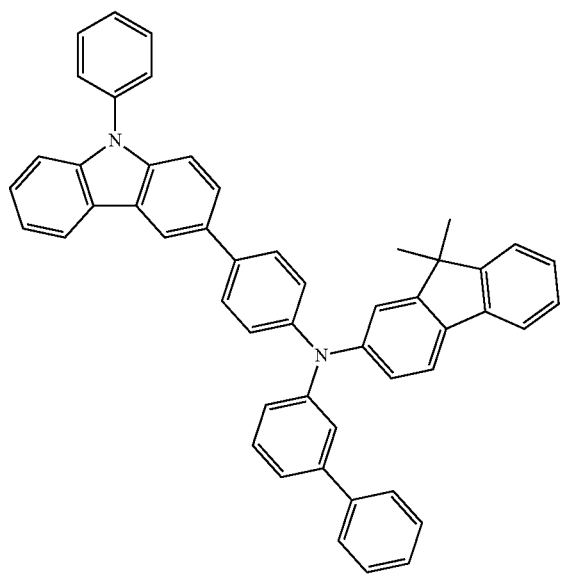
HT3
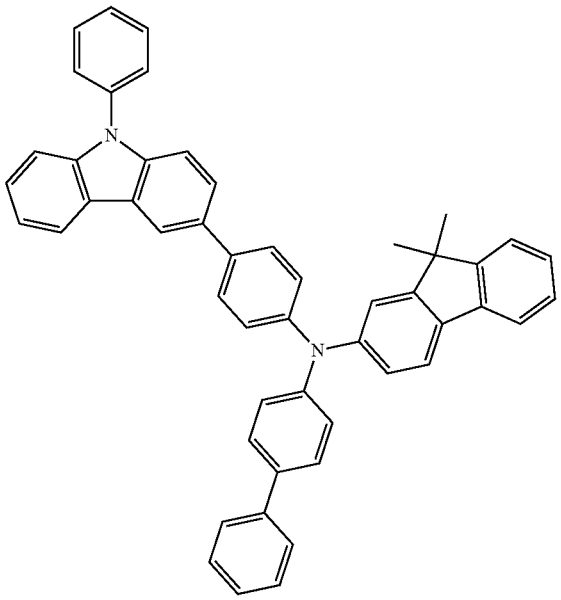
HT4
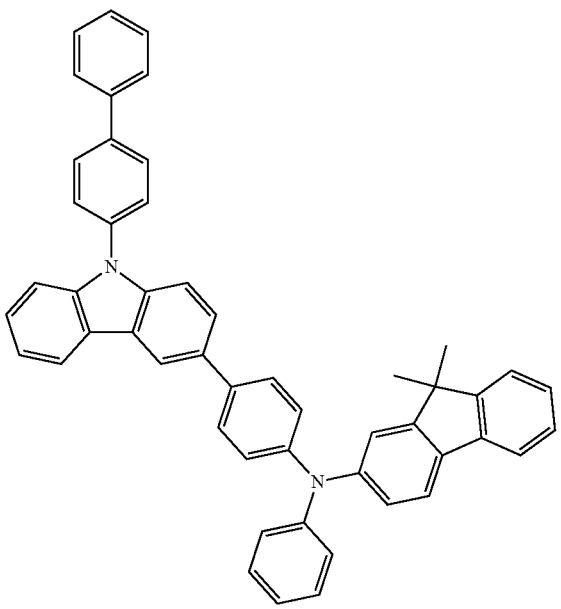

HT5
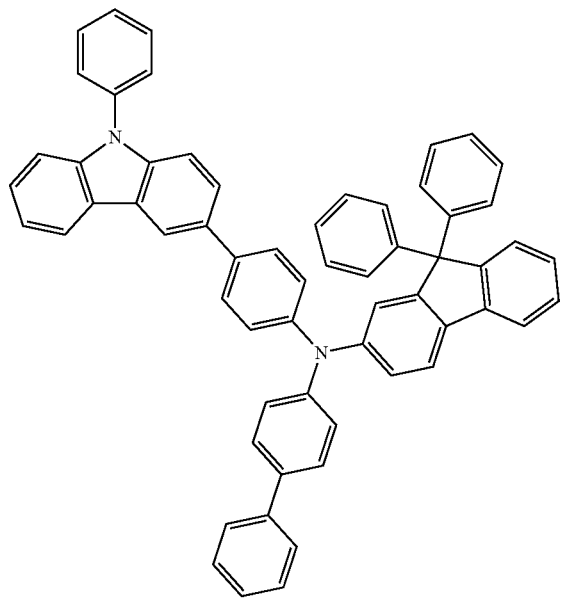
HT7
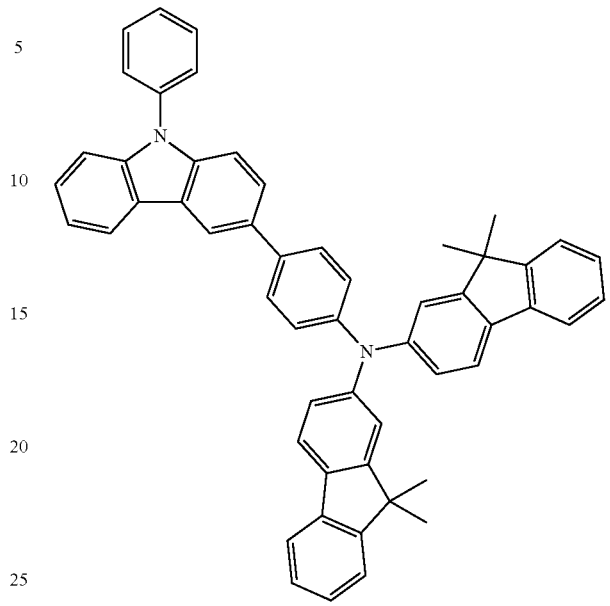
HT6
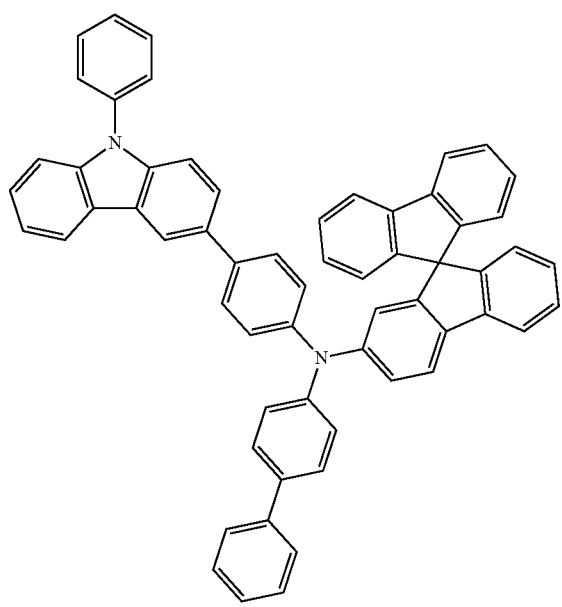
HT8
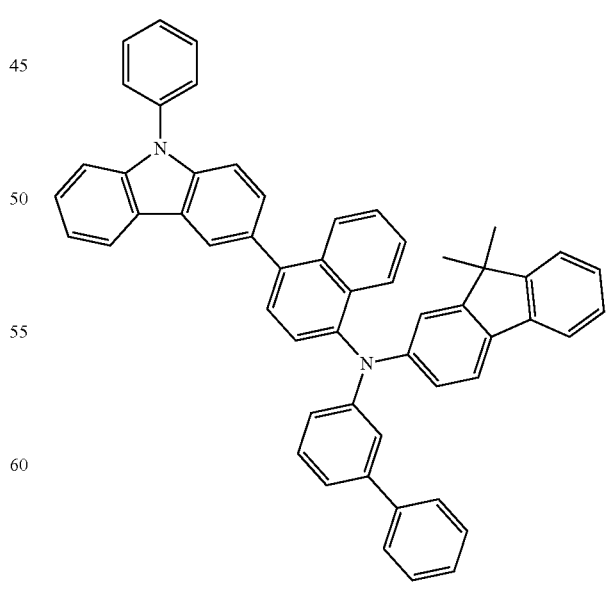

HT9
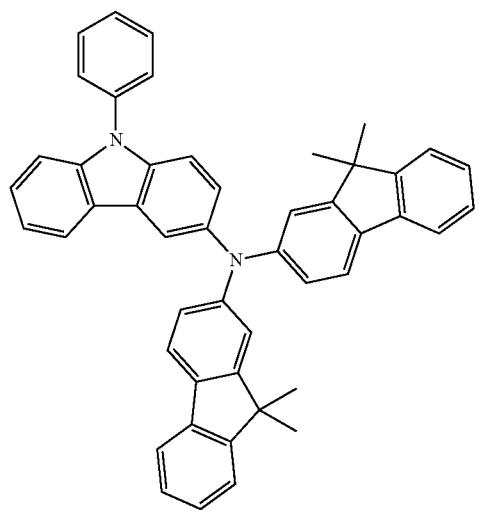
HT11
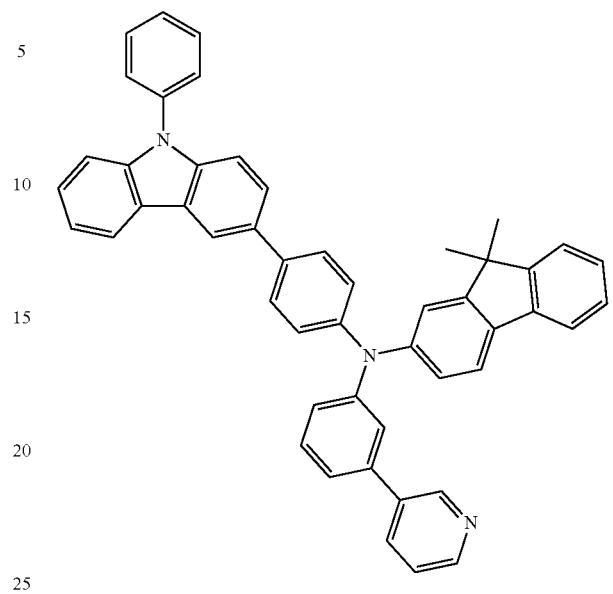
HT10
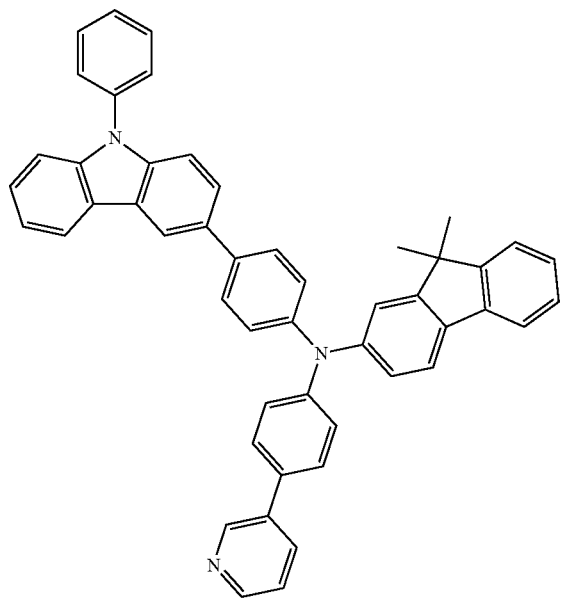
HT12
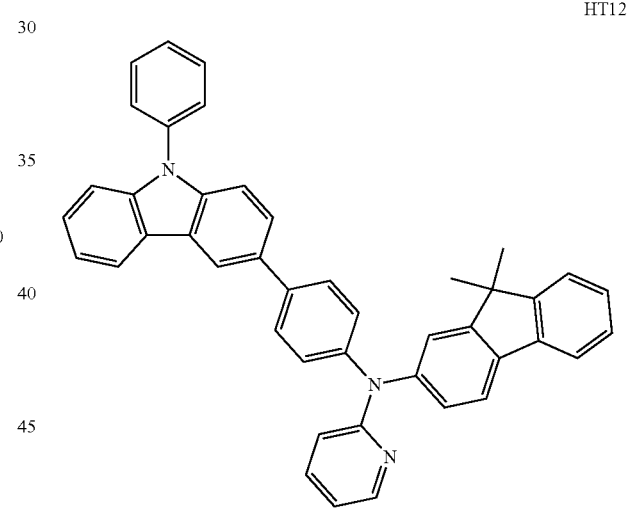
HT13
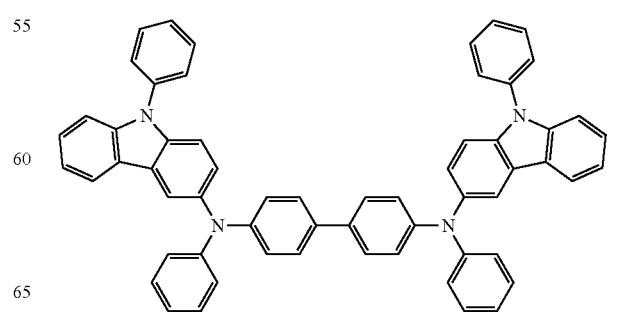

HT14

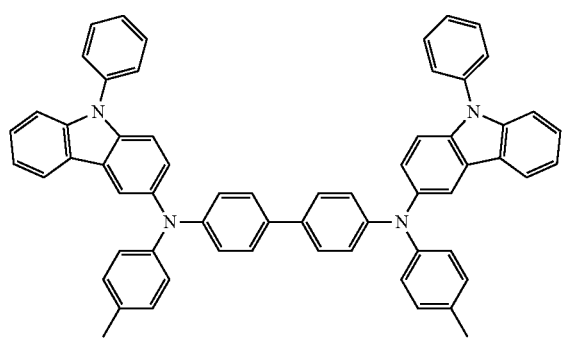

HT15

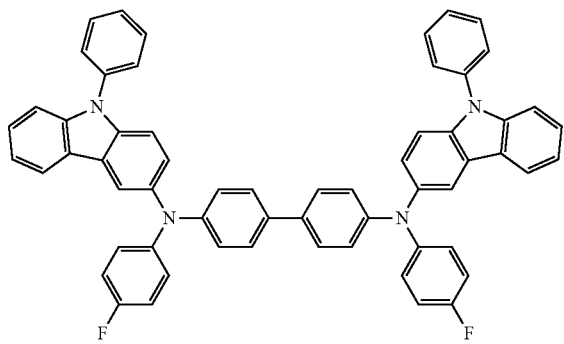

HT16

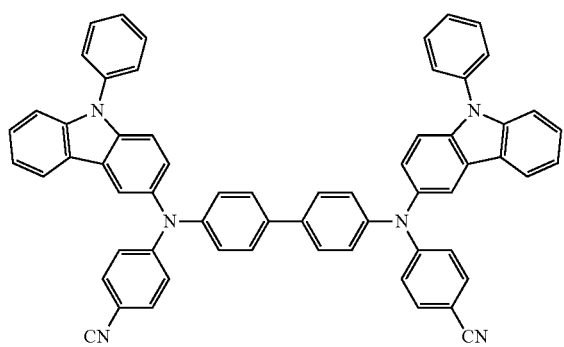

HT17

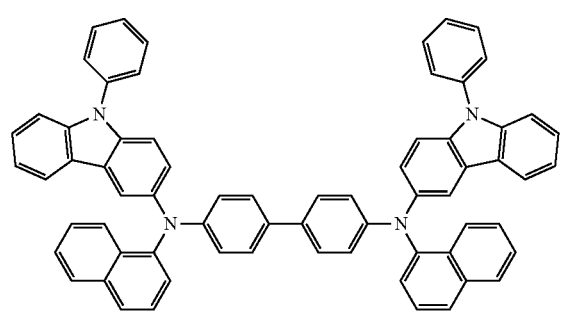

HT18

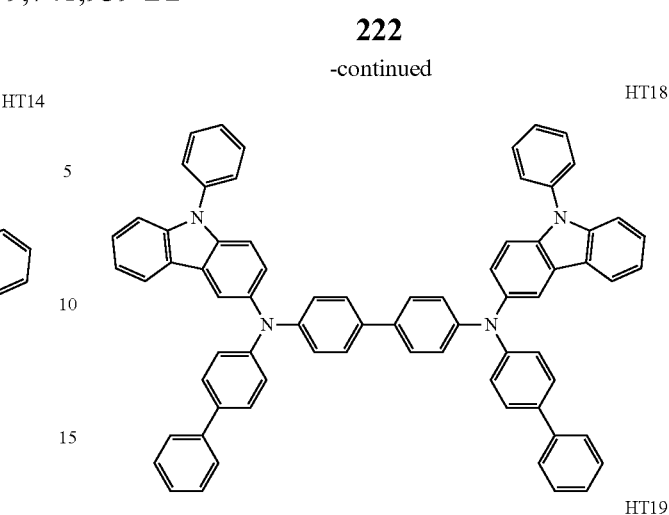

HT19

HT20

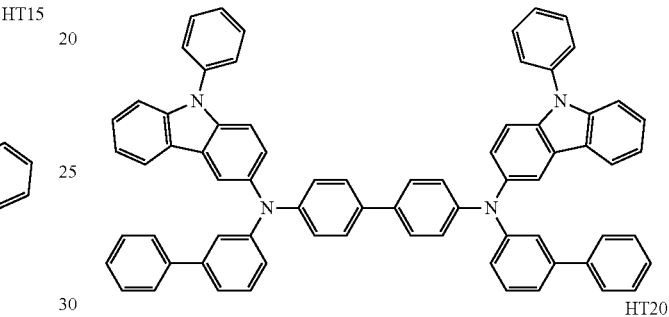

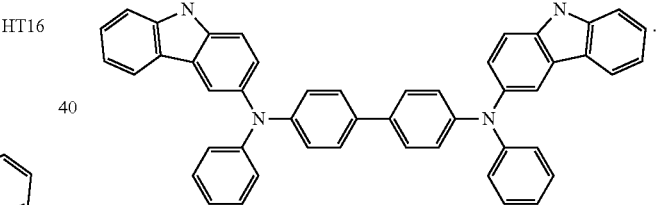

A thickness of the hole transport region may be in a range of about 100 Å to about 10,000 Å, for example, about 100 Å to about 1,000 Å. When the hole transport region Includes a hole injection layer and a hole transport layer, the thickness of the hole injection layer may be in a range of about 100 Å to about 10,000 Å, or in a range of about 100 Å to about 1,000 Å, and the thickness of the hole transport layer may be in a range of about 50 Å to about 2,000 Å, for example, about 100 Å to about 1,500 Å. When the thicknesses of the hole transport region, the hole injection layer, and the hole transport layer are within any of these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or unhomogeneously dispersed in the hole transport region.

The charge-generation material may be, for example, a p-dopant. The p-dopant may be one of a quinone derivative, a metal oxide, and a cyano group-containing compound, but is not limited thereto. Non-limiting examples of the p-dopant Include quinone derivatives (such as tetracyanoquinonedimethane (TCNQ) and/or 2,3,5,6-tetrafluoro-tetracyano-1,4-benzoquinonedimethane (F4-TCNQ)); metal oxides (such as a tungsten oxide and/or a molybdenum oxide); and Compound HT-D1 illustrated below:

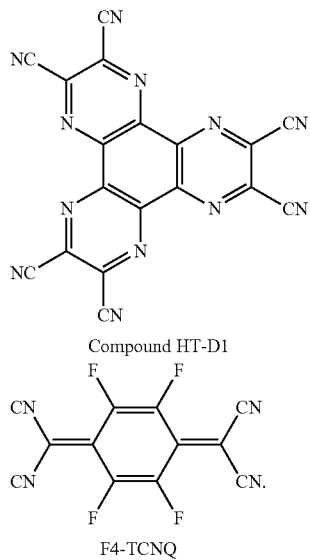

Compound HT-D1

F4-TCNQ

The hole transport region may further include, in addition to the hole injection layer and the hole transport layer, at least one of a buffer layer and an electron blocking layer. Since the buffer layer may compensate for an optical resonance distance according to a wavelength of light emitted from the emission layer, light-emission efficiency of a formed organic light-emitting device may be improved. As a material included in the buffer layer, materials that are included in the hole transport region may be used. In some embodiments, the electron blocking layer prevents (or substantially blocks) the injection of electrons from the electron transport region.

An emission layer may be formed on the first electrode 110 or the hole transport region by using one or more suitable methods, such as vacuum deposition, spin coating, casting, a LB method, ink-jet printing, laser-printing, and/or laser-induced thermal Imaging. When the emission layer is formed by vacuum deposition and/or spin coating, deposition and coating conditions for the emission layer may be similar to the deposition and coating conditions for the hole injection layer.

When the organic light-emitting device 10 is a full color organic light-emitting device, the emission layer may be patterned into a red emission layer, a green emission layer, or a blue emission layer, corresponding to a sub pixel. In some embodiments, the emission layer may have a stacked structure of a red emission layer, a green emission layer, and a blue emission layer, or may include a red-light emission material, a green-light emission material, and a blue-light emission material, which are mixed with each other in a single layer, to emit white light.

The emission layer may include a host and a dopant.

In some embodiments, the host may include a compound represented by Formula 301 below.

$$Ar_{301}-[(L_{301})_{xb1}-R_{301}]_{xb2}.$$  Formula 301

In Formula 301,
$Ar_{301}$ may be selected from:
a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;
a naphthalene group, a heptalene group, a fluorene group, a spiro-fluorene group, a benzofluorene group, a dibenzofluorene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si $(Q_{301})(Q_{302})(Q_{303})$ (where $Q_{301}$ to $Q_{303}$ are each Independently selected from a hydrogen, a $C_1$-$C_{60}$ alkyl group, a $C_2$-$C_{60}$ alkenyl group, a $C_1$-$C_{60}$ aryl group, and a $C_1$-$C_{10}$ heteroaryl group);
$L_3$ so may be the same as described in connection with $L_1$;
$R_{301}$ may be selected from:
a $C_1$-$C_{20}$ alkyl group and a $C_1$-$C_{20}$ alkoxy group;
a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazol group, and a triazinyl group; and
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3;

xb2 may be selected from 1, 2, 3, and 4.

For example, in Formula 301, $L_{301}$ may be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and $R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but embodiments of the present invention are not limited thereto.

For example, the host may include a compound represented by Formula 301A below:

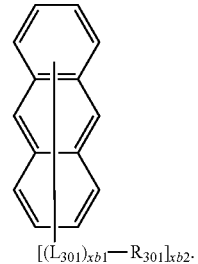

Formula 301A $[(L_{301})_{xb1}\!-\!R_{301}]_{xb2}$.

Descriptions of substituents of Formula 301A are the same as the descriptions provided herein.

The compound represented by Formula 301 may include at least one of Compounds H1 to H42, but is not limited thereto:

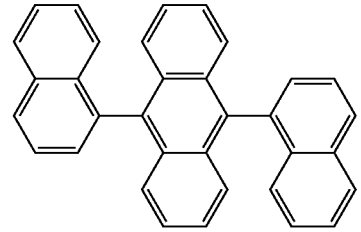

H1

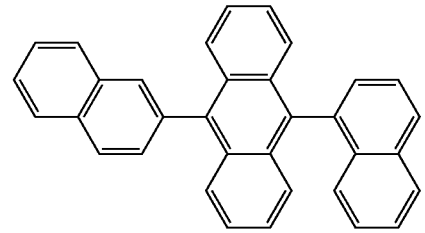

H2

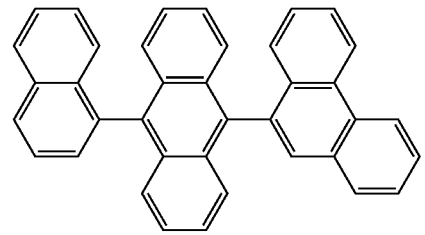

H3

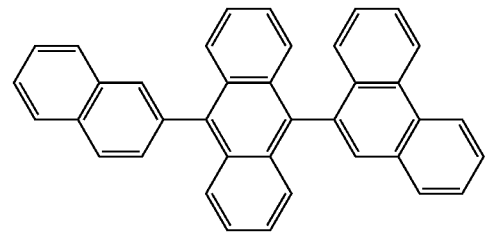

H4

-continued
H5
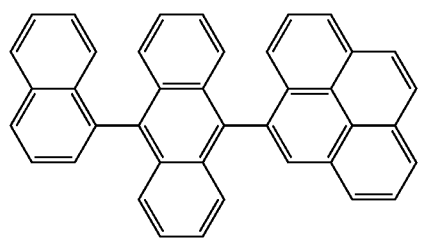
H6
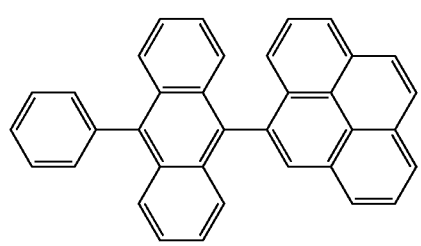
H7
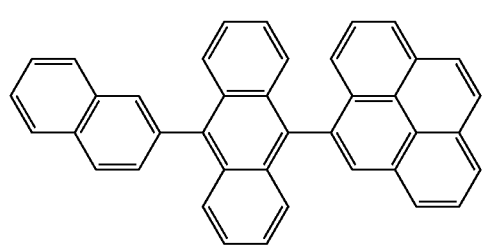
H8
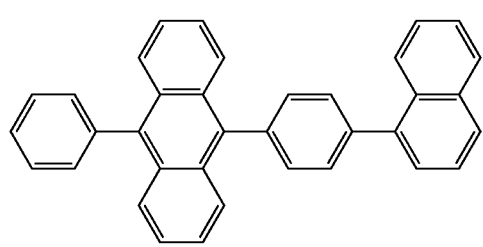
H9
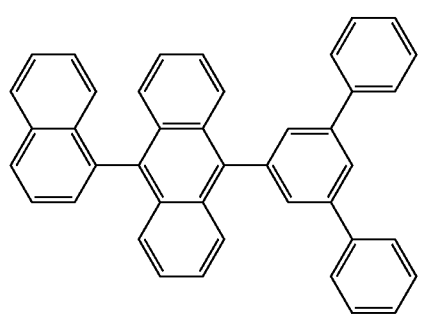
H10
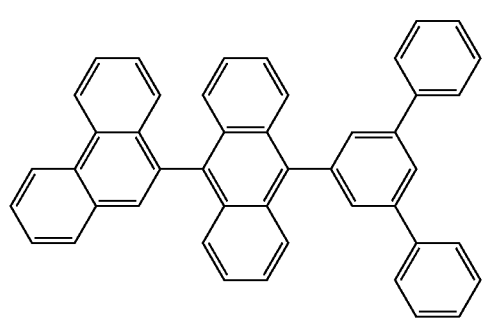
-continued
H11
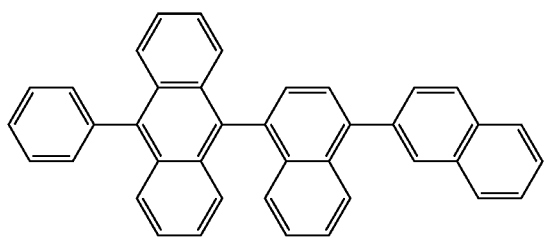
H12
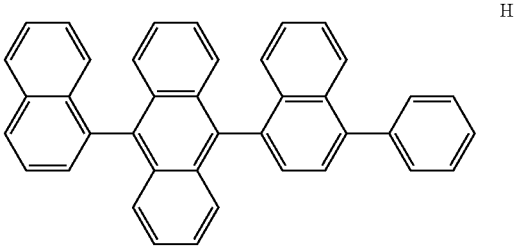
HT13
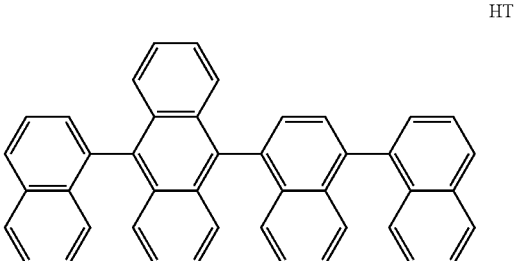
HT14
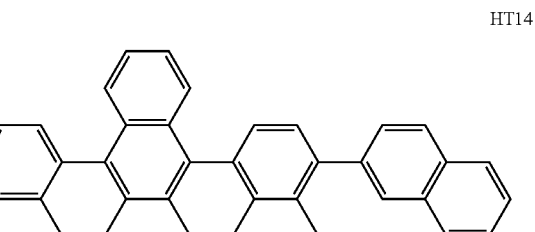
HT15
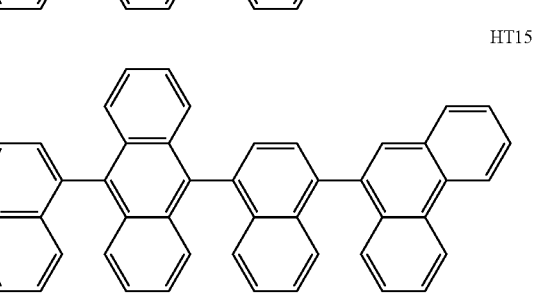
HT16
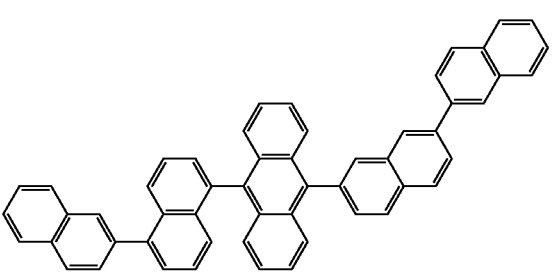

HT17
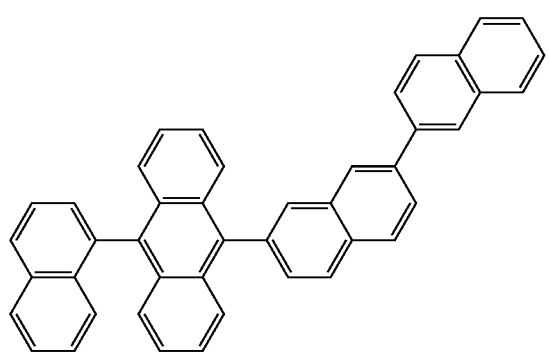
H18
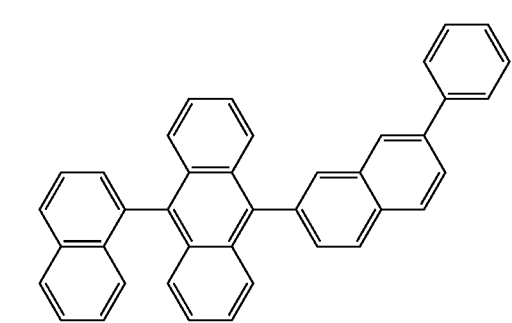
H19
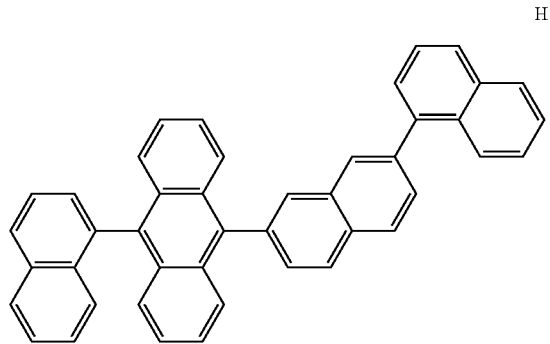
H20
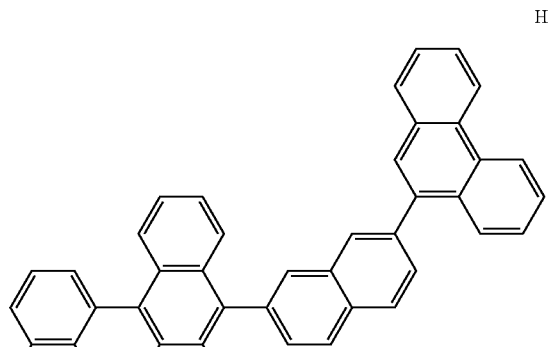
H21
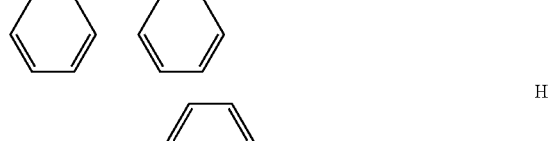
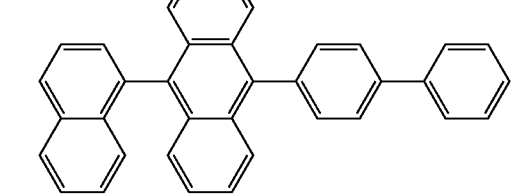
H22
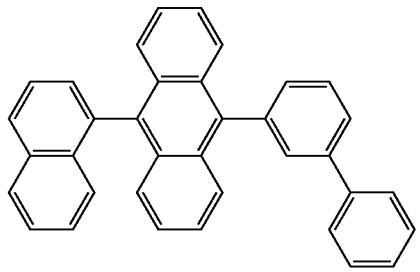
H23
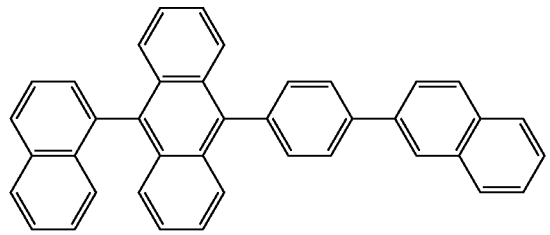
H24
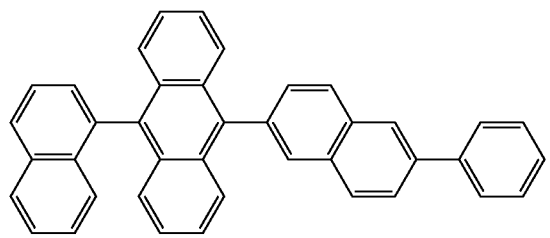
H25
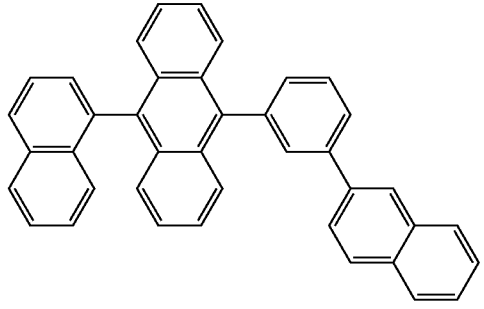
H26
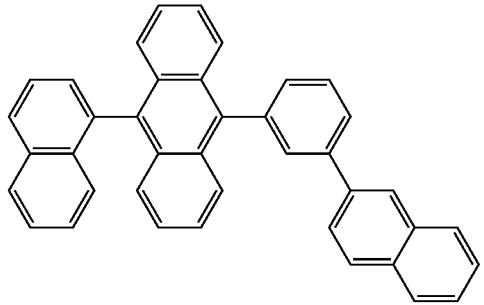

H27
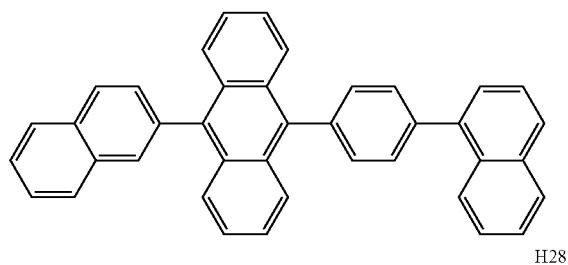
H28
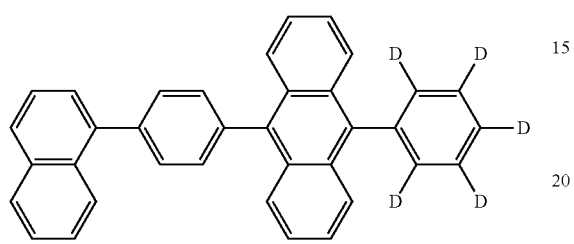
H29
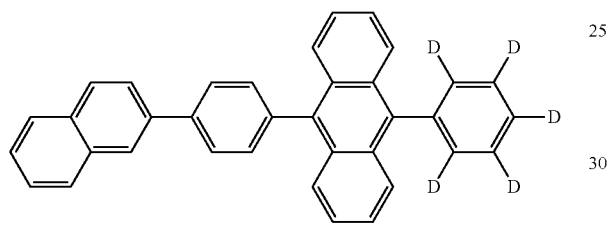
H30
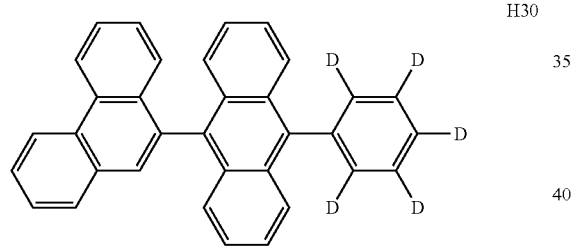
H31
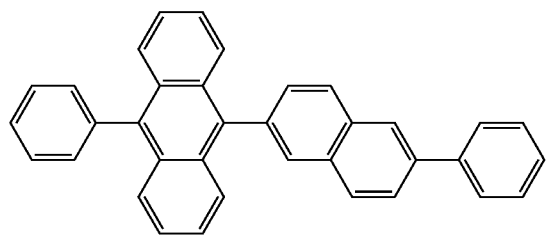
H32
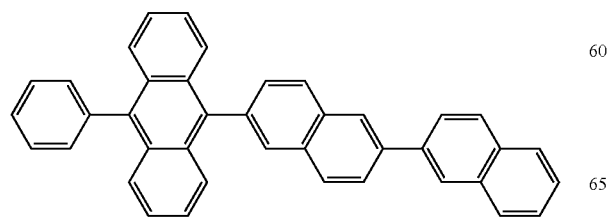
H33
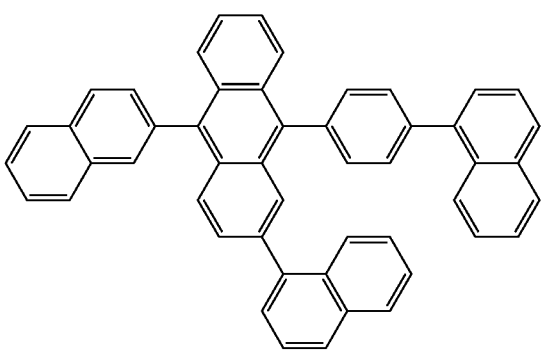
H34
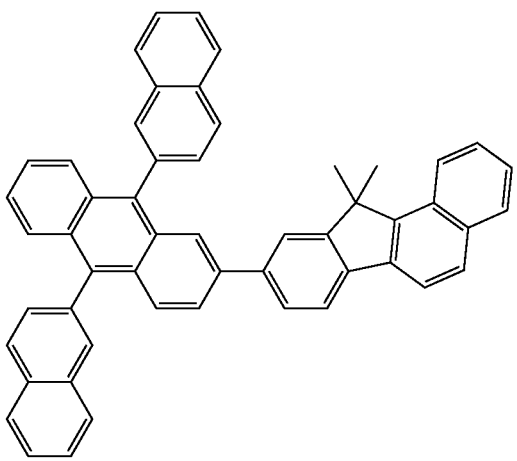
H35
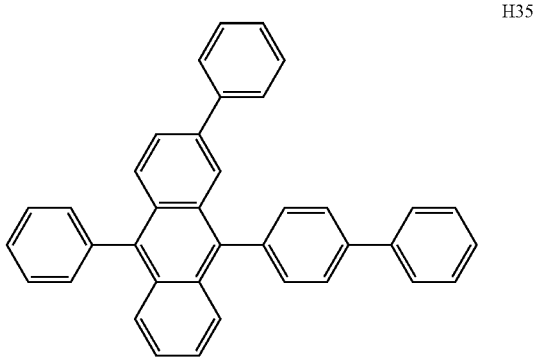

233
-continued
H36
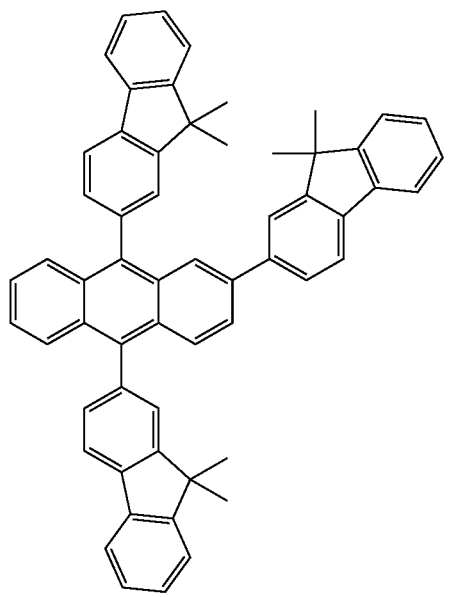
H37
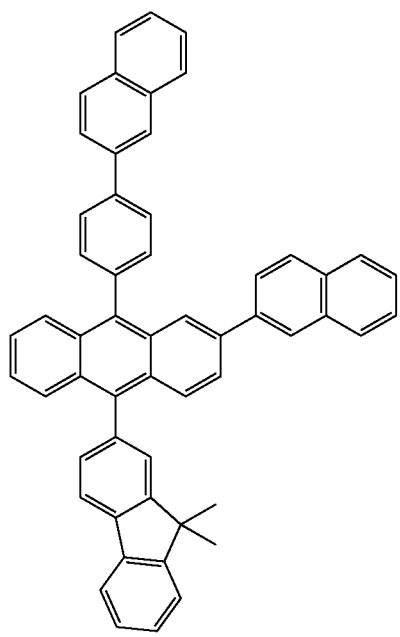
H38
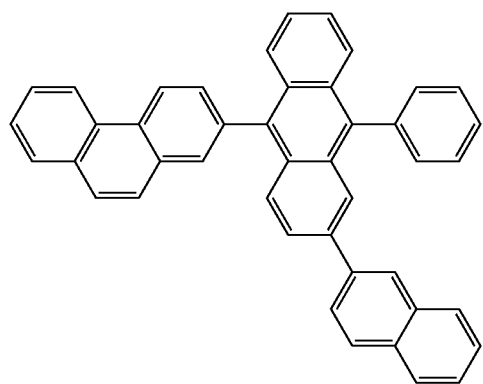
234
-continued
H39
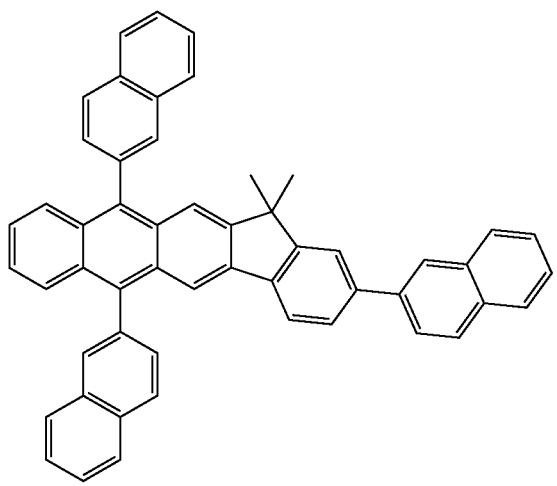
H40
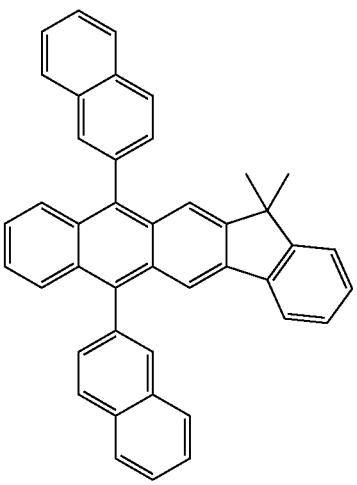
H41
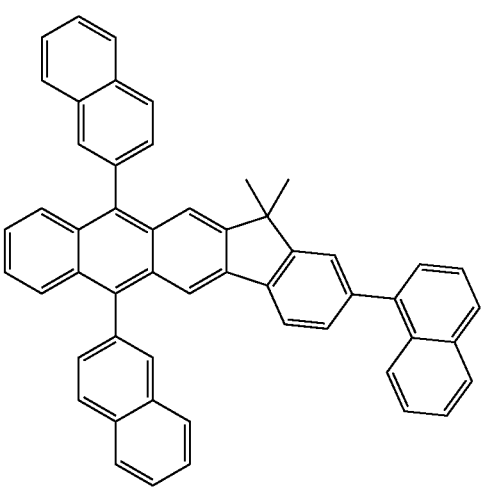

H42
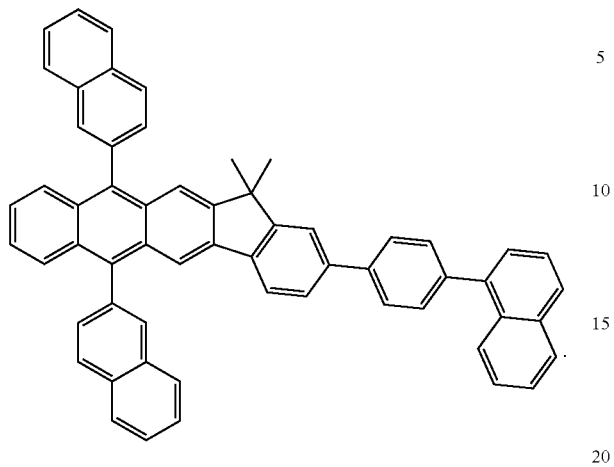
In some embodiments, the host may include at least one of Compounds 43 to H49 below, but Is not limited thereto:
H43
H44
H45
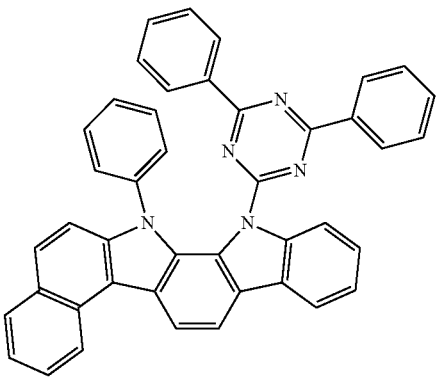
H46
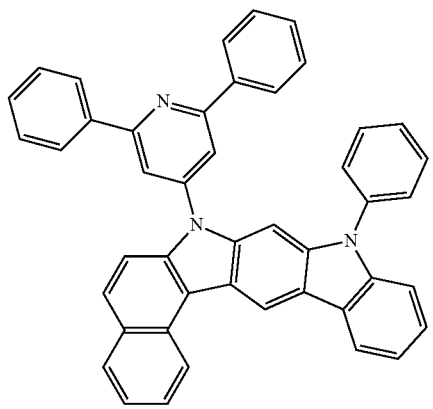
H47
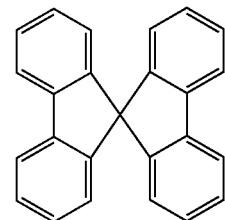
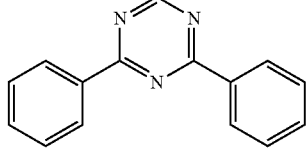
H48
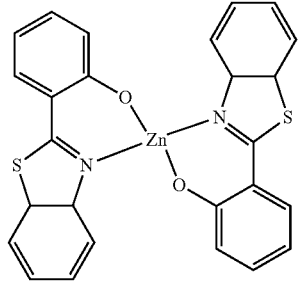

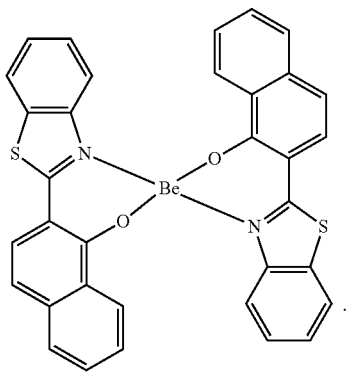

H49

The dopant may include the condensed cyclic compound represented by Formula 1.

in some embodiments, the dopant may include a compound represented by Formula 501 below.

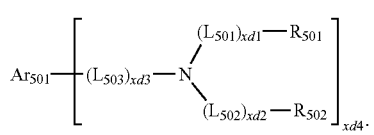

Formula 501

In Formula 501, $Ar_{501}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene group, a heptalene group, a fluorene group, a spiro-fluorene group, a benzofluorene group, a dibenzofluorene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_6$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (where $Q_{501}$ to $Q_{501}$ to $Q_{503}$ are each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

$L_{501}$ to $L_{503}$ may be the same as defined in connection with $L_1$;

$R_{501}$ and $R_{502}$ may be each Independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may be each independently selected from 0, 1, 2, and 3; and xb4 may be selected from 1, 2, 3, and 4.

When the host is a fluorescent host, it may include at least one of Compounds FD1 to FD9:

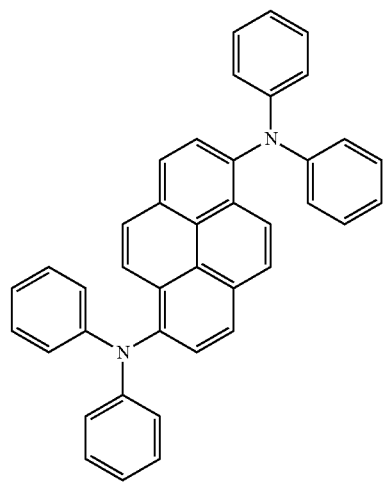

FD1

-continued
FD2
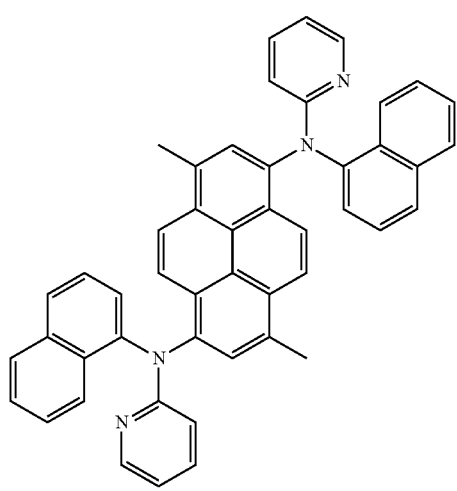
FD3
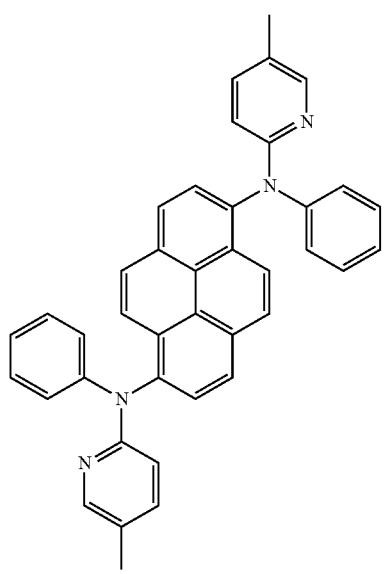
FD4
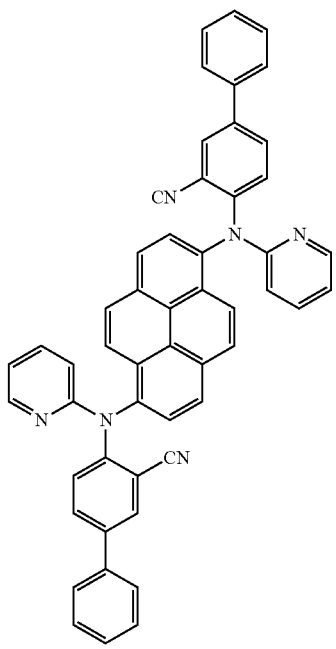
FD5
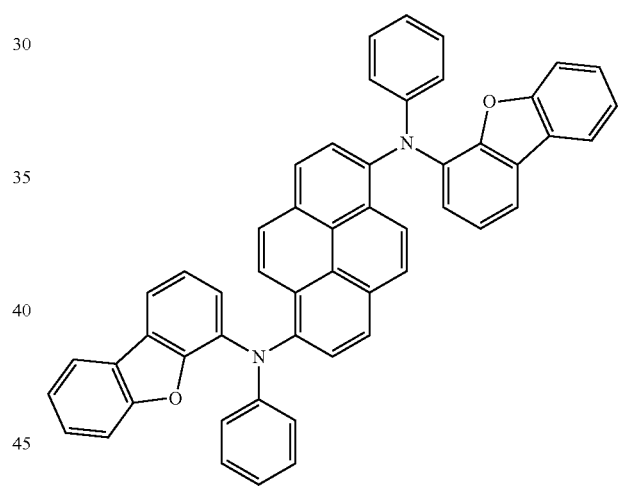
FD6
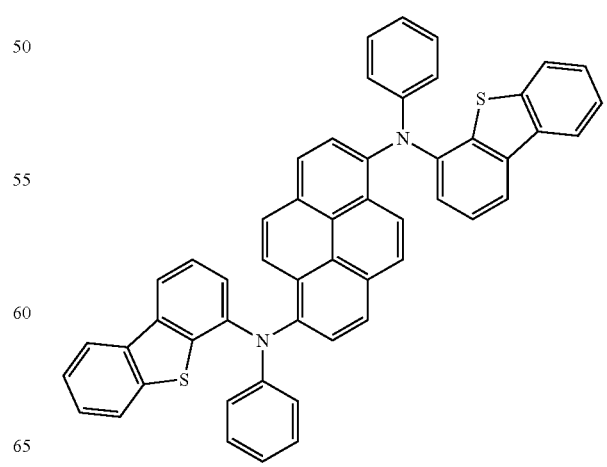

-continued

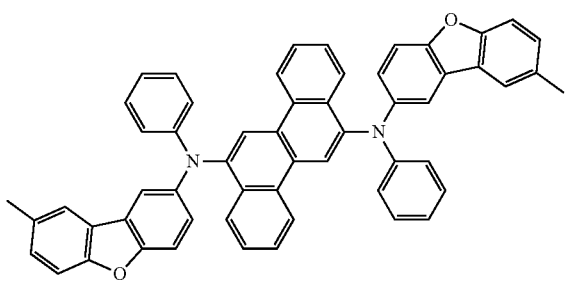
FD7

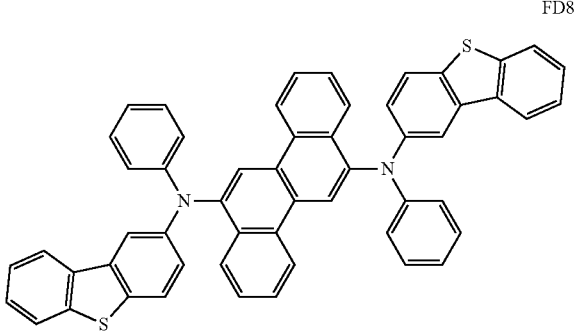
FD8

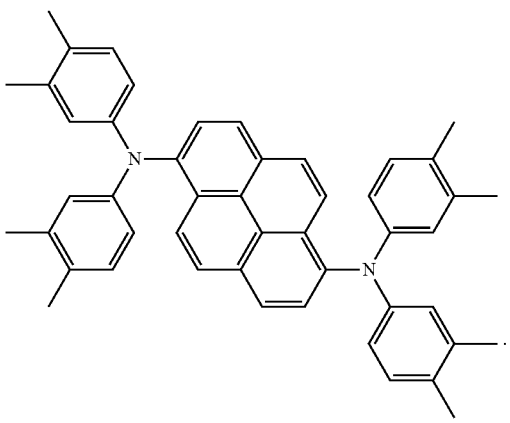
Compound FD9

An amount of the dopant in the emission layer may be, in general, in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within any of these ranges, excellent light-emission characteristics may be obtained without a substantial increase in driving voltage.

An electron transport region may be positioned on the emission layer.

The electron transport region may include at least one selected from a hole blocking layer, an electron transport layer (ETL), and an electron injection layer, but is not limited thereto.

For example, the electron transport region may have a structure of electron transport layer/electron injection layer or a structure of hole blocking layer/electron transport layer/electron injection layer, where the layers of each structure are sequentially stacked on the emission layer in the stated order, but the structure of the electron transport region is not limited thereto.

According to some embodiments, the organic layer 150 of the organic light-emitting device may include an electron transport region between the emission layer and the second electrode 190.

When the electron transport region includes a hole blocking layer, the hole blocking layer may be formed on the emission layer using one or more suitable methods, such as vacuum deposition, spin coating casting, a LB method, ink-jet printing, laser-printing, and/or laser-induced thermal Imaging. When the hole blocking layer is formed by vacuum deposition and/or spin coating, deposition and coating conditions for the hole blocking layer may be similar to the deposition and coating conditions for the hole injection layer.

The hole blocking layer may include, for example, at least one of BCP and Bphen, but is not limited thereto.

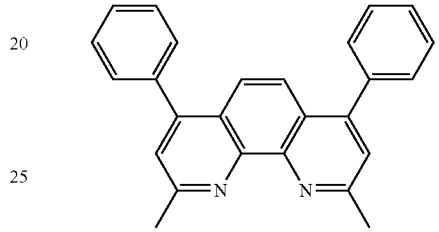
BCP

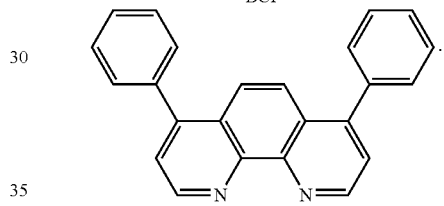
Bphen

A thickness of the hole blocking layer may be in a range of about 20 Å to about 1,000 Å, for example, about 30 Å to about 300 Å. When the thickness of the hole blocking layer is within any of these ranges, the hole blocking layer may have improved hole blocking ability without a substantial Increase in driving voltage.

The electron transport region may include an electron transport layer. The electron transport layer may be formed on the emission layer or the hole blocking layer using one or more suitable methods, such as vacuum deposition, spin coating casting, a LB method, ink-Jet printing, laser-printing, and/or laser-induced thermal imaging. When an electron transport layer is formed by vacuum deposition and/or spin coating, deposition and coating conditions for the electron transport layer may be similar to the deposition and coating conditions for the hole injection layer.

In some embodiments, the electron transport layer may include at least one compound selected from a compound represented by Formula 601 and a compound represented by Formula 602 Illustrated below:

$$Ar_{601}\text{-}[(L_{601})_{xe1}\text{-}E_{601}]_{xe2}.$$  Formula 601

In Formula 601,
$Ar_{601}$ may be selected from:
a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene group, a heptalene group, a fluorene group, a spiro-fluorene group, a benzofluorene group, a dibenzofluorene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (where $Q_{301}$ to $Q_{303}$ are each independently a hydrogen, a $C_1$-$C_{60}$ alkyl group, a $C_2$-$C_{60}$ alkenyl group, a $C_6$-$C_{60}$ aryl group, or a $C_1$-$C_{60}$ heteroaryl group);

$L_{601}$ may be the same as described in connection with $L_{201}$;

$E_{601}$ may be selected from:

a pyrrolyl group, a thiophenyl group, a furanyl group, an imidazolyl group, a pyrazolyl group, a thiazolyl group, an isothiazolyl group, an oxazolyl group, an Isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

xe1 may be selected from 0, 1, 2, and 3; and xe2 may be selected from 1, 2, 3, and 4.

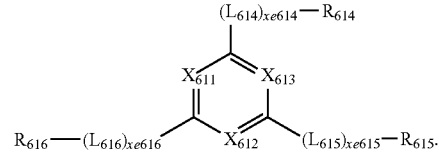

Formula 602

In Formula 602, $X_{611}$ is N or C-($L_{611}$)$_{xe611}$-$R_{611}$, $X_{612}$ is N or C-($L_{612}$)$_{xe612}$-$R_{612}$, $X_{613}$ is N or C-($L_{613}$)$_{xe613}$-$R_{613}$ and, at least one of $X_{611}$ to $X_{613}$ is N;

$L_{611}$ to $L_{616}$ may be the same as described in connection with $L_1$;

$R_{611}$ to $R_{616}$ may each Independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; xe611 to xe616 may be each independently selected from 0, 1, 2, and 3.

The compound represented by Formula 601 and the compound represented by Formula 602 may be each independently selected from Compounds ET1 to ET15 illustrated below, but are not limited thereto:

ET1
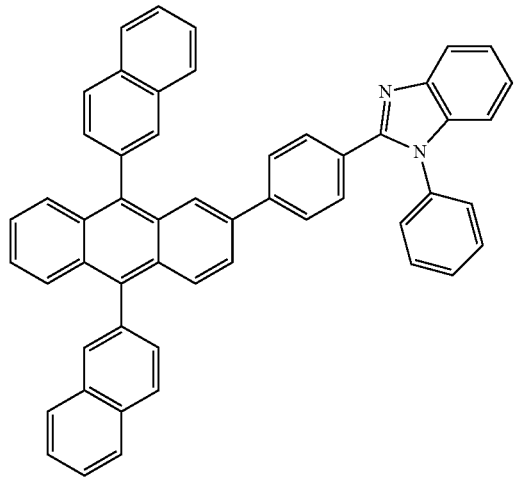

ET2
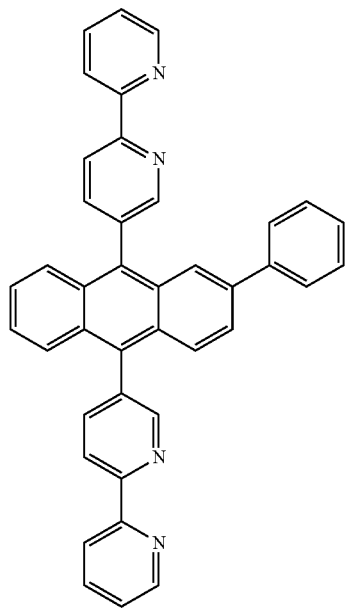

ET3
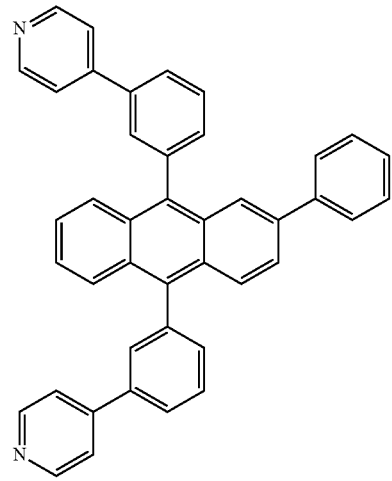

ET4
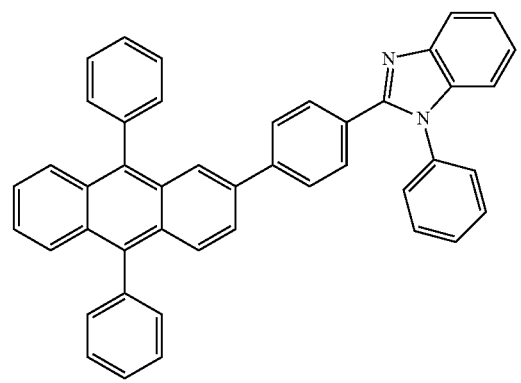

ET5
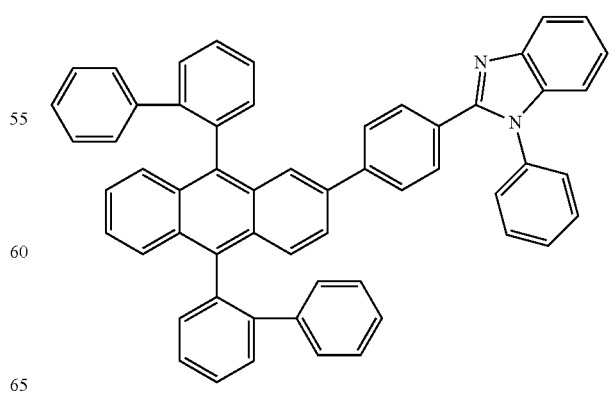

ET6
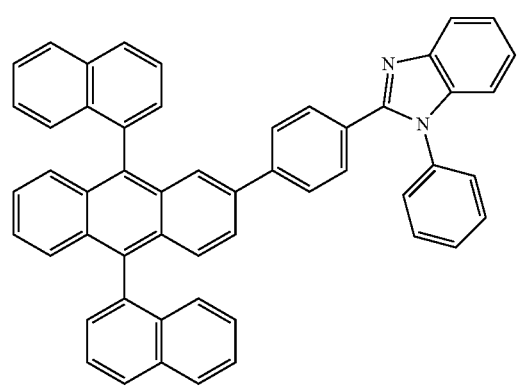
ET7
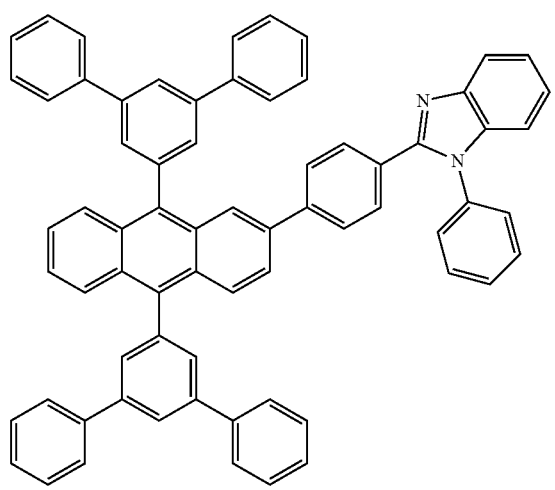
ET8
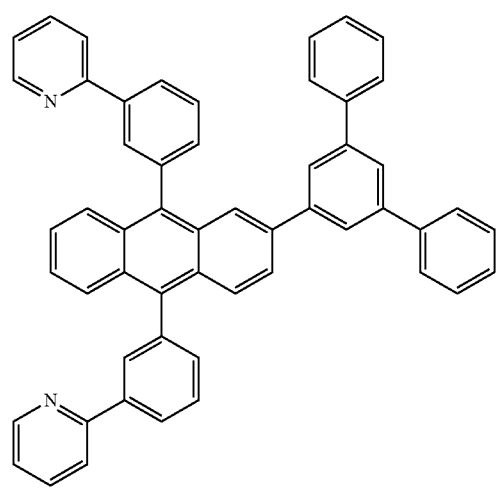
ET9
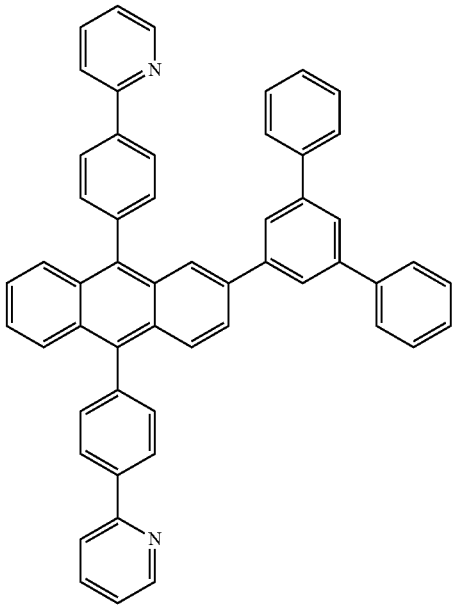
ET10
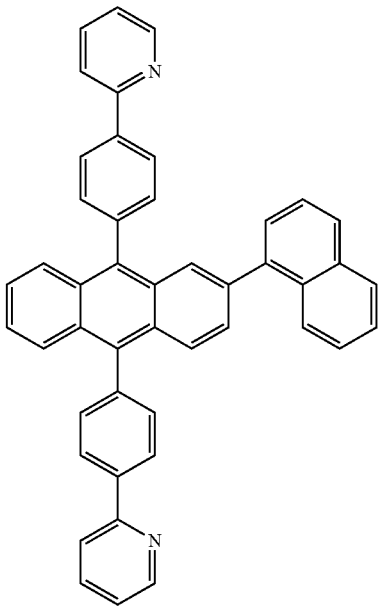

ET11
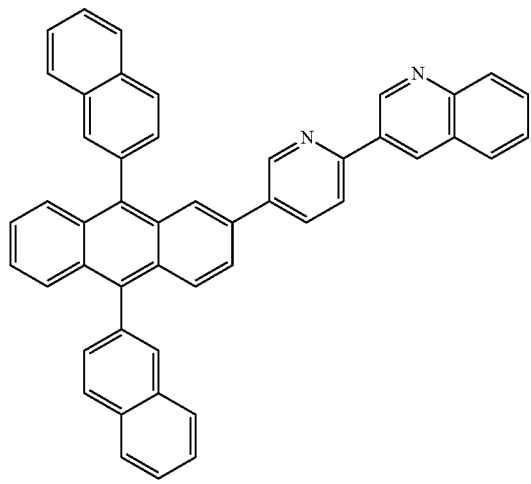
ET12
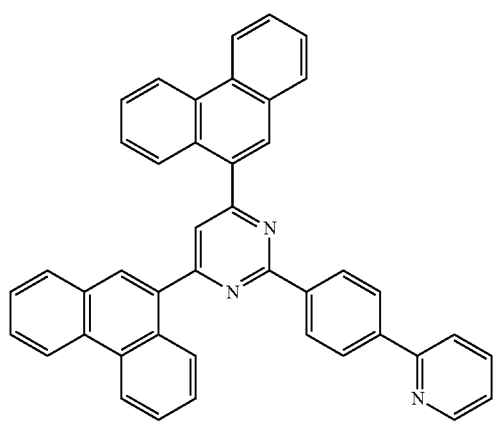
ET13
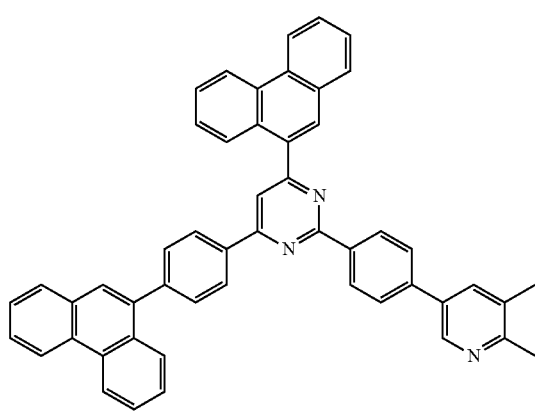
ET14
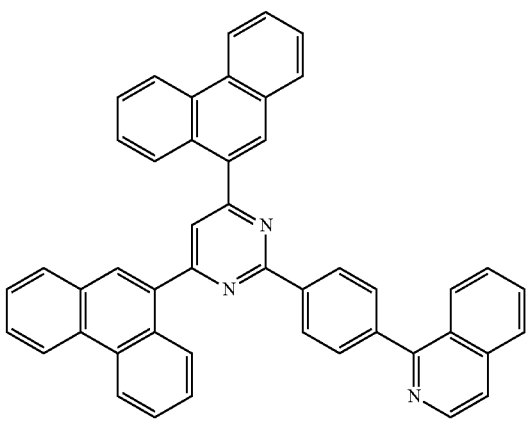
ET15
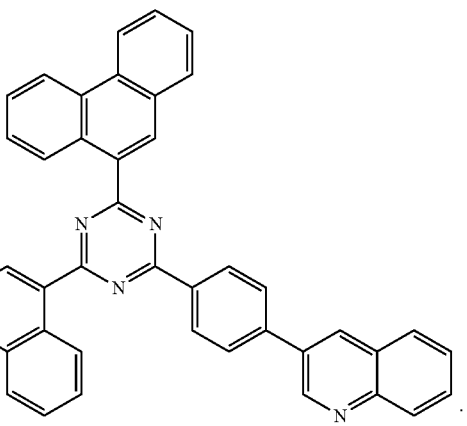
In some embodiments, the electron transport layer may further include at least one selected from BCP, Bphen, Alq3, Balq, TAZ, and NTAZ.
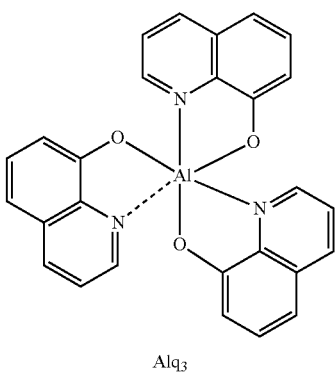
Alq3

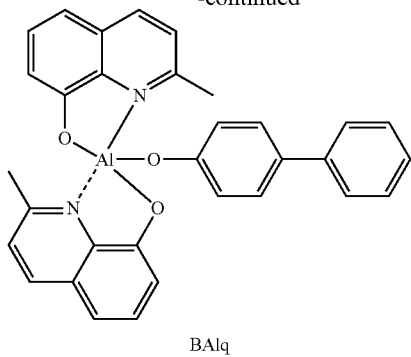

BAlq

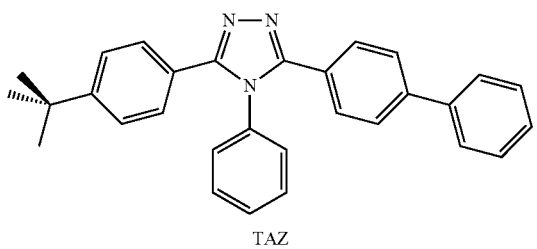

TAZ

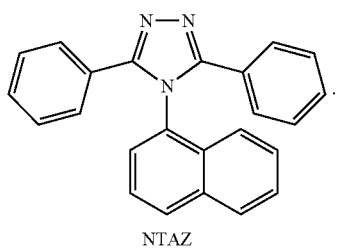

NTAZ

A thickness of the electron transport layer may be in a range of about 100 Å to about 1,000 Å, for example, about 150 Å to about 500 Å. When the thickness of the electron transport layer is within any of the ranges described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

ET-D1

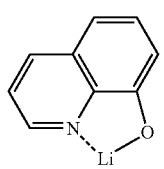

ET-D2

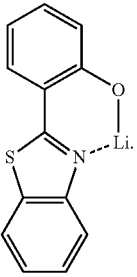

The electron transport region may include an electron Injection layer that can facilitate injection of electrons from the second electrode 190.

The electron injection layer may be formed on the electron transport layer using one or more suitable methods, such as vacuum deposition, spin coating casting, a LB method, ink-jet printing, laser-printing, and/or laser-induced thermal Imaging. When an electron injection layer is formed by vacuum deposition and/or spin coating, deposition and coating conditions for the electron Injection layer may be similar to the deposition and coating conditions for the hole injection layer.

The electron Injection layer may include at least one selected from LiF, NaCl, CsF, $Li_2O$, BaO, and LiQ.

A thickness of the electron Injection layer may be in a range of about 1 Å to about 100 Å, for example, about 3 Å to about 90 Å. When the thickness of the electron Injection layer is within any of the ranges described above, the electron injection layer may have satisfactory electron injection characteristics without a substantial Increase in driving voltage.

In some embodiments, the second electrode 190 is positioned on the organic layer 150 having the structure as described herein. The second electrode 190 may be a cathode (that is an electron injection electrode), and in this regard, a material for forming the second electrode 190 may be a material having a low work function, such as a metal, an alloy, an electrically conductive compound, or a mixture thereof. Non-limiting examples of the material for forming the second electrode 190 include lithium (Li), magnesium (Mg), aluminum (Al), aluminum-lithium (Al—Li), calcium (Ca), magnesium-indium (Mg—In), and/or magnesium-silver (Mg—Ag). In some embodiments, the material for forming the second electrode 190 may be ITO or IZO. The second electrode 190 may be a semi-transmissive electrode or a transmissive electrode.

Figure 2:
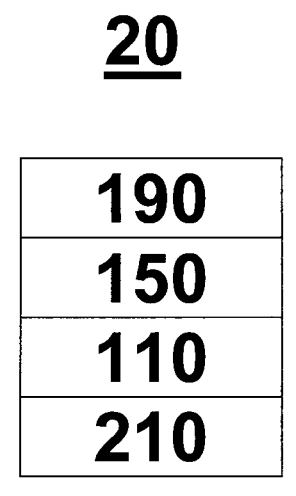

An organic light-emitting device 20 of FIG. 2 includes a first capping layer 210, the first electrode 110, the organic layer 150, and the second electrode 190, which are sequentially stacked in this stated order. An organic light-emitting device 30 of FIG. 3 includes the first electrode 110, the organic layer 150, the second electrode 190, and a second capping layer 220, which are sequentially stacked in this stated order. An organic light-emitting device 40 of FIG. 4 includes the first capping layer 210, the first electrode 110, the organic layer 150, the second electrode 190, and the second capping layer 220.

Figure 3:
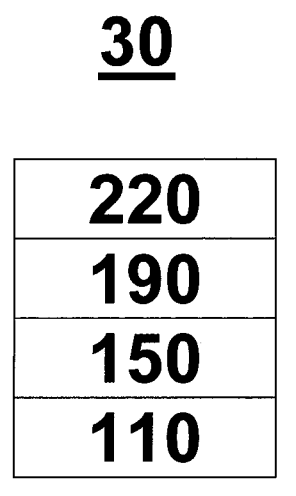
Figure 4:
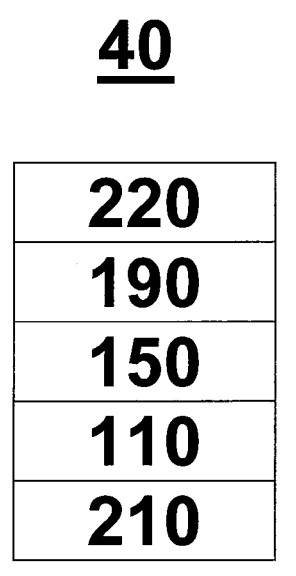

Regarding FIGS. 2 to 4, descriptions of the first electrode 110, the organic layer 150, and the second electrode 190 are the same as the descriptions presented in connection with FIG. 1.

In the organic layer 150 of each of the organic light-emitting devices 20 and 40, light generated by the emission layer may be extracted toward the outside through the first electrode 110 and the first capping layer 210. The first electrode 110 may be a semi-transmissive electrode or a transmissive electrode. In the organic layer 150 of each of the organic light-emitting devices 30 and 40, light generated by the emission layer may be extracted toward the outside through the second electrode 190 and the second capping layer 220. The second electrode 190 may be a semi-transmissive electrode or a transmissive electrode.

The first capping layer 210 and the second capping layer 220 may increase external luminescent efficiency based on the principle of constructive interference.

The first capping layer 210 illustrated in FIG. 2 and the second capping layer 220 illustrated in FIG. 3 may include the condensed cyclic compound represented by Formula 1.

At least one selected from the first capping layer 210 and the second capping layer 220 illustrated in FIG. 4 may include the condensed cyclic compound represented by Formula 1.

In some embodiments, the organic layer 150 illustrated in FIGS. 2 to 4 may not include the condensed cyclic compound represented by Formula 1.

Hereinbefore, the organic light-emitting device according to some embodiments of the present invention has been described in connection with FIGS. 1-4. However, embodiments of the present Invention are not limited thereto.

A $C_1$-$C_{10}$ alkyl group as used herein refers to a linear or branched aliphatic hydrocarbon monovalent group having 1 to 60 carbon atoms in the main chain, and non-limiting examples thereof include a methyl group, an ethyl group, a propyl group, an isobutyl group, a sec-butyl group, a ter-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (where $A_{101}$ is the $C_1$-$C_{60}$ alkyl group), and non-limiting examples thereof include a methoxy group, an ethoxy group, and an isopropyloxy group.

A $C_2$-$C_{60}$ alkenyl group as used herein refers to a hydrocarbon group having at least one carbon-carbon double bond at one or more positions along a carbon chain of the $C_2$-$C_{60}$ alkyl group (e.g., In the middle or at either terminal end of the $C_2$-$C_{60}$ alkyl group), and non-limiting examples thereof include an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group having at least one carbon-carbon triple bond at one or more positions along a carbon chain of the $C_2$-$C_{60}$ alkyl group (e.g., in the middle or at either terminal end of the $C_2$-$C_{60}$ alkyl group), and non-limiting examples thereof include an ethynyl group and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent hydrocarbon monocyclic group having 3 to 10 carbon atoms as ring atoms, and non-limiting examples thereof include a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent monocyclic group having at least one hetero atom selected from N, O, Si, P, and S as a ring-forming atom and 1 to 10 carbon atoms as the remaining ring atoms, and non-limiting examples thereof include a tetrahydrofuranyl group and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms as ring atoms and at least one carbon-carbon double bond in the ring thereof and does not have aromaticity, and non-limiting examples thereof include a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one hetero atom selected from N, O, Si, P, and S as a ring-forming atom, 1 to 10 carbon atoms as the remaining ring atoms, and at least one double bond in its ring. Non-limiting examples of the $C_1$-$C_{10}$ heterocycloalkenyl group include a 2,3-hydrofuranyl group and a 2,3-hydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms as ring atoms, and a $C_6$-$C_{60}$ arylene group as used herein refers to a divalent group having a carbocyclic aromatic system having 6 to 60 carbon atoms as ring atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and/or the $C_6$-$C_{60}$ arylene group include two or more rings, the rings may be fused to each other.

A $C_1$-$C_{60}$ heteroaryl group as used herein refers to a monovalent group having a carbocyclic aromatic system that has at least one hetero atom selected from N, O, Si, P, and S as a ring-forming atom, and 1 to 60 carbon atoms as the remaining ring atoms. A $C_1$-$C_{60}$ heteroarylene group as used herein refers to a divalent group having a carbocyclic aromatic system that has at least one hetero atom selected from N, O, P, and S as a ring-forming atom, and 1 to 60 carbon atoms as the remaining ring atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and/or the $C_1$-$C_{60}$ heteroarylene group include two or more rings, the rings may be fused to each other.

A $C_6$-$C_{60}$ aryloxy group as used herein refers to a group represented by —$OA_{102}$ (where $A_{102}$ is the $C_6$-$C_{60}$ aryl group), and a $C_6$-$C_{60}$ arylthio group as used herein refers to a group represented by —$SA_{103}$ (where $A_{103}$ is the $C_6$-$C_{60}$ aryl group).

A monovalent non-aromatic condensed polycyclic group as used herein refers to a monovalent group (for example, having 8 to 60 carbon atoms) that has two or more rings condensed to each other, only carbon atoms as ring-forming atoms, and does not have overall aromaticity. A non-limiting example of the monovalent non-aromatic condensed polycyclic group is a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group as used herein refers to a monovalent group (for example, having 1 to 60 carbon atoms) that has two or more rings condensed to each other, has at least one heteroatom selected from N, O, Si, P, and S, and carbon atoms, as ring-forming atoms, and does not have overall aromaticity. A non-limiting example of the monovalent non-aromatic condensed heteropolycyclic group is a carbazolyl group. A divalent non-aromatic condensed heteropolycyclic group as used herein refers to a divalent group having the same structure as the monovalent non-aromatic condensed heteropolycyclic group.

At least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and/or substituted monovalent non-aromatic condensed heteropolycyclic group may be selected from:

- a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
- a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), and —B($Q_{14}$)($Q_{15}$);
- a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;
- a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_3$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, —Si($Q_{21}$)($Q_{22}$)($Q_{23}$), and —B($Q_{24}$)($Q_{25}$); and
- —Si($Q_{31}$)($Q_{32}$)($Q_{33}$) and —B($Q_{34}$)($Q_{35}$),
- where $Q_{11}$ to $Q_{15}$, $Q_{21}$ to $Q_{25}$, and $Q_{31}$ to $Q_{35}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

The term "Ph" as used herein refers to a phenyl group, the term "Me" as used herein refers to a methyl group, the term "Et" as used herein refers to an ethyl group, and the term "ter-Bu" or "Bu$^t$" as used herein refers to a tert-butyl group.

Hereinafter, an organic light-emitting device according to some embodiments will be described in detail with reference to Synthesis Examples and Examples. The expression "B was used instead of A" used in describing Synthesis Examples means that a molar equivalent of A was identical to a molar equivalent of B.

EXAMPLES

Synthesis Example 1

Synthesis of Compound 1

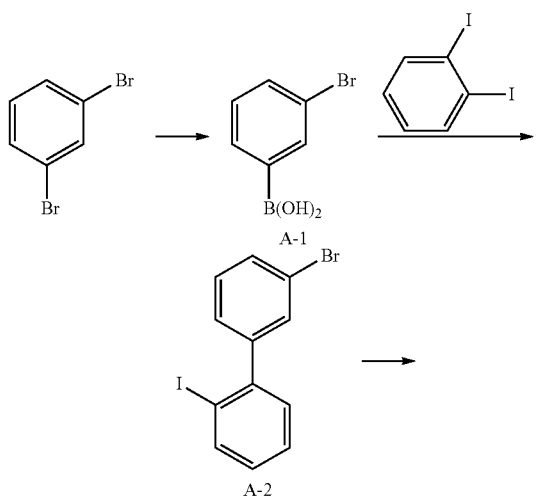

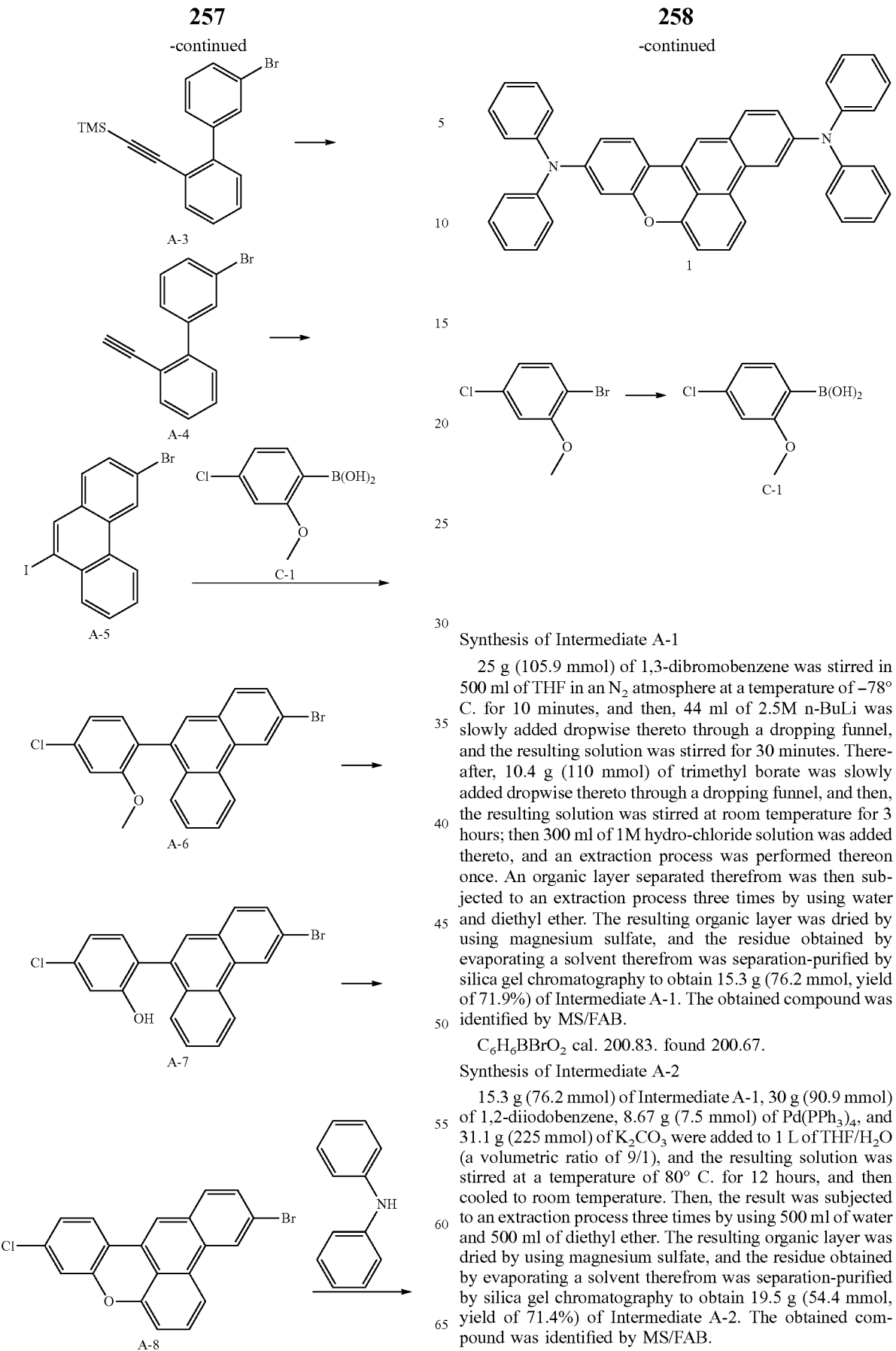

Synthesis of Intermediate A-1

25 g (105.9 mmol) of 1,3-dibromobenzene was stirred in 500 ml of THF in an $N_2$ atmosphere at a temperature of −78° C. for 10 minutes, and then, 44 ml of 2.5M n-BuLi was slowly added dropwise thereto through a dropping funnel, and the resulting solution was stirred for 30 minutes. Thereafter, 10.4 g (110 mmol) of trimethyl borate was slowly added dropwise thereto through a dropping funnel, and then, the resulting solution was stirred at room temperature for 3 hours; then 300 ml of 1M hydro-chloride solution was added thereto, and an extraction process was performed thereon once. An organic layer separated therefrom was then subjected to an extraction process three times by using water and diethyl ether. The resulting organic layer was dried by using magnesium sulfate, and the residue obtained by evaporating a solvent therefrom was separation-purified by silica gel chromatography to obtain 15.3 g (76.2 mmol, yield of 71.9%) of Intermediate A-1. The obtained compound was identified by MS/FAB.

$C_6H_6BBrO_2$ cal. 200.83. found 200.67.

Synthesis of Intermediate A-2

15.3 g (76.2 mmol) of Intermediate A-1, 30 g (90.9 mmol) of 1,2-diiodobenzene, 8.67 g (7.5 mmol) of $Pd(PPh_3)_4$, and 31.1 g (225 mmol) of $K_2CO_3$ were added to 1 L of $THF/H_2O$ (a volumetric ratio of 9/1), and the resulting solution was stirred at a temperature of 80° C. for 12 hours, and then cooled to room temperature. Then, the result was subjected to an extraction process three times by using 500 ml of water and 500 ml of diethyl ether. The resulting organic layer was dried by using magnesium sulfate, and the residue obtained by evaporating a solvent therefrom was separation-purified by silica gel chromatography to obtain 19.5 g (54.4 mmol, yield of 71.4%) of Intermediate A-2. The obtained compound was identified by MS/FAB.

$C_{12}H_8BrI$ cal. 359.00. found 359.14.

Synthesis of Intermediate A-3

19.5 g (54.4 mmol) of Intermediate A-2, 600 mg (2.7 mmol) of Pd(OAc)$_2$, 1.5 g (5.72 mmol) of PPh$_3$, 1.1 g (5.77 mmol) of CuI, and 375 ml (272 mmol) of triethylamine were mixed, and the mixture was stirred at a temperature of 60° C. in N$_2$ atmosphere for 12 hours. When the reaction stopped, the reaction product was cooled to room temperature, and then subjected to an extraction process 5 times by using diethyl ether. The obtained organic layer was dried by using magnesium sulfate and the residue obtained by evaporating a solvent therefrom was separation-purified by silica gel chromatography to obtain 15.7 g (47.6 mmol, yield of 87.5%) of Intermediate A-3. The obtained compound was identified by MS/FAB.

C$_{17}$H$_{17}$BrSi cal. 329.31. found 328.96.

Synthesis of Intermediate A-4

15.7 g (47.6 mmol) of Intermediate A-3 and 27.6 g (200 mmol) of K$_2$CO$_3$ were mixed with 600 ml of MeOH/CH$_2$Cl$_2$ (a volumetric ratio of 2:1), and the resulting solution was stirred at room temperature for 1 hour. When the reaction stopped, the mixture was filtered through filtering paper, and an organic solvent was removed from the remaining solution by evaporation. The obtained residue was then subjected to an extraction process two times by using water and dichloromethane. An organic layer separated therefrom was dried by using magnesium sulfate and the residue obtained by evaporating a solvent therefrom was separation-purified by silica gel chromatography to obtain 10.9 g (42.5 mmol, yield of 89.3%) of Intermediate A-4. The obtained compound was identified by MS/FAB.

C$_{14}$H$_9$Br cal. 257.13. found 257.42.

Synthesis of Intermediate A-5

10.9 g (42.5 mmol) of Intermediate A-4 was sufficiently dissolved in 500 ml of methylene chloride, and the resulting solution was stirred in an ice bath at a temperature of 0° C. for 30 minutes. Then, 7.3 g (45 mmol) of iodine chloride was added thereto and then stirred for 30 minutes. A reaction solution obtained therefrom was subjected to an extraction process five times by using 500 ml of water and ethylacetate. An organic layer separated therefrom was dried by using magnesium sulfate and the residual obtained by evaporating a solvent therefrom was recrystallized by using a mixed solution including methylene chloride and n-hexane to obtain 14.1 g (36.9 mmol, yield of 86.7%) of Intermediate A-5. The obtained compound was identified by MS/FAB.

C$_{14}$H$_8$BrI cal. 383.03. found 383.31.

Synthesis of Intermediate A-6

5.17 g (13 mmol, yield of 71.2%) of Intermediate A-6 was obtained by the same or substantially the same method as the one used to synthesize Intermediate A-2, except that Intermediate A-5 and Intermediate C-1 were respectively used instead of 1,2-diiodobenzene and Intermediate A-1. The obtained compound was identified by MS/FAB.

C$_{21}$H$_{14}$BrClO cal. 397.70. found 397.65.

Synthesis of Intermediate C-1

14.4 g (77.2 mmol, yield of 68.4%) of Intermediate C-1 was obtained by the same or substantially the same method as the one used to synthesize Intermediate A-1, except that 1-bromo-4-chloro-2-methoxybenzene was used instead of 1,3-dibromobenzene. The obtained compound was identified by MS/FAB.

C$_7$H$_8$BClO$_3$ cal. 186.40. found 186.47.

Synthesis of Intermediate A-7

5.17 g (13 mmol) of Intermediate A-6 and 6.72 g (40 mmol) of sodium ethanethiolate were mixed with 250 ml of DMF, and then, the mixture was stirred at a temperature of 130° C. 4 hours after, the reaction product was cooled to room temperature, and then, subjected to an extraction process 6 times by using water and ethylacetate. An organic layer separated therefrom was dried by using magnesium sulfate, and the residual obtained by evaporating a solvent therefrom was separation-purified by silica gel chromatography to obtain 4.64 g (12.1 mmol, yield of 93.1%) of Intermediate A-7. The obtained compound was identified by MS/FAB.

C$_{20}$H$_{12}$BrClO cal. 383.67. found 383.59.

Synthesis of Intermediate A-8

4.64 g (12.1 mmol) of Intermediate A-7 and 5.15 g (36 mmol) of copper(I) oxide were added to 250 ml of nitrobenzene, and the resulting solution was stirred at a temperature of 190° C. for 48 hours while heating. The reaction solution was then cooled to room temperature and subjected to an extraction process 4 times by using 150 ml of water and 150 ml of diethylether. An organic layer separated therefrom was dried by using magnesium sulfate and the residual obtained by evaporating a solvent therefrom was separation-purified by silica gel chromatography to obtain 3.66 g (9.6 mmol, yield of 79.3%) of Intermediate A-8. The obtained compound was identified by MS/FAB.

C$_{20}$H$_{10}$BrClO cal. 381.65. found 381.74.

Synthesis of Compound 1

600 mg (1.57 mmol) of Intermediate A-8, 762 mg (4.5 mmol) of diphenylamine, 495 mg (0.5 mmol) of tris(dibenzylideneacetone)dipalladium(0), 100 mg (0.5 mmol) of tri (tert-butyl)phosphine, and 432 mg (4.5 mmol) of sodium tert-butoxide were added to 10 ml of toluene, and the mixture was stirred at a temperature of 80° C. for 2 hours. The resulting reaction solution was cooled to room temperature, and then subjected to an extraction process three times by using 20 ml of water and 20 ml of diethylether. An organic layer separated therefrom was dried by using magnesium sulfate, and the residual obtained by evaporating a solvent therefrom was separation-purified by silica gel chromatography to obtain 681 mg (1.13 mmol, yield of 72%) of Compound 1. The obtained compound was identified by MS/FAB and $^1$H NMR.

C$_{44}$H$_{30}$N$_2$S cal. 602.74. found 602.71.

Synthesis Example 2

Synthesis of Compound 144

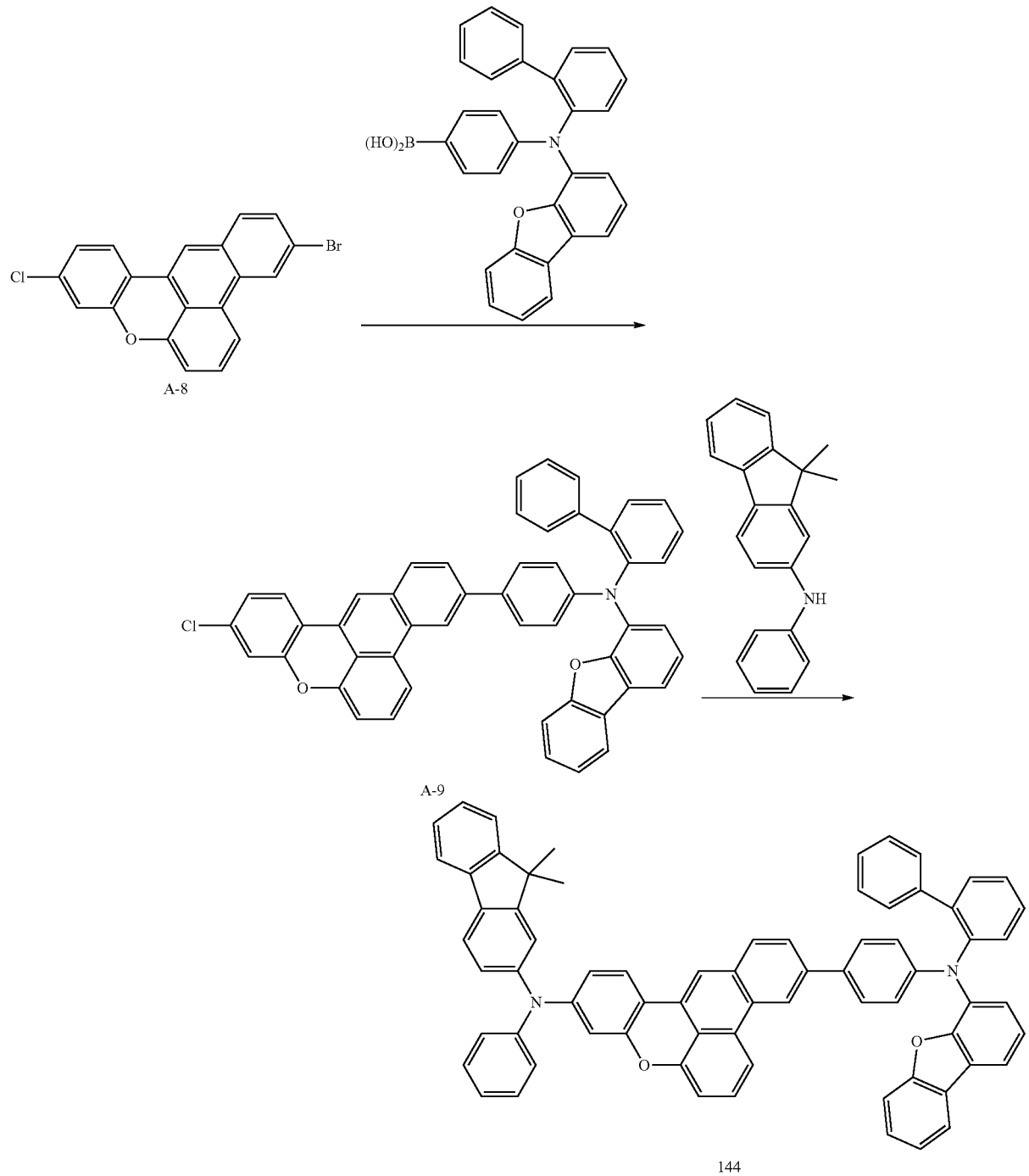

Synthesis of Intermediate A-9

600 mg (1.57 mmol) of Intermediate A-8, 730 mg (1.6 mmol) of (4-([1,1'-biphenyl]-2-yl(dibenzo[b,d]furan-4-yl)amino)phenyl)boronic acid, 173 mg (0.15 mmol) of Pd(PPh$_3$)$_4$, and 620 mg (2.25 mmol) of K$_2$CO$_3$ were added to 35 ml of a mixture of THF/H$_2$O (a volumetric ratio of 9/1), and the resulting solution was stirred at a temperature of 80% for 12 hours, and then cooled to room temperature. Then, the resulting reaction mixture was subjected to an extraction process by using 50 ml of water and 50 ml of diethyl ether. An organic layer separated therefrom was dried by using magnesium sulfate, and the residual obtained by evaporating a solvent therefrom was separation-purified by silica gel chromatography to obtain 762 mg (1.07 mmol, yield of 71.3%) of Intermediate A-9. The obtained compound was identified by MS/FAB.

$C_{50}H_{30}ClNO_2$ cal. 712.25. found 712.08.

Synthesis of Compound 144

762 mg (1.07 mmol) of Intermediate A-9, 542 mg (2.1 mmol) of 9-methyl-N-phenyl-9H-fluoren-2-amine, 192 mg (0.21 mmol) of tris(dibenzylideneacetone)dipalladium(0), 19 mg (0.21 mmol) of tri(tert-butyl)phosphine, and 288 mg (3 mmol) of sodium tert-butoxide were added to 10 ml of toluene, and the mixture was stirred at a temperature of 80° C. for 2 hours. The resulting reaction solution was cooled to room temperature, and then, subjected to an extraction process three times by using 20 ml of water and 20 ml of diethylether. An organic layer separated therefrom was dried by using magnesiumsulfate, and the residual obtained by evaporating a solvent therefrom was separation-purified by silica gel column chromatography to obtain 749 mg (0.76 mmol, yield of 71%) of Compound 144. The obtained compound was identified by MS/FAB and $^1$H NMR. $C_{71}H_{48}N_2O_2$ cal. 961.18. found 960.98.

Synthesis Example 3

Synthesis of Compound 1A

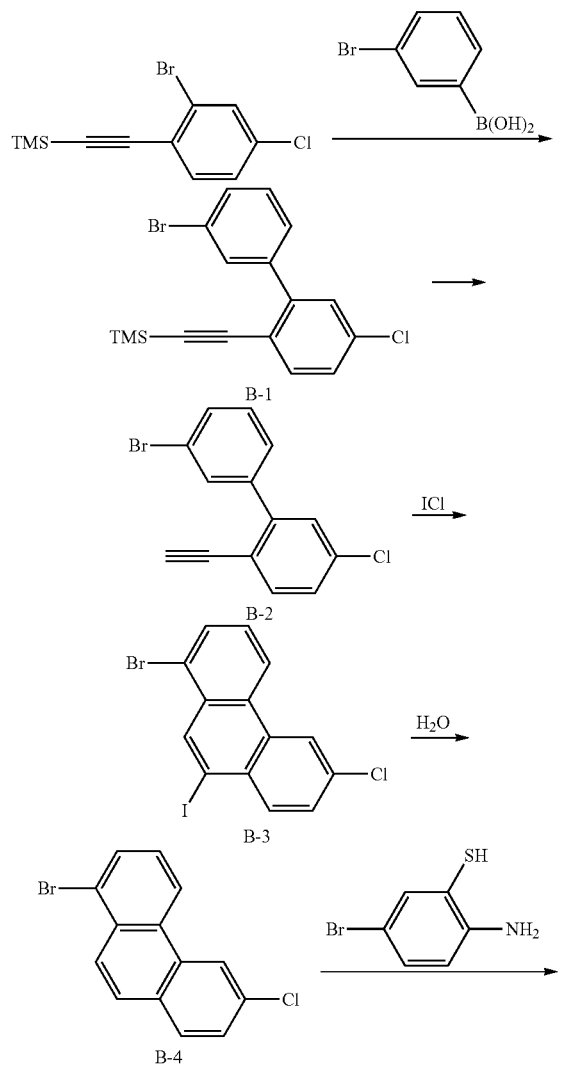

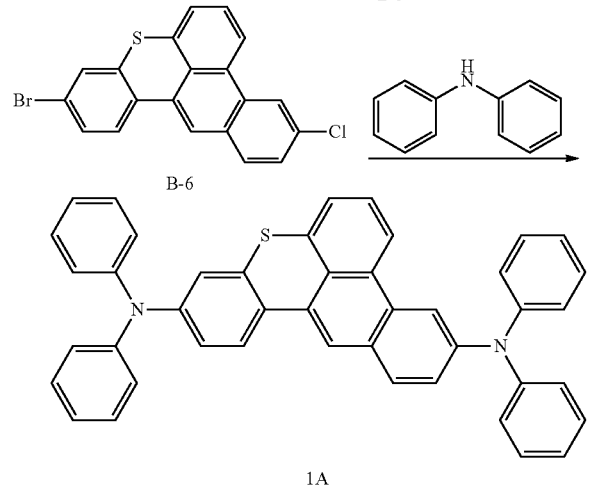

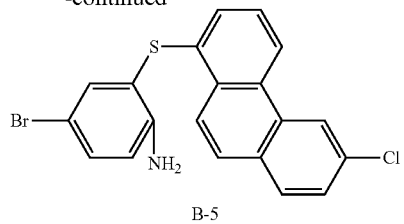

Synthesis of Intermediate B-1

8.63 g (30.0 mmol) of ((2-bromo-4-chlorophenyl)ethynyl)trimethylsilane, 6.03 g (30.0 mmol) of (3-bromophenyl)boronic acid, 1.37 g (1.5 mmol) of Pd(PPh$_3$)$_4$, and 12.44 g (90.0 mmol) of K$_2$CO$_3$ were dissolved in 250 ml of a mixed solution including THF/H$_2$O (a volumetric ratio of 9/1), and then, the resulting mixture was stirred at a temperature of 80° C. for 12 hours. The resulting reaction solution was cooled to room temperature, and then subjected to an extraction process three times by using 200 ml of water and 200 ml of ethylether. The obtained organic layer was dried with magnesium sulfate and the residual obtained by removing a solvent used herein by evaporation was separation-purified by silica gel column chromatography to obtain 7.86 g (21.6 mmol, yield of 72%) of Intermediate B-1. The obtained compound was identified by MS/FAB. $C_{17}H_{16}BrClSi$ cal. 363.75. found 363.69.

Synthesis of Intermediate B-2

7.86 g (21.6 mmol) of Intermediate B-1 and 13.82 g (100.0 mmol) of K$_2$CO$_3$ were dissolved in 200 ml of methanol, and the resulting solution was stirred at room temperature for 30 minutes. The resulting reaction mixture was filtered to separate the remaining K$_2$CO$_3$, and the residual solvent was removed therefrom by evaporation. Then, the resulting product was dissolved in 200 ml of methylene chloride, and then subjected to an extraction process by using water. An organic layer separated therefrom was dried by using magnesium sulfate, and the residual obtained by evaporating a solvent therefrom was separation-purified by silica gel chromatography to obtain 5.92 g (20.3 mmol, yield of 94%) of Intermediate B-2. The obtained compound was identified by MS/FAB. $C_{14}H_8BrCl$ cal. 291.57. found 291.63.

Synthesis of Intermediate B-3

5.92 g (20.3 mmol) of Intermediate B-2 was sufficiently dissolved in 200 ml of methylene chloride, and the resulting solution was stirred in an ice bath at a temperature of 0° C. for 30 minutes, and then 3.3 g of Iodine chloride was added thereto and stirred for 30 minutes. The resulting reaction solution was subjected to an extraction process 5 times by using 250 ml of water and ethylacetate. An organic layer separated therefrom was dried by using magnesium sulfate, and the residual obtained by evaporating a solvent therefrom was re-crystallized by using a mixed solution including methylene chloride and n-hexane to obtain 7.20 g (17.3 mmol, yield of 85%) of Intermediate B-3. The obtained compound was identified by MS/FAB.

$C_{14}H_7BrCl$ cal. 417.47. found 417.43.

Synthesis of Intermediate B-4

1.25 g (3.0 mmol) of Intermediate B-3 was dissolved in 50 ml of THF, and then, at a temperature of −78° C., 1.2 ml (3.0 mmol, 2.5M in Hexane) of n-BuLi was slowly added dropwise thereto, and the resulting solution was stirred at a temperature of −78° C. for 1 hour. Then, 0.27 ml (15.0 mmol) of $H_2O$ was slowly added dropwise thereto, and then stirred at room temperature for 6 hours. When the reaction stopped, 40 ml of water was added thereto, and then, the resulting mixture was subjected to an extraction process three times by using 30 ml of diethylether. An organic layer separated therefrom was dried with magnesium sulfate and the residual obtained by evaporating a solvent therefrom was separation-purified by silica gel column chromatography to obtain 797 mg (2.73 mmol, yield of 91%) of Intermediate B-4. The obtained compound was identified by MS/FAB.

$C_{14}HsBrCl$ cal. 291.57. found 291.64.

Synthesis of Intermediate B-5

797 mg (2.73 mmol) of Intermediate B-4, 612 mg (3.0 mmol) of 2-amino-5-bromobenzenethiol, and 300 mg (2.2 mmol) of $K_2CO_3$ were added to 20 ml of DMF, and the resulting solution was stirred at a temperature of 150° C. for 48 hours while heating. The reaction solution was cooled to room temperature, and then subjected to an extraction process three times by using 50 ml of water and 40 ml of diethylether. An organic layer separated therefrom was dried by using magnesium sulfate and the residual obtained by evaporating a solvent therefrom was separation-purified by silica gel column chromatography to obtain 792 mg (1.91 mmol, yield of 70%) of Intermediate B-5. The obtained compound was identified by MS/FAB.

$C_{20}H_{13}BrClNS$ cal. 414.74. found 414.76.

Synthesis of Intermediate B-6

792 mg (1.91 mmol) of Intermediate B-5, 1.73 g (25 mmol) of sodium nitrite, 0.8 ml of HCl, 8 ml of glacial acetic acid, and 1.2 ml of water were stirred in an ice bath for 1 hour, and then the resulting solution was stirred at room temperature for 12 hours. The reaction solution was heated to a temperature of 90° C., and then, an aqueous solution of 1.59 g (10 mmol) of copper sulfate dissolved in 30 ml of water and 1.5 ml of acetic acid was added dropwise thereto for 1 hour. The resulting mixture was stirred for 30 minutes, and then cooled to room temperature and subjected to an extraction process four times by using 20 ml of water and 20 ml of diethylether. An organic layer separated therefrom was dried by using magnesium sulfate and the residual obtained by evaporating a solvent therefrom was separation-purified by silica gel column chromatography to obtain 708 mg (1.78 mmol, yield of 93%) of Intermediate B-6. The obtained compound was identified by MS/FAB.

$C_{20}H_{10}BrClS$ cal. 397.71. found 397.69.

Synthesis of Compound 1A 708 mg (1.78 mmol) of Intermediate B-6, 762 mg (4.5 mmol) of diphenylamine, 495 mg (0.54 mmol) of tris(dibenzylideneacetone)dipalladium(0), 108 mg (0.54 mmol) of tri(tert-butyl)phosphine, and 513 mg (5.34 mmol) of sodium tert-butoxide were added to 10 ml of toluene, and the resulting mixture was stirred at a temperature of 80° C. for 2 hours. The reaction solution was cooled to room temperature, and then, was subjected to an extraction process three times by using 20 ml of water and 20 ml of diethylether. An organic layer separated therefrom was dried by using magnesium sulfate and the residual obtained by evaporating a solvent therefrom was separation-purified by silicagel column chromatography to obtain 749 mg (1.21 mmol, yield of 68%) of Compound 1A. The obtained compound was identified by MS/FAB and $^1H$ NMR.

$C_{44}H_{30}N_2S$ cal. 618.80. found 618.77.

Synthesis Example 4

Synthesis of Compound 2

894 mg (1.07 mmol, yield of 70.3%) of Compound 2 was prepared in the same or substantially the same manner as the one used to synthesize Compound 1 in Synthesis Example 1, except that 9,9-dimethyl-N-phenyl-9H-fluoren-2-amine was used instead of diphenylamine. The obtained compound was identified by MS/FAB and $^1H$ NMR.

Synthesis Example 5

Synthesis of Compound 5

794 mg (1.13 mmol, yield of 72.7%) of Compound 5 was prepared in the same or substantially the same manner as the one used to synthesize Compound 1 in Synthesis Example 1, except that N-phenylnaphthalen-1-amine was used instead of diphenylamine. The obtained compound was identified by MS/FAB and $^1H$ NMR.

Synthesis Examples

Synthesis of Compound 7

636 mg (0.84 mmol, yield of 59.8%) of Compound 7 was prepared in the same or substantially the same manner as in Synthesis Example 1, except that N-([1,1'-biphenyl]-2-yl)pyridin-3-amine was used instead of diphenylamine. The obtained compound was identified by MS/FAB and $^1H$ NMR.

Synthesis Example 7

Synthesis of Compound 8

914 mg (1.21 mmol, yield of 78.7%) of Compound 8 was prepared in the same or substantially the same manner as the one used to synthesize Compound 1 in Synthesis Example 1, except that N-phenyl-[1,1'-biphenyl]-4-amine was used instead of diphenylamine. The obtained compound was identified by MS/FAB and $^1H$ NMR.

Synthesis Example 8

Synthesis of Compound 9

689 mg (0.98 mmol, yield of 65.3%) of Compound 9 was prepared in the same or substantially the same manner as the one used to synthesize Compound 1 in Synthesis Example 1, except that N-phenylnaphthalen-2-amine was used instead of diphenylamine. The obtained compound was identified by MS/FAB and $^1H$ NMR.

Synthesis Example 9

Synthesis of Compound 13

960 mg (1.02 mmol, yield of 71.4%) of Compound 13 was prepared in the same or substantially the same manner as the one used to synthesize Compound 1 in Synthesis Example 1, except that 5'-fluoro-N-phenyl-[1,1':3',1''-terphenyl]-4'-amine was used instead of diphenylamine. The obtained compound was identified by MS/FAB and $^1$H NMR.

Synthesis Example 10

Synthesis of Compound 15

785 mg (0.84 mmol, yield of 61.7%) of Compound 15 was prepared in the same or substantially the same manner as the one used to synthesize Compound 1 in Synthesis Example 1, except that N-([1,1'-biphenyl]-2-yl)dibenzo[b,d]furan-4-amine was used instead of diphenylamine. The obtained compound was identified by MS/FAB and $^1$H NMR.

Synthesis Example 11

Synthesis of Compound 19

930 mg (1.19 mmol, yield of 78.6%) of Compound 19 was prepared in the same or substantially the same manner as the one used to synthesize Compound 1 in Synthesis Example 1, except that N-phenyldibenzo[b,d]furan-2-amine was used instead of diphenylamine. The obtained compound was identified by MS/FAB and $^1$H NMR.

Synthesis Example 12

Synthesis of Compound 172

935 mg (1.03 mmol, yield of 72.4%) of Compound 172 was prepared in the same or substantially the same manner as the one used to synthesize Compound 1 in Synthesis Example 1, except that di([1,1'-biphenyl]-4-yl)amine was used instead of diphenylamine. The obtained compound was identified by MS/FAB and $^1$H NMR.

Synthesis Example 13

Synthesis of Compound 26

950 mg (2.5 mmol) of Intermediate A-8, 810 mg (3 mmol) of N-phenylphenanthren-2-amine, 229 mg (0.25 mmol) of tris(dibenzylideneacetone)dipalladium(0), 50 mg (0.5 mmol) of tri(tert-butyl)phosphine, and 720 mg (7.5 mmol) of sodium tert-butoxide were added to 25 ml of toluene, and the resulting mixture was stirred at a temperature of 80° C. for 2 hours. The reaction solution was cooled to room temperature, and then subjected to an extraction process three times by using 40 ml of water and 40 ml of diethylether. An organic layer separated therefrom was dried by using magnesium sulfate, and the residual obtained by evaporating a solvent therefrom was separation-purified by silica gel chromatography. The result was added to 20 ml of toluene together with 340 mg (2 mmol) of diphenylamine, 137 mg (0.15 mmol) of tris(dibenzylideneacetone)dipalladium(0), 30 mg (0.3 mmol) of tri(tert-butyl)phosphine, and 577 mg (6 mmol) of sodium tert-butoxide and then, stirred at a temperature of 80° C. for 3 hours. The obtained reaction solution was cooled to room temperature, and then subjected to an extraction process three times by using 30 ml of water and 30 ml of diethylether, and an organic layer separated therefrom was dried by using magnesium sulfate and the residual obtained by evaporating a solvent therefrom was separation-purified by silica gel column chromatography to obtain 900 mg (1.28 mmol, yield of 51.2%) of Compound 26. The obtained compound was identified by MS/FAB and $^1$H NMR.

Synthesis Example 14

Synthesis of Compound 29

865 mg (1.12 mmol, yield of 49.7%) of Compound 29 was prepared in the same or substantially the same manner as in Synthesis Example 13, except that 5'-fluoro-N-phenyl-[1,1':3',1''-terphenyl]-4'-amine was used instead of N-phenylphenanthrene-2-amine. The obtained compound was identified by MS/FAB and $^1$H NMR.

Synthesis Example 15

Synthesis of Compound 30

774 mg (0.97 mmol, yield of 41.3%) of Compound 30 was prepared in the same or substantially the same manner as in Synthesis Example 13, except that 4-((5'-fluoro-[1,1':3',1''-terphenyl]-4'-yl)amino)benzonitrile was used instead of N-phenylphenanthrene-2-amine. The obtained compound was identified by MS/FAB and $^1$H NMR.

Synthesis Example 16

Synthesis of Compound 38

993 mg (1.18 mmol, yield of 53.8%) of Compound 38 was prepared in the same or substantially the same manner as in Synthesis Example 13, except that N-([1,1'-biphenyl]-2-yl)dibenzo[b,d]furan-4-amine and N-phenyl-4-(trimethylsilyl)aniline were used instead of N-phenylphenanthrene-2-amine and diphenylamine, respectively.

The obtained compound was identified by MS/FAB and $^1$H NMR.

Synthesis Example 17

Synthesis of Compound 54

1.12 g (1.53 mmol, yield of 69.4%) of Compound 54 was prepared in the same or substantially the same manner as in Synthesis Example 13, except that N-phenylnaphthalen-2-amine and N-phenyl-[1,1'-biphenyl]-2-amine(N-phenyl-[1,1'-biphenyl]-2-amine) were used instead of N-phenylphenanthrene-2-amine and diphenylamine, respectively. The obtained compound was identified by MS/FAB and $^1$H NMR.

Synthesis Example 18

Synthesis of Compound 57

1.18 g (1.36 mmol, yield of 65.7%) of Compound 57 was prepared in the same or substantially the same manner as in Synthesis Example 13, except that N-([1,1'-biphenyl]-2-yl)-9,9-dimethyl-9H-fluoren-2-amine and N-phenyl-[1,1'-bi-

Synthesis Example 19

Synthesis of Compound 72

1.31 g (1.62 mmol, yield of 73.1%) of Compound 72 was prepared in the same or substantially the same manner as Synthesis Example 13, except that 9,9-dimethyl-N-phenyl-9H-fluoren-2-amine and N-phenyldibenzo[b,d]furan-4-amine were used instead of N-phenylphenanthrene-2-amine and diphenylamine, respectively. The obtained compound was identified by MS/FAB and $^1$H NMR.

Synthesis Example 20

Synthesis of Compound 88

1.01 g (1.14 mmol, yield of 59.1%) of Compound 88 was prepared in the same or substantially the same manner as in Synthesis Example 13, except that 9,9-dimethyl-N-phenyl-9H-fluoren-2-amine and N-([1,1'-biphenyl]-2-yl)dibenzo[b,d]furan-4-amine were used instead of N-phenylphenanthrene-2-amine and diphenylamine, respectively. The obtained compound was identified by MS/FAB and $^1$H NMR.

Syntheses Example 21

Synthesis of Compound 90

1.25 g (1.33 mmol, yield of 65.8%) of Compound 90 was prepared in the same or substantially the same manner as in Synthesis Example 13, except that 5'-fluoro-N-phenyl-[1,1':3',1''-terphenyl]-4'-amine and N-([1,1'-biphenyl]-2-yl)dibenzo[b,d]furan-4-amine were used instead of N-phenylphenanthrene-2-amine and diphenylamine, respectively. The obtained compound was identified by MS/FAB and $^1$H NMR.

Synthesis Example 22

Synthesis of Compound 174

1.02 g (1.27 mmol, yield of 72.4%) of Compound 174 was prepared in the same manner as in Synthesis Example 13, except that N-phenylnaphthalen-1-amine and di([1,1'-biphenyl]-4-yl)amine were used instead of N-phenylphenanthrene-2-amine and diphenylamine, respectively. The obtained compound was identified by MS/FAB and $^1$H NMR.

Synthesis Example 23

Synthesis of Compound 129

785 mg (0.96 mmol, yield of 71.3%) of Compound 129 was prepared in the same or substantially the same manner as the one used to synthesize Intermediate A-9 and Compound 144 in Synthesis Example 2, except that (4-(dibenzo[b,d]furan-4-yl(phenyl)amino)phenyl)boronic acid was used instead of (4-([1,1'-biphenyl]-2-yl(dibenzo[b,d]furan-4-yl)amino)phenyl)boronic acid and N-phenylnaphthalen-2-amine was used instead of 9,9-methyl-N-phenyl-9H-fluoren-2-amine. The obtained compound was identified by MS/FAB and $^1$H NMR.

Synthesis Example 24

Synthesis of Compound 134

823 mg (0.93 mmol, yield of 70.7%) of Compound 134 was prepared in the same or substantially the same manner as the one used to synthesize Intermediate A-9 in Synthesis Example 2, except that (4-(dibenzo[b,d]furan-4-yl(phenyl)amino)phenyl)boronic acid was used instead of (4-([1,1'-biphenyl]-2-yl(dibenzo[b,d]furan-4-yl)amino)phenyl)boronic acid. The obtained compound was identified by MS/FAB and $^1$H NMR.

Synthesis Example 25

Synthesis of Compound 183

900 mg (1.08 mmol, yield of 74.1%) of Compound 183 was prepared in the same or substantially the same manner as the one used to synthesize Intermediate A-9 and Compound 144 in Synthesis Example 2, except that (4-(di([1,1'-biphenyl]-4-yl)amino)phenyl)boronic acid was used instead of (4-([1,1'-biphenyl]-2-yl(dibenzo[b,d]furan-4-yl)amino)phenyl)boronic acid and diphenylamine was used instead of 9,9-methyl-N-phenyl-9H-fluoren-2-amine. The obtained compound was identified by MS/FAB and $^1$H NMR.

Synthesis Example 26

Synthesis of Compound 167

800 mg (2.10 mmol) of Intermediate A-8, 1.45 g (5 mmol) of (4-(diphenylamino)phenyl)boronic acid, 580 mg (0.5 mmol) of Pd(PPh$_3$)$_4$, and 900 mg (6.5 mmol) of K$_2$CO$_3$ were added to 60 ml of a mixed solution including THF/H$_2$O (a volumetric ratio of 9/1), and the resulting mixture was stirred at a temperature of 80° C. for 12 hours. The resulting solution was cooled to room temperature, and then subjected to an extraction process three times by using 80 ml of water and 80 ml of diethyl ether. An organic layer separated therefrom was dried by using magnesium sulfate, and the residual obtained by evaporating a solvent therefrom was separation-purified by silica gel chromatography to obtain 955 mg (1.28 mmol, yield of 60.9%) of Compound 167. The obtained compound was identified by MS/FAB and $^1$H NMR.

Synthesis Example 27

Synthesis of Compound 185

1.05 g (1.35 mmol, yield of 64.3%) of Compound 185 was obtained in the same or substantially the same manner as in Synthesis Example 26, except that (4-(naphthalen-1-yl(phenyl)amino)phenyl)boronic acid was used instead of (4-(diphenylamino)phenyl)boronic acid. The obtained compound was identified by MS/FAB and $^1$H NMR.

Synthesis Example 28

Synthesis of Compound 2A 783 mg (1.09 mmol, yield of 61.2%) of Compound 2A was prepared in the same or substantially the same manner as the one used to synthesize Compound 1A in Synthesis Example 3, except that N-phenylnaphthalen-2-amine was used instead of diphenylamine. The obtained compound was identified by MS/FAB and $^1$H NMR.

Synthesis Example 29

Synthesis of Compound 3A 859 mg (1.01 mmol, yield of 56.7%) of Compound 3A was prepared in the same or substantially the same manner the one as used to synthesize Compound 1A in Synthesis Example 3, except that 9,9-dimethyl-N-phenyl-9H-fluoren-2-amine was used instead of diphenylamine. The obtained compound was identified by MS/FAB and $^1$H NMR.

Synthesis Example 30

Synthesis of Compound 5A 862 mg (1.08 mmol, yield of 60.7%) of Compound 5A was prepared in the same or substantially the same manner as the one used to synthesize Compound 1A In Synthesis Example 3, except that N-phenyldibenzo[b,d]furan-4-amine was used instead of diphenylamine. The obtained compound was identified by MS/FAB and $^1$H NMR.

Synthesis Example 31

Synthesis of Compound 9A 847 mg (1.14 mmol, yield of 64.0%) of Compound 9A was prepared in the same or substantially the same manner as the one used to synthesize Compound 1A in Synthesis Example 3, except that N-phenyldibenzo[b,d]thiophen-3-amine was used instead of diphenylamine. The obtained compound was identified by MS/FAB and $^1$H NMR.

Synthesis Example 32

Synthesis of Compound 11A 999 mg (1.05 mmol, yield of 59.0%) of Compound 11A was prepared in the same or substantially the same manner as the one used to synthesize Compound 1A in Synthesis Example 3, except that N-([1,1'-biphenyl]-2-yl)dibenzo[b,d]furan-4-amine was used instead of diphenylamine. The obtained compound was identified by MS/FAB and $^1$H NMR.

Synthesis Example 33

Synthesis of Compound 15A 995 mg (2.5 mmol) of Intermediate B-6, 1005 mg (3 mmol) of N-([1,1'-biphenyl]-2-yl)dibenzo[b,d]furan-3-amine, 229 mg (0.25 mmol) of tris(dibenzylideneacetone)dipalladium(0), 50 mg (0.5 mmol) of tri(tert-butyl)phosphine, and 720 mg (7.5 mmol) of sodium tert-butoxide were added to 25 ml of toluene, and the resulting mixture was stirred at a temperature of 80° C. for 2 hours. The reaction solution was cooled to room temperature, and then subjected to an extraction process three times by using 40 ml of water and 40 ml of diethylether. An organic layer separated therefrom was dried by using magnesium sulfate, and the residual obtained by evaporating a solvent therefrom was separation-purified by silica gel chromatography. The resulting product was added to 20 ml of toluene together with 670 mg (2 mmol) of N-([1,1'-biphenyl]-2-yl)dibenzo[b,d]furan-2-amine, 137 mg (0.15 mmol) of tris(dibenzylideneacetone)dipalladium, 30 mg (0.3 mmol) of tri(tert-butyl)phosphine, and 577 mg (6 mmol) of sodium tert-butoxide, and then stirred at a temperature of 80° C. for 3 hours. The resulting reaction solution was cooled to room temperature, and then subjected to an extraction process three times by using 30 ml of water and 30 ml of diethylether. An organic layer separated therefrom was dried by using magnesium sulfate and the residual obtained by evaporating a solvent therefrom was separation-purified by silica gel column chromatography to obtain 1159 mg (1.22 mmol, yield of 48.8%) of Compound 15A. The obtained compound was identified by MS/FAB and $^1$H NMR.

Synthesis Example 34

Synthesis of Compound 17A 812 mg (1.13 mmol, yield of 63.5%) of Compound 17A was prepared in the same or substantially the same manner as the one used to synthesize Compound 1A in Synthesis Example 3, except that N-phenylnaphthalen-1-amine was used instead of diphenylamine. The obtained compound was identified by MS/FAB and $^1$H NMR.

Synthesis Example 35

Synthesis of Compound 25A 909 mg (1.31 mmol, yield of 52.5%) of Compound 25A was obtained in the same or substantially the same manner as in Synthesis Example 33, except that diphenylamine (3 mmol) was used instead of N-([1,1'-biphenyl]-2-yl)dibenzo[b,d]furan-3-amine (3 mmol) and N-phenyl-[1,1'-biphenyl]-4-amine (2 mmol) was used instead of N-([1,1'-biphenyl]-2-y)dibenzo[b,d]furan-2-amine (2 mmol). The obtained compound was identified by MS/FAB and $^1$H NMR.

Synthesis Example 36

Synthesis of Compound 27A 988 mg (1.26 mmol, yield of 50.3%) of Compound 27A was obtained in the same or substantially the same manner as in Synthesis Example 33, except that diphenylamine (3 mmol) was used instead of N-([1,1'-biphenyl]-2-yl)dibenzo[b,d]furan-3-amine (3 mmol) and N-([1,1'-biphenyl]-2-y)dibenzo[b,d]furan-4-amine (2 mmol) was used instead of N-([1,1'-biphenyl]-2-yl)dibenzo[b,d]furan-2-amine (2 mmol). The obtained compound was identified by MS/FAB and $^1$H NMR.

Synthesis Example 37

Synthesis of Compound 32A 911 mg (1.31 mmol, yield of 52.4%) of Compound 32A was obtained in the same or substantially the same manner as in Synthesis Example 36, except that N-([1,1'-biphenyl]-2-yl)pyridin-3-amine (2 mmol) was used instead of N-([1,1'-biphenyl]-2-yl)dibenzo[b,d]furan-4-amine (2 mmol). The obtained compound was identified by MS/FAB and $^1$H NMR.

Synthesis Example 38

Synthesis of Compound 50A 829 mg (1.12 mmol, yield of 44.6%) of Compound 50A was obtained in the same or substantially the same manner as in Synthesis Example 33, except that N-phenylnaphthalen-2-amine (3 mmol) was used instead of N-([1,1'-biphenyl]-2-yl)dibenzo[b,d]furan-3-amine (3 mmol) and N-phenyl-4-(trimethylsilyl)aniline (2 mmol) was used instead of N-([1,1'-biphenyl]-2-yl)dibenzo[b,d]furan-2-amine (2 mmol). The obtained compound was identified by MS/FAB and $^1$H NMR.

Synthesis Example 39

Synthesis of Compound 56A 968 mg (1.16 mmol, yield of 46.4%) of Compound 56A was obtained in the same or substantially the same manner as in Synthesis Example 38, except that N-([1,1'-biphenyl]-2-yl)dibenzo[b,d]furan-4-amine (2 mmol) was used instead of N-phenyl-4-(trimethylsilyl)aniline (2 mmol). The obtained compound was identified by MS/FAB and $^1$H NMR.

Synthesis Example 40

Synthesis of Compound 72A 1102 mg (1.19 mmol, yield of 47.6%) of Compound 72A was obtained in the same or substantially the same manner as in Synthesis Example 33, except that N-([1,1'-biphenyl]-2-yl)-9,9-dimethyl-9H-fluoren-3-amine (3 mmol) was used instead of N-([1,1'-biphenyl]-2-yl)dibenzo[b,d]furan-3-amine (3 mmol), and 9,9-dimethyl-N-phenyl-9H-fluoren-2-amine (2 mmol) was used instead of N-([1,1'-biphenyl]-2-yl)dibenzo[b,d]furan-2-amine (2 mmol). The obtained compound was identified by MS/FAB and $^1$H NMR.

Synthesis Example 41

Synthesis of Compound 83A 855 mg (1.09 mmol, yield of 43.6%) of Compound 83A was obtained in the same or substantially the same manner as in Synthesis Example 33, except that N-([1,1'-biphenyl]-2-yl)dibenzo[b,d]furan-4-amine (3 mmol) was used instead of N-([1,1'-biphenyl]-2-yl)dibenzo[b,d]furan-3-amine (3 mmol), and diphenylamine(2 mmol) was used instead of N-([1,1'-biphenyl]-2-yl)dibenzo[b,d]furan-2-amine (2 mmol). The obtained compound was identified by MS/FAB and $^1$H NMR.

Synthesis Example 42

Synthesis of Compound 88A 973 mg (1.02 mmol, yield of 40.9%) of Compound 88A was obtained in the same or substantially the same manner as in Synthesis Example 41, except for 5'-fluoro-N-phenyl-[1,1':3',1''-terphenyl]-4'-amine was used instead of diphenylamine. The obtained compound was identified by MS/FAB and $^1$H NMR.

Synthesis Example 43

Synthesis of Compound 71A 1164 mg (1.21 mmol, yield of 48.3%) of Compound 71A was obtained in the same or substantially the same manner as in Synthesis Example 33, except that N-([1,1'-biphenyl]-2-yl)-9,9-dimethyl-9H-fluoren-3-amine (3 mmol) was used instead of N-([1,1'-biphenyl]-2-yl)dibenzo[b,d]furan-3-amine (3 mmol), and di([1,1'-biphenyl]-4-yl)amine (2 mmol) was used instead of N-([1,1'-biphenyl]-2-yl)dibenzo[b,d]furan-2-amine (2 mmol). The obtained compound was identified by MS/FAB and $^1$H NMR.

Synthesis Example 44

Synthesis of Compound 106A

Synthesis of Intermediate B-6(1)

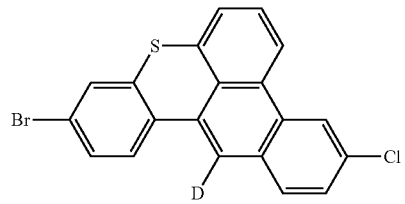

B-6(1)

Intermediate B-6(1) was prepared in the same or substantially the same manner as the one used to synthesize Intermediate B-1 to Intermediate B-6 in Synthesis Example 3, except that in synthesizing Intermediate B-4, D$_2$O was used Instead of H$_2$O.

Synthesis of Compound 106A 709 mg (1.06 mmol, yield of 42.3%) of Compound 106A was obtained in the same or substantially the same manner as in Synthesis Example 33, except that Intermediate B-6(1) was used instead of intermediate B-6, diphenylamine (3 mmol) was used instead of N-([1,1'-biphenyl]-2-yl)dibenzo[b,d]furan-3-amine (3 mmol), and N-phenylnaphthalen-2-amine (2 mmol) was used instead of N-([1,1'-biphenyl]-2-yl)dibenzo[b,d]furan-2-amine (2 mmol). The obtained compound was identified by MS/FAB and $^1$H NMR.

Synthesis Example 45

Synthesis of Compound 110A 821 mg (1.12 mmol, yield of 44.6%) of Compound 110A was obtained in the same or substantially the same manner as the one used to synthesize Compound 106A in Synthesis Example 44, except that 2,4,6-trimethyl-N-phenylaniline (3 mmol) was used instead of diphenylamine (3 mmol), and N-phenyl-4-(trimethylsilyl)aniline (2 mmol) was used instead of N-phenylnaphthalen-2-amine (2 mmol). The obtained compound was identified by MS/FAB and $^1$H NMR.

Synthesis Example 46

Synthesis of Compound 120A

Synthesis of Intermediate B-6(2)

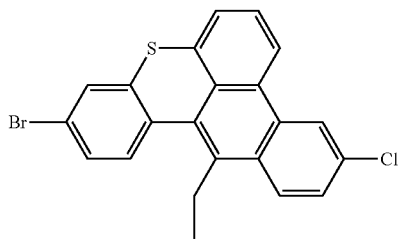

B-6(2)

Intermediate B-6(2) was prepared in the same or substantially the same manner as the one used to synthesize Intermediate B-1 to Intermediate B-6 in Synthesis Example 3, except that in synthesizing Intermediate B-4, ethyl iodide was used instead of $H_2O$.

Synthesis of Compound 120A 1225 mg (1.22 mmol, yield of 48.6%) of Compound 120A was obtained in the same or substantially the same manner as in Synthesis Example 33, except that Intermediate B-6(2) was used instead of Intermediate B-6, N-([1,1'-biphenyl]-2-yl)-9,9-dimethyl-9H-fluoren-2-amine (3 mmol) was used instead of N-([1,1'-biphenyl]-2-yl)dibenzo[b,d]furan-3-amine (3 mmol), and N-([1,1'-biphenyl]-2-yl)dibenzo[b,d]furan-4-amine (2 mmol) was used instead of N-([1,1'-biphenyl]-2-yl)dibenzo[b,d]furan-2-amine (2 mmol). The obtained compound was identified by MS/FAB and $^1$H NMR.

Synthesis Example 47

Synthesis of Compound 125A

Synthesis of Intermediate B-6(3)

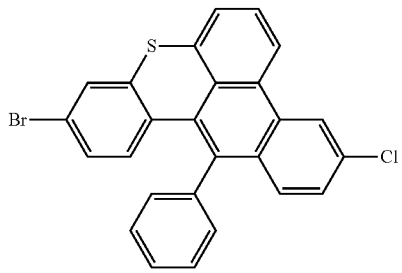

B-6(3)

Intermediate B-6(3) was obtained in the same or substantially the same manner as the one used to synthesize Intermediate B-1 to Intermediate B-6 in Synthesis Example 3, except that in synthesizing Intermediate B-4, 1-bromobenzene was used instead of $H_2O$.

Synthesis of Compound 125A 774 mg (1.04 mmol, yield of 41.5%) of Compound 125A was obtained in the same or substantially the same manner as in Synthesis Example 33, except that Intermediate B-6(3) was used instead of Intermediate B-6, N-phenylnaphthalen-2-amine (3 mmol) was used instead of N-([1,1'-biphenyl]-2-yl)dibenzo[b,d]furan-3-amine (3 mmol), and diphenylamine (2 mmol) was used instead of N-([1,1'-biphenyl]-2-yl)dibenzo[b,d]furan-2-amine (2 mmol). The obtained compound was identified by MS/FAB and $^1$H NMR.

Synthesis Example 48

Synthesis of Compound 137A 622 mg (1.57 mmol) of Intermediate B-6, 463 mg (1.6 mmol) of (4-(diphenylamino)phenyl)boronic acid, 173 mg (0.15 mmol) of Pd(PPh$_3$)$_4$, and 620 mg (225 mmol) of K$_2$CO$_3$ were added to 35 ml of a mixture including THF/H$_2$O (a volumetric ratio of 9/1), and the resulting solution was stirred at a temperature of 80° C. for 12 hours, and then cooled to room temperature and subjected to an extraction process three times by using 500 ml of water and 500 ml of diethyl ether. An organic layer separated therefrom was dried by using magnesium sulfate, and the residual obtained by evaporating a solvent was separation-purified by silica gel chromatography. 600 mg (1.07 mmol) of the resulting product was added to 10 ml of toluene together with 366 mg (2.1 mmol) of diphenylamine, 192 mg (0.21 mmol) of tris(dibenzylideneacetone)dipalladium(0), 19 mg (0.21 mmol) of tri(tert-butyl)phosphine, and 288 mg (3 mmol) of sodium tert-butoxide and then, the resulting mixture was stirred at a temperature of 80° C. for 2 hours. The reaction solution was cooled to room temperature, and then subjected to an extraction process three times by using 20 ml of water and 20 ml of diethylether. An organic layer separated therefrom was dried by using magnesium sulfate and the residual obtained by evaporating a solvent therefrom was separation-purified by silica gel column chromatography to obtain 535 mg (0.77 mmol, yield of 72.3%) of Compound 137A. The obtained compound was identified by MS/FAB and $^1$H NMR.

Synthesis Example 49

Synthesis of Compound 142A 656 mg (0.735 mmol, yield of 68.7%) of Compound 142A was obtained in the same or substantially the same manner as in Synthesis Example 48, except that (6-([1,1'-biphenyl]-4-yl(phenyl)amino)naphthalen-2-yl)boronic acid was used instead of (4-(diphenylamino)phenyl)boronic acid, and N-phenyl-4-(trimethylsilyl)aniline was used instead of diphenylamine. The obtained compound was identified by MS/FAB and $^1$H NMR.

Synthesis Example 50

Synthesis of Compound 160A 623 mg (1.57 mmol) of Intermediate B-6(1) was added to 35 ml of toluene together with 514 mg (1.6 mmol) of di([1,1'-biphenyl]-4-yl)amine, 192 mg (0.21 mmol) of tris(dibenzylideneacetone)dipalladium(0), 19 mg (0.21 mmol) of tri(tert-butyl)phosphine, and 288 mg (3 mmol) of sodium tert-butoxide, and the resulting mixture was stirred at a temperature of 80° C. for 2 hours. The reaction solution was cooled to room temperature, and then subjected to an extraction process three times by using 500 ml of water and 500 ml of diethyl ether. An organic layer separated therefrom was dried by using magnesium sulfate and the residual obtained by evaporating a solvent therefrom was separation-purified by silica gel column chromatography. 683 mg (1.07 mmol) of the resulting product was added to 15 ml of a mixture including THF/H$_2$O (a volumetric ratio of 9/1) together with 764 mg (1.6 mmol) of (4-((9,9-dimethyl-9H-fluoren-2-yl)(4-(trimethylsilyl)phenyl)amino)phenyl)boronic acid, 115 mg (0.10 mmol) of Pd(PPh$_3$)$_4$, and 413 mg (150 mmol) of K$_2$CO$_3$, and the resulting solution was stirred at a temperature of 80° C. for 12 hours, and then cooled to room temperature and subjected to an extraction process three times by using 30 ml of water and 20 ml of diethyl ether. An organic layer separated therefrom was dried by using magnesium sulfate, and the residual obtained by evaporating a solvent was separation-purified by silica gel chromatography to obtain 674 mg (0.65 mmol, yield of 60.5%) of Compound 160 Å. The obtained compound was identified by MS/FAB and $^1$H NMR.

Synthesis Example 51

Synthesis of Compound 161A 475 mg (0.67 mmol, yield of 62.4%) of Compound 161A was obtained in the same or substantially the same manner as in Synthesis Example 50, except that Intermediate B-6(2) was used instead of Intermediate B-6(1), diphenylamine was used instead of di([1,1'-biphenyl]-4-yl)amine, and (4-(diphenylamino)phenyl)boronic acid was used instead of (4-((9,9-dimethyl-9H-fluoren-2-yl)(4-(trimethylsilyl)phenyl)amino) phenyl)boronic acid. The obtained compound was identified by MS/FAB and $^1$H NMR.

Synthesis Example 52

Synthesis of Compound 164A 741 mg (1.57 mmol) of Intermediate B-6(3), 463 mg (1.6 mmol) of (4-(diphenylamino)phenyl)boronic acid, 173 mg (0.15 mmol) of Pd(PPh$_3$)$_4$, and 620 mg (225 mmol) of K$_2$CO$_3$ were added to 35 ml of a mixture Including THF/H$_2$O (a volumetric ratio of 9/1), and the resulting solution was stirred at a temperature of 80° C. for 12 hours, and then cooled to room temperature and subjected to an extraction process three times by using 500 ml of water and 500 ml of diethyl ether. An organic layer separated therefrom was dried by using magnesium sulfate, and the residual obtained by evaporating a solvent was separation-purified by silica gel chromatography. 896 mg (1.07 mmol) of the resulting product was added to 15 ml of a mixture including THF/H$_2$O (a volumetric ratio of 9/1) together with 543 mg (4-(diphenylamino)naphthalen-1-yl)boronic acid, 115 mg (0.10 mmol) of Pd(PPh$_3$)$_4$, and 413 mg (150 mmol) of K$_2$CO$_3$, and then stirred at a temperature of 80° C. for 12 hours, and then cooled to room temperature, and subjected to an extraction process three times by using 30 ml of water and 20 ml of diethyl ether. An organic layer separated therefrom was dried by using magnesium sulfate, and the residual obtained by evaporating a solvent was separation-purified by silica gel chromatography to obtain 592 mg (0.66 mmol, yield of 61.4%) of Compound 164A. The obtained compound was Identified by MS/FAB and $^1$H NMR.

MS/FAB and $^1$H NMR of the compounds synthesized in Synthesis Examples 1 to 52 are shown in Table 1 below:

TABLE 1

| Compound | $^1$H NMR (CDCl$_3$, 400 MHz) | MS/FAB found | MS/FAB calc. |
|---|---|---|---|
| 2 | 8.29(s, 1H), 8.01(s, 1H), 7.55-7.50(m, 3H), 7.43-7.37(m, 2H), 7.33-7.29(m, 3H), 7.23-7.20(m, 2H), 7.15(dd, 1H), 7.05-6.97(m, 9H), 6.86(dd, 1H), 6.75(dd, 1H), 6.72-6.68(m, 3H), 6.61-6.56(m, 3H), 6.46-6.41(m, 4H), 1.86(s, 12H) | 835.12 | 835.06 |
| 9 | 8.34(s, 1H), 8.07(d, 1H), 7.63(ss, 2H), 7.5(ss, 1H), 7.4-7.22(m, 13H), 7.11(dd, 1H), 7.06(dd, 1H), 6.98-6.89(m, 5H), 6.79(dd, 1H), 6.69(t, 1H), 6.62-6.58(m, 2H), 6.62(dd, 1H), 6.36-6.28(m, 4H) | 702.74 | 702.86 |
| 13 | 8.42(s, 1H), 8.14(d, 1H), 7.53-7.45(m, 9H), 7.4-7.34(m, 12H), 7.29-7.27(m, 2H), 7.22(dd, 2H), 7.16(dd, 2H), 7.04-6.98(m, 6H), 6.82(dd, 1H), 6.63-6.59(m, 2H), 6.5(t, 1H), 6.41(dd, 1H), 6.3-6.21(m, 4H) | 943.17 | 943.11 |
| 15 | 8.31(s, 1H), 8.05(d, 1H), 7.58(d, 2H), 7.48-7.43(m, 5H), 7.4-7.22(m, 17H), 7.11(dd, 1H), 7.03-6.99(m, 4H), 6.92-6.83(m, 8H), 6.77(dd, 1H), 6.45(s, 1H), 6.37(dd, 1H) | 934.95 | 935.09 |
| 19 | 8.16(s, 1H), 7.92(d, 1H), 7.5(dd, 2H), 7.43(dd, 2H), 7.34-7.16(m, 12H), 7.09(dd, 1H), 6.99-6.91(m, 6H), 6.85(dd, 1H), 6.76(t, 1H), 6.67-6.58(m, 3H), 6.49-6.44(m, 4H) | 782.87 | 782.90 |
| 26 | 8.33(s, 1H), 8.12(dd, 1H), 8.08(dd, 1H), 7.93(d, 1H), 7.64(dd, 1H), 7.49(dd, 2H), 7.44-7.32(m, 7H), 7.16(dd, 1H), 7.04-6.94(m, 8H), 6.73(t, 1H), 6.68(t, 3H), 6.56(dd, 1H), 6.40-6.36(m, 6H) | 702.65 | 702.86 |
| 29 | 8.36(s, 1H), 8.13(d, 1H), 7.61-7.27(m, 16H), 7.18-7.11(m, 7H), 6.99(dd, 1H), 6.88(t, 1H), 6.85-6.79(m, 3H), 6.72(dd, 1H), 6.56(dd, 4H), 6.48(dd, 2H) | 772.76 | 772.92 |
| 30 | 8.12(s, 1H), 7.85(d, 1H), 7.28-7.19(m, 6H), 7.15-6.98(m, 11H), 6.92(d, 1H), 6.82-6.75(m, 5H), 6.68(dd, 1H), 6.50-6.41(m, 5H), 6.31(dd, 1H), 6.15(dd, 4H) | 798.01 | 797.93 |
| 38 | 8.30(s, 1H), 8.00(d, 1H), 7.48(d, 1H), 7.37-7.32(m, 3H), 7.28-7.07(m, 12H), 6.97(dd, 1H), 6.89-6.66(m, 8H), 6.59(dd, 1H), 6.53(t, 1H), 6.49-6.41(m, 3H), 6.35(dd, 1H), 6.25(dd, 2H), 0.66(s, 9H) | 840.96 | 841.10 |
| 54 | 8.23(s, 1H), 7.97(d, 1H), 7.56(d, 1H), 7.34-7.17(m, 14H), 7.08-6.84(m, 10H), 6.72(d, 1H), 6.63-6.55(m, 3H), 6.41(dd, 1H), 6.31(dd, 2H), 6.23(dd, 2H) | 729.10 | 728.89 |

TABLE 1-continued

| Compound | $^1$H NMR (CDCl$_3$, 400 MHz) | MS/FAB found | MS/FAB calc. |
|---|---|---|---|
| 57 | 8.46(s, 1H), 8.18(d, 1H), 7.62(dd, 2H), 7.48-7.44(m, 6H), 7.39-7.31(m, 8H), 7.26-7.22(m, 1H), 7.18-6.91(m, 11H), 6.83-6.78(m, 2H), 6.65-6.57(m, 3H), 6.46-6.43(m, 2H), 6.31-6.22(m, 3H), 1.68 (s, 6H) | 871.04 | 871.10 |
| 72 | 8.42(s, 1H), 8.12(d, 1H), 7.61(s, 1H), 7.56-7.39(m, 6H), 7.32-7.10(m, 6H), 6.97-6.81(m, 9H), 6.64-6.52(m, 4H), 6.45-6.42(m, 2H), 6.32-6.11(m, 4H), 1.72 (s, 6H) | 809.03 | 808.98 |
| 88 | 8.31(s, 1H), 8.09(d, 1H), 7.7(d, 1H), 7.66(d, 1H), 7.61-7.31(m, 16H), 7.24-7.07(m, 11H), 6.95(dd, 1H), 6.9(t, 1H), 6.79(d, 1H), 6.74(t, 1H), 6.69-6.64(m, 3H), 1.69(s, 6H) | 884.99 | 885.08 |
| 90 | 8.27(s, 1H), 8.01(d, 1H), 7.54(d, 1H), 7.44-7.18(m, 22H), 7.13-7.07(m, 3H), 6.99-6.75(m, 10H), 6.6(t, 1H), 6.41(t, 1H), 6.32(d, 1H), 6.21(dd, 2H) | 939.03 | 939.10 |
| 129 | 8.34(s, 1H), 8.20(d, 1H), 8.00(s, 1H), 7.88(d, 1H), 7.77-7.66(m, 3H), 7.59-7.29(m, 13H), 7.20(dd, 1H), 7.07-6.96(m, 6H), 6.88(dd, 1H), 6.78(t, 1H), 6.69(dd, 2H), 6.61(dd, 3H), 6.45(dd, 2H), 6.36(dd, 2H) | 819.07 | 818.98 |
| 134 | 8.26(s, 1H), 8.12(d, 1H), 7.93(s, 1H), 7.81(d, 1H), 7.69(dd, 1H), 7.6(d, 1H), 7.56-7.46(m, 4H), 7.34-7.19(m, 7H), 7.14(dd, 1H), 7.03-6.96(m, 6H), 6.92(dd, 2H), 6.83(dd, 1H), 6.69-6.53(m, 7H), 6.39(dd, 2H), 6.32(dd, 2H), 1.76(s, 6H) | 885.16 | 885.08 |
| 1 | 8.43(s, 1H), 8.12(d, 1H), 7.46(d, 1H), 7.42(d, 1H), 7.38(d, 1H), 7.29(t, 1H), 7.09(d, 1H), 6.94-6.84(m, 9H), 6.62(t, 1H), 6.56(dd, 4H), 6.41(dd, 1H), 6.23(dd, 4H), 6.17(dd, 4H) | 602.66 | 602.74 |
| 5 | 8.40(s, 1H), 8.13(d, 1H), 7.9(dd, 2H), 7.67(d, 2H), 7.41(d, 2H), 7.37-7.26(m, 5H), 7.17-7.08(m, 5H), 7.03(d, 1H), 6.97-6.91(m, 4H), 6.71(d, 1H), 6.64(dd, 1H), 6.59-6.51(m, 4H), 6.37(dd, 1H), 6.17(dd, 2H). 6.1(dd. 2H) | 702.92 | 702.86 |
| 7 | 8.31(s, 1H), 8.01(d, 1H), 7.93(dd, 2H), 7.66(dd, 2H), 7.29-7.12(m, 13H), 7.03-6.86(m, 9H), 6.79(dd, 1H), 6.68(t, 2H), 6.65-6.58(m, 3H), 6.44(dd, 1H), 6.33(dd, 1H) | 756.78 | 756.91 |
| 8 | 8.33(s, 1H), 8.09(d, 1H), 7.62(dd, 1H), 7.55(dd, 1H), 7.49-7.46(m, 5H), 7.4-7.36(m, 9H), 7.33-7.29(m, 2H), 7.15(d, 1H), 7.10-7.07(m, 5H), 6.86(dd, 1H), 6.79-6.67(m, 7H), 6.56-6.50(m, 4H) | 754.97 | 754.93 |
| 144 | 8.39(s, 1H), 8.25(d, 1H), 8.05(s, 1H), 7.93(d, 1H), 7.8(dd, 1H), 7.71(d, 1H), 7.67-7.56(m, 4H), 7.53-7.29(m, 12H), 7.24(dd, 1H), 7.15-6.90(m, 11H), 6.77-6.71(m, 2H), 6.64-6.61(m, 2H), 6.55(dd, 2H), 6.45(dd, 2H), 1.59(s, 6H) | 961.11 | 961.18 |
| 167 | 8.29(s, 1H), 8.14(d, 1H), 7.93(s, 1H), 7.81(d, 1H), 7.69(dd, 2H), 7.33-7.19(m, 7H), 6.98-6.90(m, 9H), 6.76-6.70(m, 4H), 6.57-6.54(m, 4H), 6.06-6.02(m, 8H) | 755.01 | 754.93 |
| 172 | 8.56(s, 1H), 8.27(d, 1H), 7.81(d, 1H), 7.61(dd, 1H), 7.55-7.50(m, 9H), 7.45-7.39(m, 17H), 7.35-7.31(m, 4H), 7.23(dd, 1H), 7.14(dd, 1H), 7.14(dd, 1H), 6.81(dd, 1H), 6.75(dd, 4H), 6.68(dd, 4H), 6.6(dd, 1H). | 907.17 | 907.13 |
| 174 | 8.60(s, 1H), 8.28(d, 1H), 8.01(d, 1H), 7.77(d, 1H), 7.56(dd, 1H), 7.51-7.11(m, 21H), 7.05(d, 1H), 6.99-6.93(m, 2H), 6.71-6.47(m, 9H), 6.13(dd, 2H) | 805.04 | 804.99 |
| 183 | 8.24(s, 1H), 8.10(d, 1H), 7.91(s, 1H), 7.78(d, 1H), 7.65(dd, 1H), 7.44(d, 1H), 7.34(dd, 4H), 7.29-7.18(m, 13H), 7.1(dd, 1H), 6.96-6.92(m, 4H), 6.76-6.73(m, 4H), 6.66(t, 1H), 6.61-6.57(m, 4H), 6.47(dd, 1H), 6.29(dd, 4H) | 831.11 | 831.03 |
| 185 | 8.30(s, 1H), 8.06(d, 1H), 7.88(dd, 1H), 7.85(dd, 1H), 7.69(d, 1H), 7.63(dd, 2H), 7.41(d, 1H), 7.36-7.24(m, 9H), 7.17-6.92(m, 10H), 6.75-6.59(m, 5H), 6.4(dd, 2H), 6.19(dd, 2H), 6.15(dd, 2H) | 779.02 | 778.95 |
| 1A | 8.44(s, 1H), 8.07(d, 1H), 7.64(m, 2H), 7.59(dd, 1H), 7.51(m, 2H), 7.07-7.03(m, 8H), 6.98(dd, 1H), 6.85(d, 1H), 6.70(t, 4H), 6.60(dd, 1H), 6.42(dd, 4H), 6.35(dd, 4H) | 618.04 | 618.80 |
| 5A | 8.52(s, 1H), 8.13(d, 1H), 7.74(dd, 2H), 7.68-7.55(m, 9H), 7.43(t, 2H), 7.37(t, 2H), 7.11-7.06(m, 5H), 7.03-6.98(m, 5H), 6.73(t, 2H), 6.63(dd, 1H), 6.52(dd, 2H), 6.43(dd, 2H) | 798.84 | 798.96 |

TABLE 1-continued

| Compound | ¹H NMR (CDCl₃, 400 MHz) | MS/FAB found | MS/FAB calc. |
|---|---|---|---|
| 9A | 8.49(s, 1H), 8.10(d, 1H), 8.04(d, 2H), 7.95(d, 2H), 7.69(d, 2H), 7.64(dd, 1H), 7.60-7.51(m, 4H), 7.36(t, 2H), 7.30(t, 2H), 7.09-7.02(m, 7H), 6.96(dd, 2H), 6.91(d, 1H), 6.67(t, 3H), 6.53(d, 2H), 6.49(d, 2H) | 831.01 | 831.08 |
| 17A | 8.47(s, 1H), 8.08(d, 1H), 7.95(dd, 2H), 7.83(d, 1H), 7.73(dd, 2H), 7.65(dd, 1H), 7.58(dd, 1H), 7.52(m, 1H), 7.44(m, 3H), 7.36(t, 2H), 7.23(t, 2H), 7.18(t, 2H), 7.03(t, 4H), 6.85(d, 1H), 6.80(dd, 1H), 6.76(t, 2H), 6.68(t, 3H), 6.31(dd, 2H), 6.23(dd, 2H) | 718.99 | 718.92 |
| 25A | 8.52(s, 1H), 8.11(d, 1H), 7.74(d, 1H), 7.64(d, 1H), 7.59(dd, 1H), 7.52(m, 2H), 7.46(dd, 2H), 7.38-7.35(m, 4H), 7.30-7.26(m, 1H), 7.01(t, 7H), 6.80(d, 1H), 6.64(t, 3H), 6.58(d, 2H), 6.54(dd, 1H), 6.33(dd, 6H) | 694.92 | 694.90 |
| 71A | 8.53(s, 1H), 8.13(d, 1H), 7.85(d, 1H), 7.67-7.60(m, 3H), 7.55(d, 2H), 7.51-7.47(m, 6H), 7.42-7.36(m, 11H), 7.34-7.28(m, 3H), 7.12-7.07(m, 4H), 7.04-7.02(m, 2H), 6.97(m, 2H), 6.81(d, 2H), 6.68(d, 4H), 6.46(m, 2H), 2.19(s, 6H) | 936.21 | 963.25 |
| 110A | 8.12(d, 1H), 7.90(d, 1H), 7.74(d, 1H), 7.65(d, 1H), 7.59(dd, 1H), 7.52(t, 1H), 7.30(d, 2H), 7.03-6.98(m, 5H), 6.76(d, 1H), 6.65-6.58(m, 7H), 6.33(dd, 2H), 6.22(dd, 2H), 2.71(d, 9H), 0.91(s, 9H) | 733.98 | 734.07 |
| 142A | 8.58(s, 1H), 8.15(d, 1H), 8.05(d, 1H), 7.91(m, 2H), 7.75(d, 1H), 7.66-7.44(m, 7H), 7.40-7.32(m, 6H), 7.28-7.23(m, 4H), 6.98(t, 6H), 6.59-6.55(m, 4H), 6.46(d, 2H), 6.25(d, 2H), 6.18(d, 2H), 0.49(s, 9H) | 893.31 | 893.24 |
| 160A | 8.18(s, 1H), 8.11(d, 1H), 7.71(q, 2H), 7.63-7.51(m, 4H), 7.45(d, 4H), 7.37-7.32(m, 11H), 7.28-7.21(m, 5H), 7.03(d, 2H), 6.78(d, 1H), 6.70-6.65(m, 5H), 6.59-6.53(m, 5H), 6.40(d, 1H), 2.09(s, 6H), 0.85(s, 9H) | 1036.32 | 1036.44 |
| 164A | 8.34(d, 1H), 8.28(d, 1H), 8.05(d, 1H), 8.03(t, 1H), 7.99(d, 1H), 7.85(dd, 1H), 7.75(dd, 2H), 7.69(dd, 1H), 7.57-7.50(m, 4H), 7.42-7.26(m, 8H), 7.00-6.93(m, 8H), 6.89(d, 1H), 6.58(q, 4H), 6.51(d, 2H), 6.12(dd, 4H), 6.03(dd, 4H) | 897.01 | 897.15 |
| 2A | 8.46(s, 1H), 8.07(d, 1H), 7.71(d, 2H), 7.63(d, 1H), 7.57(d, 1H), 7.55(d, 1H), 7.53(d, 1H), 7.50-7.39(m, 7H), 7.35(t, 2H), 7.30(t, 2H), 7.13(dd, 1H), 7.04(t, 4H), 6.98(dd, 1H), 6.87(dd, 1H), 6.84(d, 1H), 6.67(t, 2H), 6.59(dd, 1H), 6.42(d, 2H), 6.36(dd, 2H) | 718.96 | 718.92 |
| 3A | 8.47(s, 1H), 8.08(d, 1H), 7.65-7.61(m, 3H), 7.58(d, 1H), 7.54-7.49(m, 3H), 7.36(d, 2H), 7.27-7.23(m, 2H), 1.20(d, 1H), 7.08-6.98(m, 9H), 6.79(dd, 1H), 6.74(dd, 1H), 6.68(t, 2H), 6.62(t, 2H), 6.53(d, 1H), 6.43(d, 2H), 6.36(d, 2H), 2.44(s, 12H) | 851.18 | 851.12 |
| 11A | 8.44(s, 1H), 8.06(d, 1H), 7.66(d, 2H), 7.59(d, 1H), 7.56-7.41(m, 20H), 7.31(t, 2H), 7.08(m, 4H), 6.98(m, 9H), 6.83(dd, 1H), 6.35(dd, 1H) | 951.14 | 951.16 |
| 15A | 8.51(s, 1H), 8.1(d, 1H), 7.7-7.66(m, 3H), 7.62(d, 1H), 7.58(dd, 1H), 7.52(d, 2H), 7.51-7.43(m, 9H), 7.4-7.34(m, 6H), 7.32-7.28(m, 3H), 7.16(t, 1H), 7.1(m, 2H), 6.97-6.92(m, 5H), 6.9(dd, 1H), 6.86-6.82(m, 2H), 6.78-6.74(m, 3H), 6.59(dd, 1H) | 951.19 | 951.16 |
| 27A | 8.45(s, 1H), 8.06(d, 1H), 7.66(d, 1H), 7.59(d, 1H), 7.56-7.51(m, 6H), 7.47-7.42(m, 4H), 7.38-7.35(m, 2H), 7.31(t, 1H), 7.10-7.01(m, 6H), 6.97-6.91(m, 4H), 6.82(m, 2H), 6.68(t, 2H), 6.57(dd, 1H), 6.39(dd, 4H) | 785.03 | 784.98 |
| 32A | 8.45(s, 1H), 8.06(m, 2H), 7.84(d, 1H), 7.64(d, 1H), 7.57(d, 1H), 7.53-7.43(m, 5H), 7.39-7.34(m, 3H), 7.24(dd, 1H), 7.18(t, 1H), 7.14(d, 1H), 7.06-7.01(m, 5H), 6.96(t, 1H), 6.89(m, 2H), 6.83(d, 1H), 6.68(t, 2H), 6.57(d, 1H), 6.38(d, 4H) | 695.97 | 695.88 |

TABLE 1-continued

| Compound | ¹H NMR (CDCl₃, 400 MHz) | MS/FAB found | MS/FAB calc. |
|---|---|---|---|
| 50A | 8.42(s, 1H), 8.05(d, 1H), 7.7(m, 2H), 7.62(dd, 1H), 7.56(dd, 1H), 7.52(d, 1H), 7.50-7.33(m, 5H), 7.29(d, 3H), 7.06-7.01(m, 5H), 6.88(dd, 1H), 6.85(dd, 1H), 6.70-6.66(m, 4H), 6.69(dd, 1H), 6.45(dd, 2H), 6.41(dd, 2H), 1.45(s, 9H) | 740.98 | 741.04 |
| 56A | 8.50(s, 1H), 8.11(d, 1H), 7.75(d, 1H), 7.70(dd, 1H), 7.64-7.32(m, 19H), 7.13-7.04(m, 4H), 7.01-6.94(m, 4H), 6.9(dd, 1H), 6.87(d, 1H), 6.86(dd, 1H), 6.70(t, 1H), 6.62(dd, 1H), 6.45(dd, 2H) | 835.11 | 835.04 |
| 72A | 8.47(s, 1H), 8.09(d, 1H), 7.68-7.59(m, 5H), 7.56(d, 2H), 7.54-7.45(m, 2H), 7.44-7.41(m, 4H), 7.37-7.30(m, 2H), 7.17-7.03(m, 12H), 6.89(m, 2H), 6.83(dd, 1H), 6.76(t, 1H), 6.63(d, 1H), 6.58(m, 2H), 6.48(dd, 2H), 2.73(s, 6H), 2.69(s, 6H) | 927.29 | 927.22 |
| 83A | 8.45(s, 1H), 8.08(d, 1H), 7.70(d, 1H), 7.66(t, 2H), 7.62-7.40(m, 11H), 7.36(t, 1H), 7.16-6.98(m, 12H), 6.76(t, 2H), 6.46(m, 5H) | 785.01 | 784.98 |
| 88A | 8.47(s, 1H), 8.08(d, 1H), 7.67(d, 1H), 7.63(d, 1H), 7.59-7.30(m, 23H), 7.26(m, 1H), 7.10-6.90(m, 10H), 6.86(dd, 1H), 6.64(t, 1H), 6.35(dd, 1H), 6.28(dd, 2H) | 955.09 | 955.16 |
| 106A | 8.09(d, 1H), 7.74(d, 1H), 7.64(d, 1H), 7.60(d, 1H), 7.57(d, 1H), 7.55-7.33(m, 7H), 7.16(dd, 1H), 7.08-7.03(m, 6H), 7.01(dd, 1H), 6.86(d, 1H), 6.70(t, 3H), 6.60(dd, 1H), 6.44-6.69(m, 6H) | 669.83 | 669.86 |
| 120A | 8.10(d, 1H), 7.67(d, 1H), 7.62-7.58(m, 2H), 7.55(d, 1H), 7.52(d, 1H), 7.47-7.29(m, 17H), 7.24(m, 1H), 7.16(d, 1H), 7.11-7.05(m, 5H), 6.97-6.90(m, 6H), 6.68(dd, 1H), 6.57-6.52(m, 3H), 6.32-6.28(m, 1H), 2.42(s, 9H), 2.14(t, 2H) | 1005.27 | 1005.29 |
| 125A | 7.94(dd, 1H), 7.77(d, 1H), 7.72(m, 3H), 7.57(d, 1H), 7.52-7.29(m, 10H), 7.13(d, 1H), 7.05-7.00(m, 6H), 6.92(dd, 1H), 6.86(d, 2H), 6.69-6.64(m, 4H), 6.40(dd, 2H), 6.30(dd, 4H) | 744.91 | 744.96 |
| 137A | 8.44(s, 1H), 8.06(d, 1H), 7.94(d, 1H), 7.86(d, 1H), 7.63(m, 2H), 7.50(dd, 2H), 7.39(dd, 1H), 7.36(d, 2H), 7.06-7.02(m, 8H), 6.98(dd, 1H), 6.69(t, 4H), 6.64(d, 2H), 6.35(dd, 4H), 6.27(dd, 4H) | 694.82 | 694.90 |
| 161A | 8.05(s, 1H), 7.98(m, 1H), 7.78(d, 1H), 7.60(dd, 1H), 7.53-7.47(m, 3H), 7.39(m, 2H), 7.05-7.01(m, 8H), 6.86-6.82(m, 3H), 6.69 (t, 4H), 6.65(dd, 1H), 6.42(dd, 4H), 6.28(dd, 4H), 3.68(s, 3H) | 708.93 | 708.92 |

Example 1

A 15 Ωcm² (1200 Å) ITO glass substrate (a product of Corning) was cut to a size of 50 mm×50 mm×0.7 mm, and was ultrasonically cleaned by using isopropyl alcohol and pure water for 5 minutes each, and then UV light was Irradiated thereon for 30 minutes and the substrate was further exposed to ozone to clean. Then, the resultant structure was loaded into a vacuum deposition apparatus.

On the iTO glass substrate acting as an anode, 2-TNATA was vacuum-deposited to form a hole Injection layer having a thickness of 600 Å, and Compound 1 was vacuum-deposited on the hole injection layer to form a hole transport layer having a thickness of 300 Å, thereby completing the formation of a hole transport region.

9,10-di-naphthalene-2-yl-anthracene (ADN) acting as a host and N,N,N',N'-tetraphenyl-pyrene-1,6-diamine (TPD) acting as a dopant were co-deposited on the hole transport region at a weight ratio of 98:2 to form an emission layer having a thickness of 300 Å.

Alq₃ was vacuum-deposited on the emission layer to form an electron transport layer having a thickness of 300 Å, and LiF was deposited on the electron transport layer to form an electron injection layer having a thickness of 10 Å, thereby completing the formation of an electron transport region.

Al was vacuum-deposited on the electron transport region to form a cathode having a thickness of 3,000 Å, thereby completing the manufacture of an organic light-emitting device.

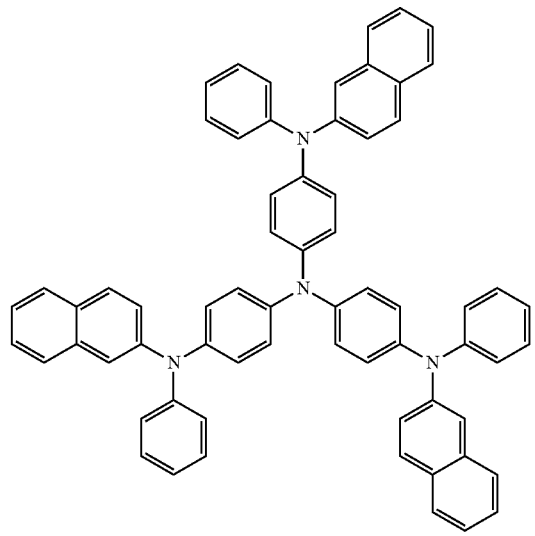

2-TNATA

-continued

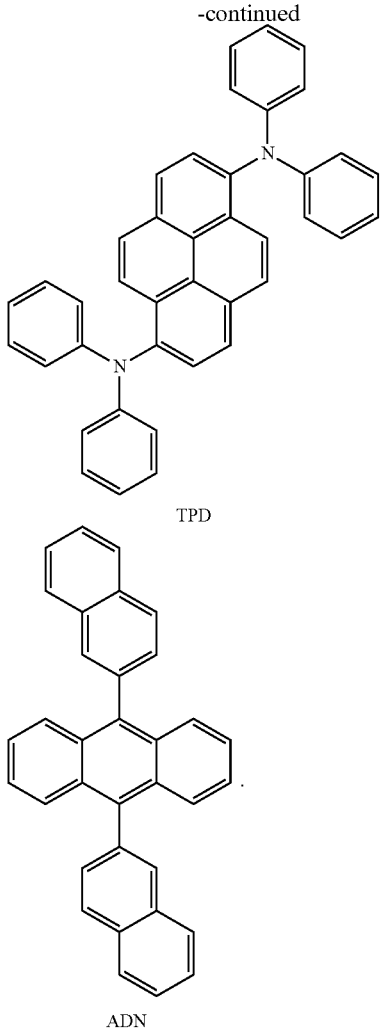

TPD

ADN

Examples 2 to 20

Organic light-emitting devices were manufactured in the same or substantially the same manner as in Example 1, except that in forming a hole transport layer, compounds shown in Table 2 were used instead of Compound 1.

Comparative Example 1

An organic light-emitting device was manufactured in the same or substantially the same manner as in Example 1, except that in forming a hole transport layer, NPB was used instead of Compound 1.

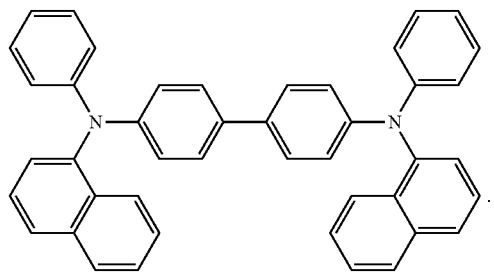

NPB

Evaluation Example 1

The driving voltage, current density, brightness, efficiency, and half-lifespan of the organic light-emitting devices manufactured according to Examples 1 to 20, and Comparative Example 1 were measured by using Keithley SMU 236 (from Keithley Instruments Inc.) and a brightness photometer $PR_{650}$ (from Photo Research, Inc.), and the results are shown in Table 2. The half-lifespan as used herein is a period of time that it takes for the brightness of the organic light-emitting device to reduce to 50% of the initial brightness.

TABLE 2

|  | Hole transport layer | Driving voltage (V) | Current Density (mA/cm$^2$) | Brightness (cd/m$^2$) | Efficiency (cd/A) | Emission color | Half lifespan (hr @100 mA/cm$^2$) |
|---|---|---|---|---|---|---|---|
| Example 1 | Compound 1 | 5.83 | 50 | 3210 | 6.42 | Blue | 376 |
| Example 2 | Compound 5 | 5.66 | 50 | 3330 | 6.66 | Blue | 359 |
| Example 3 | Compound 7 | 5.72 | 50 | 3165 | 6.33 | Blue | 292 |
| Example 4 | Compound 8 | 5.79 | 50 | 3340 | 6.68 | Blue | 366 |
| Example 5 | Compound 144 | 5.89 | 50 | 3210 | 6.42 | Blue | 319 |
| Example 6 | Compound 167 | 5.64 | 50 | 3290 | 6.58 | Blue | 368 |
| Example 7 | Compound 172 | 5.62 | 50 | 3395 | 6.79 | Blue | 389 |
| Example 8 | Compound 174 | 5.61 | 50 | 3380 | 6.76 | Blue | 393 |
| Example 9 | Compound 183 | 5.71 | 50 | 3335 | 6.67 | Blue | 368 |
| Example 10 | Compound 185 | 5.64 | 50 | 3270 | 6.54 | Blue | 356 |
| Example 11 | Compound 1A | 6.03 | 50 | 3070 | 6.14 | Blue | 342 |
| Example 12 | Compound 5A | 5.82 | 50 | 3170 | 6.34 | Blue | 327 |
| Example 13 | Compound 9A | 5.76 | 50 | 3135 | 6.27 | Blue | 278 |
| Example 14 | Compound 17A | 5.94 | 50 | 3035 | 6.07 | Blue | 354 |
| Example 15 | Compound 25A | 5.98 | 50 | 3105 | 6.21 | Blue | 326 |
| Example 16 | Compound 71A | 6.12 | 50 | 2990 | 5.98 | Blue | 372 |
| Example 17 | Compound 110A | 5.87 | 50 | 3240 | 6.48 | Blue | 318 |
| Example 18 | Compound 142A | 5.66 | 50 | 3285 | 6.57 | Blue | 347 |
| Example 19 | Compound 160A | 5.94 | 50 | 3205 | 6.41 | Blue | 336 |
| Example 20 | Compound 164A | 6.07 | 50 | 3255 | 6.51 | Blue | 327 |
| Comparative Example 1 | NPB | 7.01 | 50 | 2645 | 5.29 | Blue | 258 |

Example 1

As illustrated in Table 2, the organic light-emitting devices manufactured according to Examples 1 to 20 have lower driving voltage, higher brightness, higher efficiency, and longer half-lifespan than the organic light-emitting device manufactured according to Comparative Example 1.

Example 21

An organic light-emitting device was manufactured in the same or substantially the same manner as in Example 1, except that in forming a hole transport layer, NPB was used instead of Compound 1, and in forming an emission layer, as a dopant, Compound 2 was used instead of TPD.

Examples 22 to 36

Organic light-emitting devices were manufactured in the same or substantially the same manner as in Example 21, except that in forming an emission layer, for use as a dopant, corresponding compounds shown in Table 3 were used instead of Compound 2.

Example 37

An organic light-emitting device was manufactured in the same or substantially the same manner as in Example 21, except that in forming a hole transport layer, Compound 172 was used instead of NPB.

Examples 38 to 41

Organic light-emitting devices were each manufactured in the same or substantially the same manner as in Example 37, except that in forming an emission layer, for use as a dopant, corresponding compounds shown in Table 3 were used Instead of Compound 2.

Examples 42 to 57

Organic light-emitting devices were each manufactured in the same or substantially the same manner as in Example 21, except that in forming an emission layer, for use as a dopant, corresponding compounds shown in Table 3 were used Instead of Compound 2.

Example 58

An organic light-emitting device was manufactured in the same or substantially the same manner as in Example 42, except that in forming a hole transport layer, Compound 142A was used instead of NPB.

Examples 59 to 62

Organic light-emitting devices were each manufactured in the same or substantially the same manner as in Example 58, except that in forming an emission layer, for use as a dopant, corresponding compounds shown in Table 3 were used Instead of Compound 2A.

Comparative Example 2

An organic light-emitting device was manufactured in the same or substantially the same manner as in Example 21, except that in forming an emission layer, as a dopant, Compound A was used instead of Compound 2.

Compound A

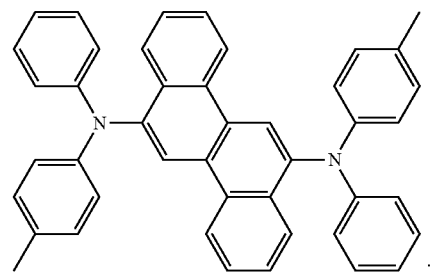

Comparative Example 3

An organic light-emitting device was manufactured in the same or substantially the same manner as in Example 21, except that in forming an emission layer, as a dopant, Compound B was used instead of Compound 2.

Compound B

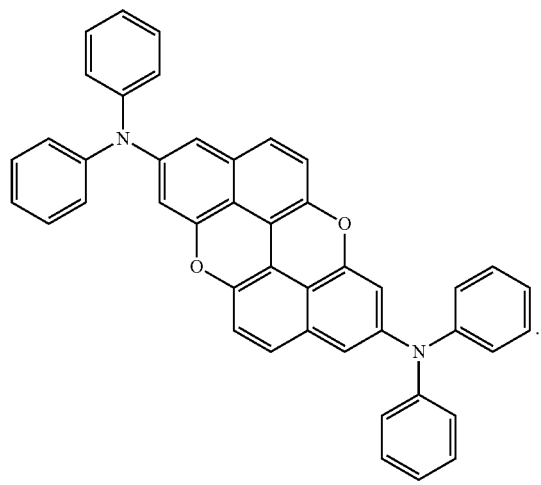

Comparative Example 4

An organic light-emitting device was manufactured in the same or substantially the same manner as in Example 21, except that in forming an emission layer, as a dopant, Compound C was used instead of Compound 2.

Compound C

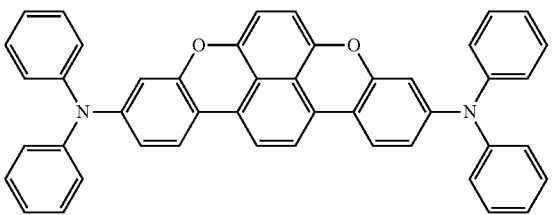

Evaluation Example 2

The driving voltage, current density, brightness, efficiency, and half-lifespan of the organic light-emitting devices manufactured according to Examples 21 to 62, and Comparative Examples 1 to 4 were measured by using Keithley SMU 236 (from Keithley Instruments Inc.) and a brightness photometer $PR_{650}$ (from Photo Research, Inc.), and the results are shown in Table 3. The half-lifespan as used herein is a period of time that it takes for the brightness of the organic light-emitting device to reduce to 50% of the initial brightness.

An organic light-emitting device including the compound according to embodiments of the present invention may have low driving voltage, high efficiency, high brightness, and long lifespan.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

TABLE 3

|  | Hole transport layer | Dopant | Driving voltage (V) | Current Density (mA/cm$^2$) | Brightness (cd/m$^2$) | Efficiency (cd/A) | Emission color | Half lifespan (hr @100 mA/cm$^2$) |
|---|---|---|---|---|---|---|---|---|
| Example 21 | NPB | Compound 2 | 6.83 | 50 | 3565 | 7.13 | Blue | 336 |
| Example 22 | NPB | Compound 9 | 6.84 | 50 | 3460 | 6.92 | Blue | 349 |
| Example 23 | NPB | Compound 13 | 6.87 | 50 | 3575 | 7.15 | Blue | 346 |
| Example 24 | NPB | Compound 15 | 6.86 | 50 | 3555 | 7.11 | Blue | 358 |
| Example 25 | NPB | Compound 19 | 6.89 | 50 | 3525 | 7.05 | Blue | 339 |
| Example 26 | NPB | Compound 26 | 6.84 | 50 | 3545 | 7.09 | Blue | 348 |
| Example 27 | NPB | Compound 29 | 6.87 | 50 | 3505 | 7.01 | Blue | 329 |
| Example 28 | NPB | Compound 30 | 6.87 | 50 | 3360 | 6.72 | Blue | 333 |
| Example 29 | NPB | Compound 38 | 6.86 | 50 | 3570 | 7.14 | Blue | 318 |
| Example 30 | NPB | Compound 54 | 6.84 | 50 | 3465 | 6.93 | Blue | 356 |
| Example 31 | NPB | Compound 57 | 6.83 | 50 | 3560 | 7.12 | Blue | 366 |
| Example 32 | NPB | Compound 72 | 6.85 | 50 | 3550 | 7.1 | Blue | 359 |
| Example 33 | NPB | Compound 88 | 6.85 | 50 | 3575 | 7.15 | Blue | 342 |
| Example 34 | NPB | Compound 90 | 6.86 | 50 | 3565 | 7.13 | Blue | 363 |
| Example 35 | NPB | Compound 129 | 6.86 | 50 | 3460 | 6.92 | Blue | 347 |
| Example 36 | NPB | Compound 134 | 6.87 | 50 | 3455 | 6.91 | Blue | 338 |
| Example 37 | Compound 172 | Compound 2 | 5.56 | 50 | 3690 | 7.38 | Blue | 397 |
| Example 38 | Compound 172 | Compound 13 | 5.55 | 50 | 3725 | 7.45 | Blue | 389 |
| Example 39 | Compound 172 | Compound 38 | 5.56 | 50 | 3755 | 7.51 | Blue | 328 |
| Example 40 | Compound 172 | Compound 57 | 5.55 | 50 | 3765 | 7.53 | Blue | 415 |
| Example 41 | Compound 172 | Compound 88 | 5.54 | 50 | 3785 | 7.57 | Blue | 408 |
| Example 42 | NPB | Compound 2A | 6.79 | 50 | 3570 | 7.14 | Blue | 343 |
| Example 43 | NPB | Compound 3A | 6.75 | 50 | 3455 | 6.91 | Blue | 321 |
| Example 44 | NPB | Compound 11A | 6.65 | 50 | 3520 | 7.04 | Blue | 307 |
| Example 45 | NPB | Compound 15A | 6.72 | 50 | 3460 | 6.92 | Blue | 342 |
| Example 46 | NPB | Compound 27A | 6.84 | 50 | 3420 | 6.84 | Blue | 347 |
| Example 47 | NPB | Compound 32A | 6.87 | 50 | 3490 | 6.98 | Blue | 351 |
| Example 48 | NPB | Compound 50A | 6.92 | 50 | 3560 | 7.12 | Blue | 319 |
| Example 49 | NPB | Compound 56A | 6.68 | 50 | 3630 | 7.26 | Blue | 342 |
| Example 50 | NPB | Compound 72A | 6.78 | 50 | 3605 | 7.21 | Blue | 327 |
| Example 51 | NPB | Compound 83A | 6.85 | 50 | 3420 | 6.84 | Blue | 342 |
| Example 52 | NPB | Compound 88A | 6.78 | 50 | 3505 | 7.01 | Blue | 324 |
| Example 53 | NPB | Compound 106A | 6.81 | 50 | 3410 | 6.82 | Blue | 337 |
| Example 54 | NPB | Compound 120A | 6.88 | 50 | 3525 | 7.05 | Blue | 314 |
| Example 55 | NPB | Compound 125A | 6.85 | 50 | 3495 | 6.99 | Blue | 319 |
| Example 56 | NPB | Compound 137A | 6.77 | 50 | 3410 | 6.82 | Blue | 346 |
| Example 57 | NPB | Compound 161A | 6.92 | 50 | 3480 | 6.96 | Blue | 327 |
| Example 58 | Compound 142A | Compound 2A | 5.42 | 50 | 3620 | 7.24 | Blue | 397 |
| Example 59 | Compound 142A | Compound 11A | 5.44 | 50 | 3685 | 7.37 | Blue | 407 |
| Example 60 | Compound 142A | Compound 56A | 5.52 | 50 | 3805 | 7.61 | Blue | 369 |
| Example 61 | Compound 142A | Compound 72A | 5.47 | 50 | 3705 | 7.41 | Blue | 401 |
| Example 62 | Compound 142A | Compound 120A | 5.61 | 50 | 3655 | 7.31 | Blue | 384 |
| Comparative Example 1 | NPB | TPD | 7.01 | 50 | 2645 | 5.29 | Blue | 258 |
| Comparative Example 2 | NPB | Compound A | 6.95 | 50 | 2420 | 4.84 | Blue | 250 |
| Comparative Example 3 | NPB | Compound B | 6.68 | 50 | 3120 | 6.24 | Blue | 294 |
| Comparative Example 4 | NPB | Compound C | 6.84 | 50 | 2745 | 5.49 | Blue | 338 |

As Illustrated in Table 3, it was confirmed that the organic light-emitting devices manufactured according to Examples 21 to 62 have higher driving voltage, higher brightness, higher efficiency, and/or longer half-lifespan than the organic light-emitting devices manufactured according to Comparative Examples 1 to 4.

While one or more exemplary embodiments have been described with reference to the figures, it will be understood by those of ordinary skill in the art that various changes in form and details may be made therein without departing from the spirit and scope as defined by the following claims and equivalents thereof.

What is claimed is:
1. A condensed cyclic compound represented by Formula 1:

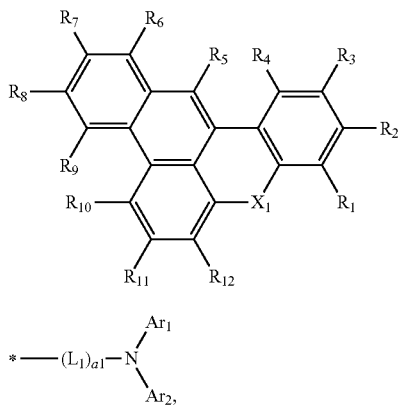

Formula 1

Formula 2

$$*\!\!-\!\!(L_1)_{a1}\!\!-\!\!N\!\!\begin{array}{c}Ar_1\\ \\Ar_2,\end{array}$$

wherein in Formulae 1 and 2, $X_1$ is O or S;

$L_1$ is each Independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 is selected from 0, 1, 2, and 3, and when a1 is two or more, a plurality of $L_1$ are identical to or different from each other;

$Ar_1$ and $Ar_2$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

$R_1$ to $R_{12}$ are each Independently selected from a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), and —B($Q_4$)($Q_5$);

at least two selected from $R_1$ to $R_{12}$ are each independently the group represented by Formula 2;

at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_1$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{10}$ heteroaryl group, a monovalent non-aromatic condensed polycyclic group, a monovalent non-aromatic condensed heteropolycyclic group, —Si($Q_{11}$)($Q_{12}$)($Q_{13}$), and —B($Q_{14}$)($Q_{15}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric add group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, —Si($Q_{21}$)($Q_{22}$)($Q_{23}$), and —B($Q_{24}$)($Q_{25}$); and —Si($Q_{31}$)($Q_{32}$)($Q_{33}$) and —B($Q_{34}$)($Q_{35}$), wherein $Q_1$ to $Q_5$, $Q_{11}$ to $Q_{15}$, $Q_{21}$ to $Q_{25}$, and $Q_{31}$ to $Q_{35}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The condensed cyclic compound of claim 1, wherein $L_1$ is selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, a isoxazolytene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrmidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

3. The condensed cyclic compound of claim 1, wherein $L_1$ is selected from a group represented by any one of Formulae 3-1 to 3-35:

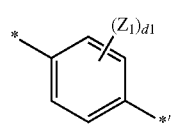

Formula 3-1

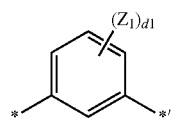

Formula 3-2

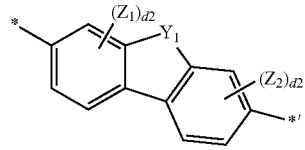

Formula 3-3

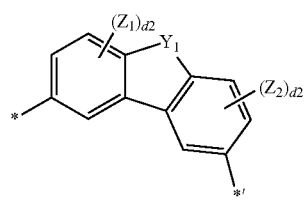

Formula 3-4

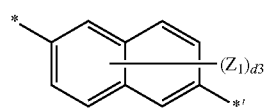

Formula 3-5

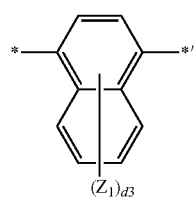

Formula 3-6

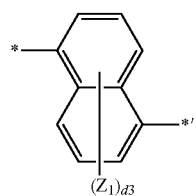

Formula 3-7

-continued

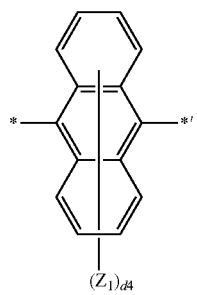

Formula 3-8

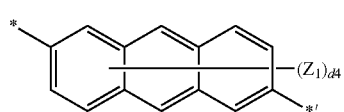

Formula 3-9

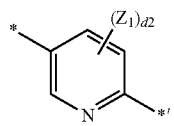

Formula 3-10

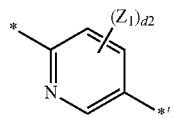

Formula 3-11

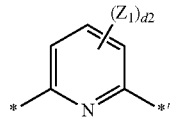

Formula 3-12

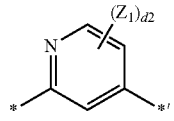

Formula 3-13

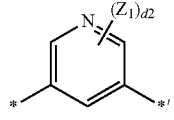

Formula 3-14

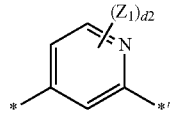

Formula 3-15

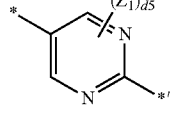

Formula 3-16

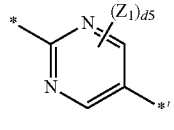

Formula 3-17

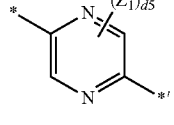

Formula 3-18

Formula 3-19
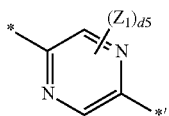

Formula 3-20
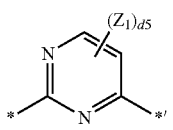

Formula 3-21
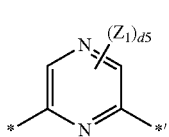

Formula 3-22
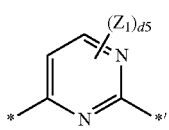

Formula 3-23
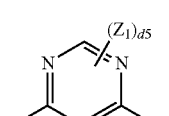

Formula 3-24
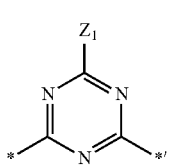

Formula 3-25
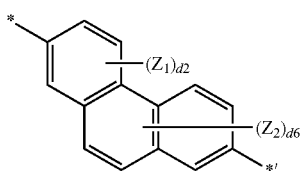

Formula 3-26
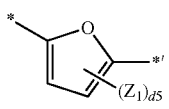

Formula 3-27
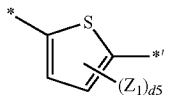

Formula 3-28
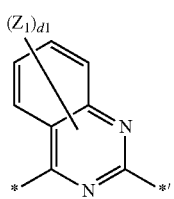

Formula 3-29
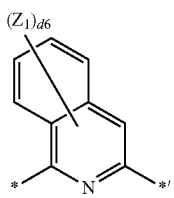

Formula 3-30
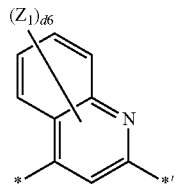

Formula 3-31
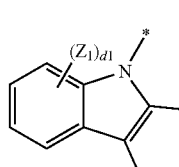

Formula 3-32
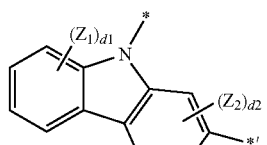

Formula 3-33
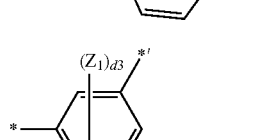

Formula 3-34
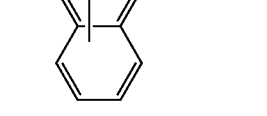

Formula 3-35
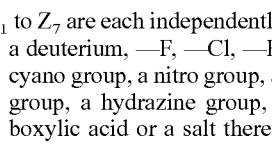

wherein in Formulae 3-1 to 3-35, $Y_1$ is O, S, $C(Z_3)(Z_4)$, $N(Z_5)$, or $Si(Z_6)(Z_7)$;

$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 is an integer selected from 1, 2, 3, and 4, d2 is an integer selected from 1, 2, and 3, d3 is an integer selected from 1, 2, 3, 4, 5, and 6, d4 is an integer selected from 1, 2, 3, 4, 5, 6, 7, and 8, d5 is 1 or 2, and d6 is an integer selected from 1, 2, 3, 4, and 5, and * and *' each indicate a binding site to a neighboring atom.

4. The condensed cyclic compound of claim 1, wherein $L_1$ is selected from a group represented by any one of Formulae 4-1 to 4-28:

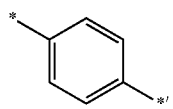

Formula 4-1

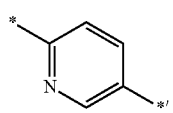

Formula 4-2

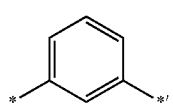

Formula 4-3

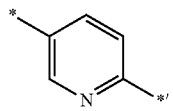

Formula 4-4

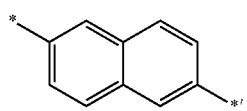

Formula 4-5

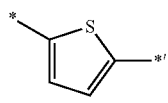

Formula 4-6

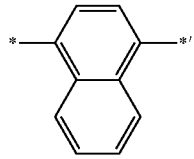

Formula 4-7

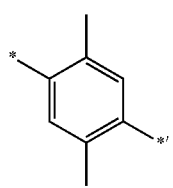

Formula 4-8

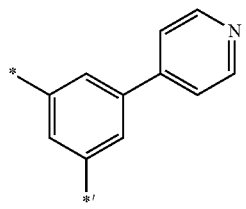

Formula 4-9

-continued

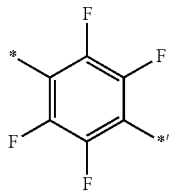

Formula 4-10

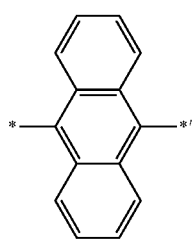

Formula 4-11

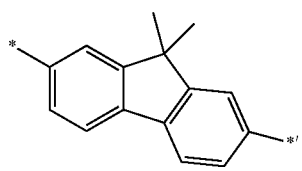

Formula 4-12

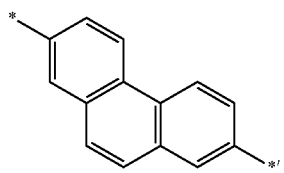

Formula 4-13

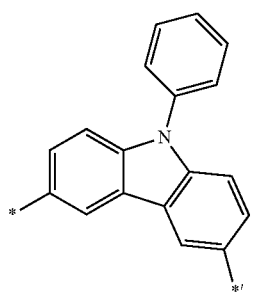

Formula 4-14

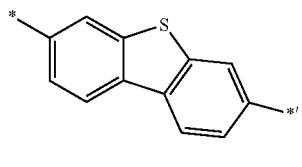

Formula 4-15

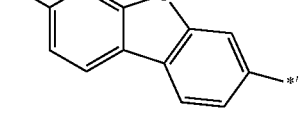

Formula 4-16

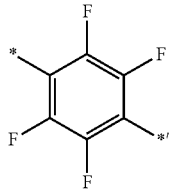

Formula 4-17

-continued

Formula 4-18
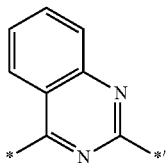

Formula 4-19
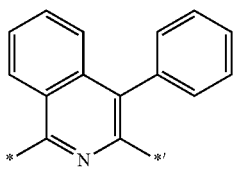

Formula 4-20
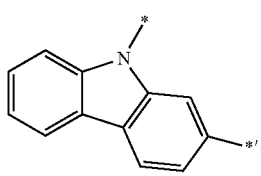

Formula 4-21
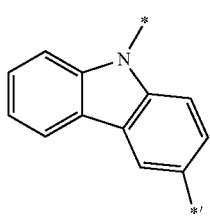

Formula 4-22
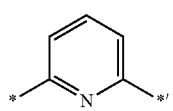

Formula 4-23
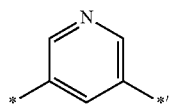

Formula 4-24
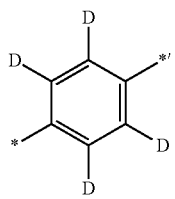

Formula 4-25
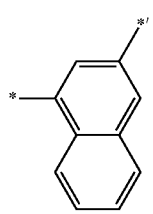

Formula 4-26
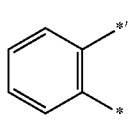

-continued

Formula 4-27
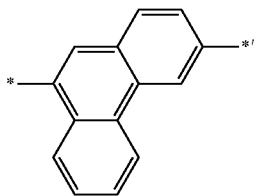

Formula 4-28
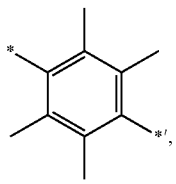

wherein * and *' in Formulae 4-1 to 4-28 each indicate a binding site to a neighboring atom.

5. The condensed cyclic compound of claim 1, wherein a1 is 0 or 1.

6. The condensed cyclic compound of claim 1, wherein $Ar_1$ and $Ar_2$ are each Independently selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an Isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzosilolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group and a dibenzocarbazolyl group, a thiadiazolyl group, an imidazopyridinyl group, an imidazopyrimidinyl group, and —Si($Q_{31}$)($Q_{32}$)($Q_{33}$); and wherein $Q_{31}$ to $Q_{33}$ are each independently selected from a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzooxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group.

7. The condensed cyclic compound of claim 1, wherein $Ar_1$ and $Ar_2$ are each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$) ($Q_{33}$), and wherein $Q_{31}$ to $Q_{33}$ are each Independently selected from a $C_1$-$C_{10}$ alkyl group, a $C_1$-$C_{10}$ alkoxy group, a phenyl group, and a naphthyl group.

8. The condensed cyclic compound of claim 1, wherein $Ar_1$ and $Ar_2$ are each independently selected from:

a phenyl group, a naphthyl group, a fluorenyl group, a phenanthrenyl group, a pyridinyl group, a pyrimidinyl group, a triazinyl group, a dibenzofuranyl group, and a dibenzothiophenyl group; and a phenyl group, a naphthyl group, a fluorenyl group, a phenanthrenyl group, a pyridinyl group, a pyrimidinyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a phenanthrenyl group, a pyridinyl group, a pyrimidinyl group, a triazinyl group, a dibenzofuranyl group, a dibenzothiophenyl group, and —Si($Q_{31}$)($Q_{32}$) ($Q_{33}$), and wherein $Q_{31}$ to $Q_{33}$ are each independently selected from a $C_1$-$C_{10}$ alkyl group, a $C_1$-$C_{10}$ alkoxy group, a phenyl group, and a naphthyl group.

9. The condensed cyclic compound of claim 1, wherein $R_1$ to $R_{12}$ are each independently selected from:

a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group, and —Si($Q_{31}$)($Q_{32}$) ($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, and a naphthyl group.

10. The condensed cyclic compound of claim 1, wherein $R_1$ to $R_{12}$ are each independently selected from:

a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, and a $C_1$-$C_{10}$ alkoxy group;

a phenyl group, a naphthyl group, a pyrimidinyl group, and a triazinyl group;

a phenyl group, a naphthyl group, a pyridinyl group, a pyrimidinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, and a naphthyl group.

11. The condensed cyclic compound of claim 1, wherein $Ar_1$ and $Ar_2$ are each independently selected from a group represented by any one of Formula 5-1 to Formula 5-42, and $R_1$ to $R_{12}$ are each independently selected from a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid and a salt thereof, a $C_1$-$C_{20}$ alkyl group, a $C_1$-$C_2$ alkoxyl group, and the group represented by any one of Formula 5-1 to Formula 5-42:

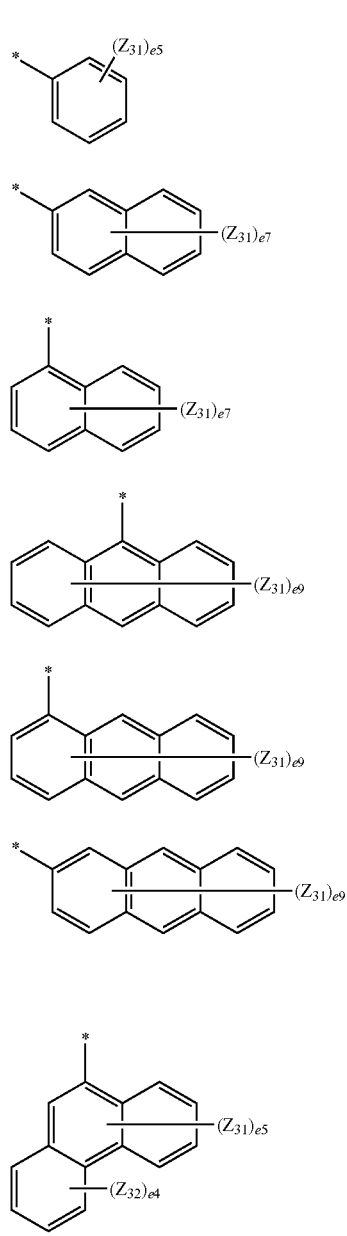

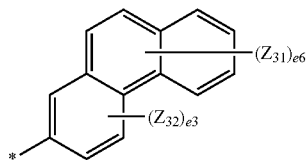

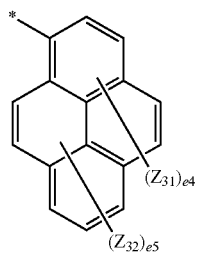

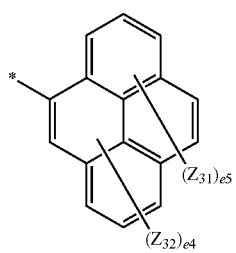

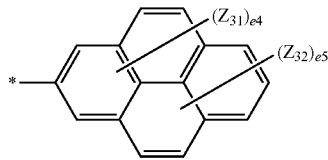

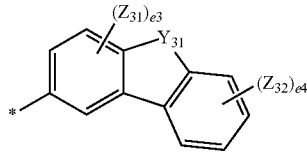

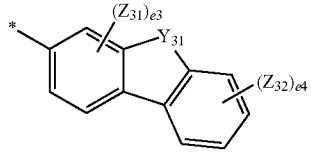

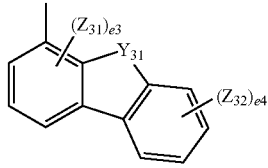

-continued
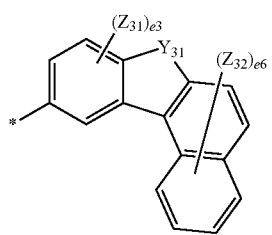
Formula 5-16
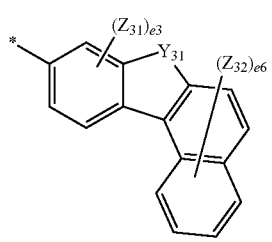
Formula 5-17
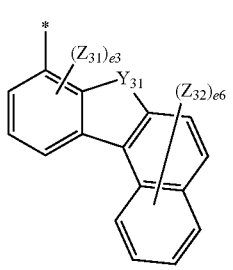
Formula 5-18
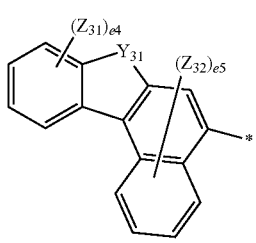
Formula 5-19
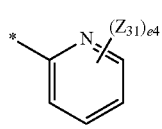
Formula 5-20
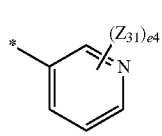
Formula 5-21
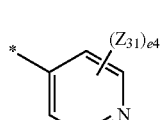
Formula 5-22
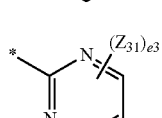
Formula 5-23
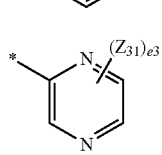
Formula 5-24
-continued
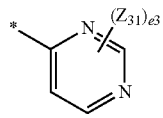
Formula 5-25
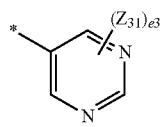
Formula 5-26
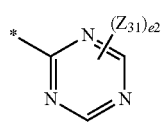
Formula 5-27
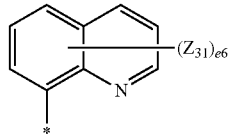
Formula 5-28
Formula 5-29
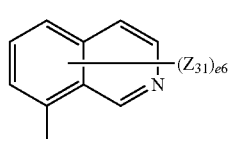
Formula 5-30
Formula 5-31
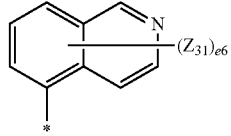
Formula 5-32
Formula 5-33
Formula 5-34
Formula 5-35

-continued

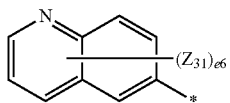
Formula 5-36

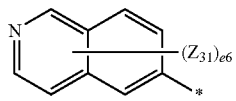
Formula 5-37

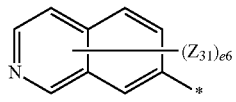
Formula 5-38

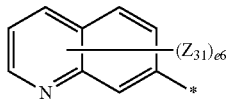
Formula 5-39

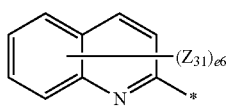
Formula 5-40

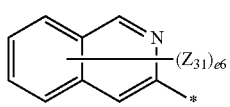
Formula 5-41

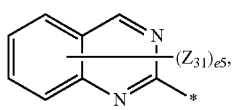
Formula 5-42 wherein in Formulae 5-1 to 5-42,
$Y_{31}$ is O, S, $C(Z_{23})(Z_{34})$, $N(Z_{35})$, or $Si(Z_{36})(Z_{37})$;
$Z_{31}$ to $Z_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spirofluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group,
e2 is 1 or 2, e3 is an integer selected from 1, 2, and 3, e4 is an integer selected from 1, 2, 3, and 4, e5 is an integer selected from 1, 2, 3, 4, and 5, e6 is an integer selected from 1, 2, 3, 4, 5, and 6, e7 is an integer selected from 1, 2, 3, 4, 5, 6, and 7, e9 is an integer selected from 1, 2, 3, 4, 5, 6, 7, 8, and 9, and * Indicates a binding site to a neighboring atom.

12. The condensed cyclic compound of claim 1, wherein $Ar_1$ and $Ar_2$ are each independently selected from a group represented by any one of Formula 6-1 to Formula 6-29, and
$R_1$ to $R_{12}$ are each Independently selected from:
a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid and a salt thereof, a $C_1$-$C_{20}$ alkyl group, a $C_1$-$C_2$ alkoxyl group, a phenyl group, a naphthyl group, a pyridinyl group, a pyrimidinyl group, and a triazinyl group:

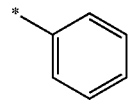
Formula 6-1

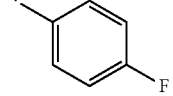
Formula 6-2

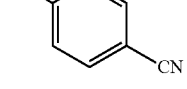
Formula 6-3

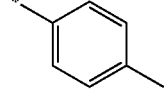
Formula 6-4

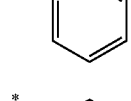
Formula 6-5

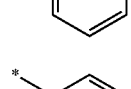
Formula 6-6

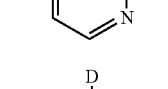
Formula 6-7

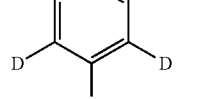
Formula 6-8

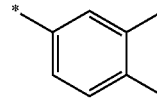
Formula 6-9

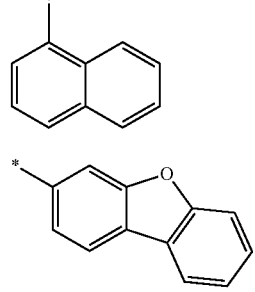
Formula 6-10

Formula 6-11

-continued
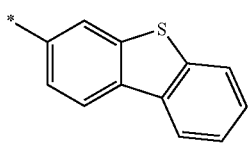
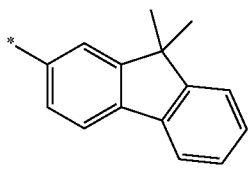
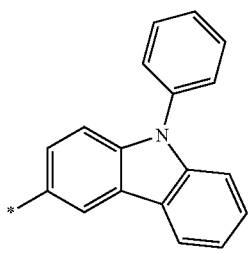
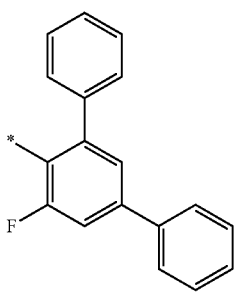
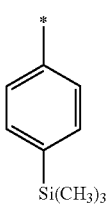
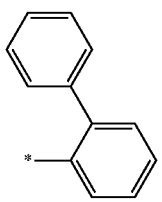
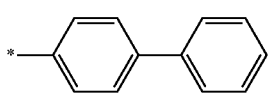
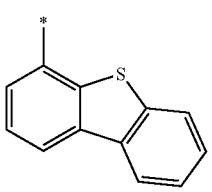
-continued
Formula 6-12
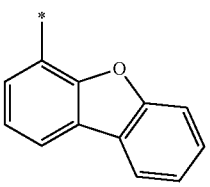
Formula 6-13
Formula 6-14
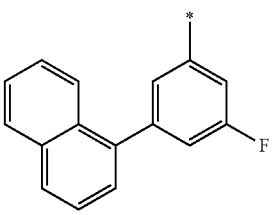
Formula 6-15
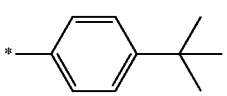
Formula 6-16
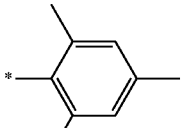
Formula 6-17
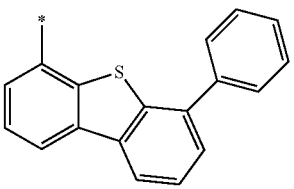
Formula 6-18
Formula 6-19
Formula 6-20
Formula 6-21
Formula 6-22
Formula 6-23
Formula 6-24
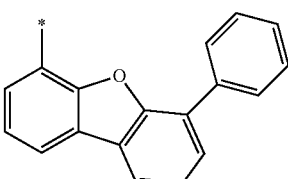
Formula 6-25
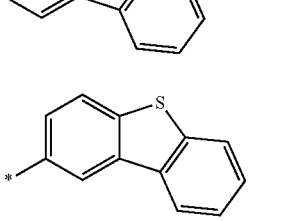
Formula 6-26
Formula 6-27
Formula 6-28
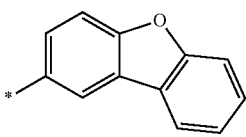

-continued

Formula 6-29

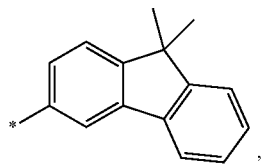

wherein * in Formulae 6-1 to 6-29 indicates a binding site to a neighboring atom.

13. The condensed cyclic compound of claim 1, wherein the condensed cyclic compound is represented by any one of Formulae 1-1 to 1-4:

Formula 1-1

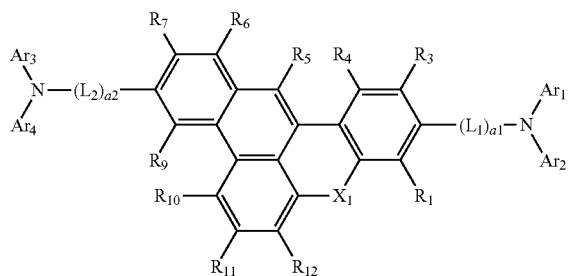

Formula 1-2

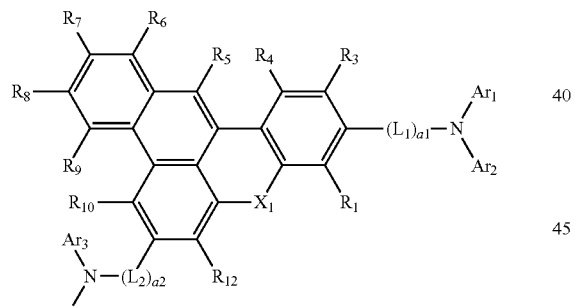

Formula 1-3

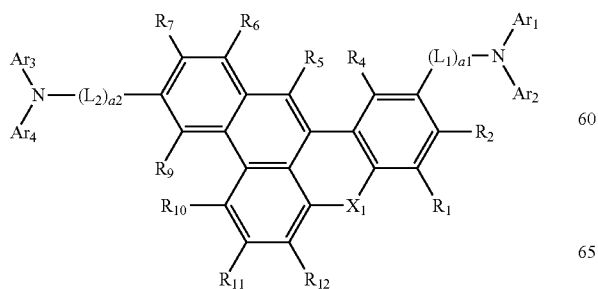

-continued

Formula 1-4

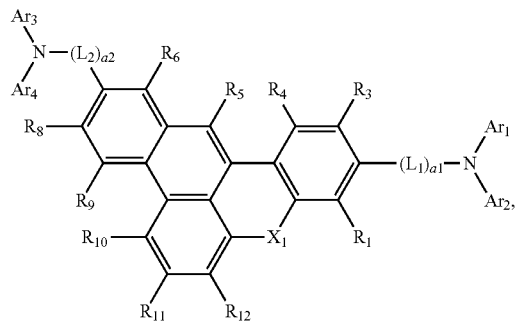

wherein in Formulae 1-1 to 1-4, descriptions of $L_2$, a2, $Ar_3$, and $Ar_4$ are the same as those of $L_1$, a1, $Ar_1$, and $Ar_2$, respectively.

14. The condensed cyclic compound of claim 1, wherein the condensed cyclic compound is represented by any one of Formulae 1-1(1) to 1-1(4):

Formula 1-1(1)

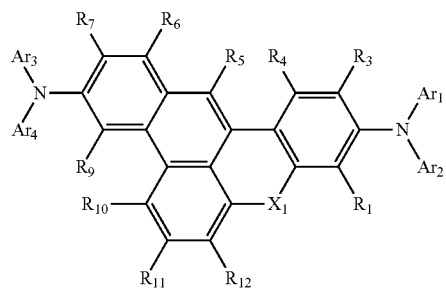

Formula 1-1(2)

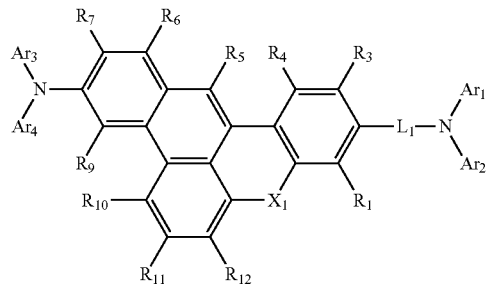

Formula 1-1(3)

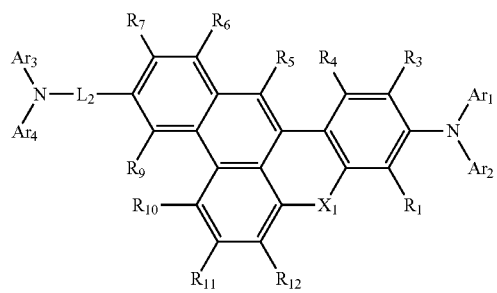

Formula 1-1(4)

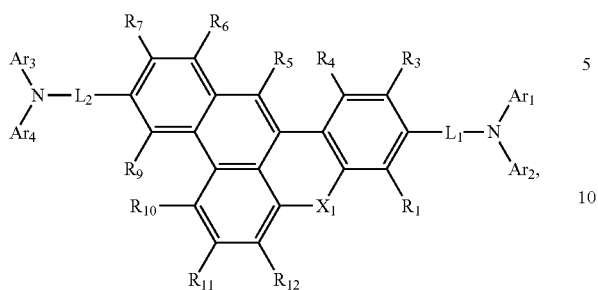

wherein in Formulae 1-1(1) to 1-1(4), descriptions of $L_2$, $a_2$, $Ar_3$, and $Ar_4$ are the same as those of $L_1$, a1, $Ar_1$, and $Ar_2$, respectively.

15. The condensed cyclic compound of claim 13, wherein
$R_1$ to $R_4$, and $R_6$ to $R_{12}$ are each a hydrogen,
$R_5$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group,
$L_1$ and $L_2$ are each independently selected from a group represented by any one of Formula 4-1 to Formula 4-28,
a1 and a2 are each independently 0 or 1, and
$Ar_1$ to $Ar_4$ are each independently selected from a group represented by any one of Formula 6-1 to Formula 6-29:

Formula 4-1

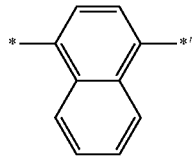

Formula 4-2

Formula 4-3

Formula 4-4

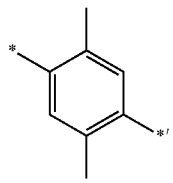

Formula 4-5

Formula 4-6

Formula 4-7

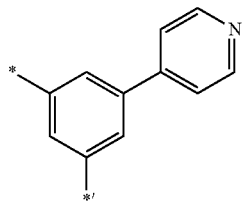

Formula 4-8

Formula 4-9

Formula 4-10

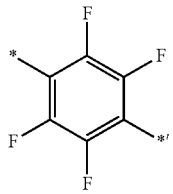

Formula 4-11

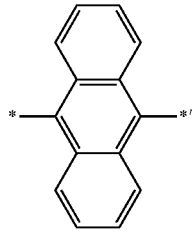

Formula 4-12

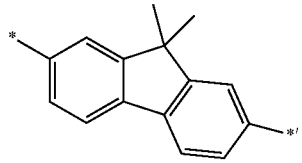

Formula 4-13

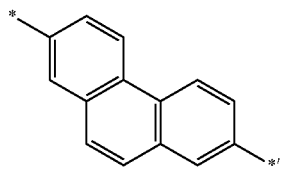

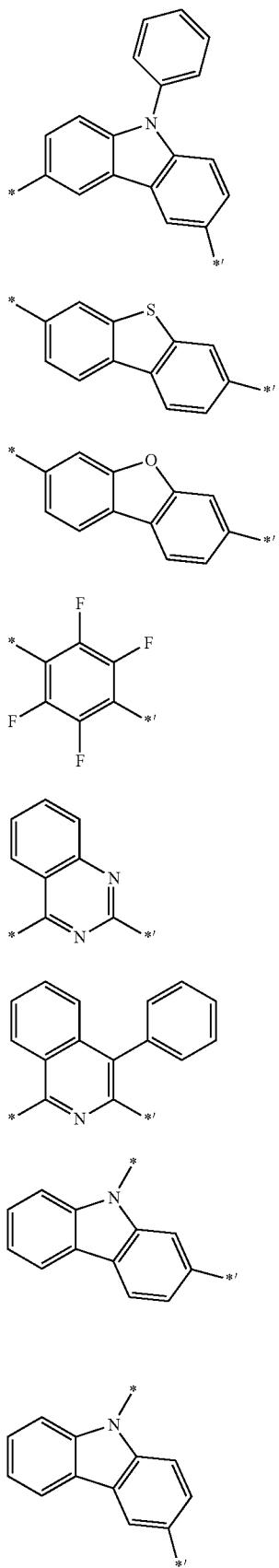
Formula 4-14
Formula 4-15
Formula 4-16
Formula 4-17
Formula 4-18
Formula 4-19
Formula 4-20
Formula 4-21
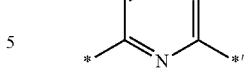
Formula 4-22
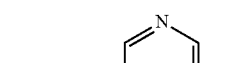
Formula 4-23
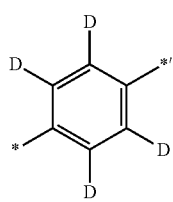
Formula 4-24
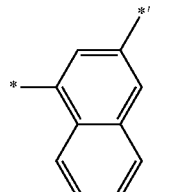
Formula 4-25
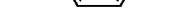
Formula 4-26
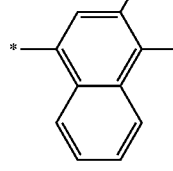
Formula 4-27
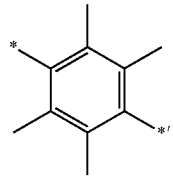
Formula 4-28
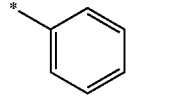
Formula 6-1
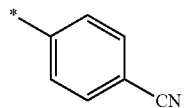
Formula 6-2
Formula 6-3
Formula 6-4

-continued
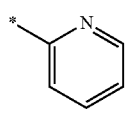
Formula 6-5
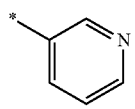
Formula 6-6
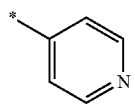
Formula 6-7
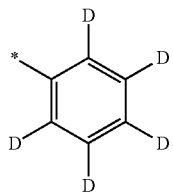
Formula 6-8
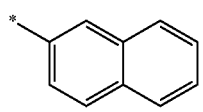
Formula 6-9
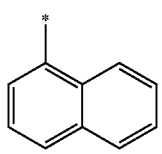
Formula 6-10
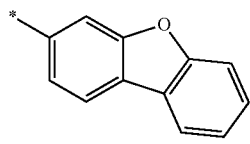
Formula 6-11
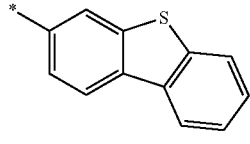
Formula 6-12
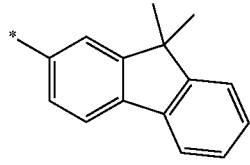
Formula 6-13
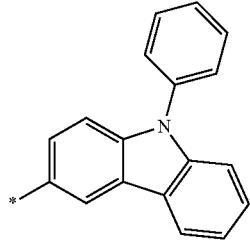
Formula 6-14
-continued
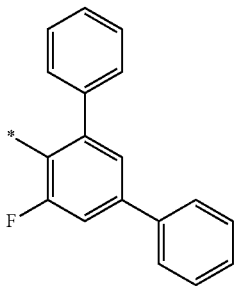
Formula 6-15
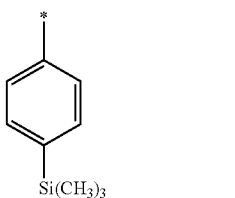
Formula 6-16
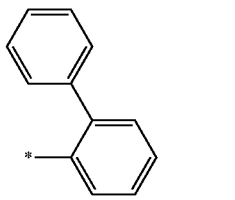
Formula 6-17
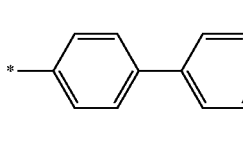
Formula 6-18
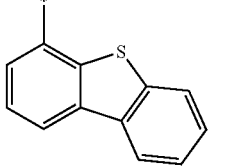
Formula 6-19
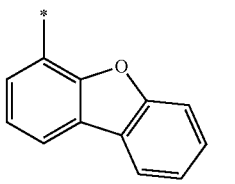
Formula 6-20
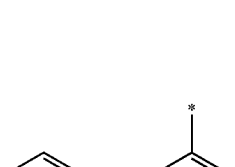
Formula 6-21
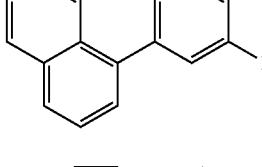
Formula 6-22
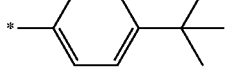

323
-continued
Formula 6-23
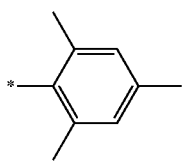
Formula 6-24
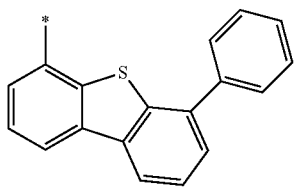
Formula 6-25
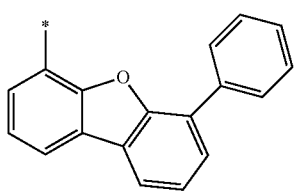
Formula 6-26
Formula 6-27
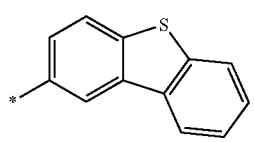
Formula 6-28
Formula 6-29
324
16. The condensed cyclic compound of claim 1, wherein the condensed cyclic compound is selected from Compounds 1 to 189 and 1A to 164A below:
1
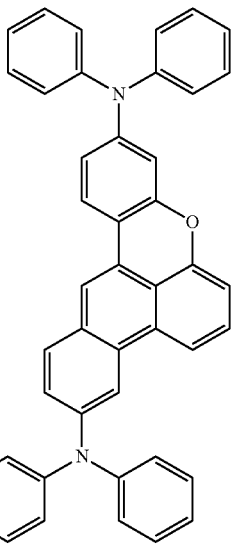
2
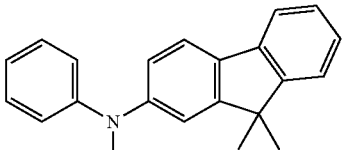
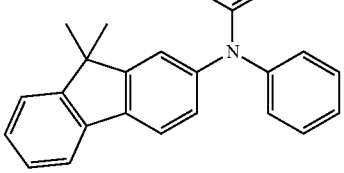

325
-continued
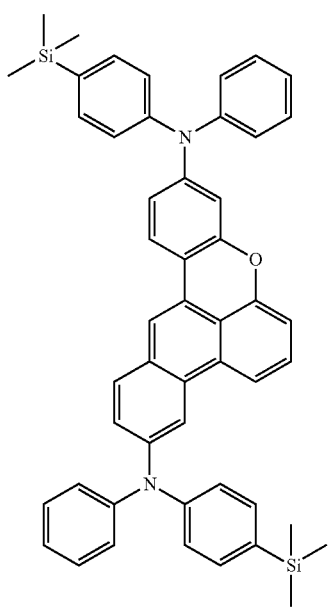
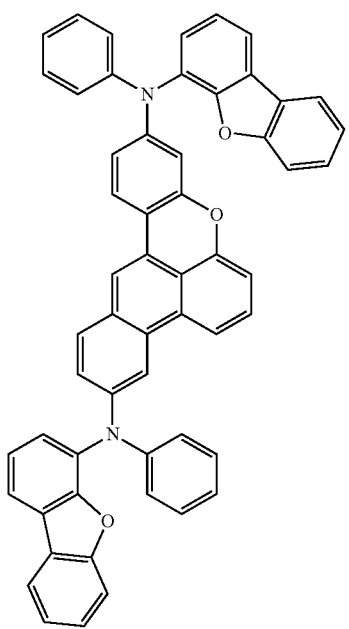
326
-continued
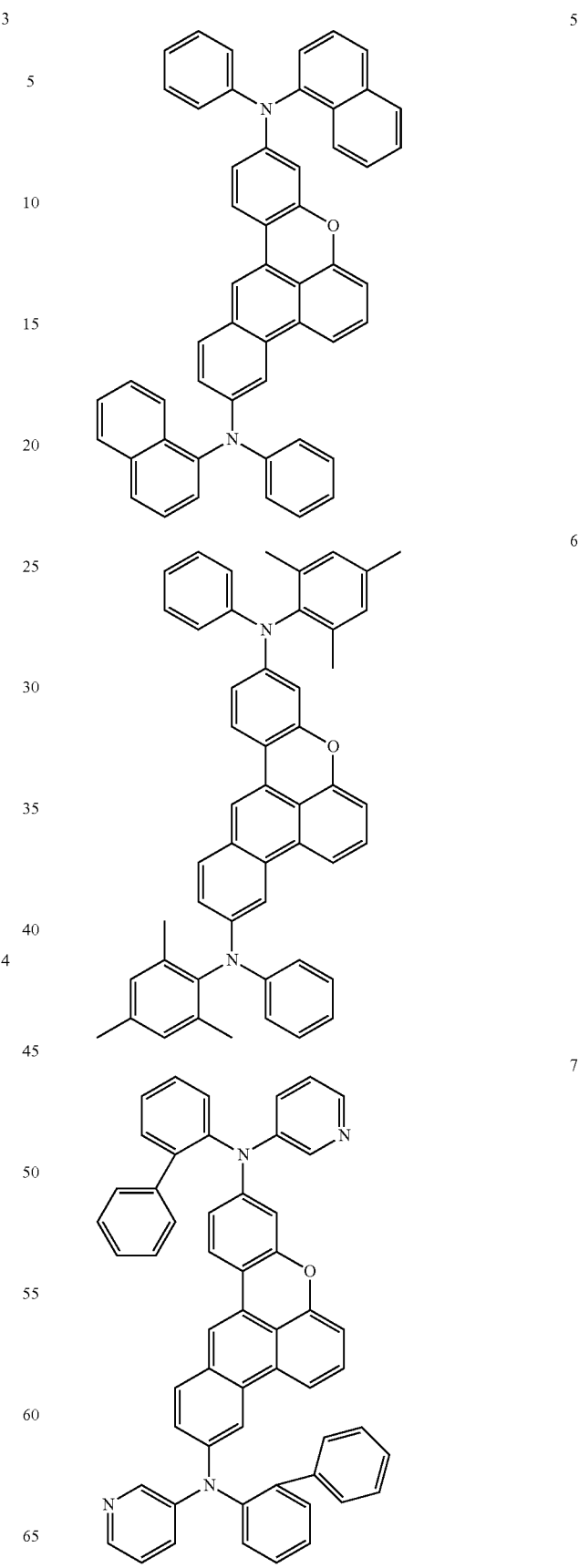

327
-continued
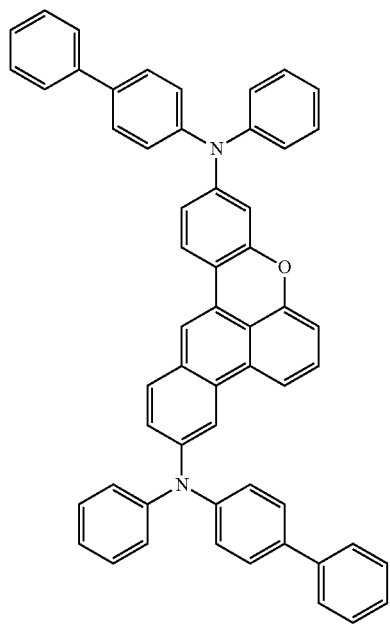
8
328
-continued
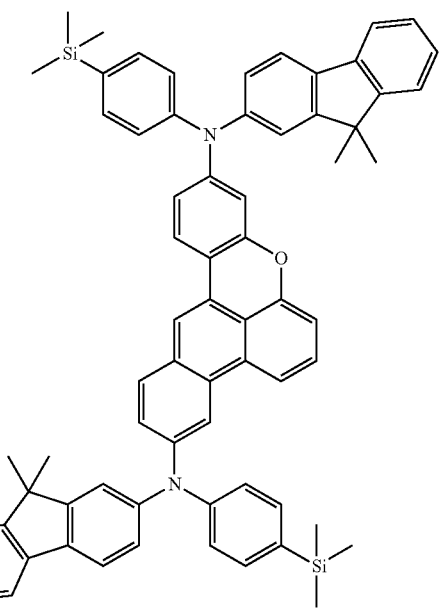
10
9
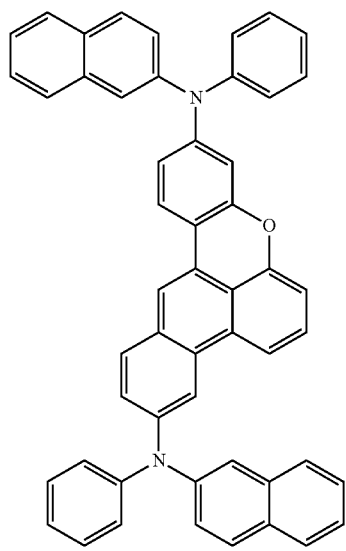
11
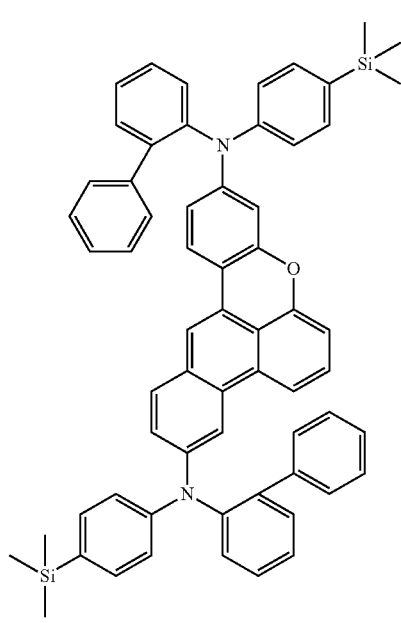

329
-continued
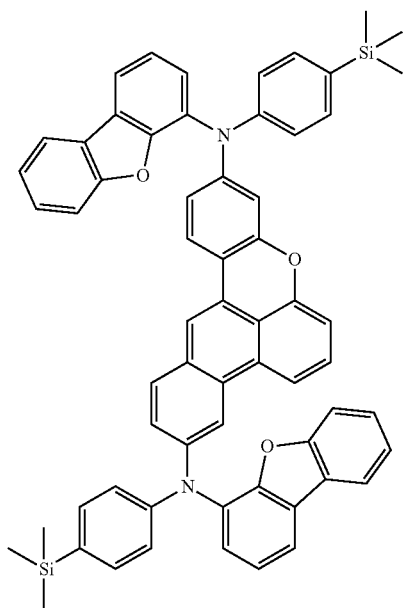
330
-continued
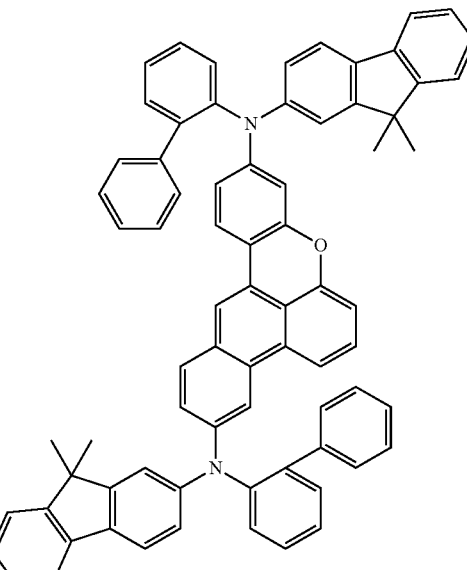
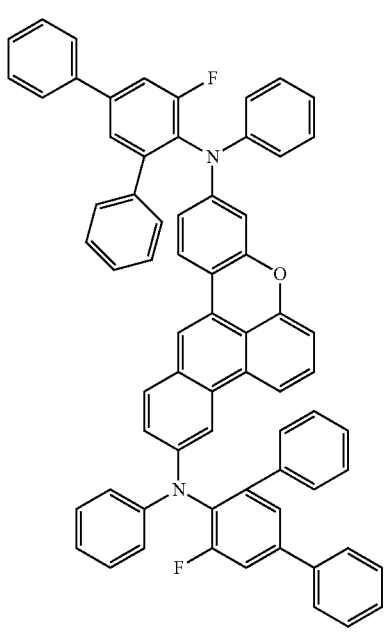

331
-continued
16
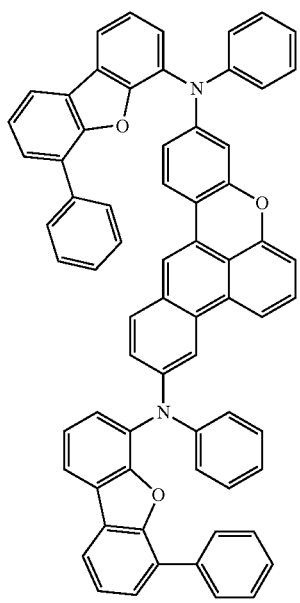
17
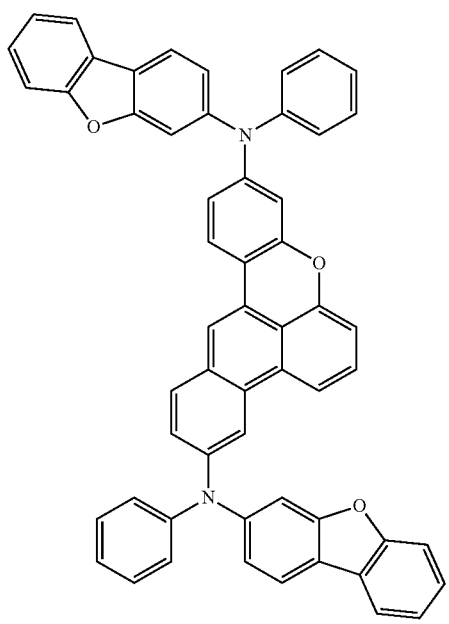
332
-continued
18
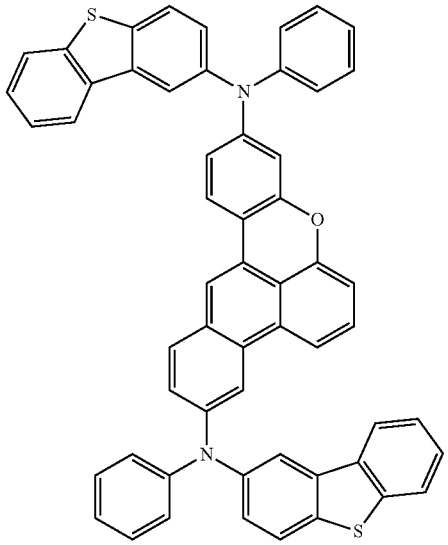
19
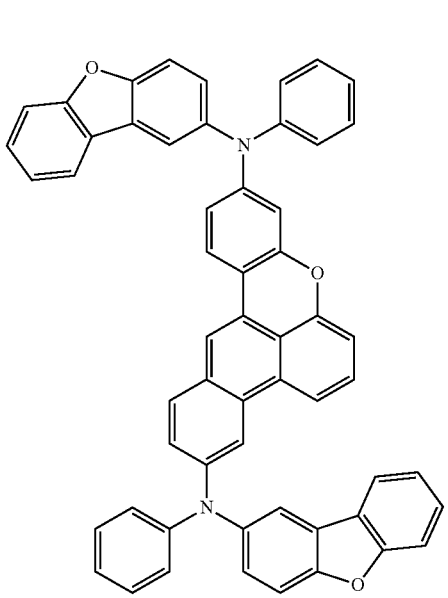

333
-continued
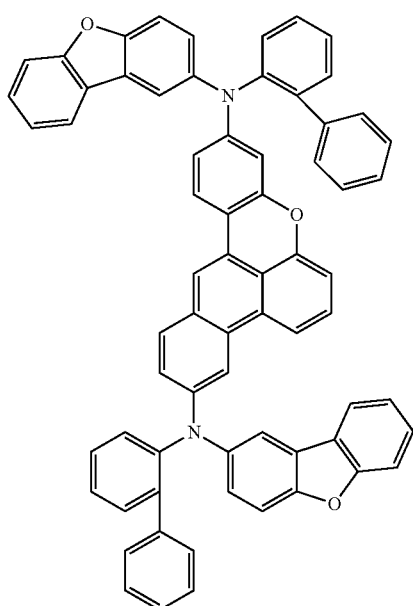
20
334
-continued
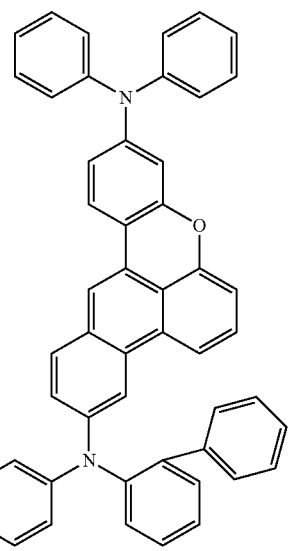
22
21
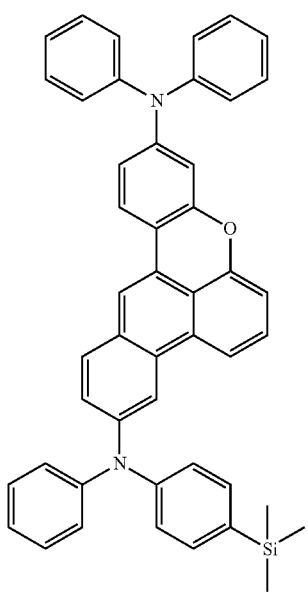
23
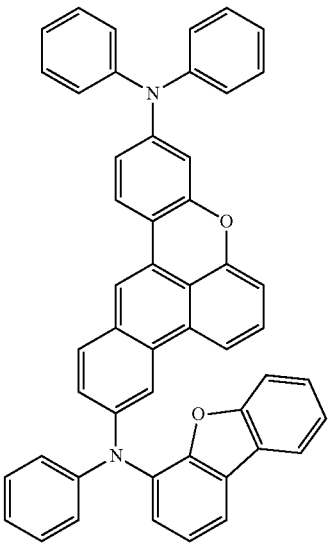

335
-continued
336
-continued
24
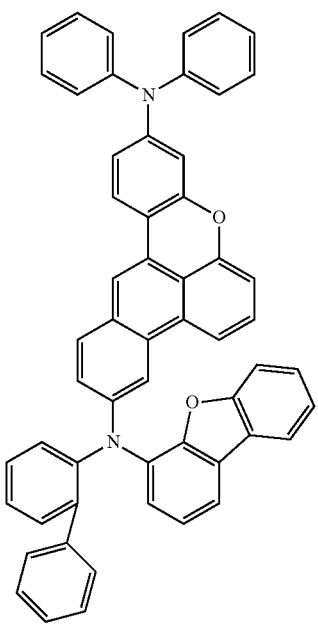
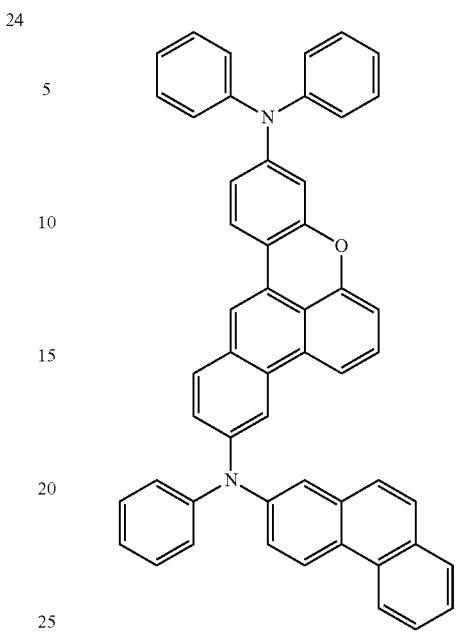
26
25
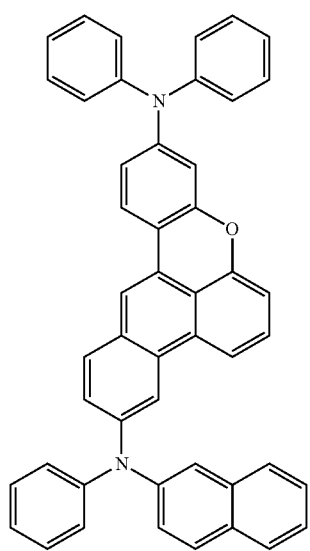
27
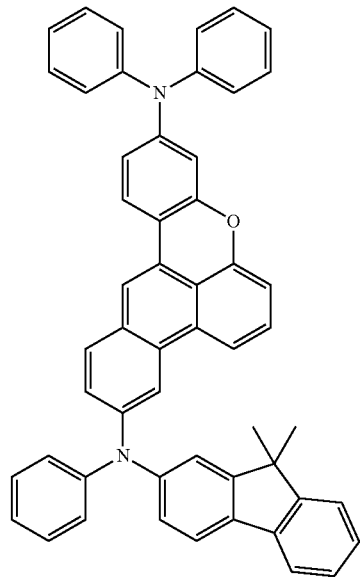

337
-continued
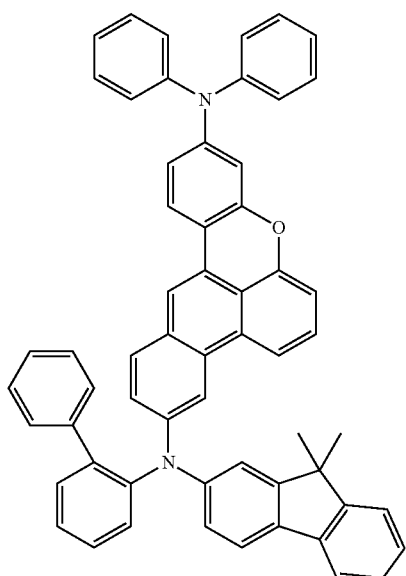
338
-continued
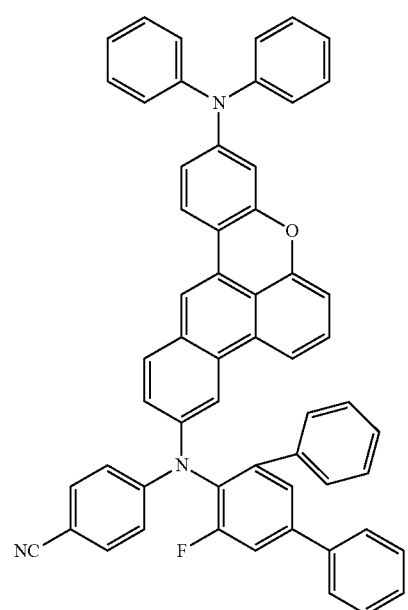
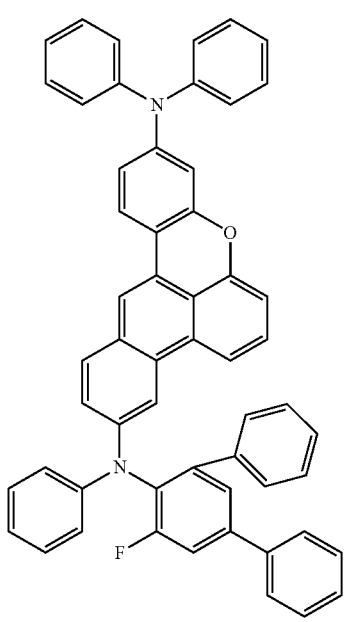
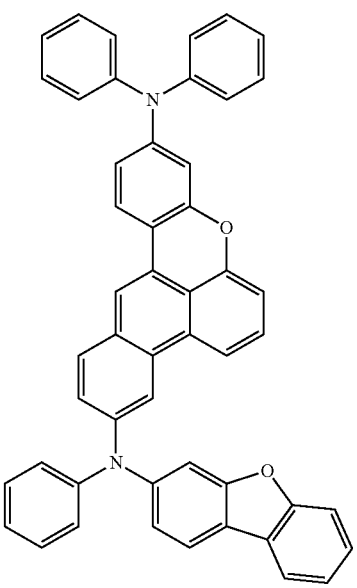

32
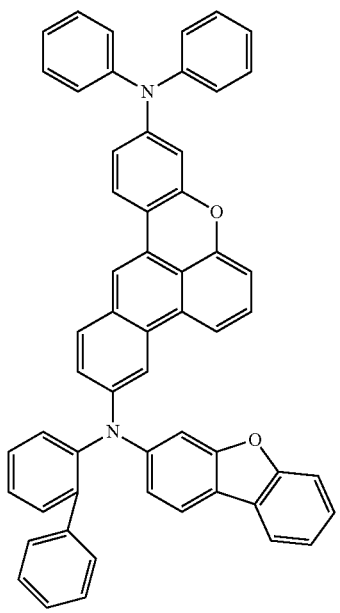
33
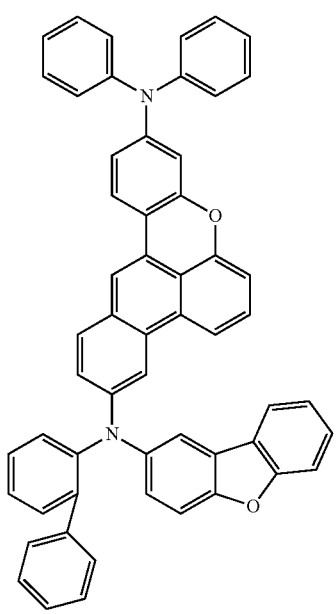
34
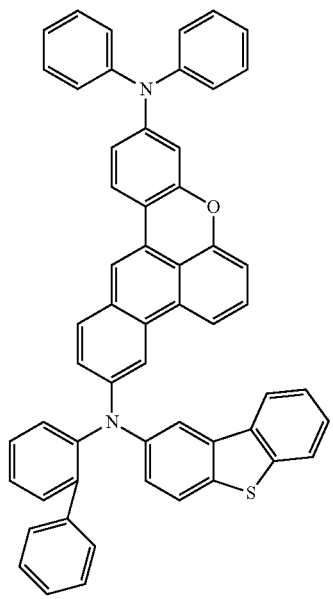
35
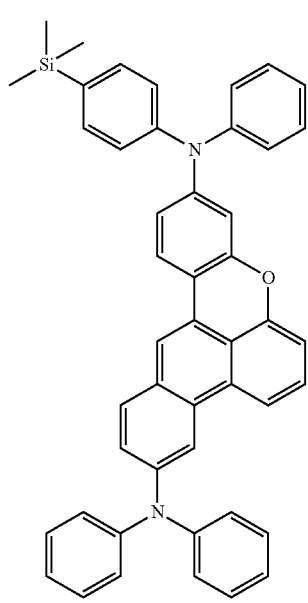

341
36
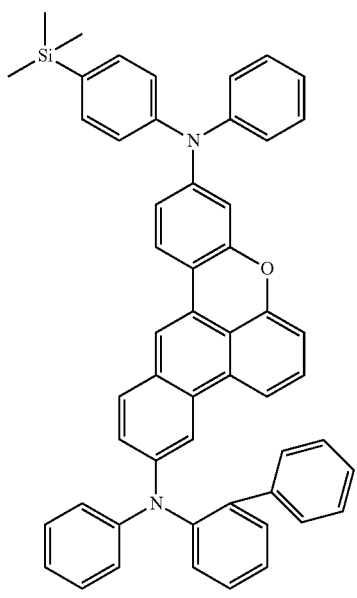
342
38
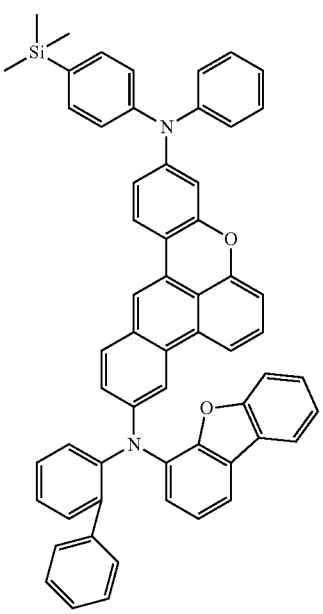
37
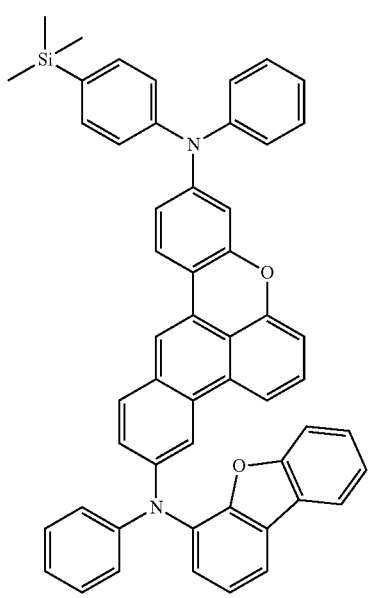
39
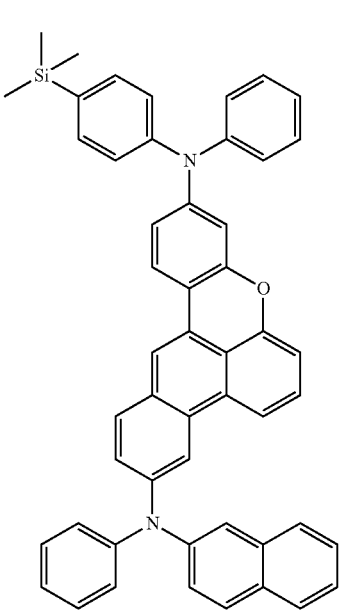

343
-continued
40
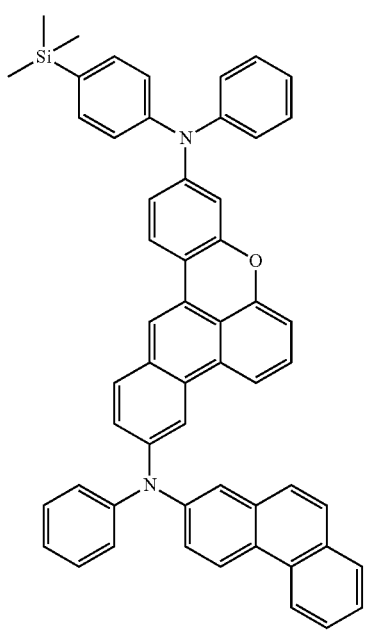
344
-continued
42
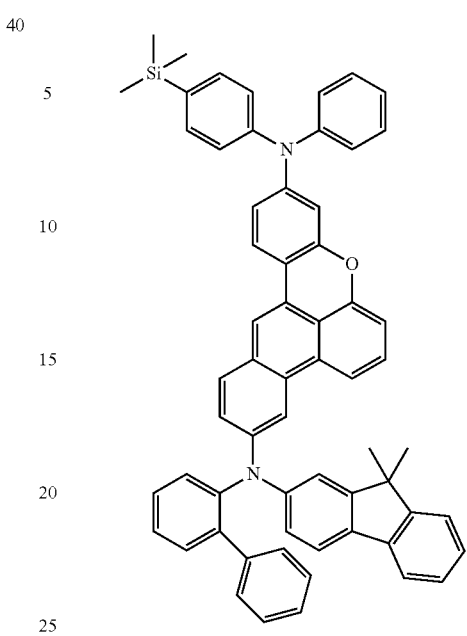
41
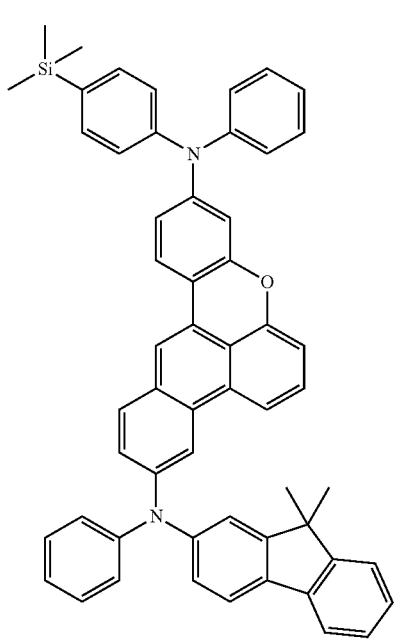
43
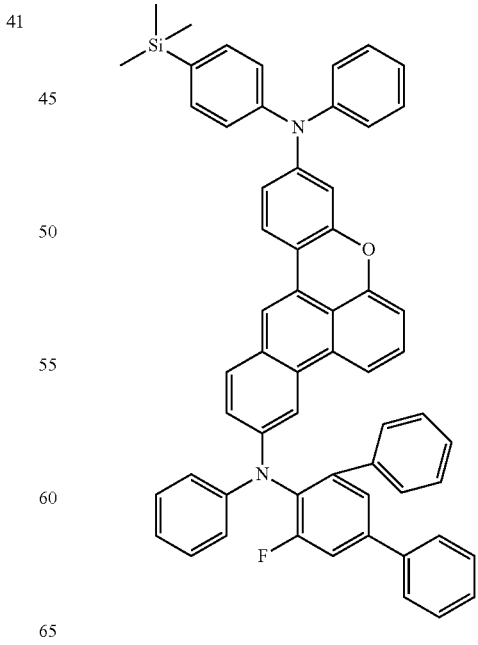

345
-continued
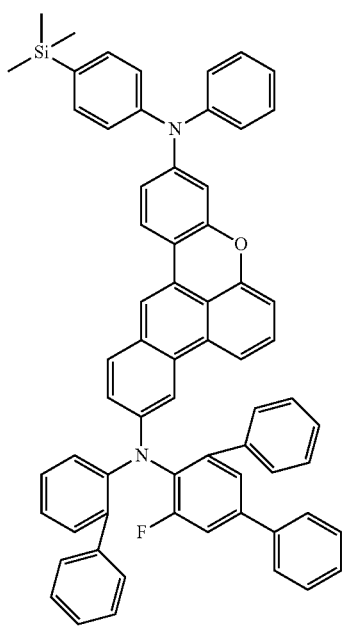
44
346
-continued
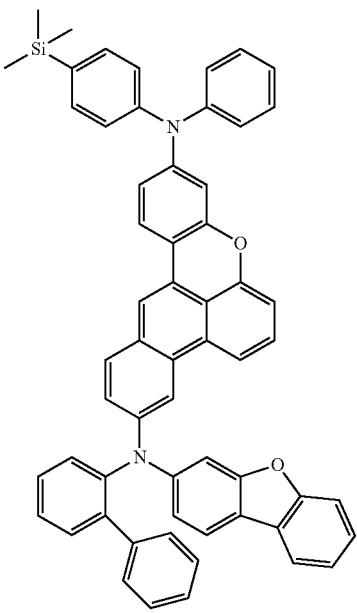
46
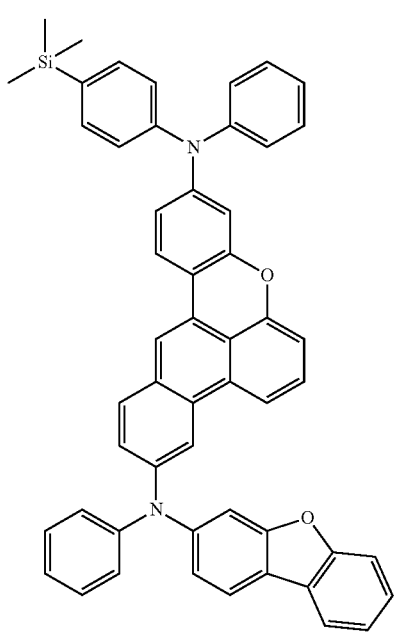
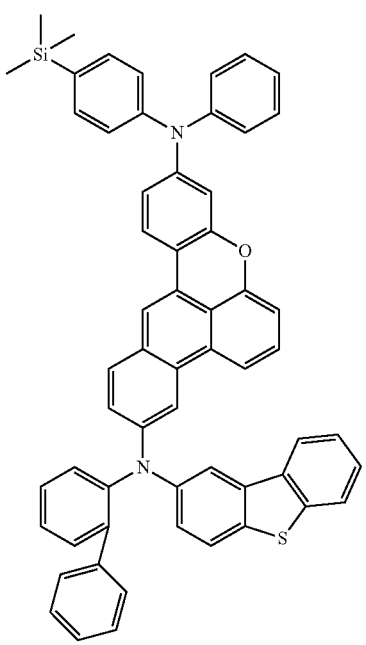
47

347
-continued
48
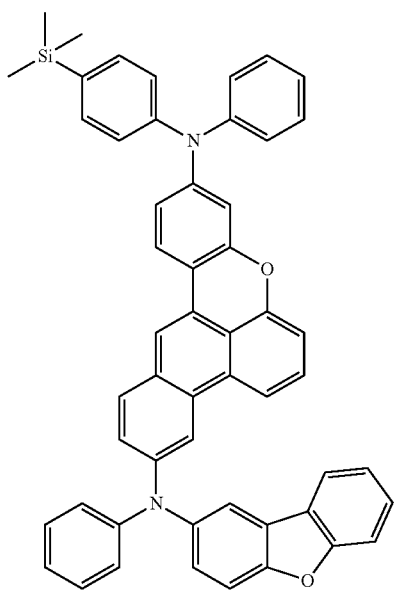
49
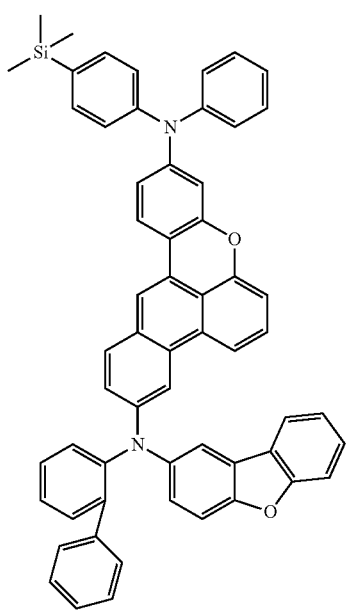
348
-continued
50
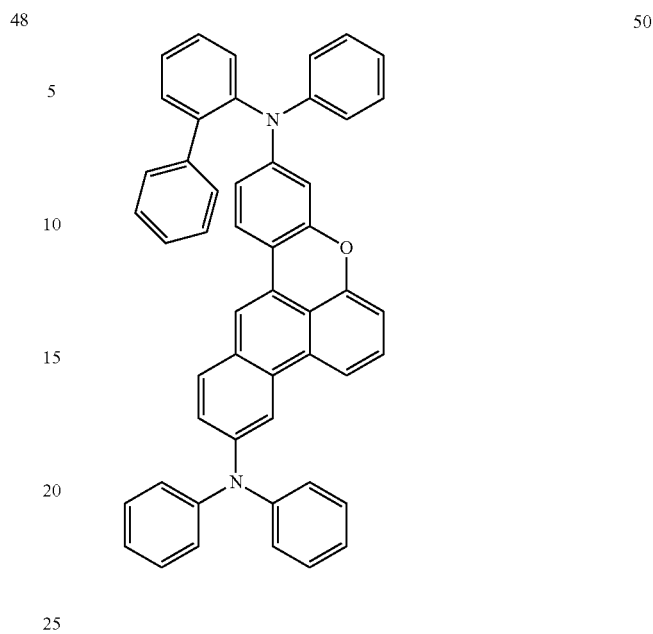
51
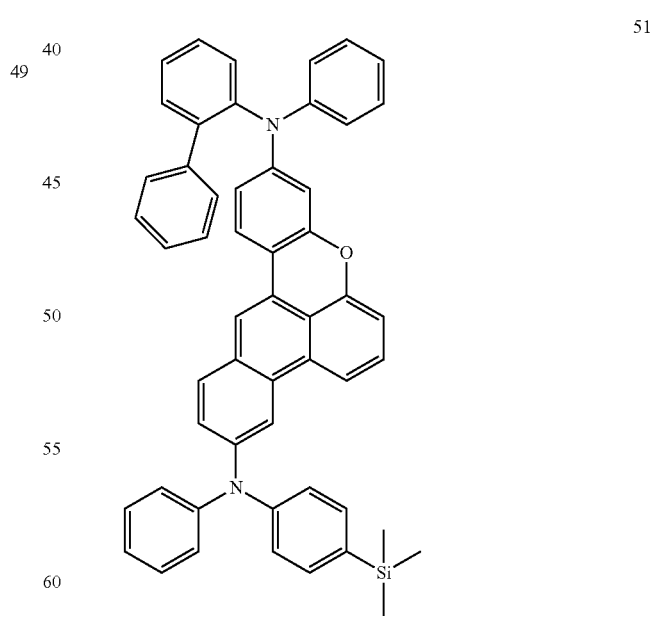

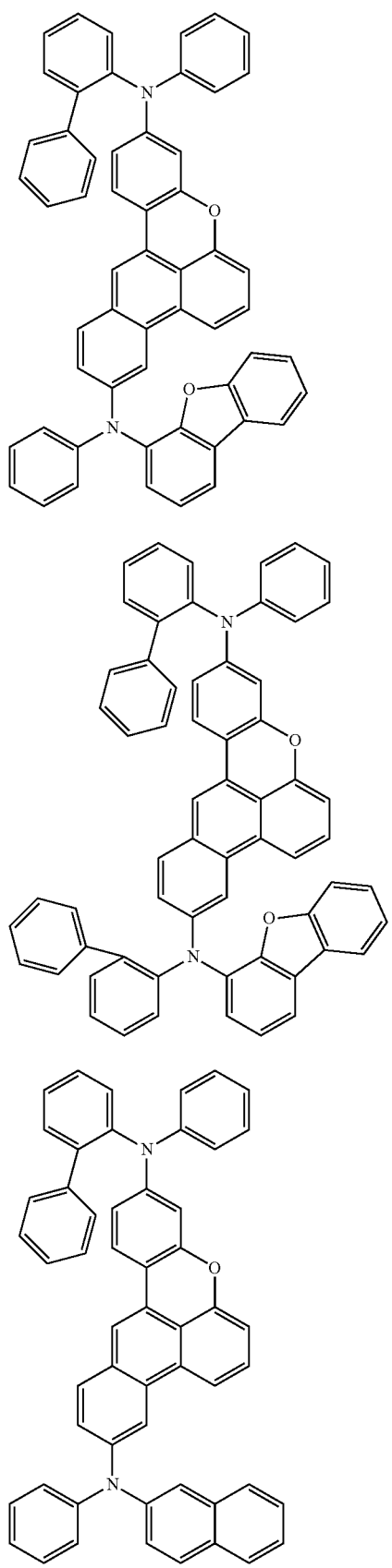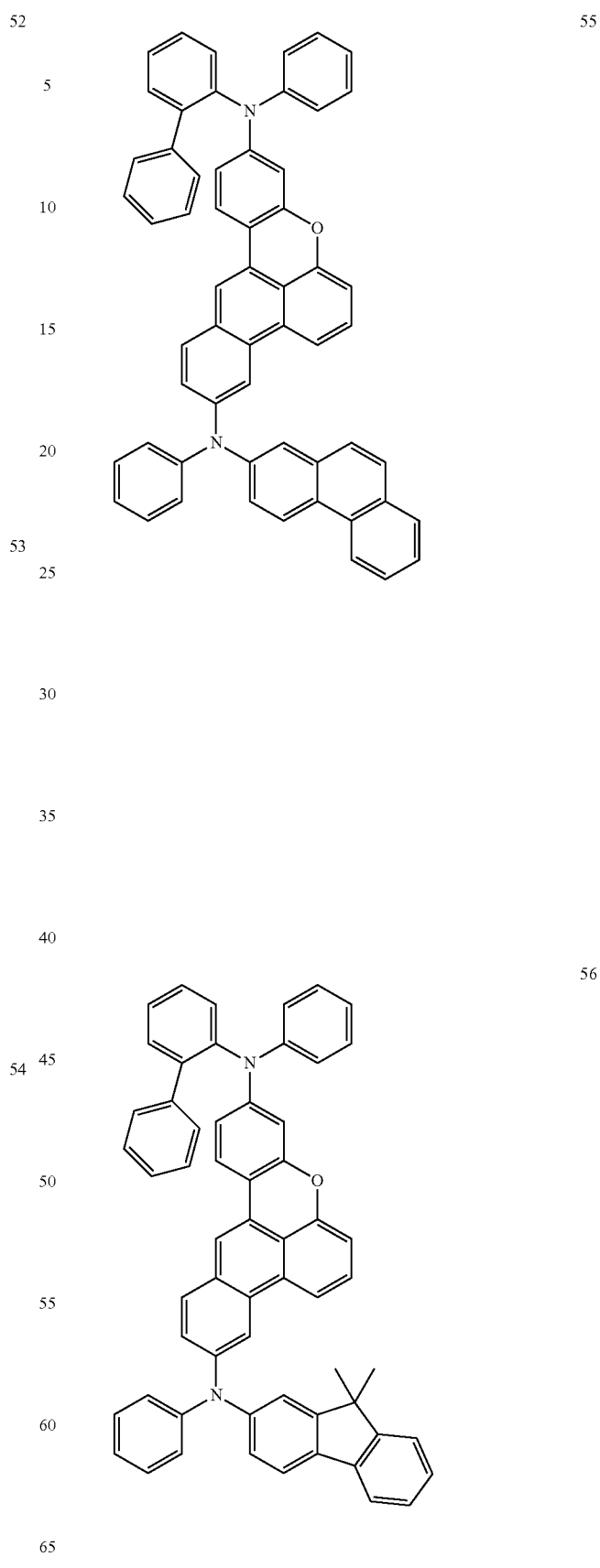

351
-continued
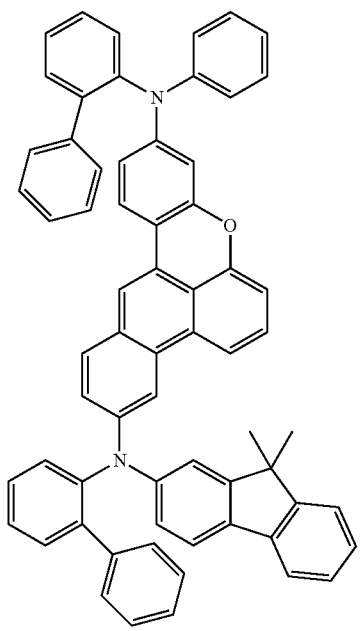
57
352
-continued
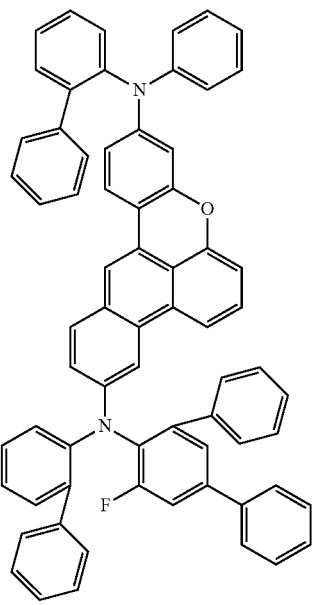
59
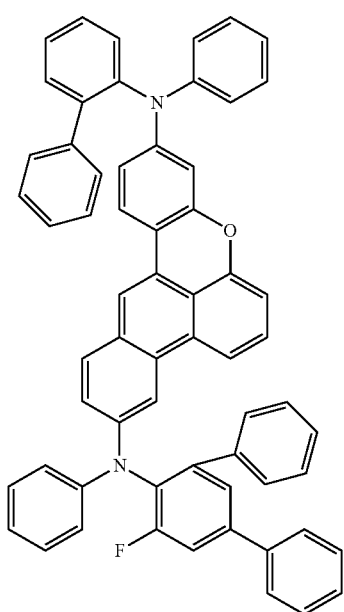
58
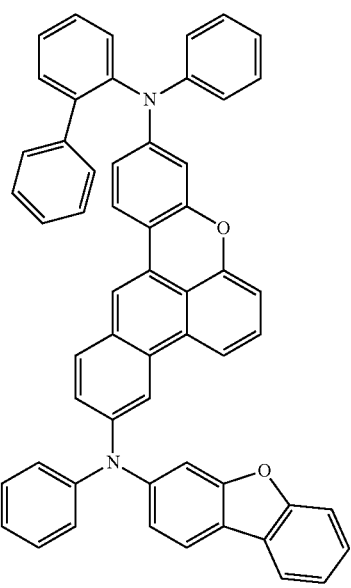
60

353
-continued
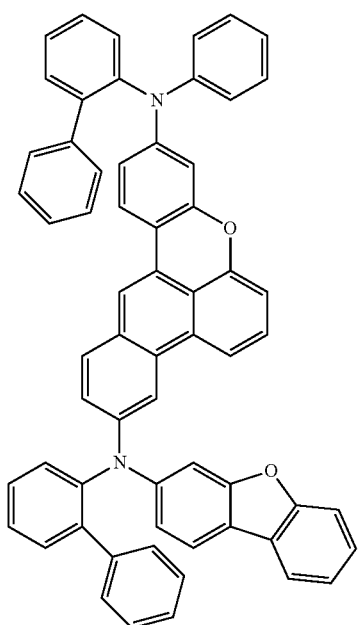
354
-continued
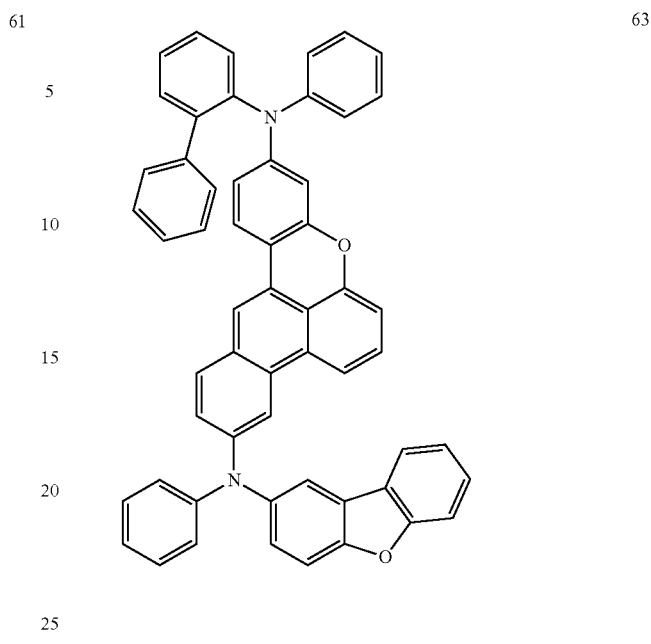
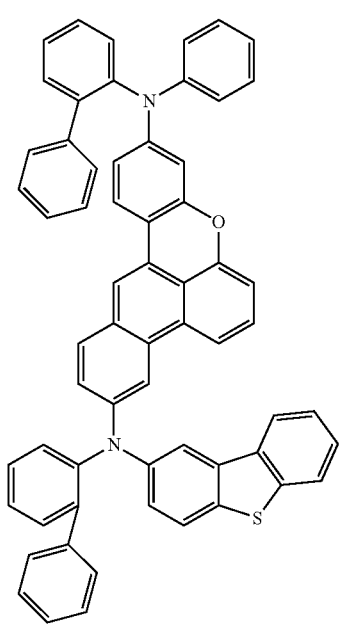
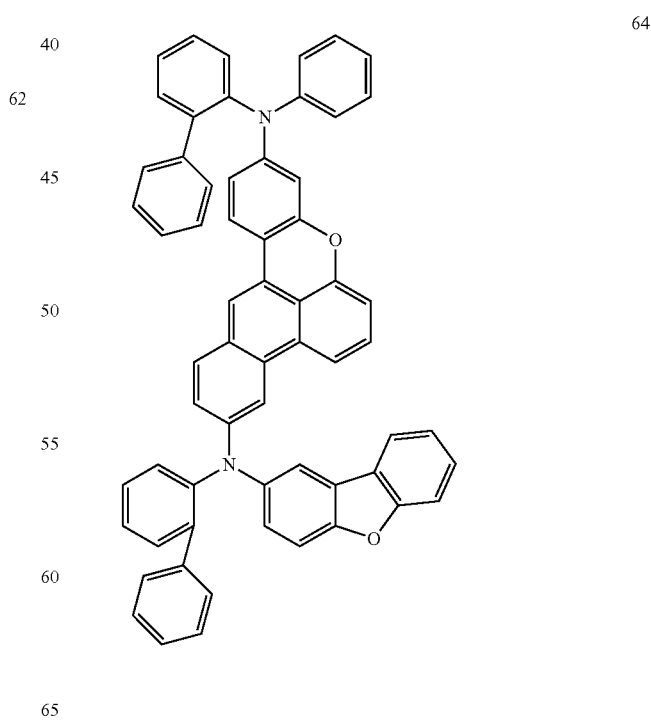

355
-continued
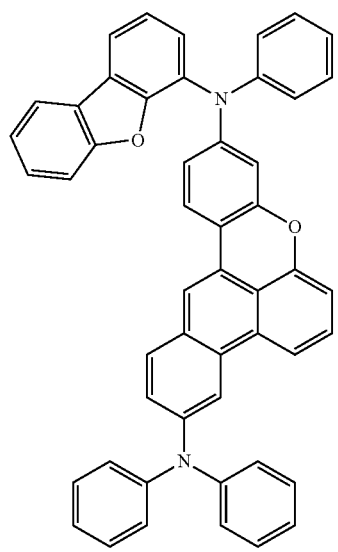
66
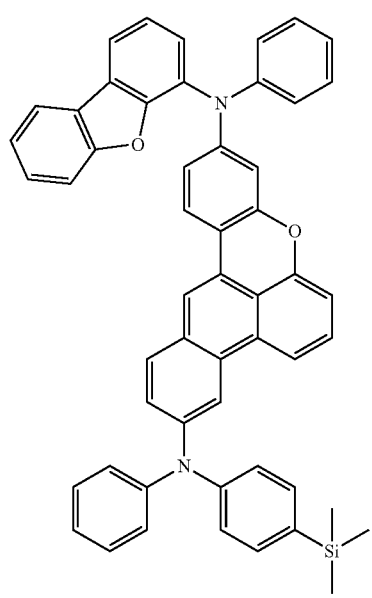
356
-continued
65
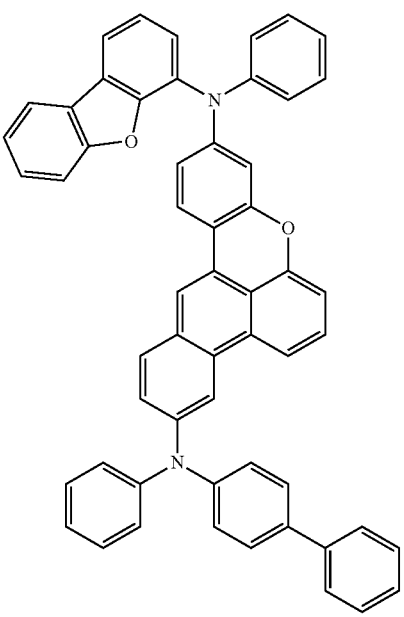
67
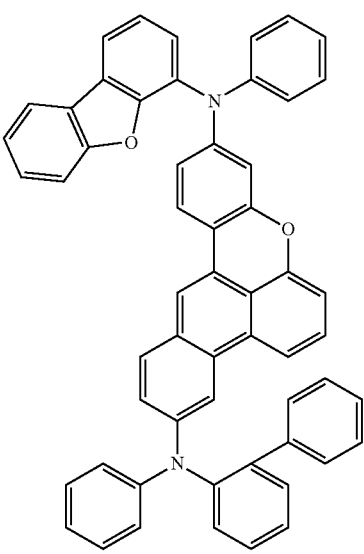
68

357
-continued
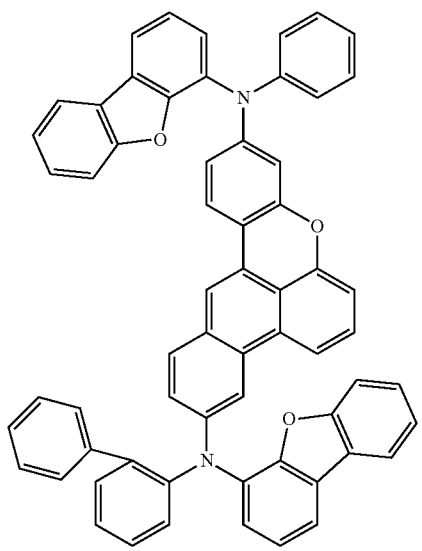
358
-continued
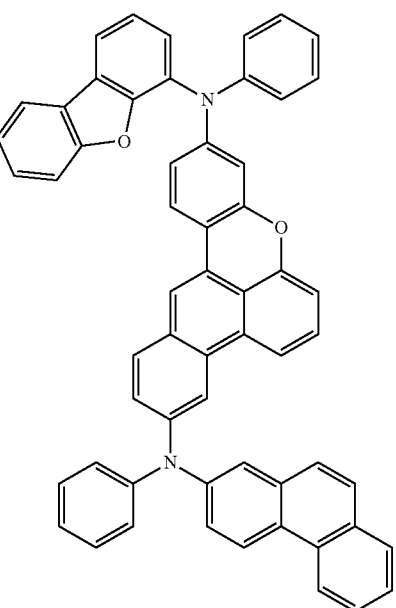
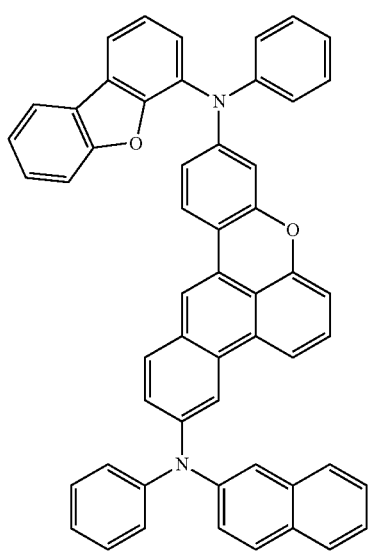
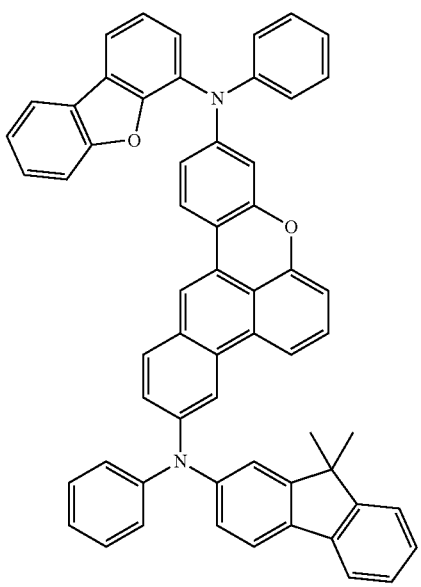

73
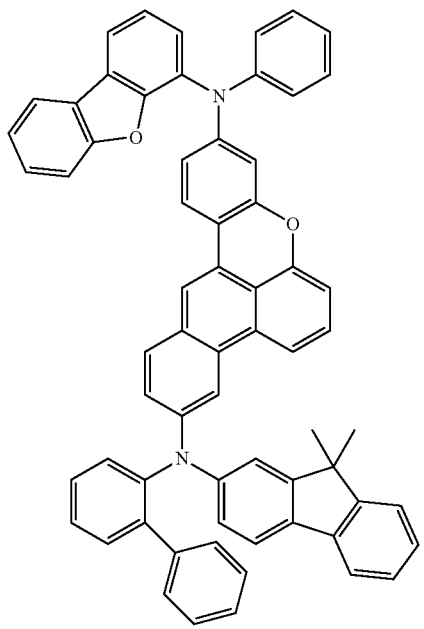
74
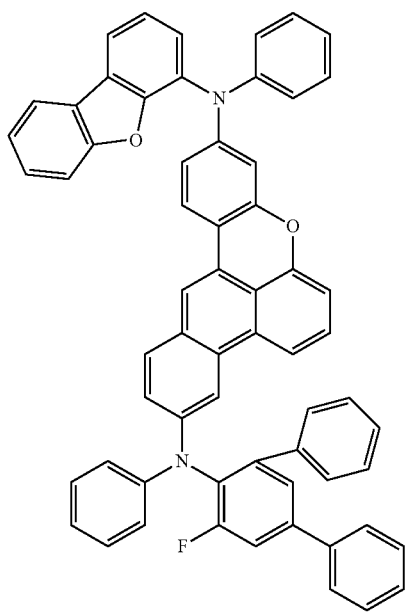
75
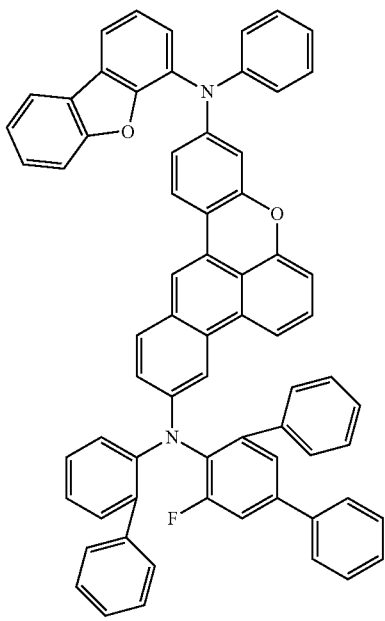
76
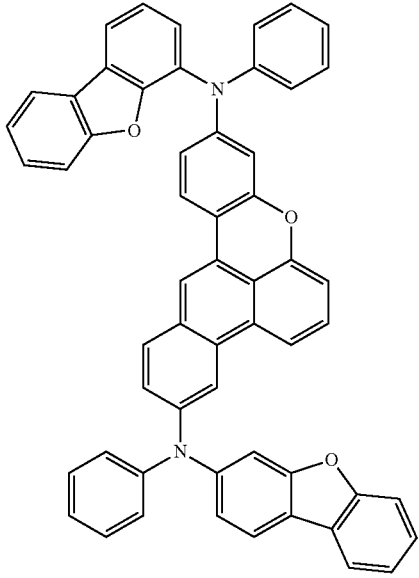

77
-continued
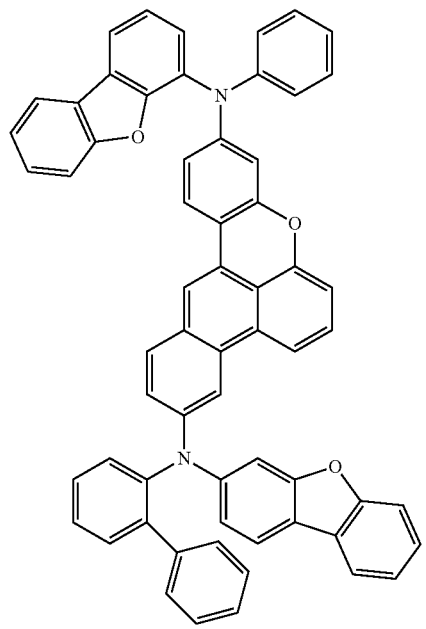
78
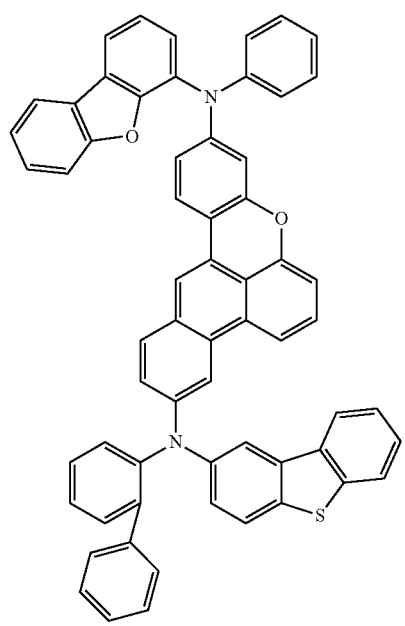
79
-continued
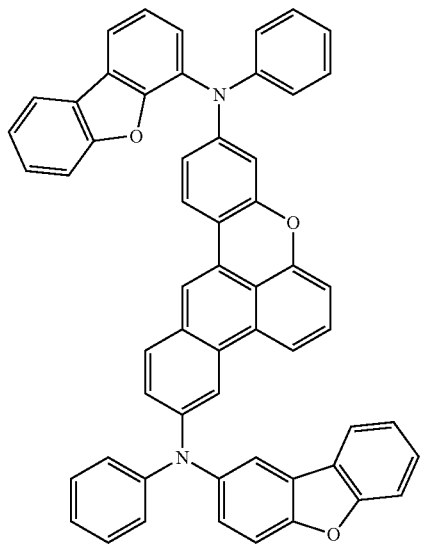
80
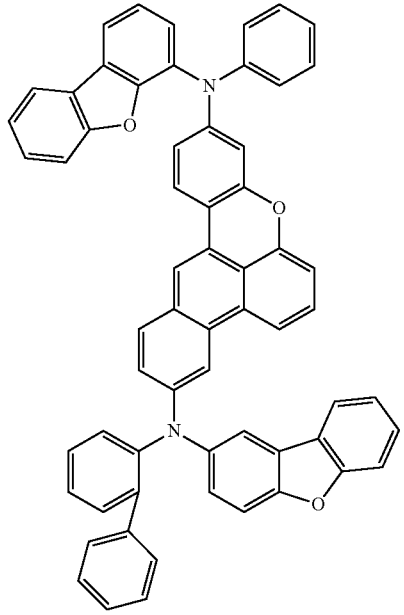

363
-continued
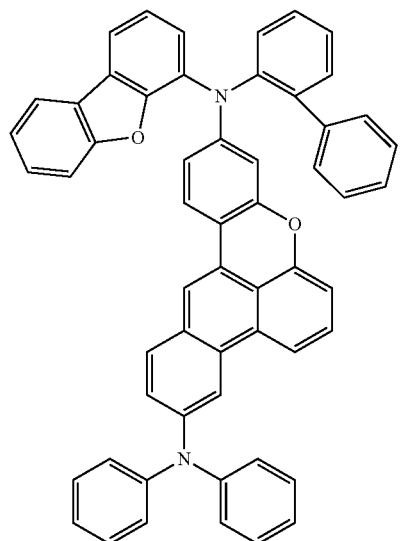
81
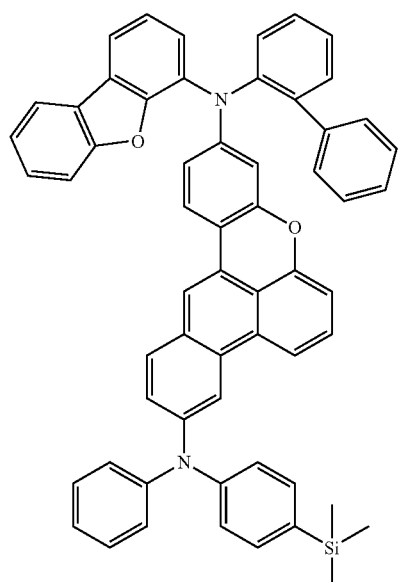
82
364
-continued
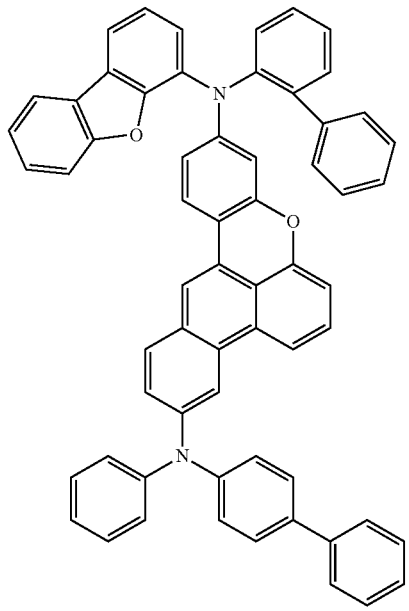
83
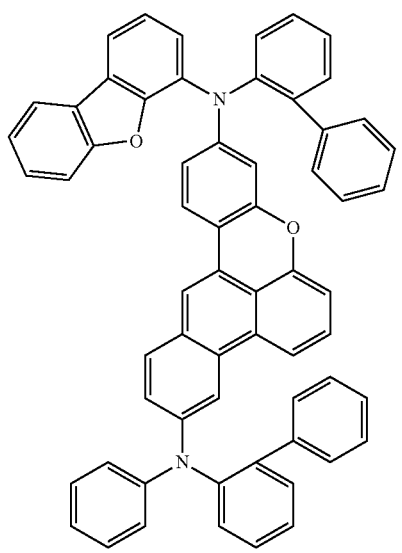
84

365
-continued
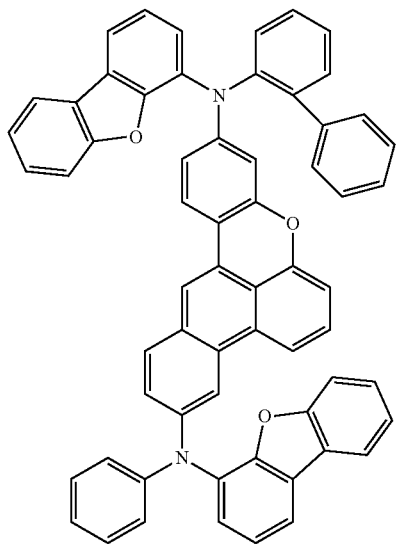
85
86
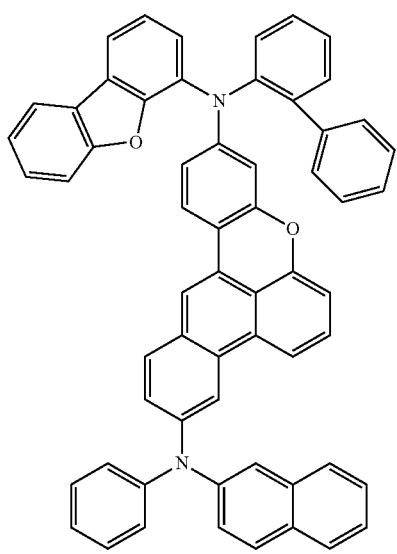
366
-continued
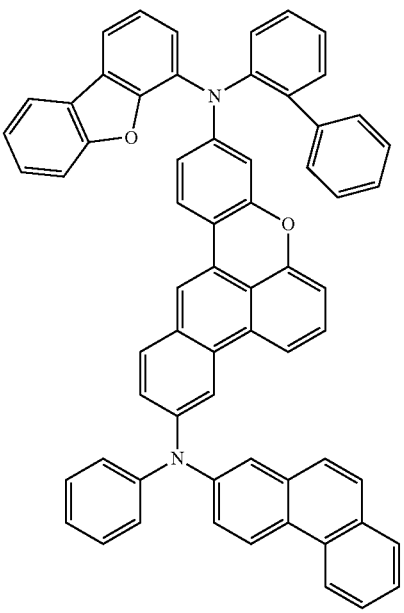
87
88
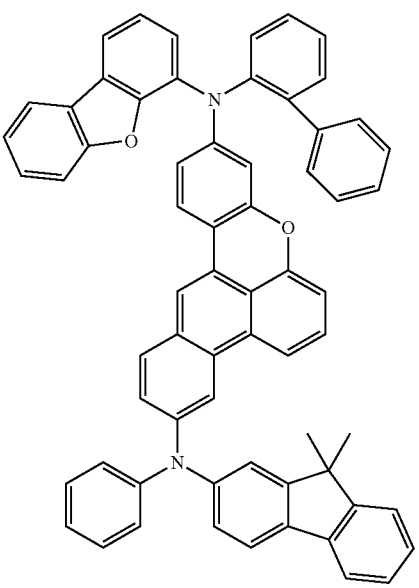

367
-continued
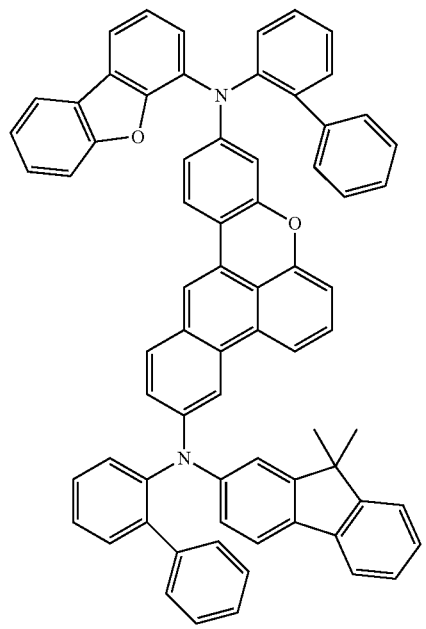
89
368
-continued
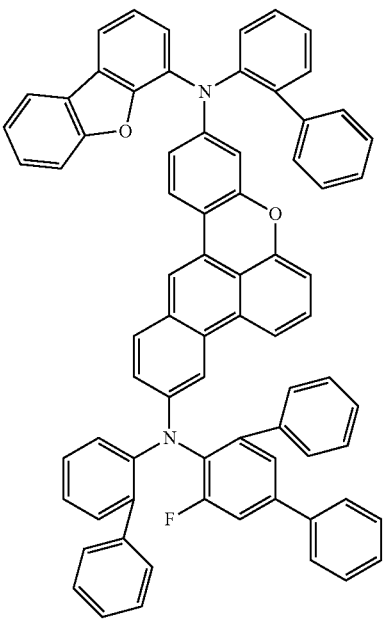
91
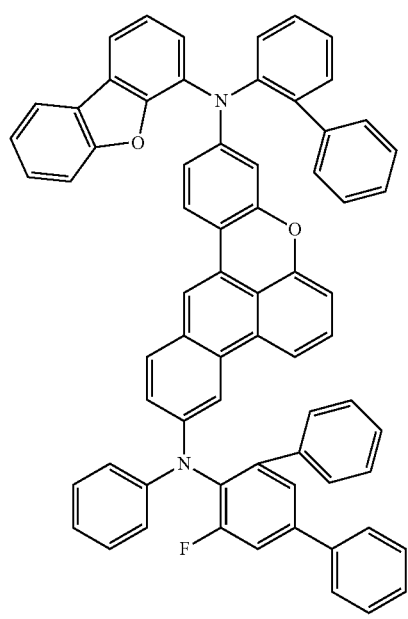
90
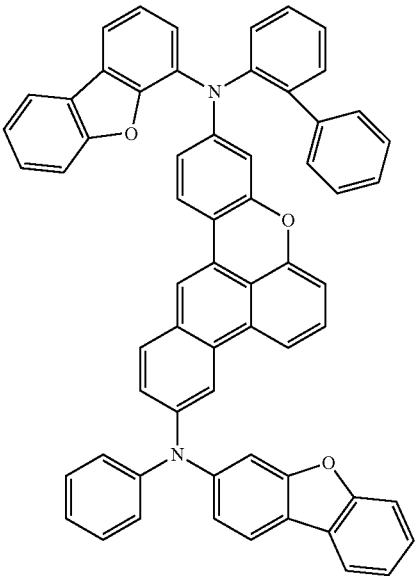
92

93
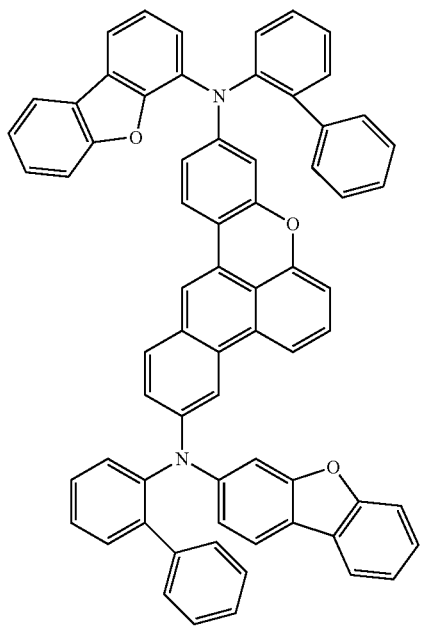
94
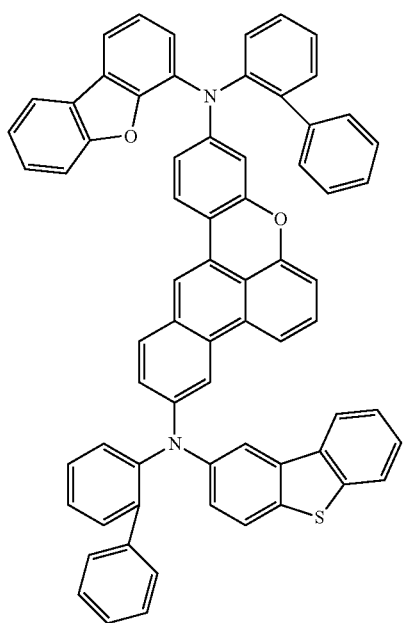
95
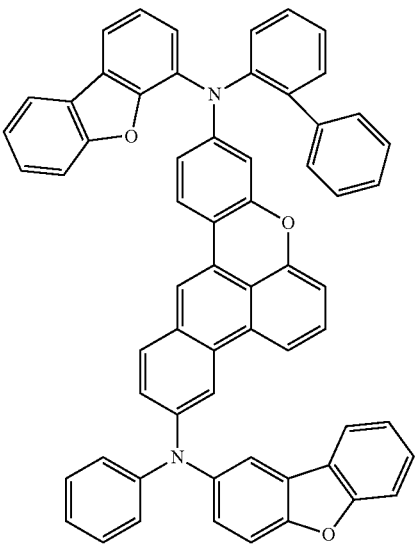
96
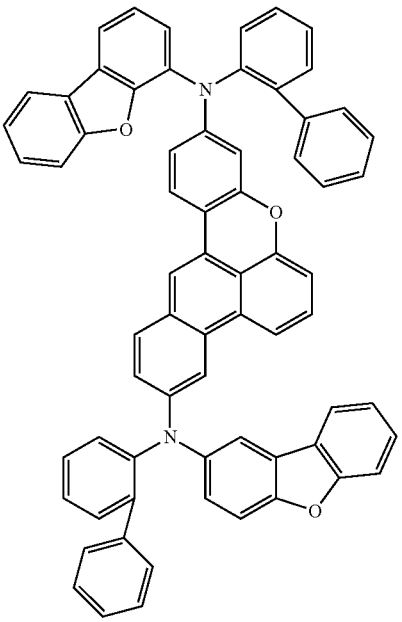

371
-continued
97
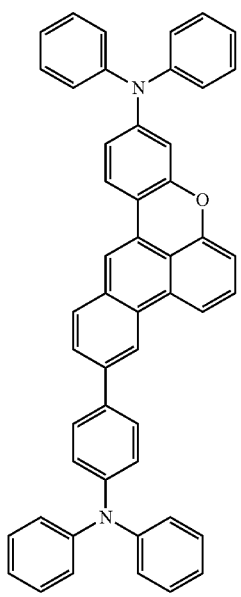
372
-continued
99
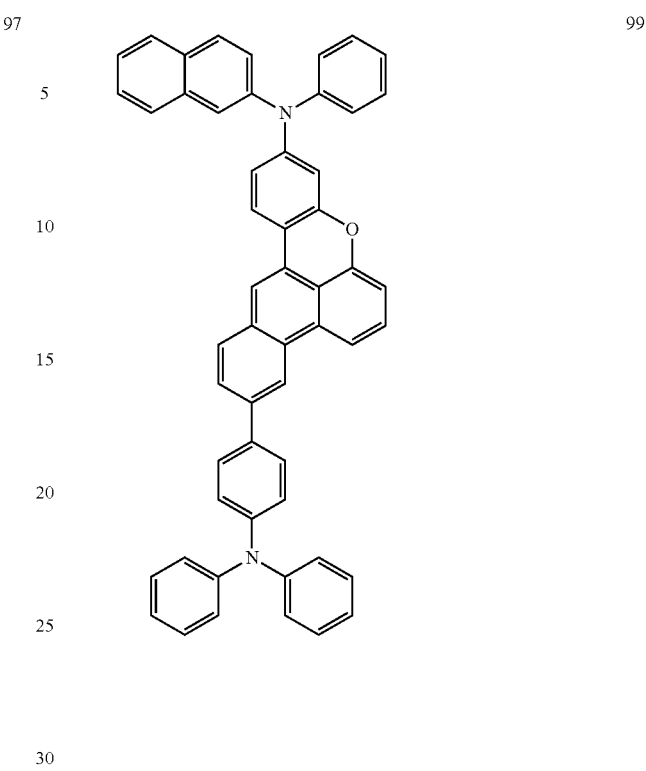
98
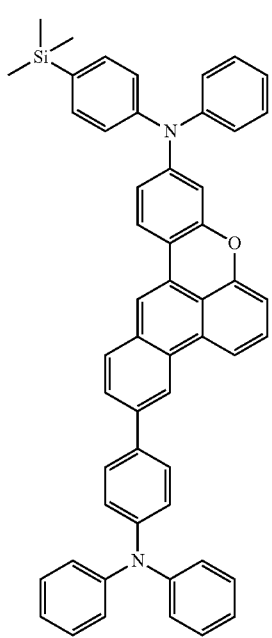
100
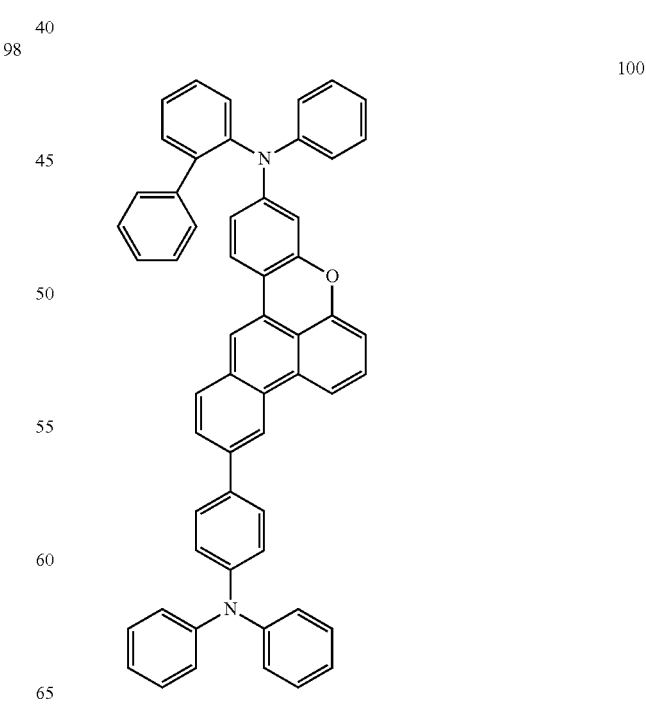

373
-continued
101
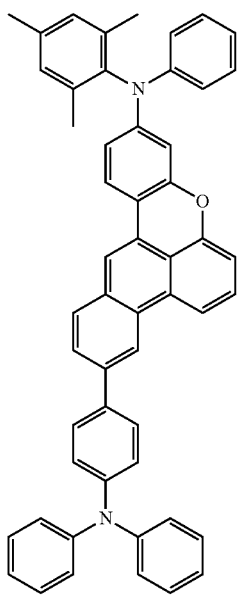
102
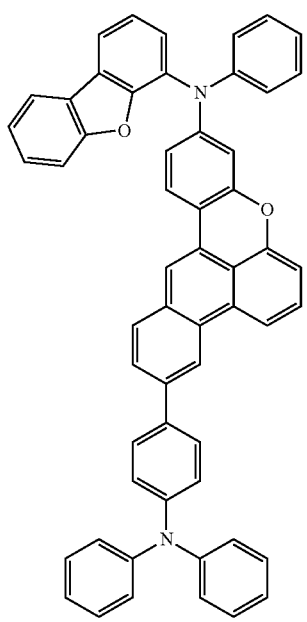
374
-continued
103
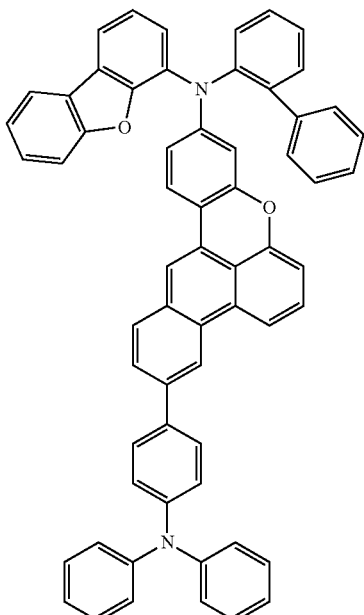
104
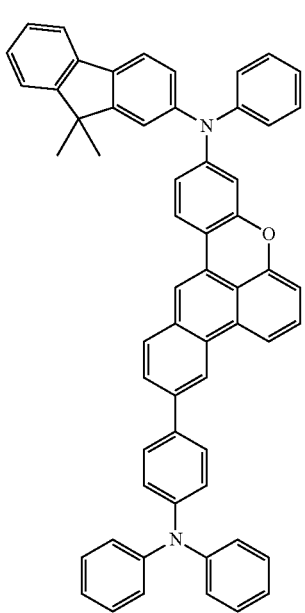

375
-continued
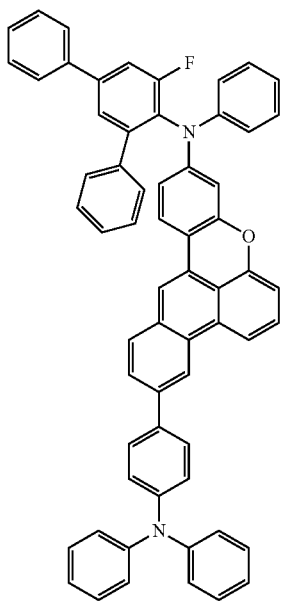
376
-continued
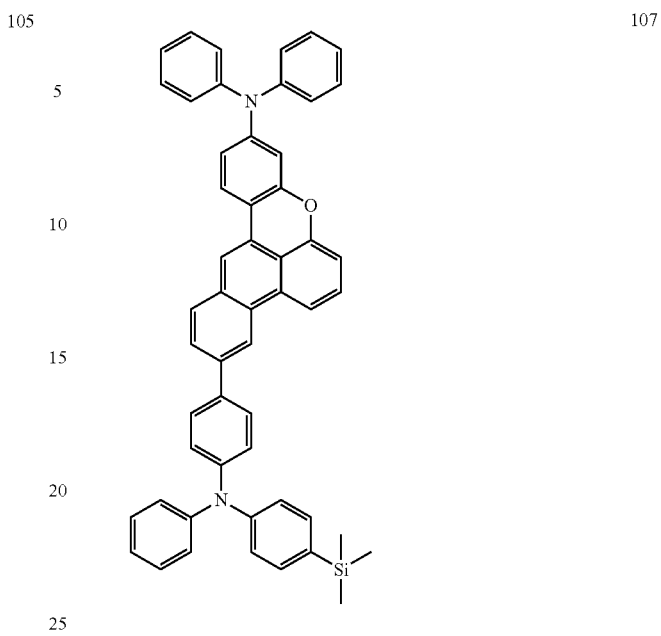
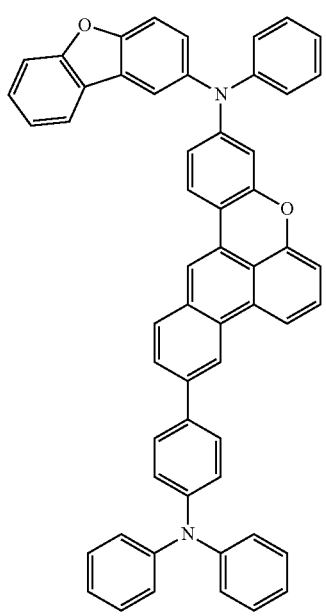
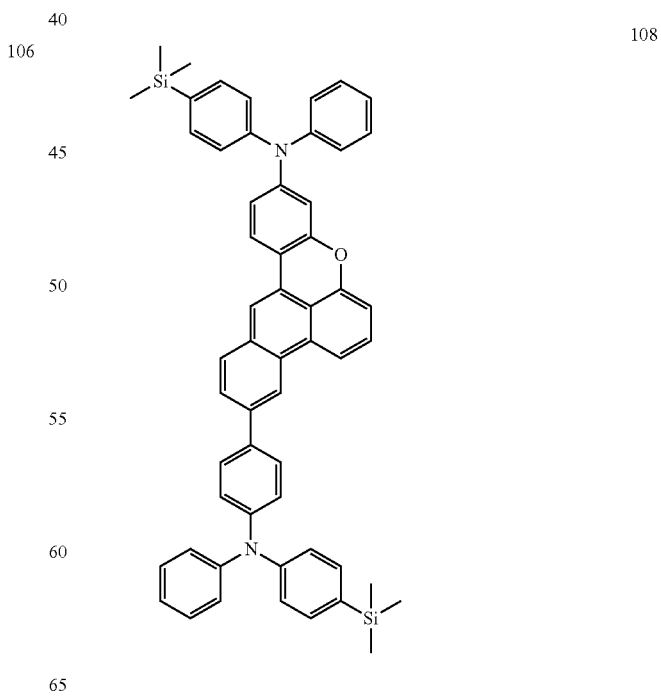

377
-continued
109
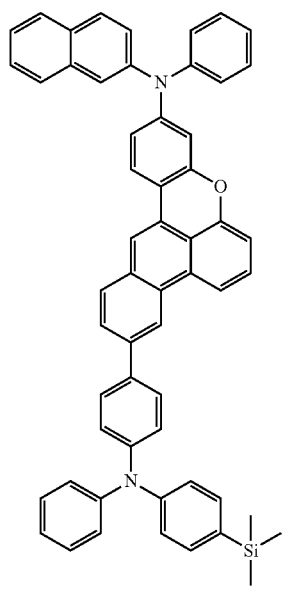
110
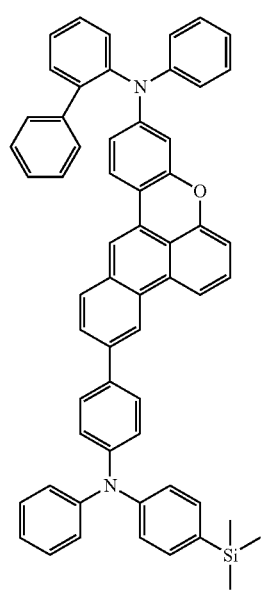
378
-continued
111
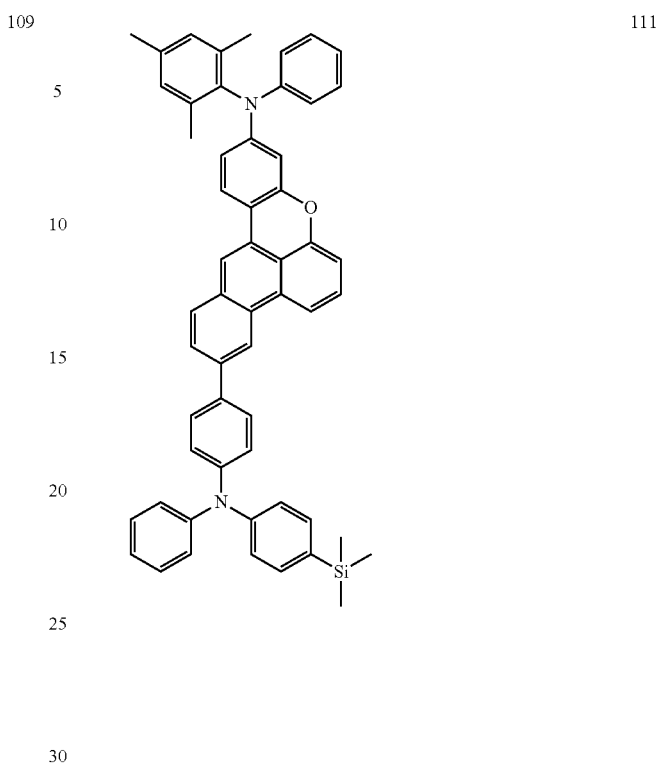
112
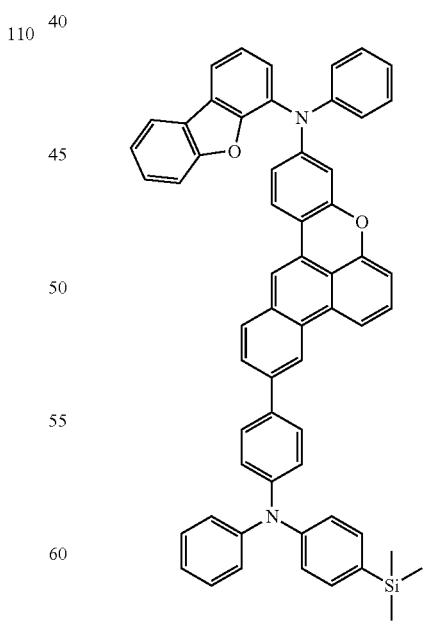

379
-continued
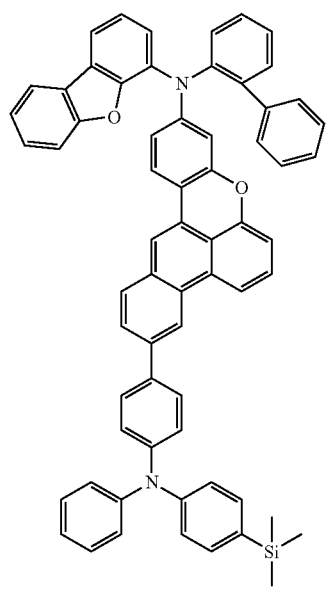
113
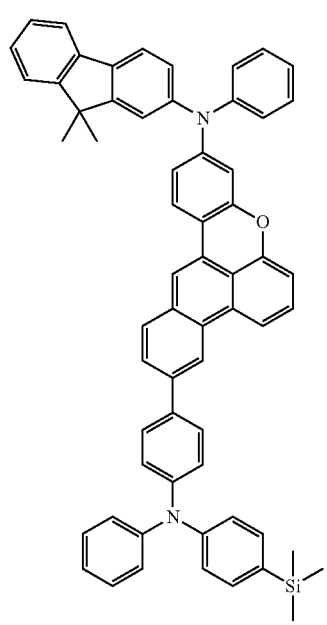
114
380
-continued
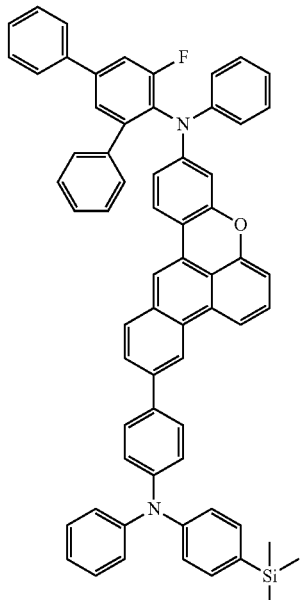
115
116

381
-continued
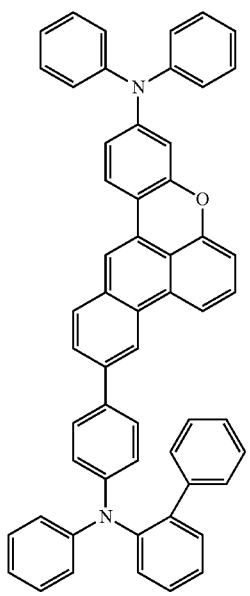
117
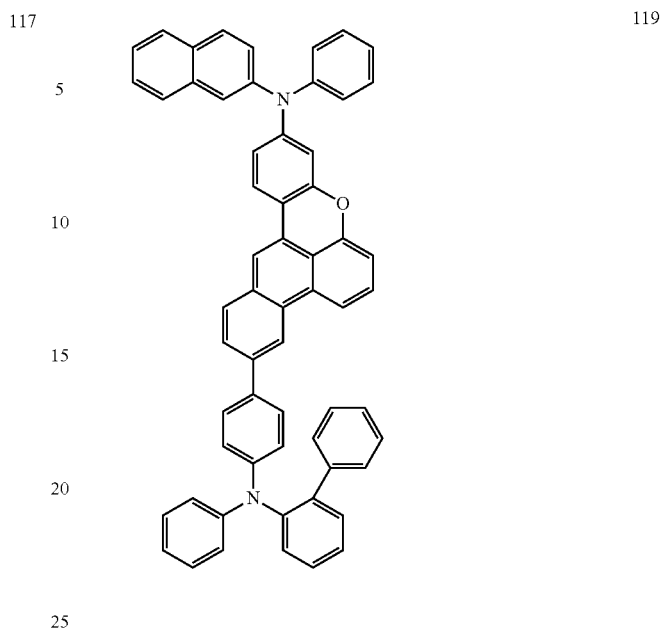
118
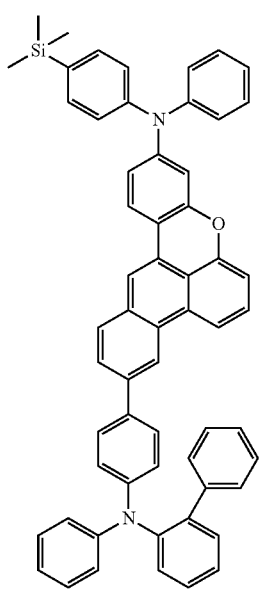
382
-continued
119
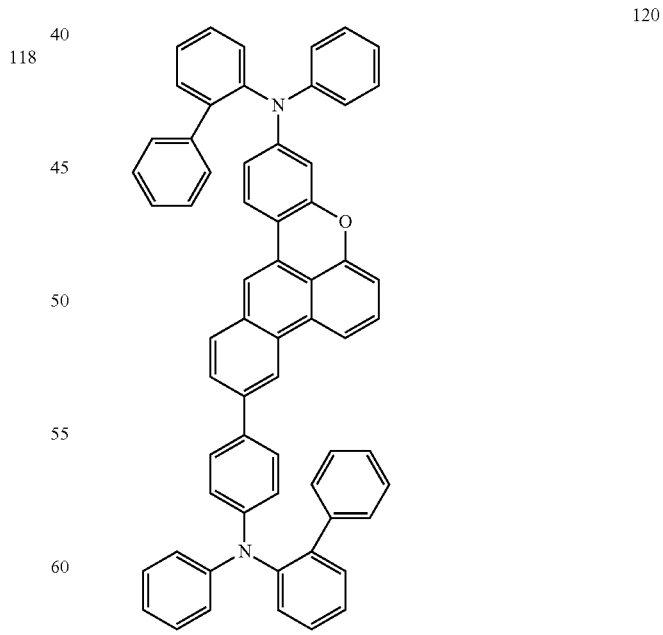
120

121
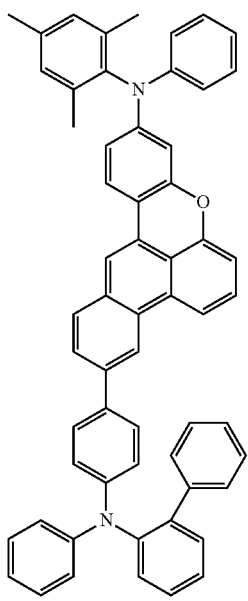
123
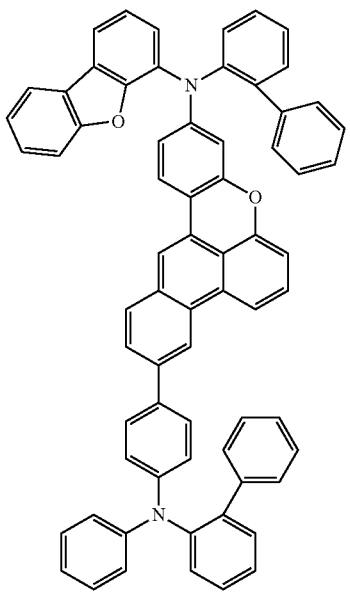
122
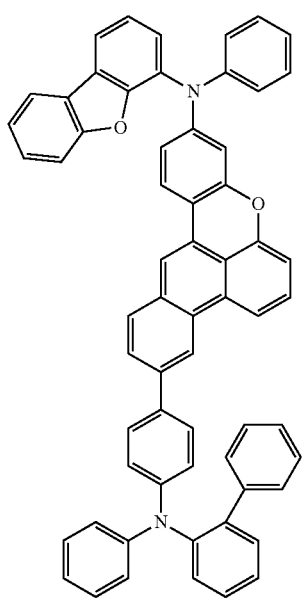
124
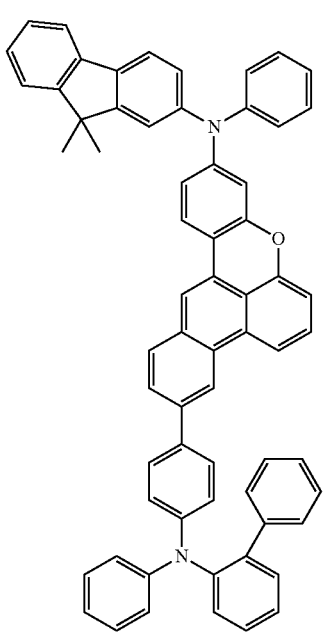

385
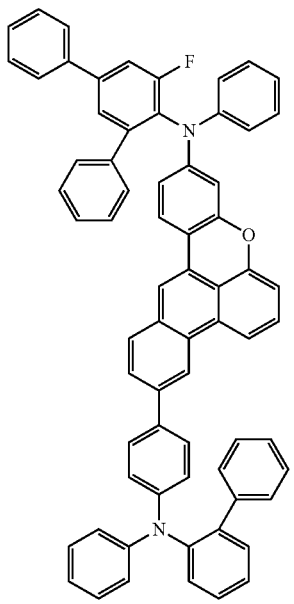
386
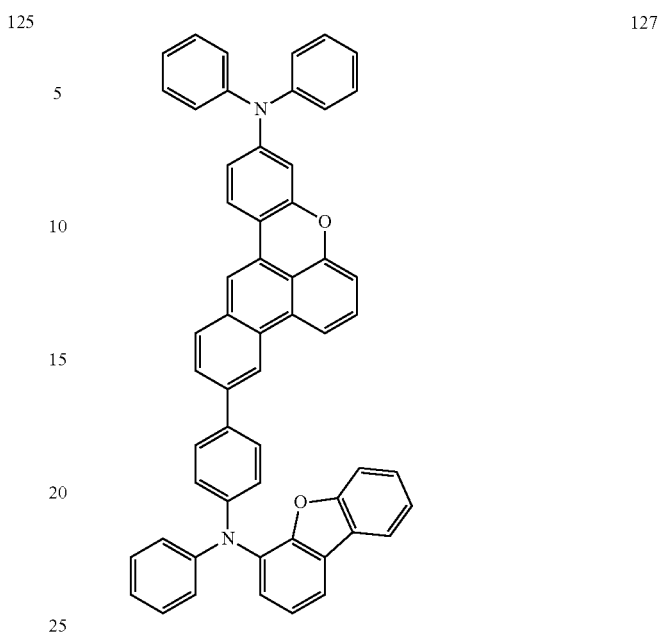
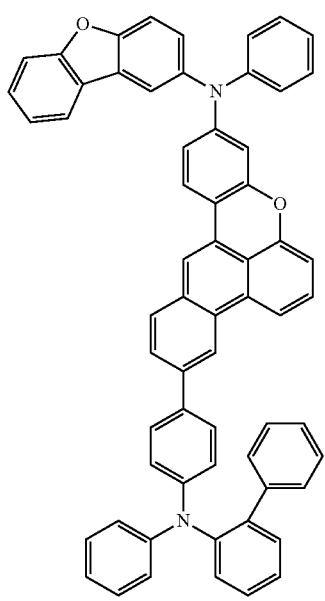
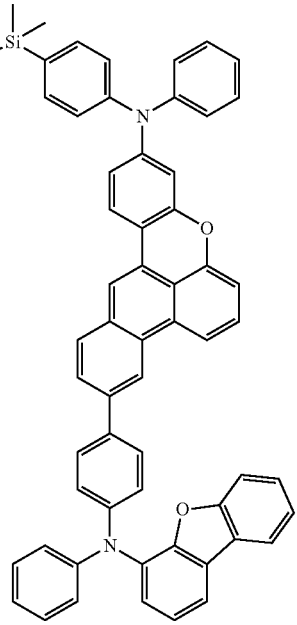

387
-continued
129
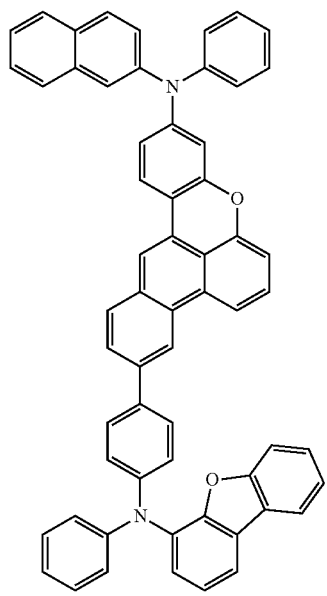
130
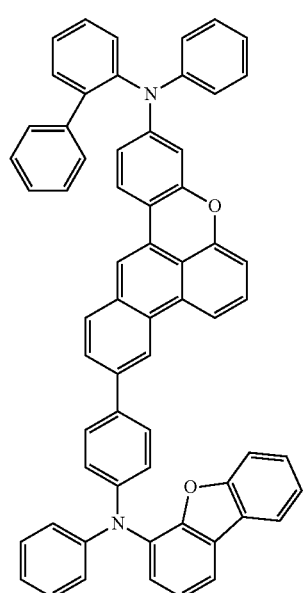
388
-continued
131
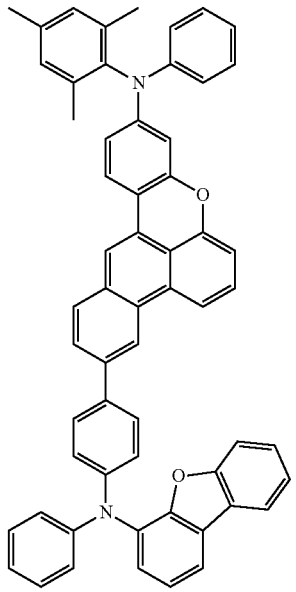
132
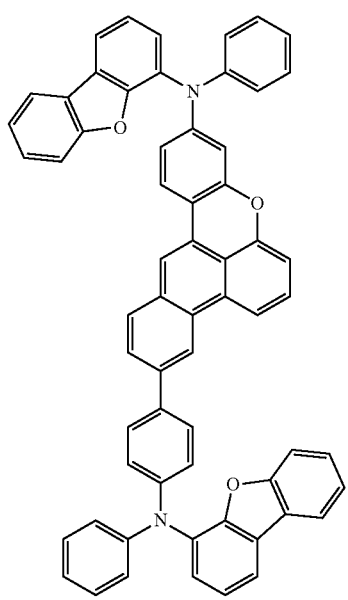

389
-continued
133
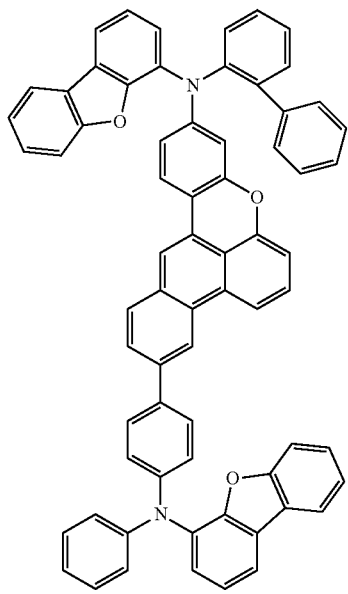
390
-continued
135
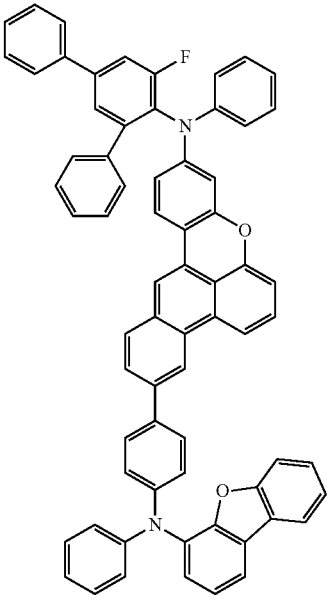
134
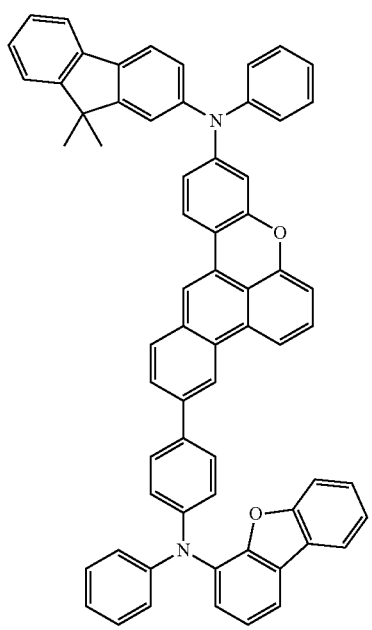
136
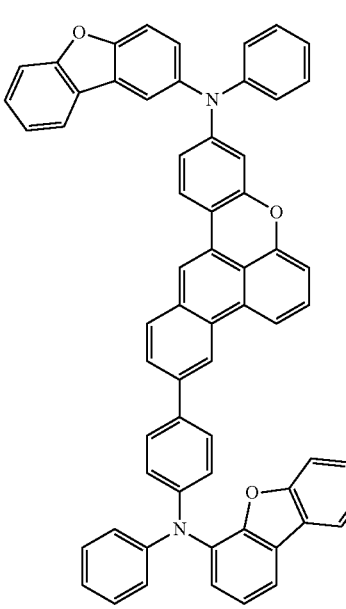

391
-continued
| 137 | 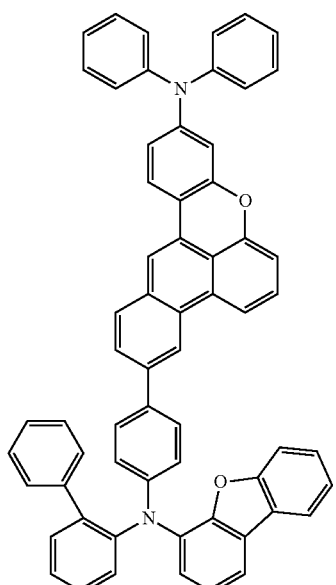 | 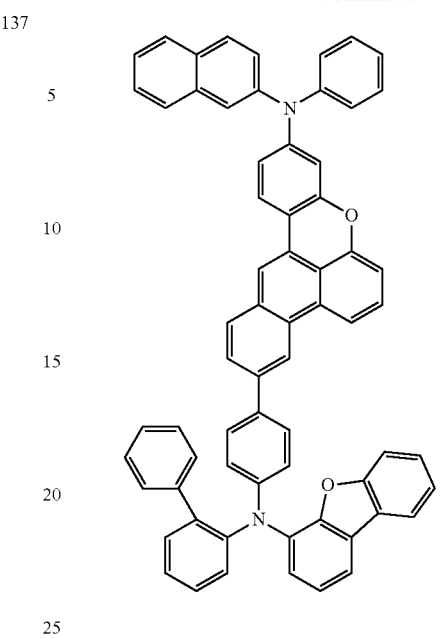 | 139 |
|---|---|---|---|
392
-continued
| 138 | 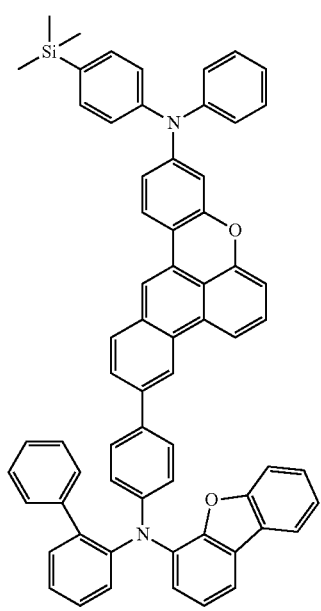 | 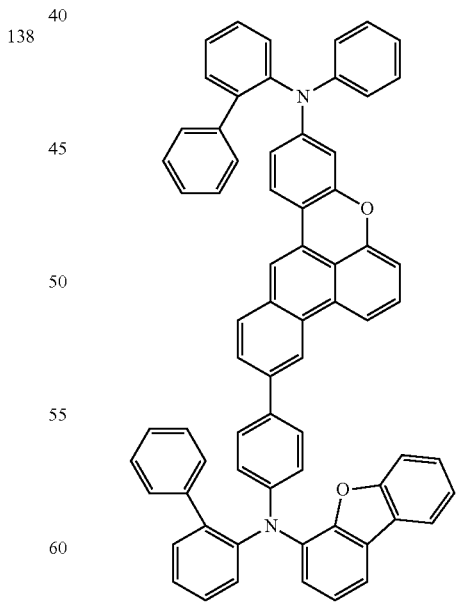 | 140 |

393
-continued
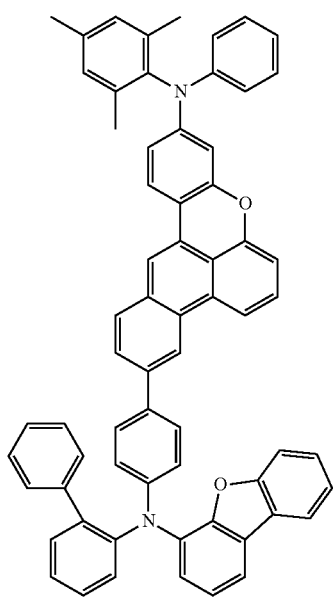
394
-continued
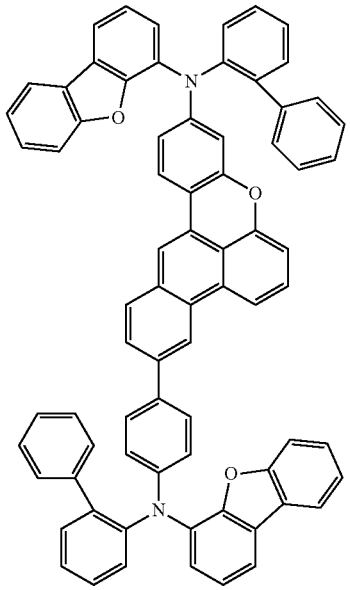
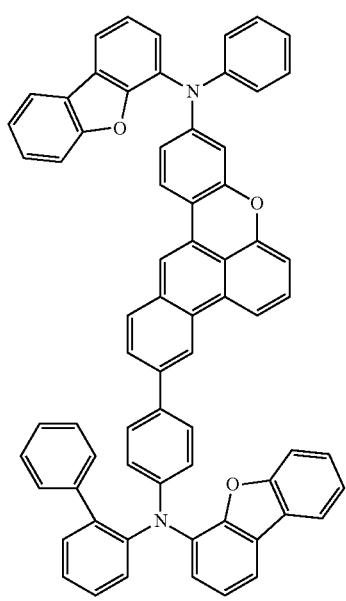
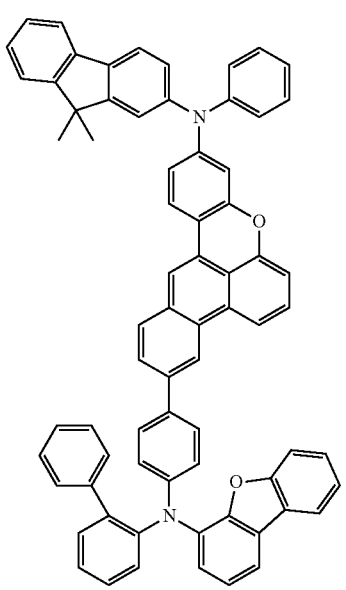

395
-continued
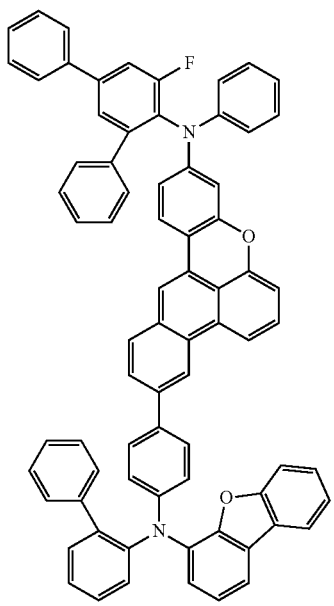
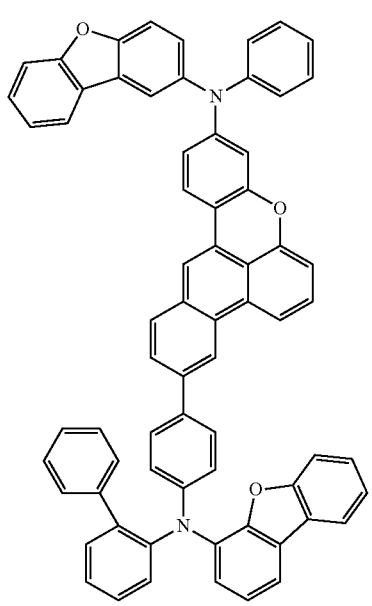
396
-continued
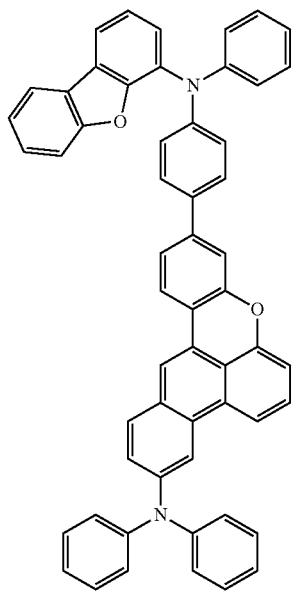
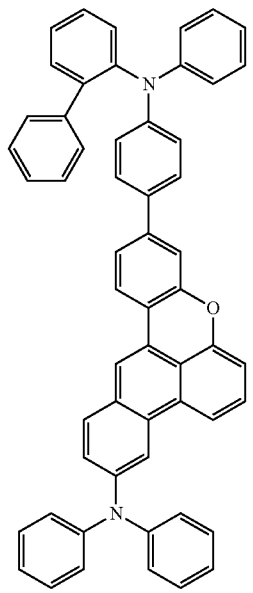

397
-continued
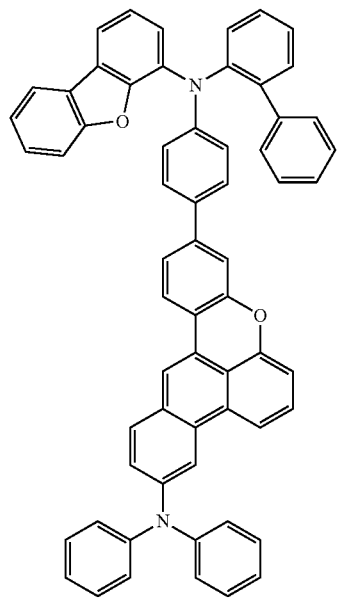
149
398
-continued
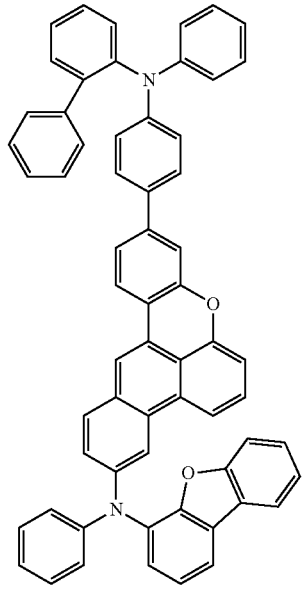
151
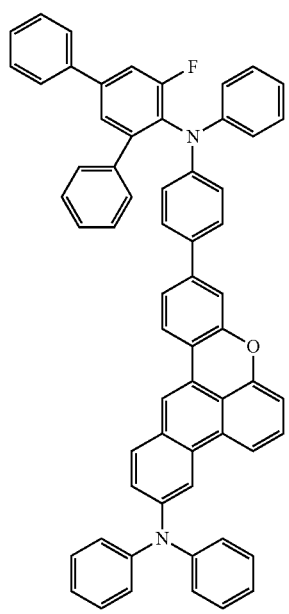
150
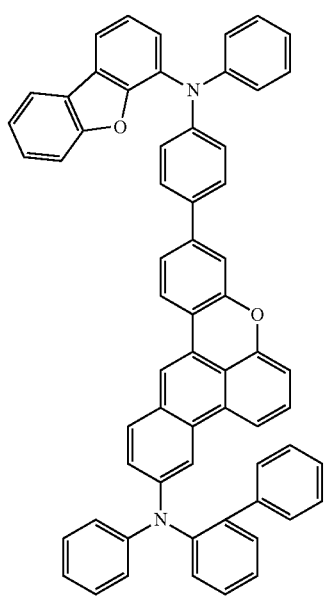
152

153
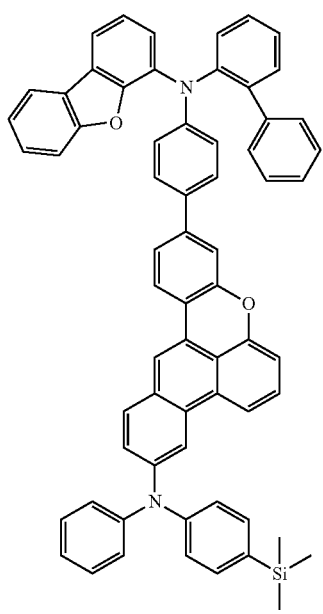
154
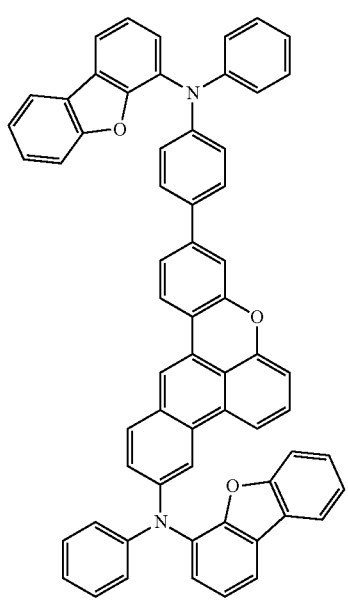
155
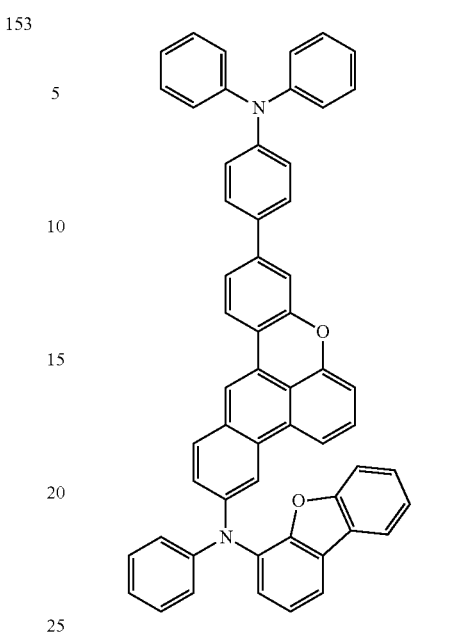
156
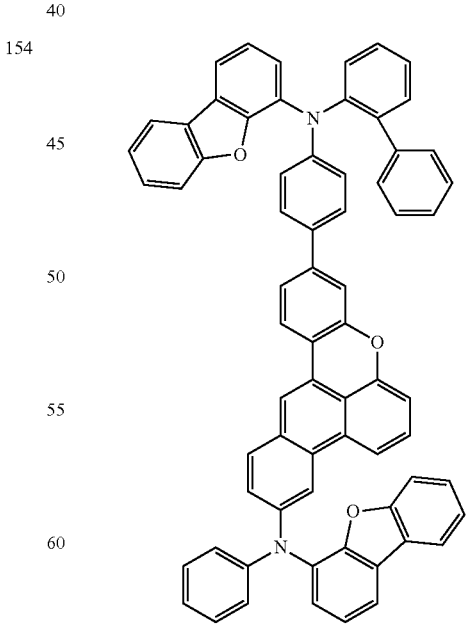

401
-continued
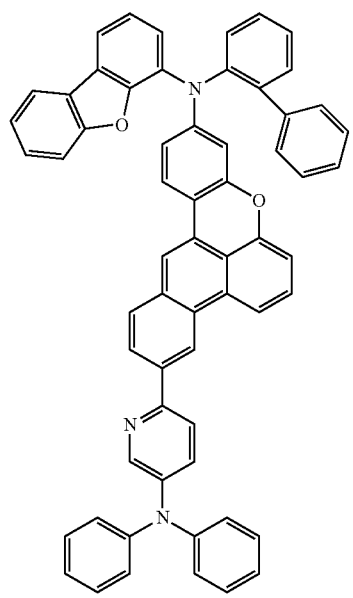
157
402
-continued
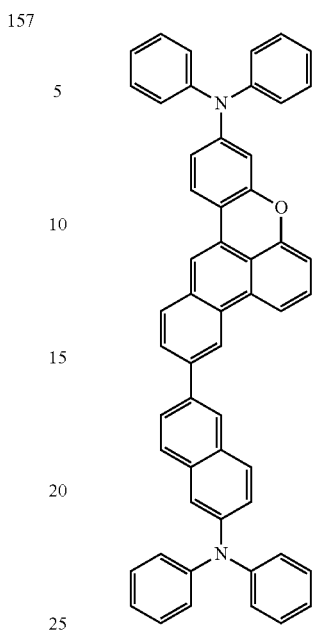
159
158
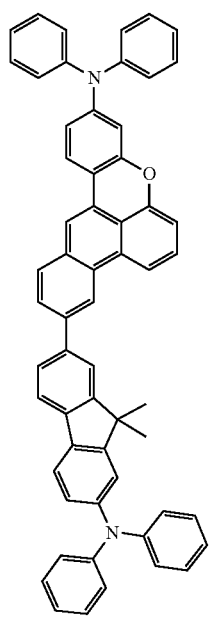
160
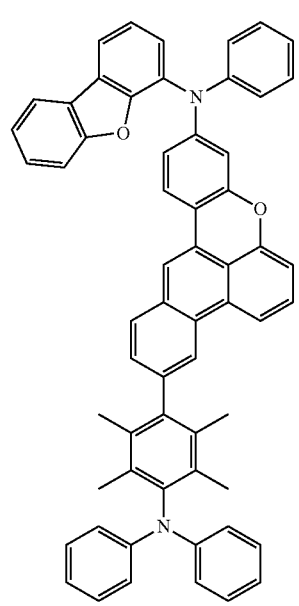

403
-continued
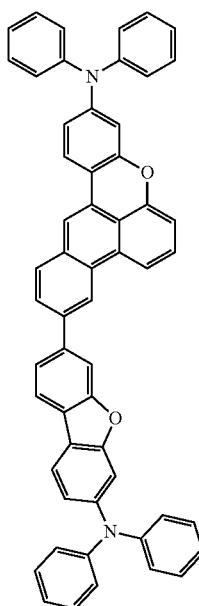
404
-continued
161
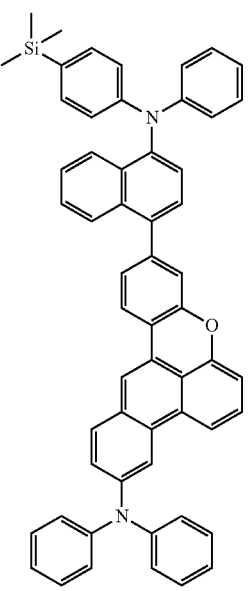
162
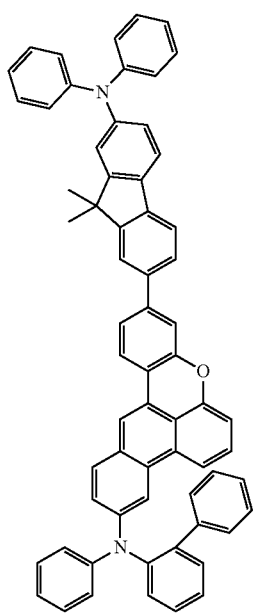
163
164

405
-continued
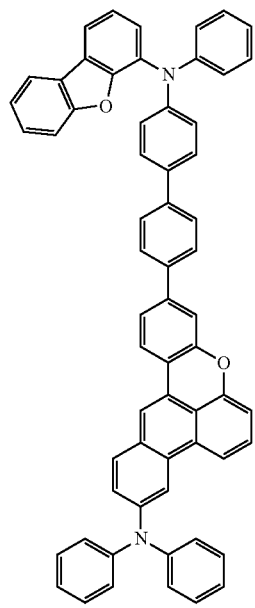
406
-continued
165
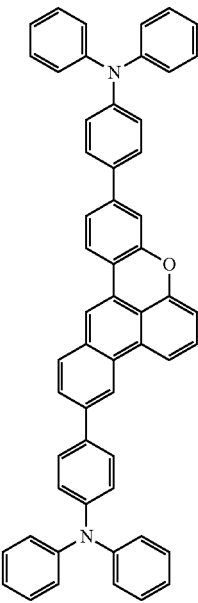
167
166
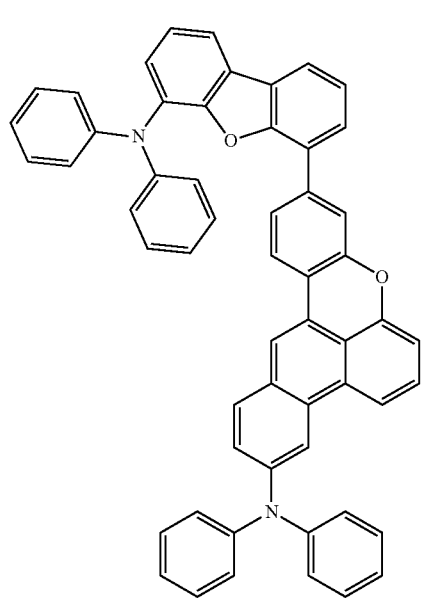
168
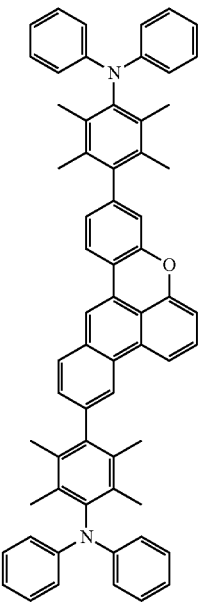

407
-continued
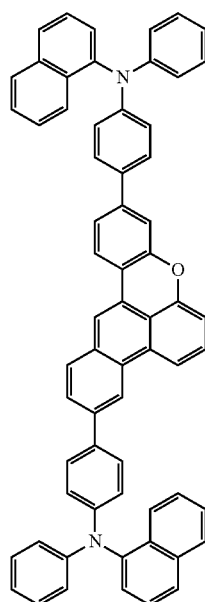
408
-continued
169
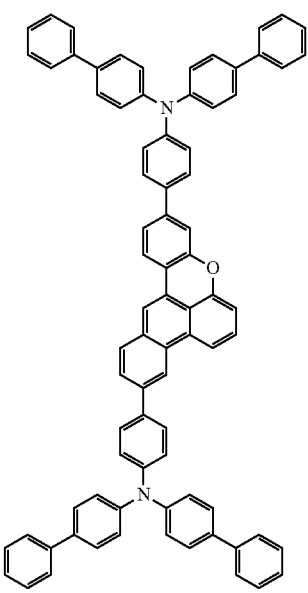
170
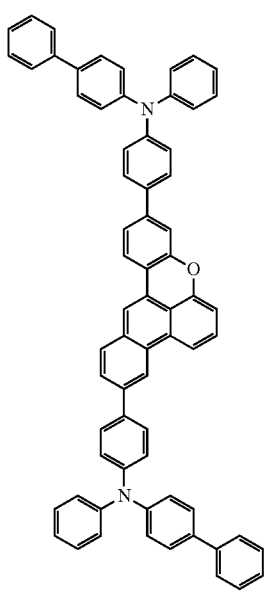
171
172
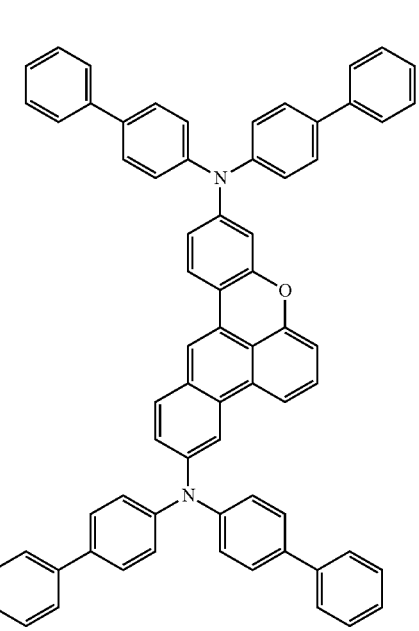

409
-continued
173
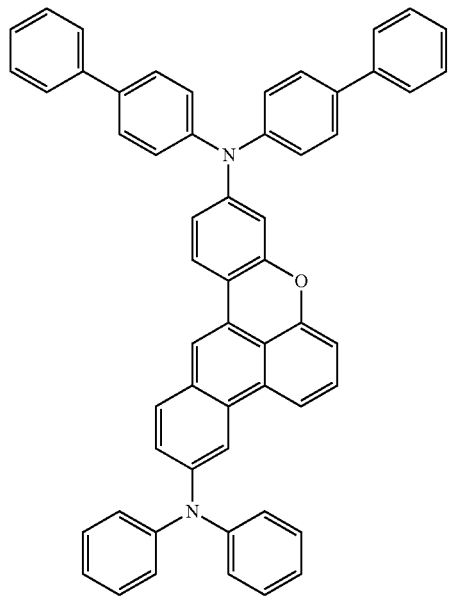
174
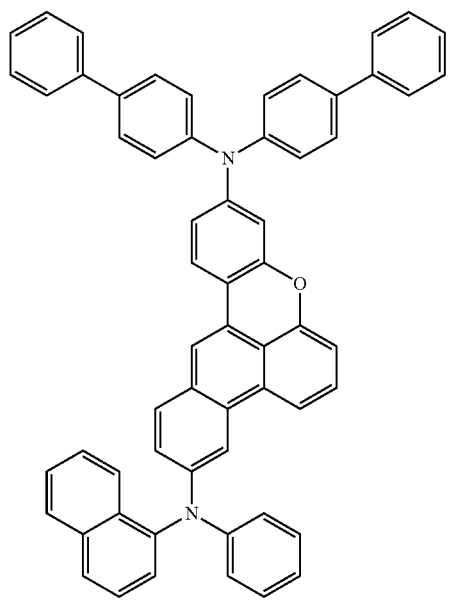
410
-continued
175
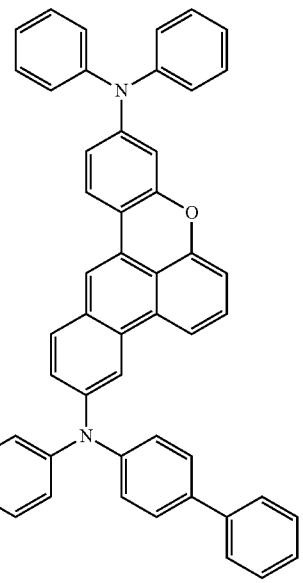
176
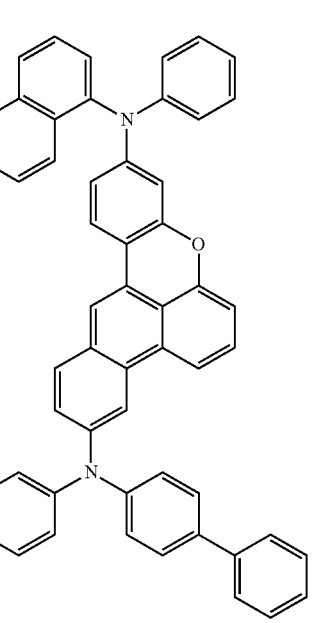

411
-continued
177
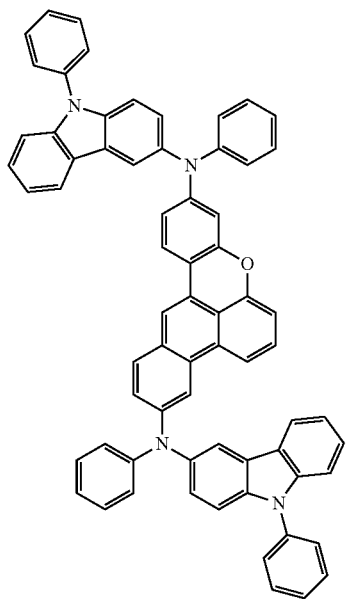
412
-continued
179
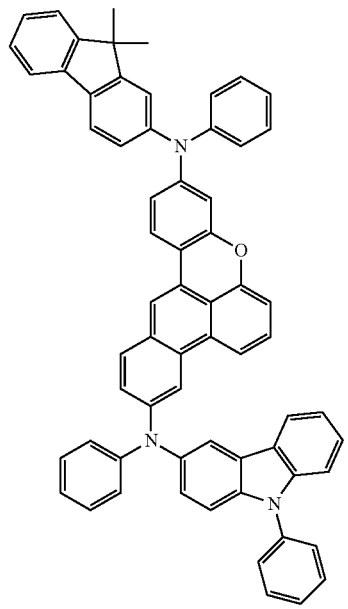
178
180

413
-continued
181
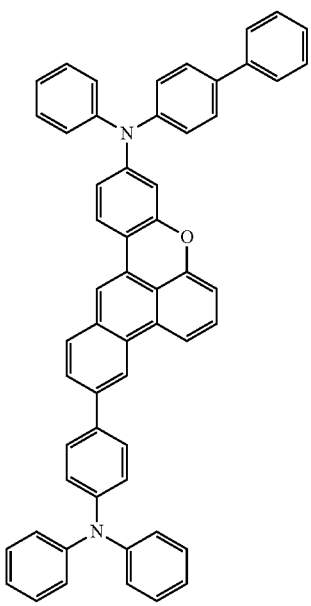
414
-continued
183
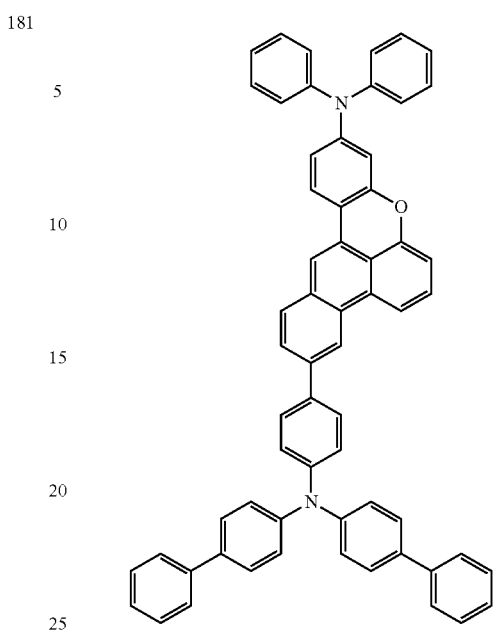
182
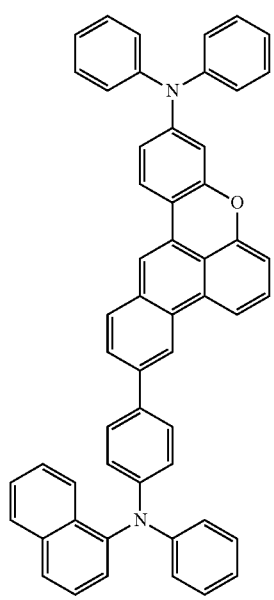
184
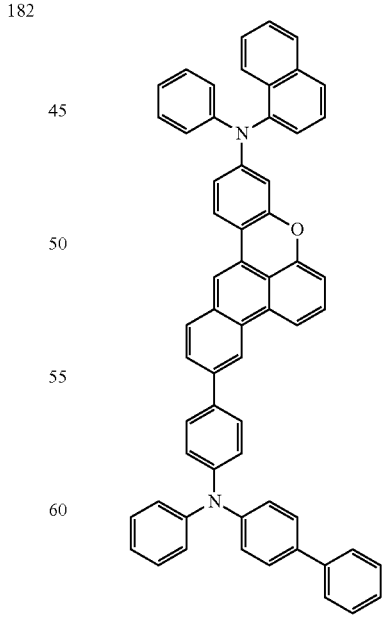

415
-continued
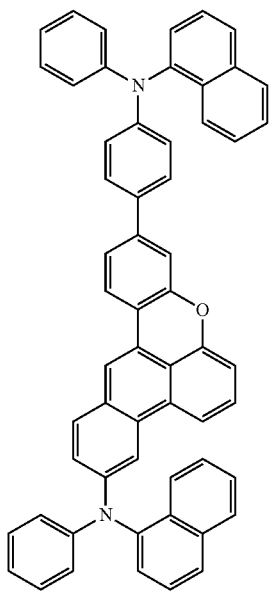
416
-continued
185
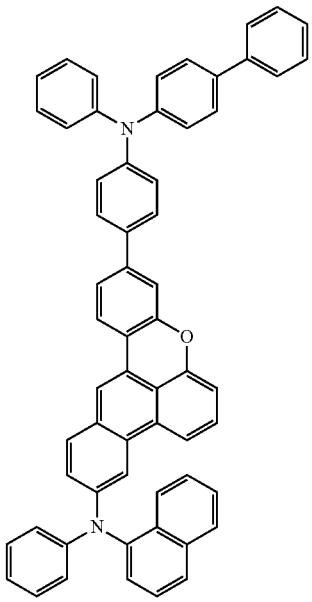
187
186
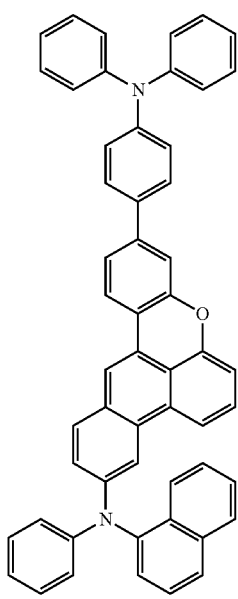
188
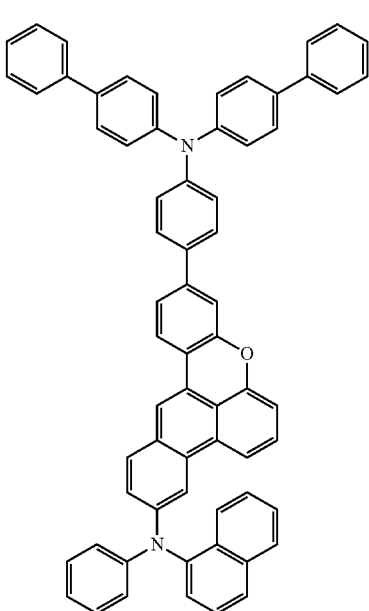

417
-continued
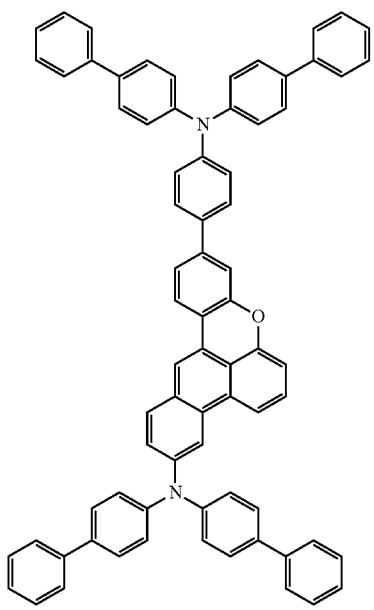
418
-continued
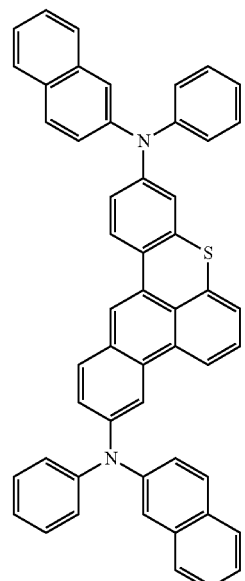
1A
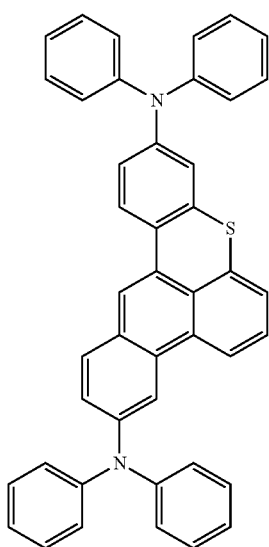
2A
3A
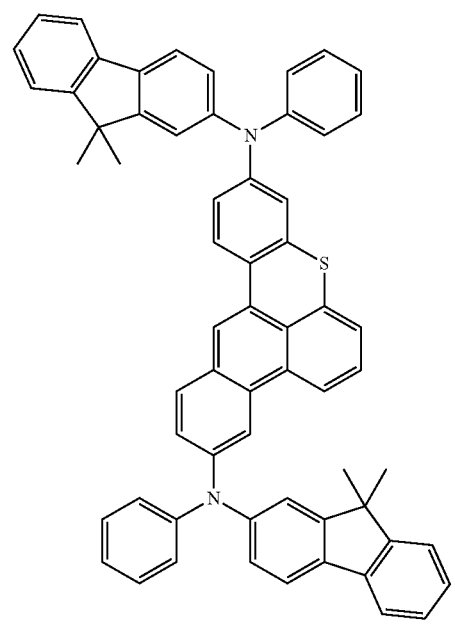

419
-continued
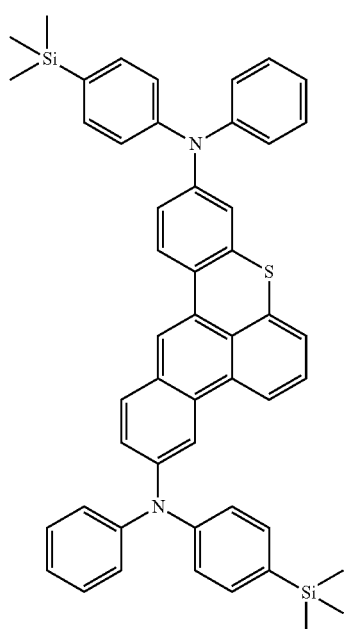
420
-continued
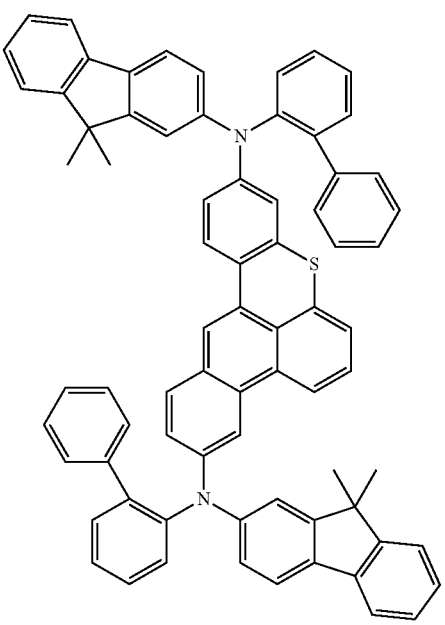
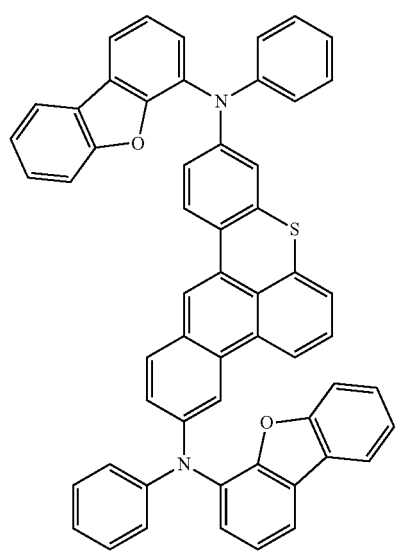
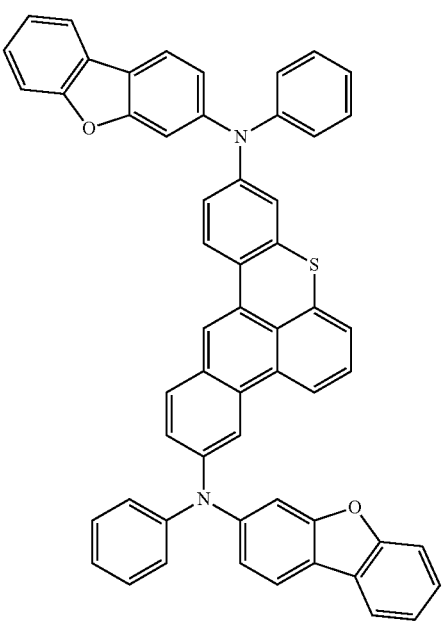

421
-continued
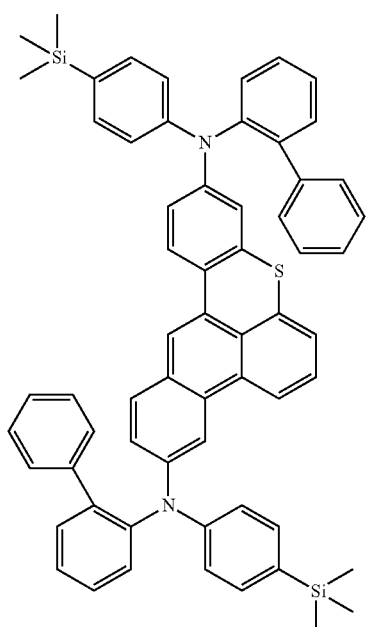
422
-continued
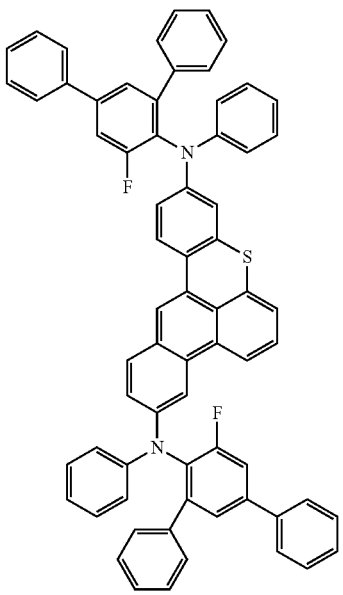
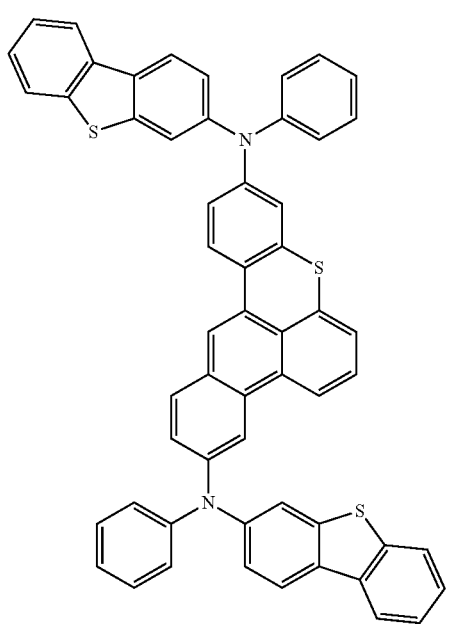
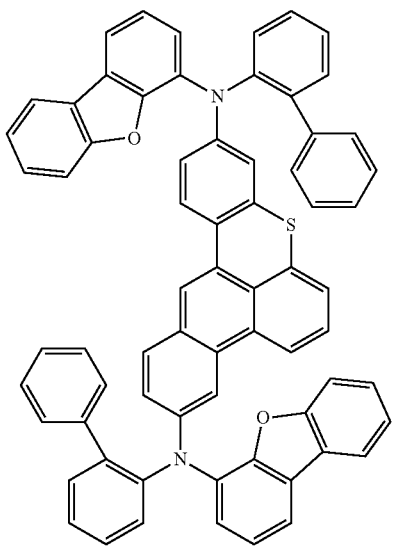

423
-continued
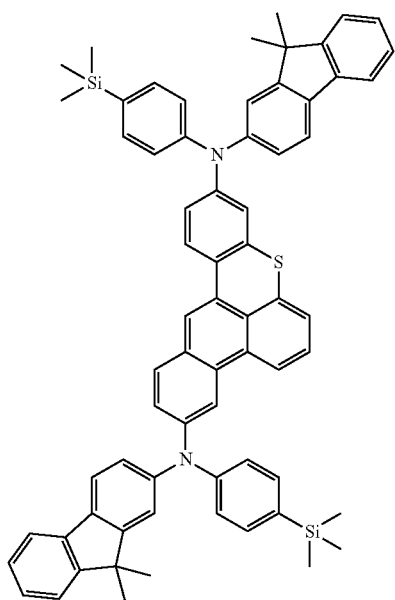
12A
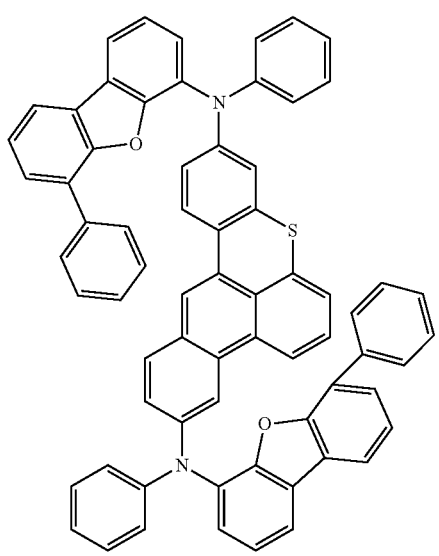
13A
424
-continued
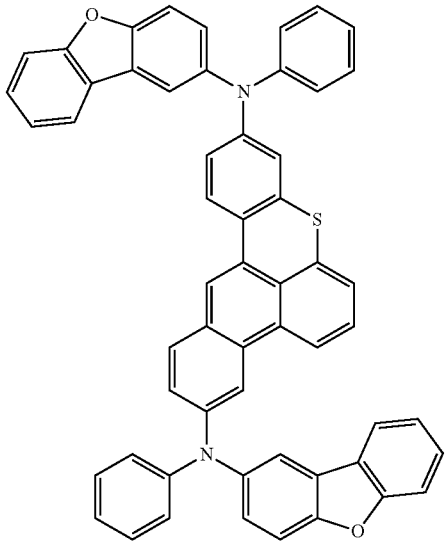
14A
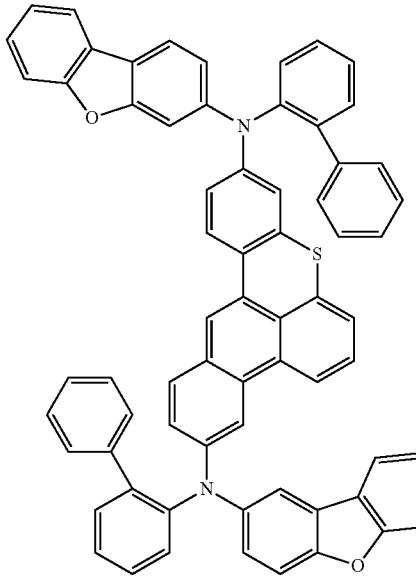
15A 425
-continued
426
-continued
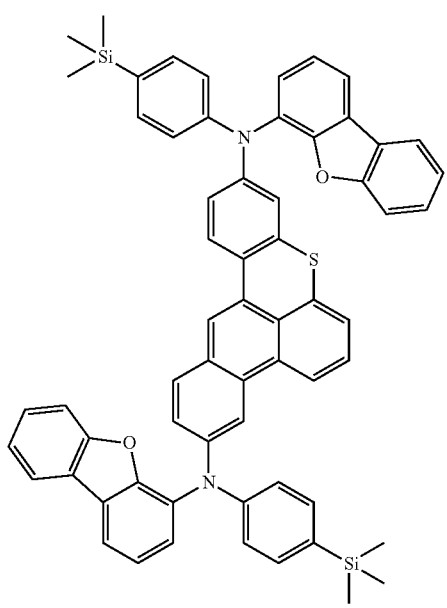
16A
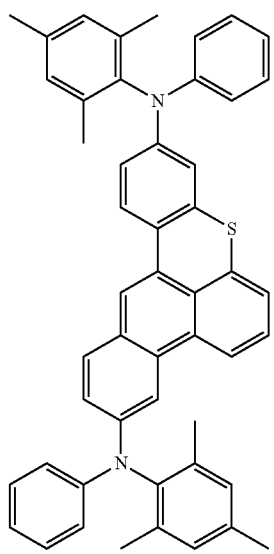
18A
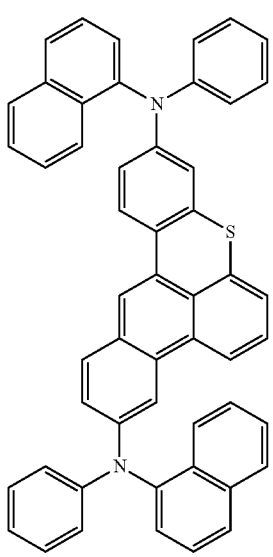
17A
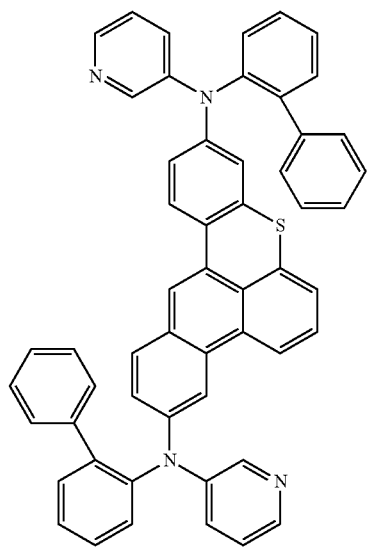
19A 427
-continued
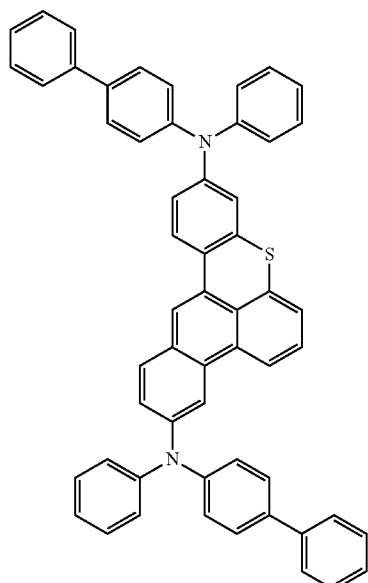
428
-continued
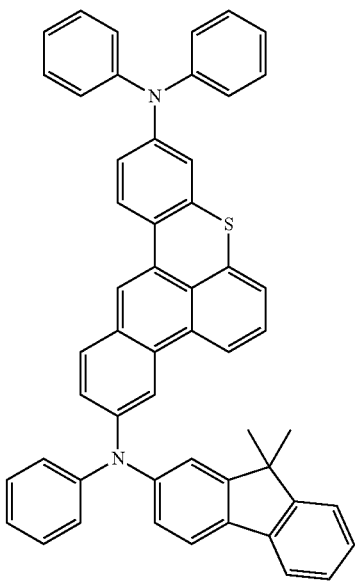
20A
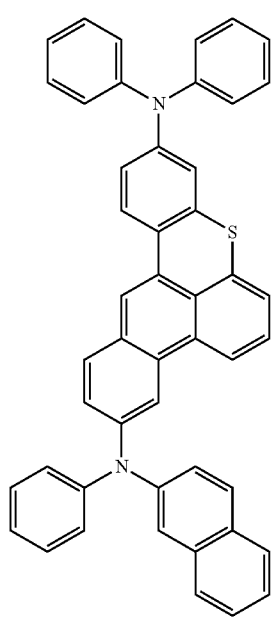
21A
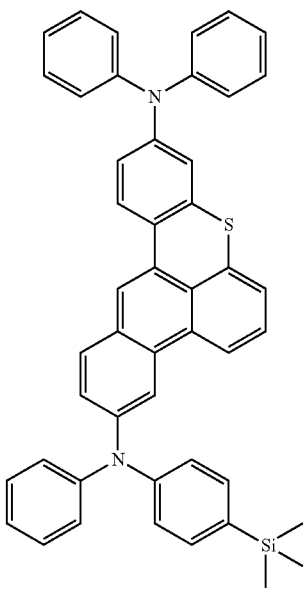
22A
23A 429
-continued
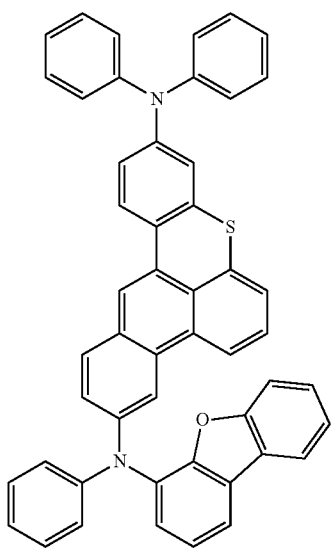
24A
430
-continued
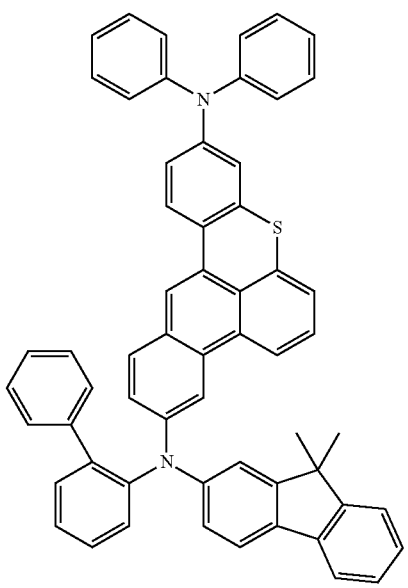
26A
25A
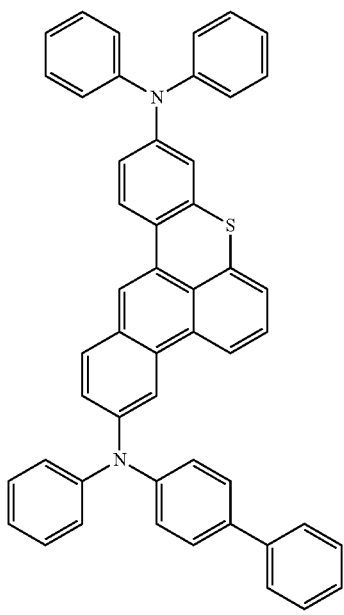
27A
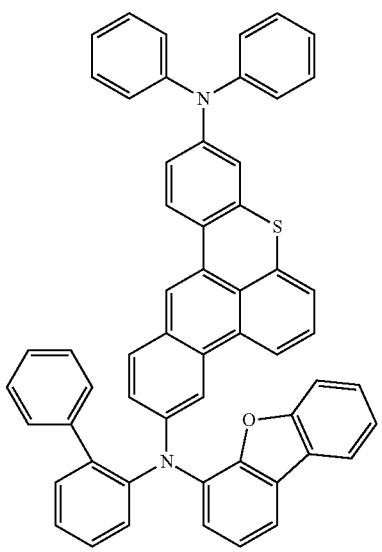

431
-continued
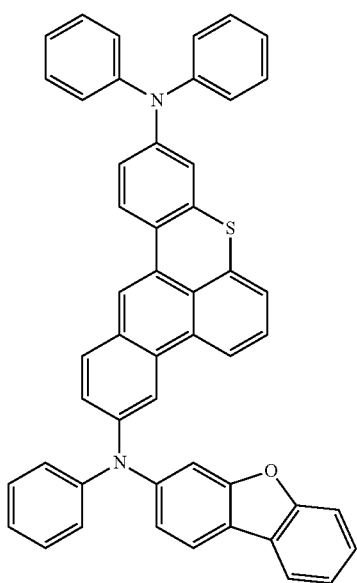
28A
432
-continued
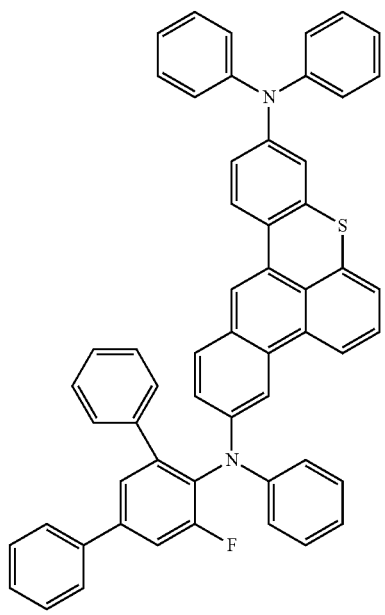
30A
29A
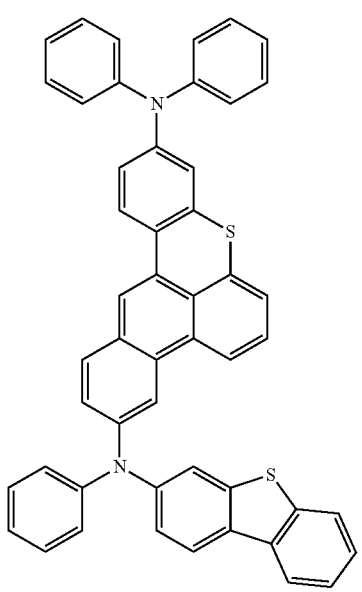
31A
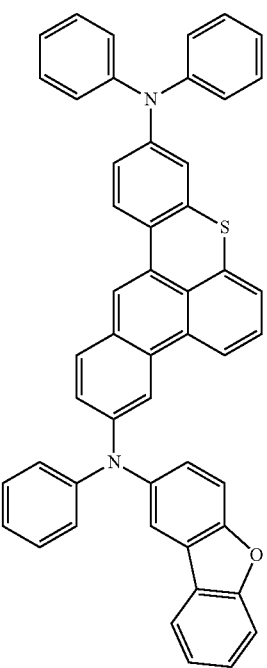

433
-continued
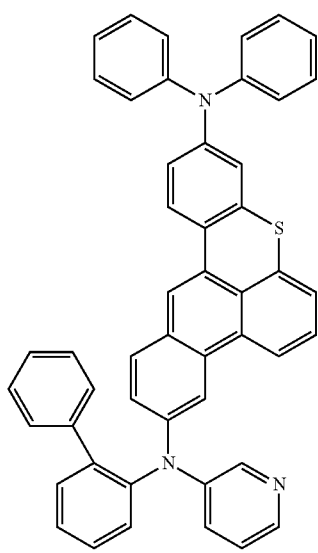
434
-continued
32A
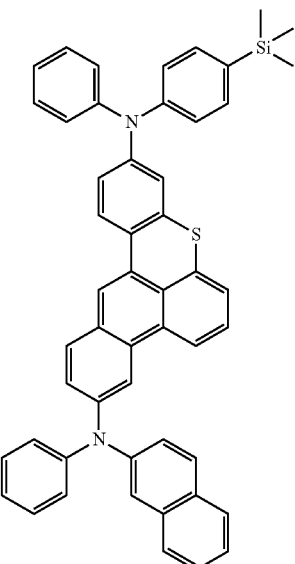
34A
33A
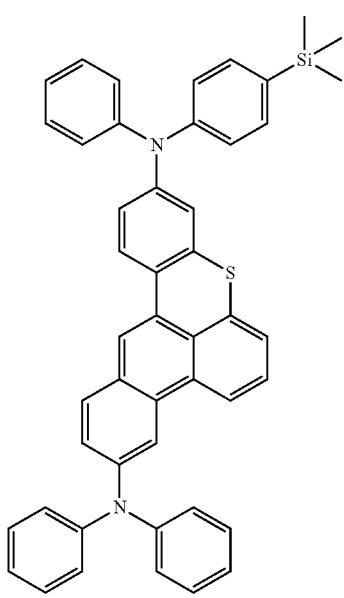
35A 435
-continued
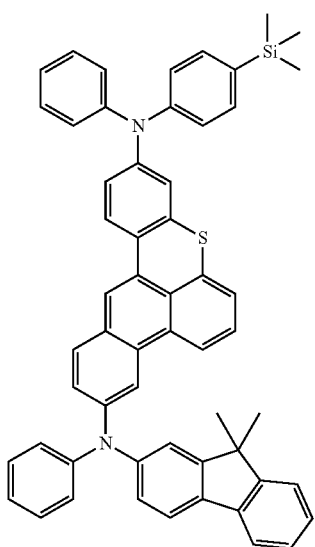
36A
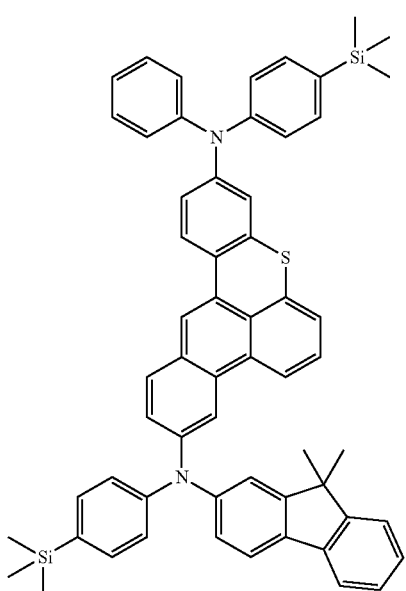
37A
436
-continued
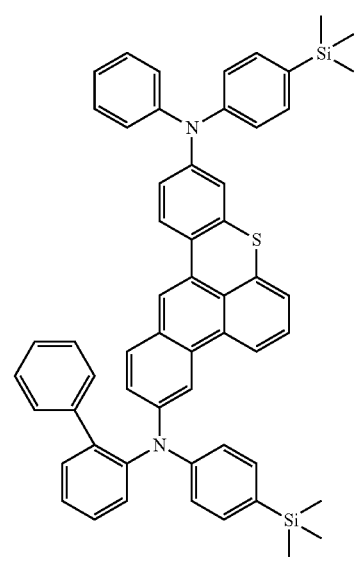
38A
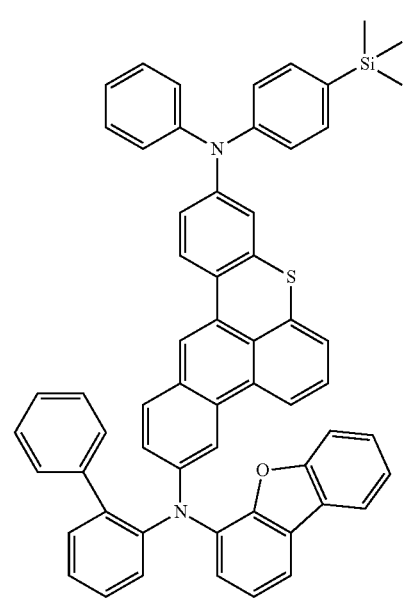
39A 437
-continued
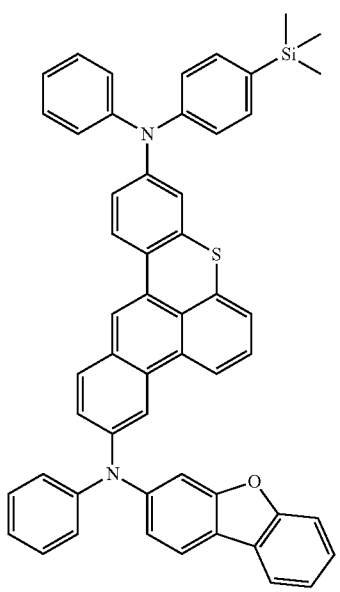
438
-continued
40A
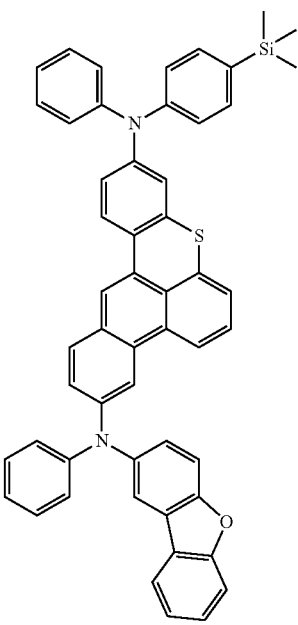
42A
41A
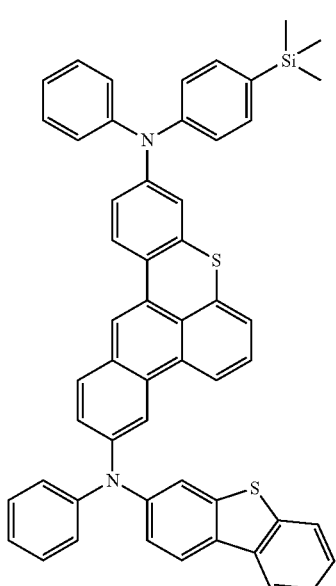
43A
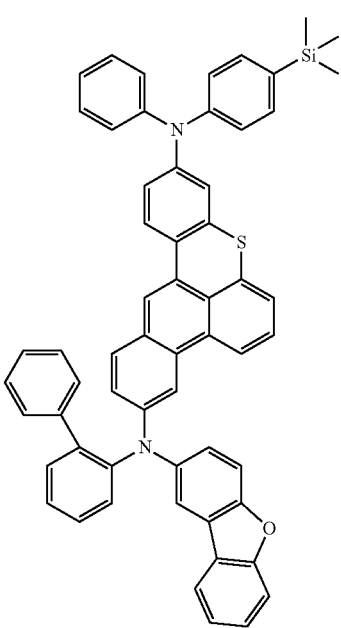

439
-continued
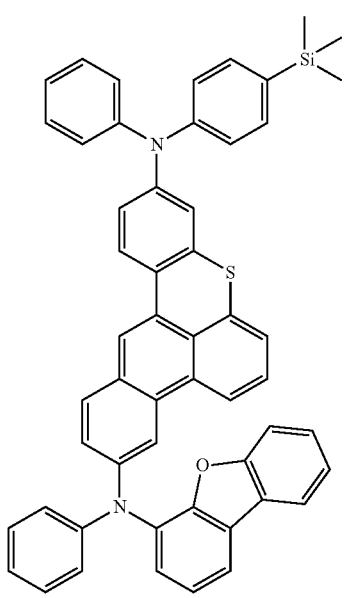
44A
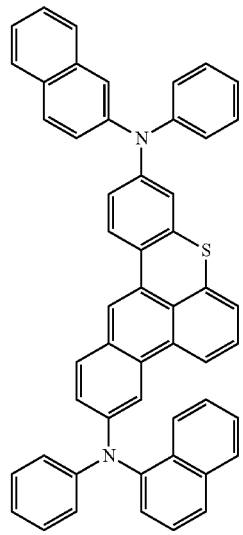
46A
440
-continued
45A
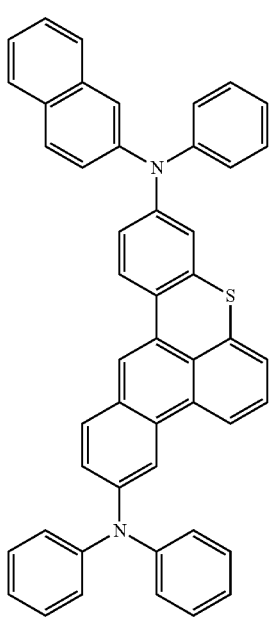
47A
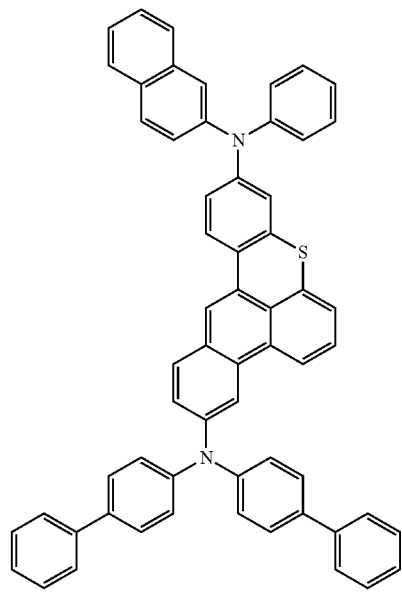

441
-continued
442
-continued
48A
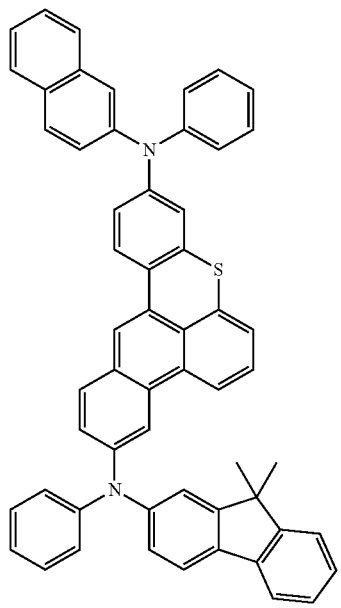
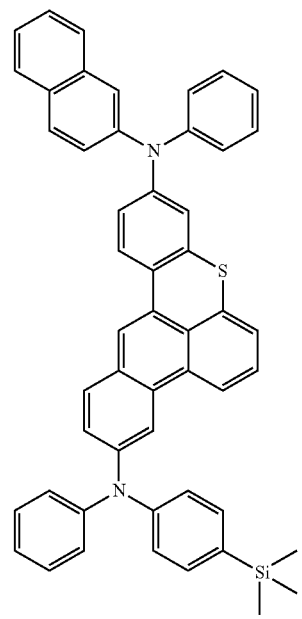
50A
49A
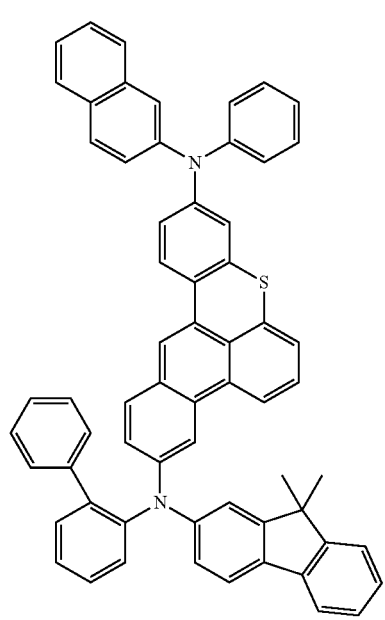
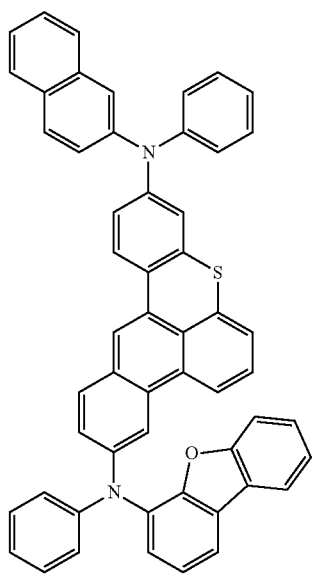
51A 443
-continued
444
-continued
52A
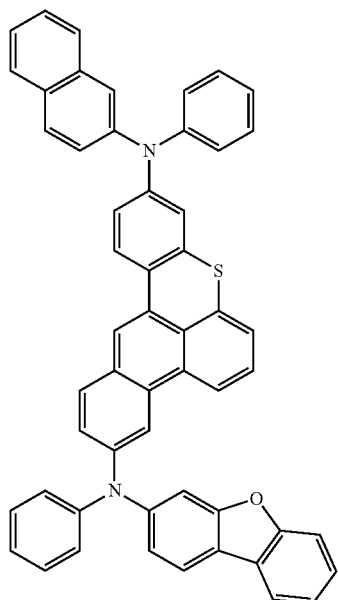
54A
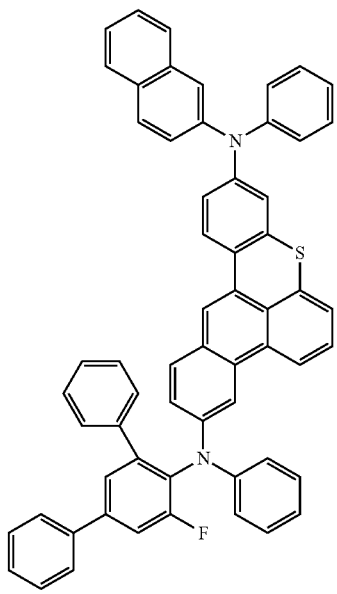
53A
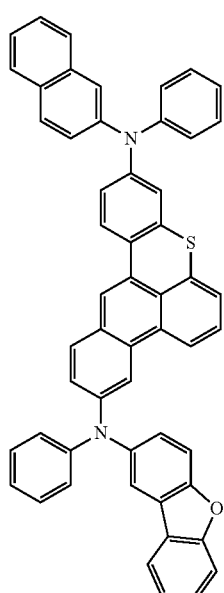
55A
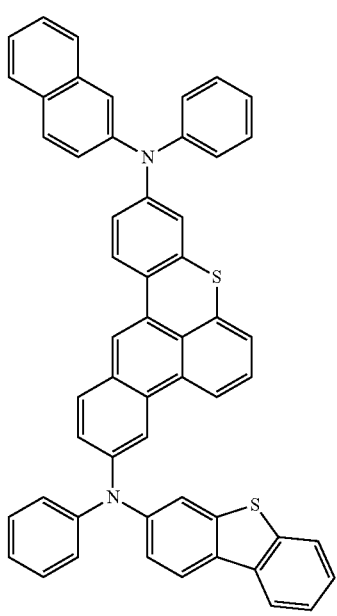

445
-continued
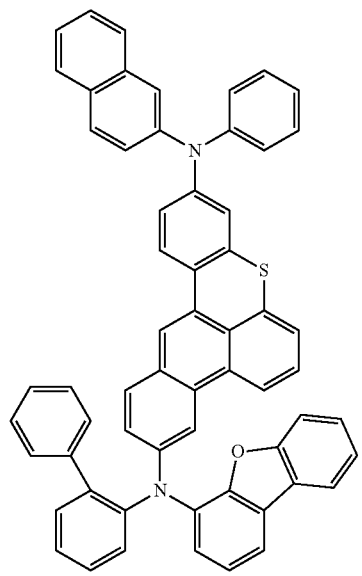
446
-continued
56A
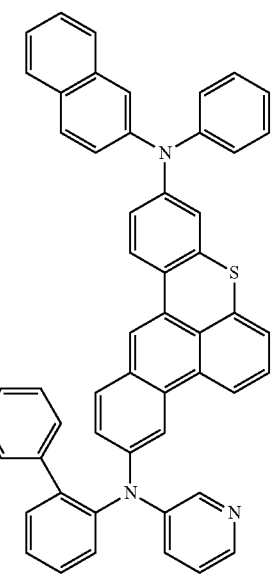
57A
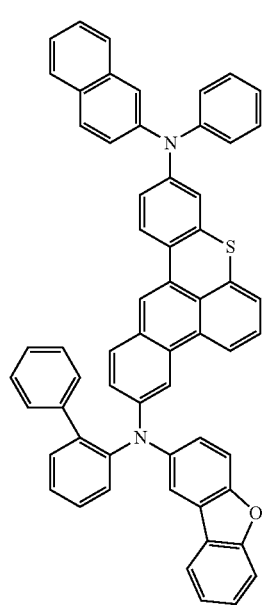
58A
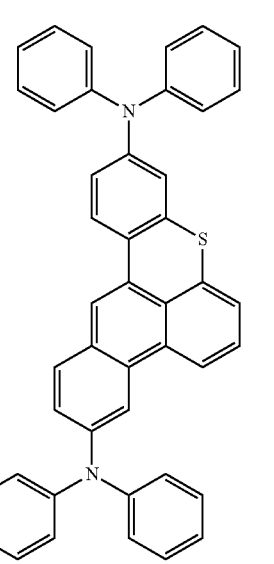
59A
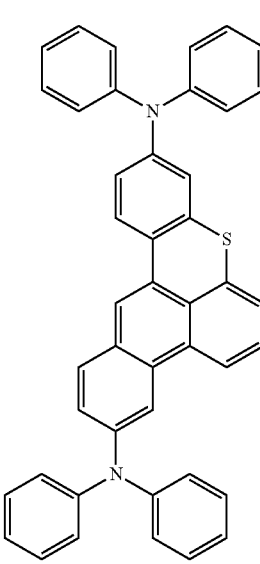
60A
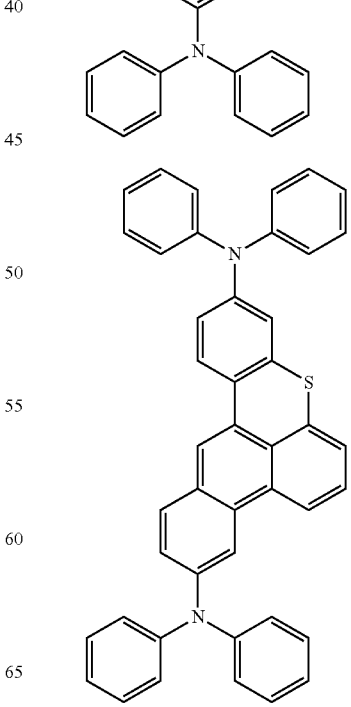

447
-continued
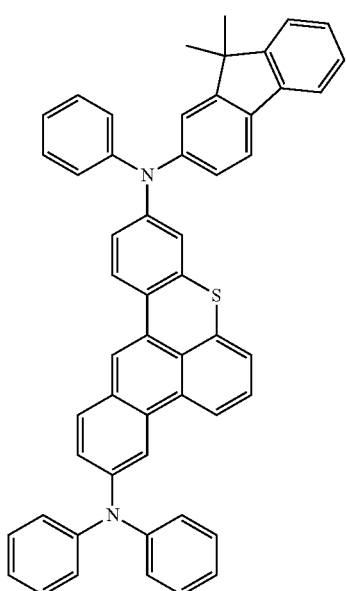
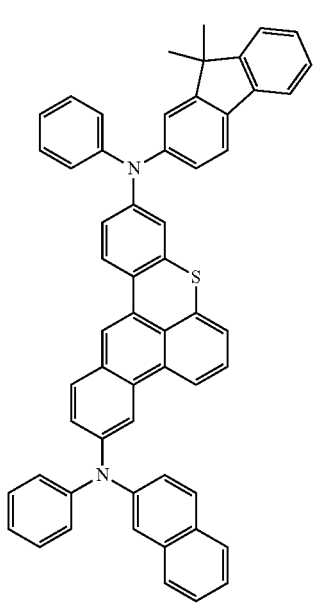
62A
448
-continued
61A
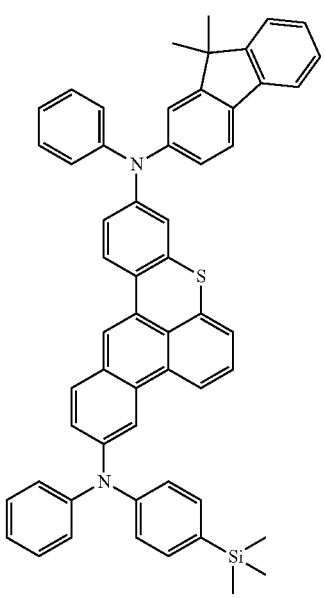
63A
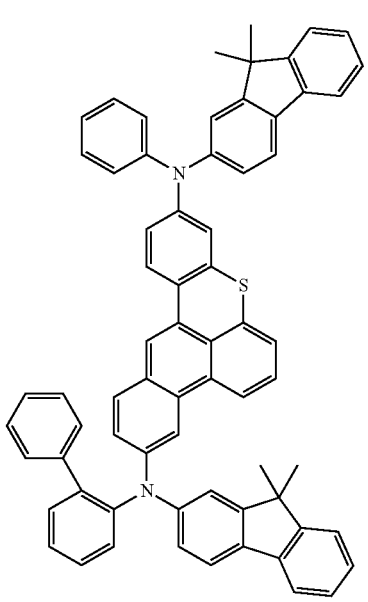
64A 449
-continued
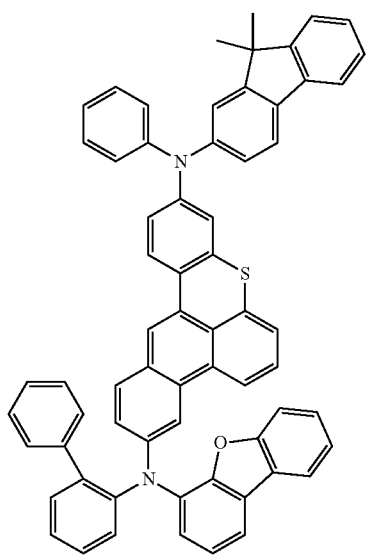
65A
450
-continued
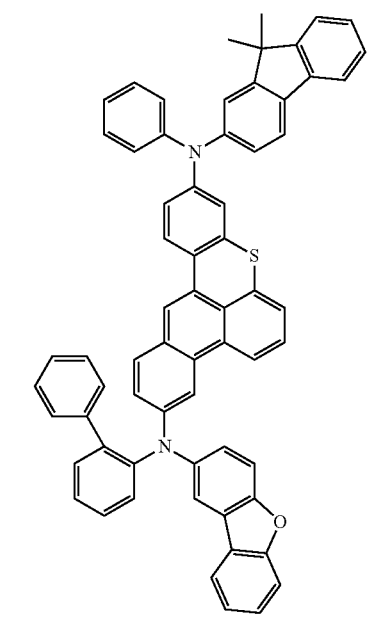
67A
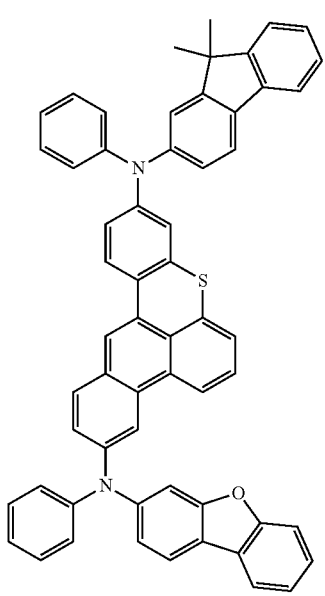
66A
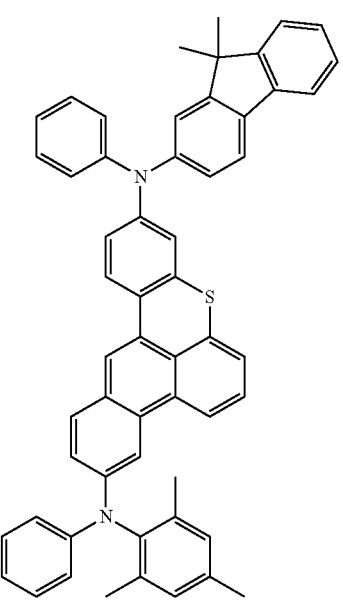
68A 451
-continued
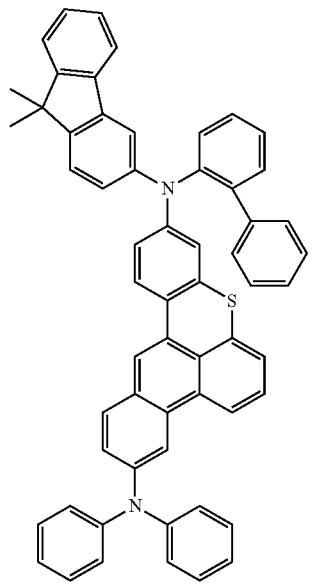
69A
452
-continued
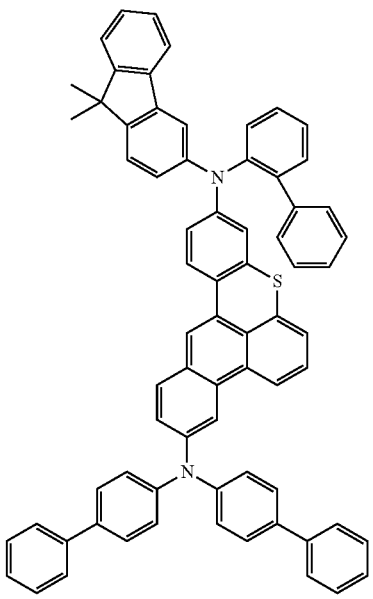
71A
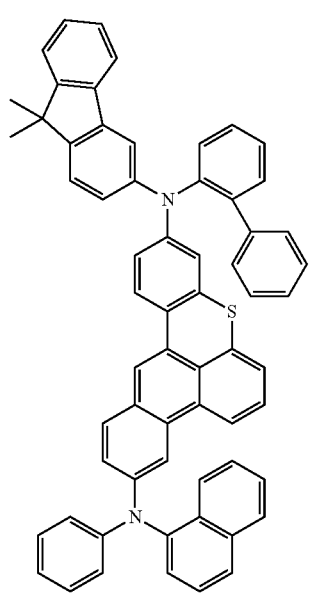
70A
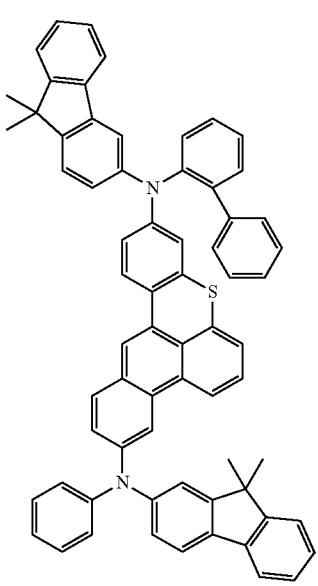
72A 453
-continued
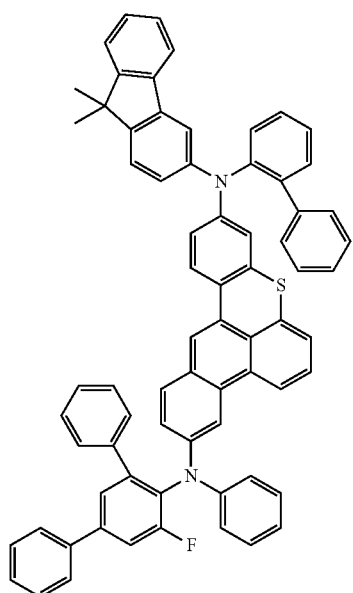
454
-continued
73A
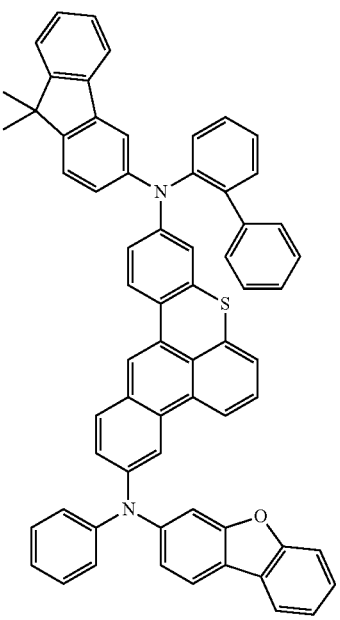
75A
74A
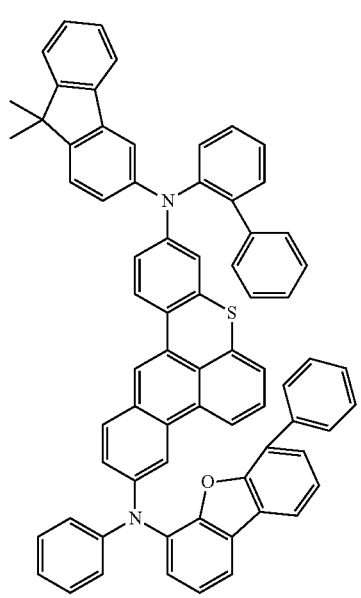
76A
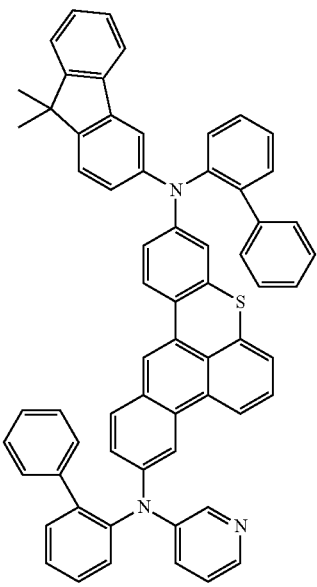

455
-continued
77A
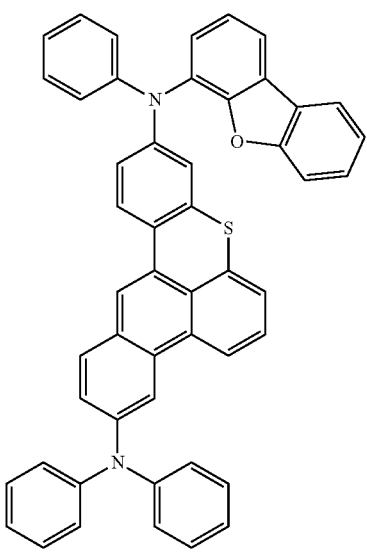
78A
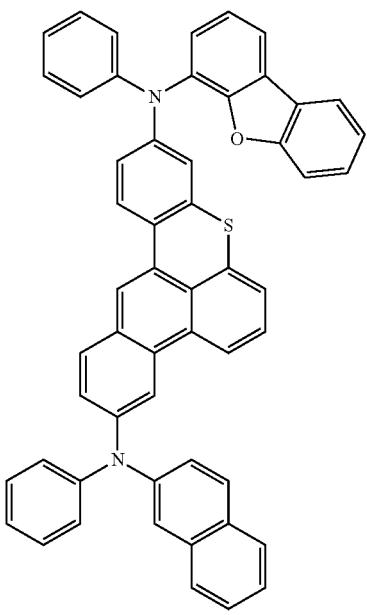
456
-continued
79A
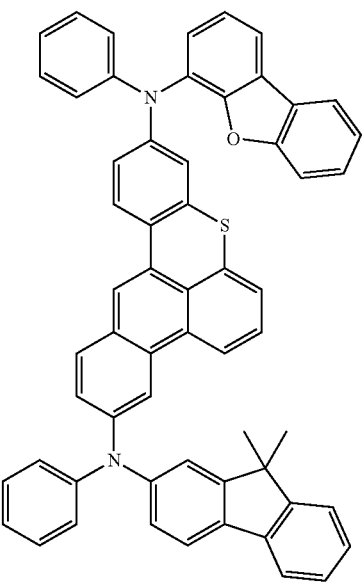
80A
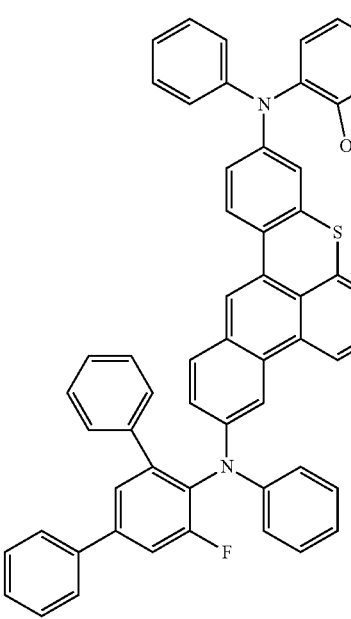

457
-continued
458
-continued
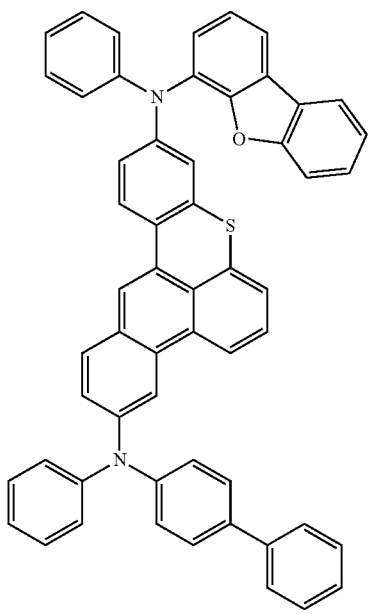
81A
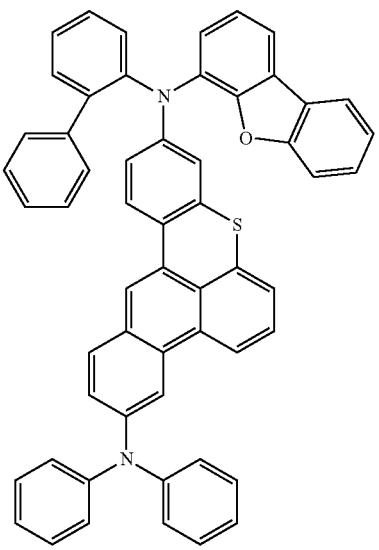
83A
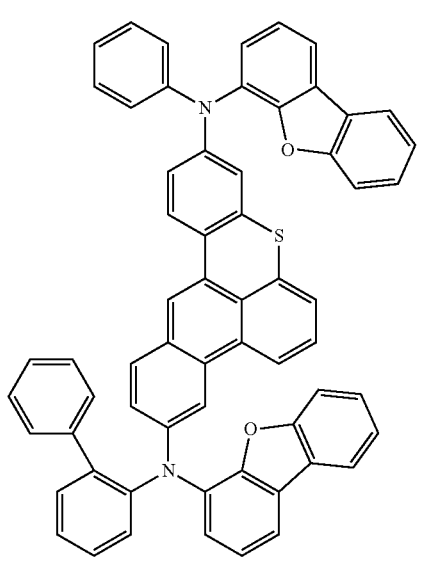
82A
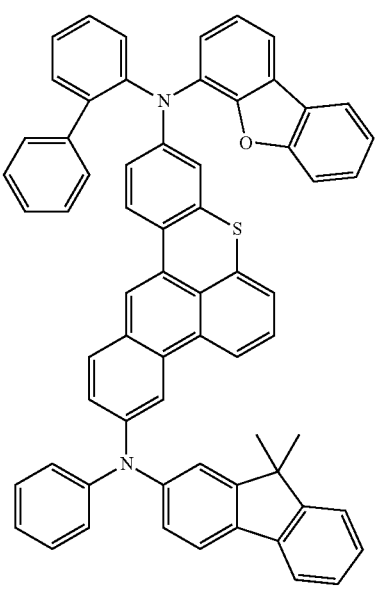
84A

459
-continued
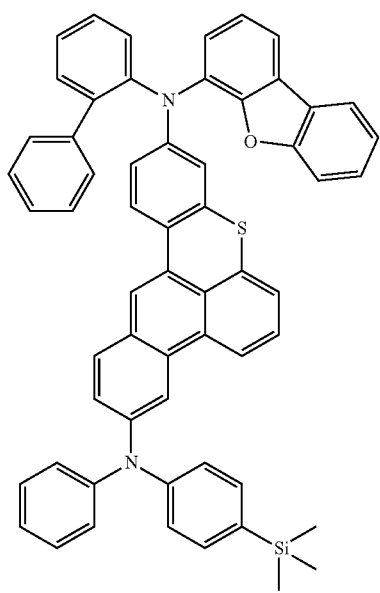
85A
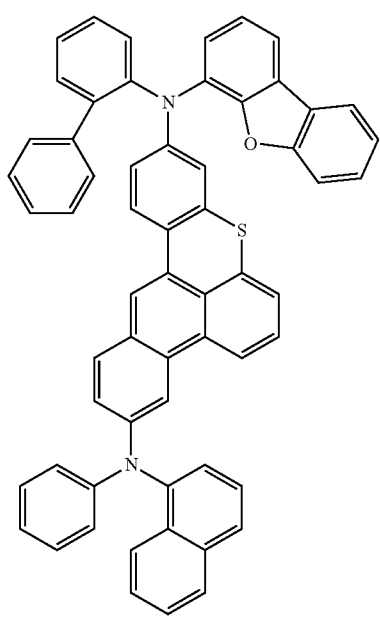
86A
460
-continued
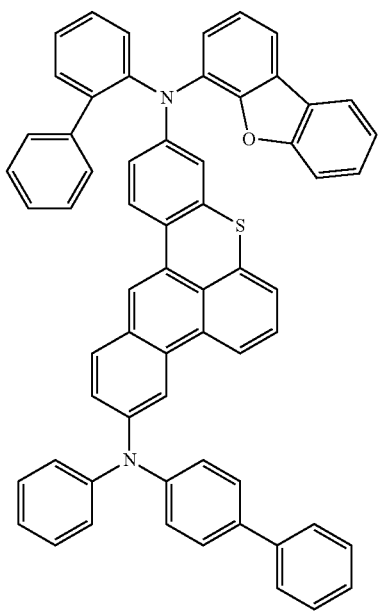
87A
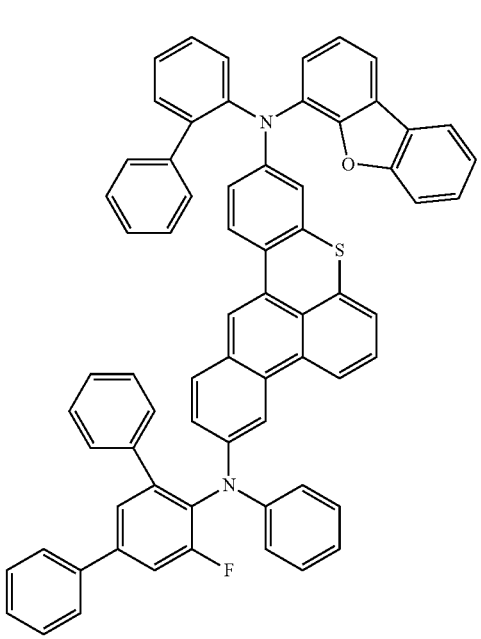
88A 461
-continued
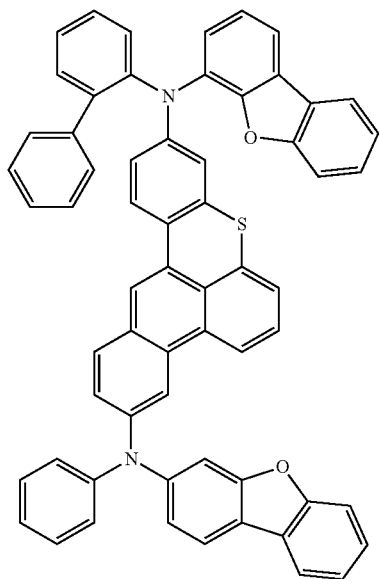
89A
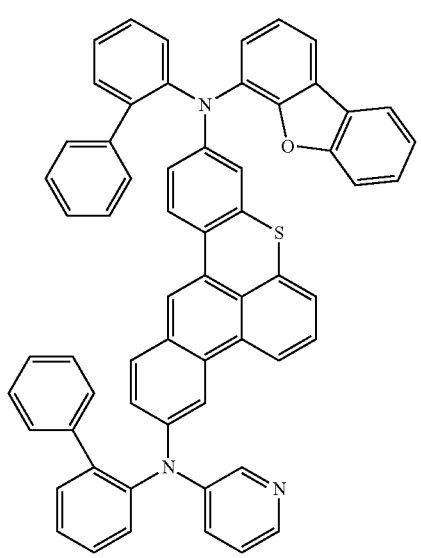
90A
462
-continued
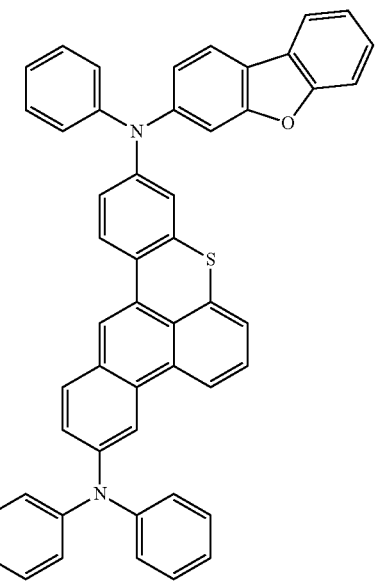
91A
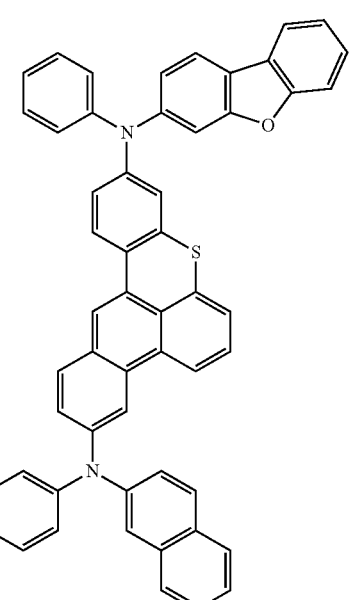
92A -continued
463
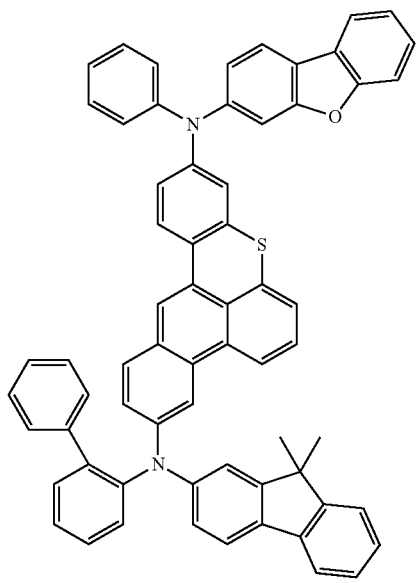
93A
464
-continued
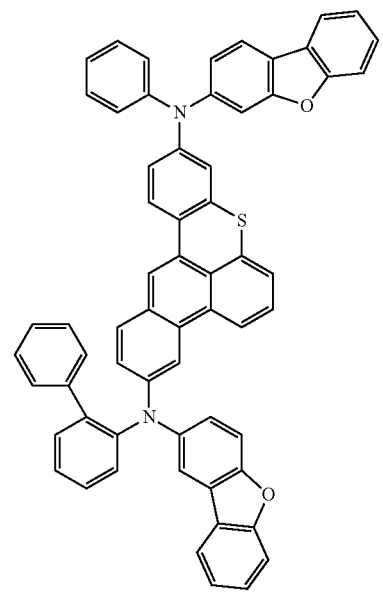
95A
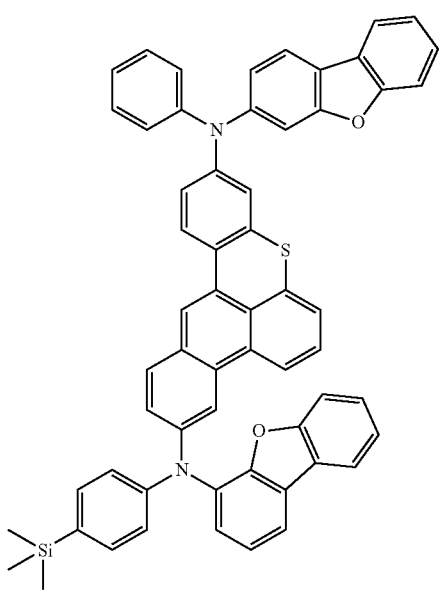
94A
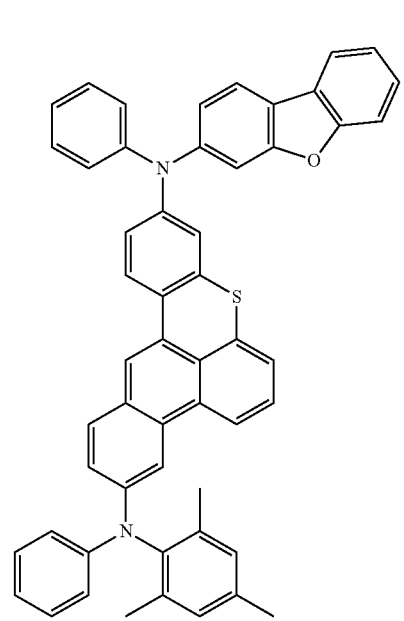
96A 465
-continued
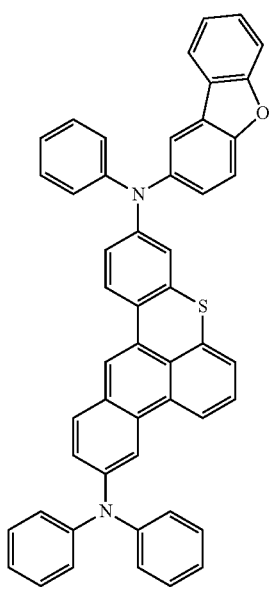
97A
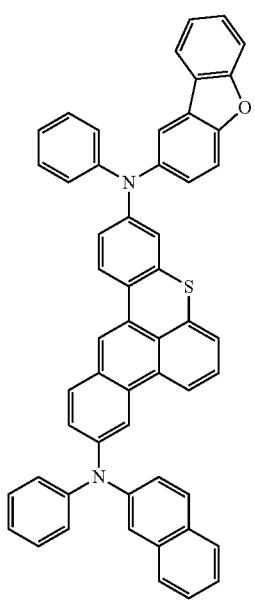
98A
466
-continued
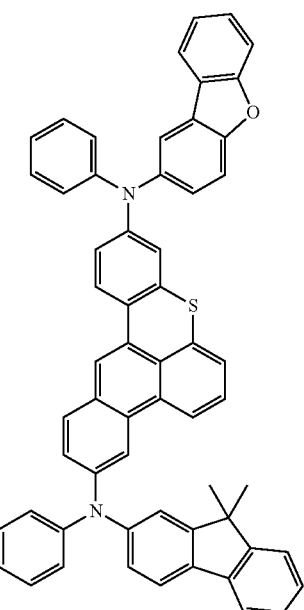
99A
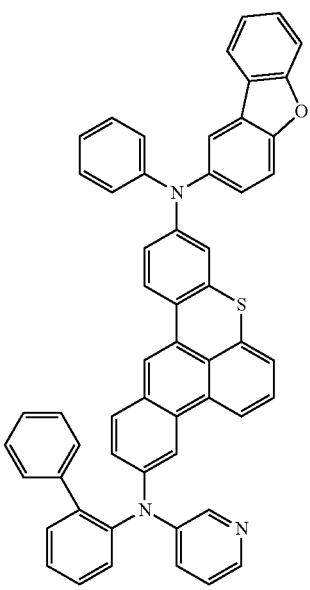
100A 467
-continued
101A
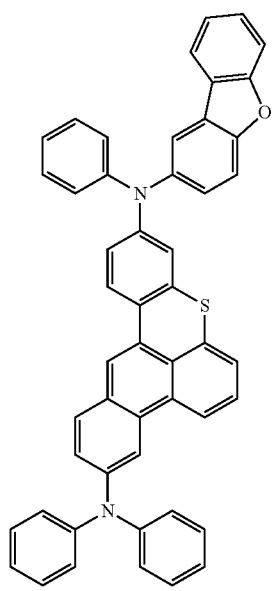
102A
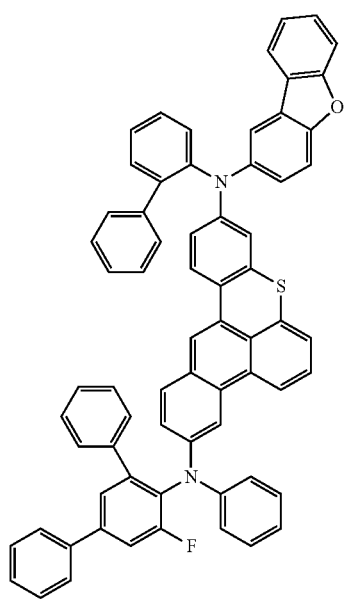
468
-continued
103A
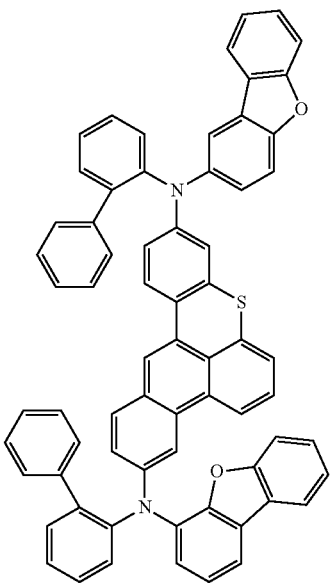
104A
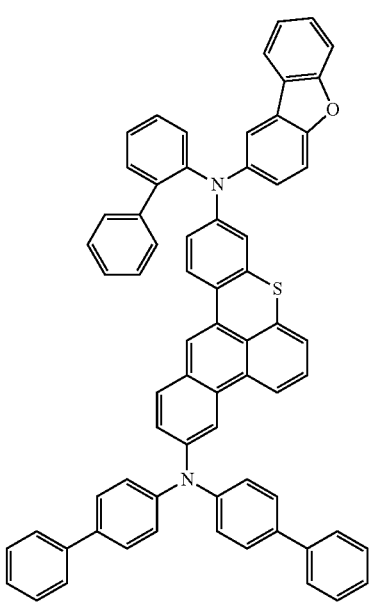

469
-continued
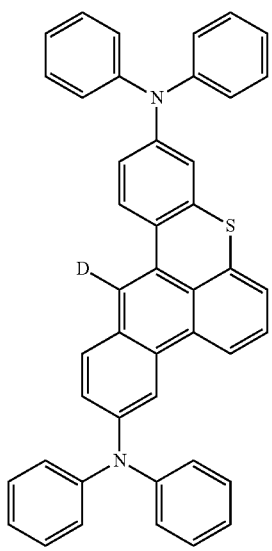
106A
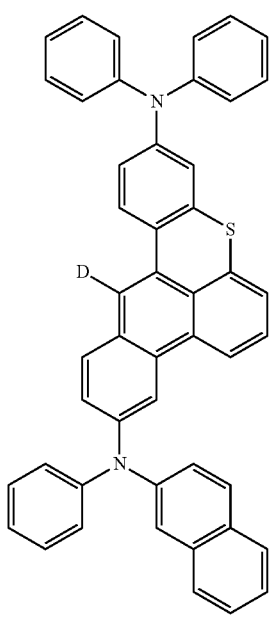
470
-continued
105A
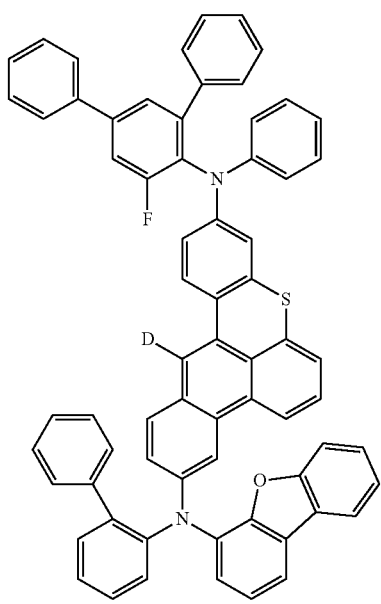
107A
106A
108A
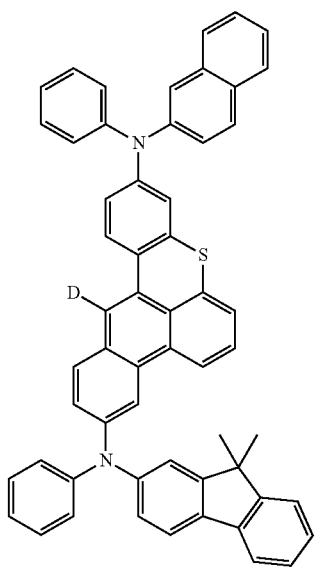

471
-continued
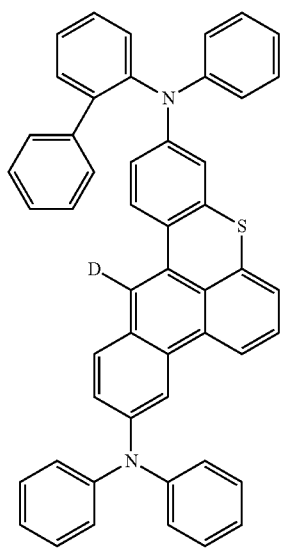
109A
472
-continued
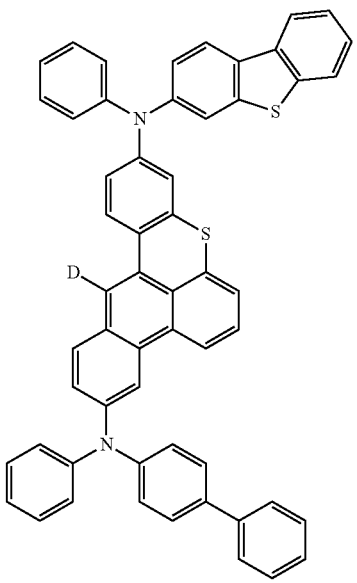
111A
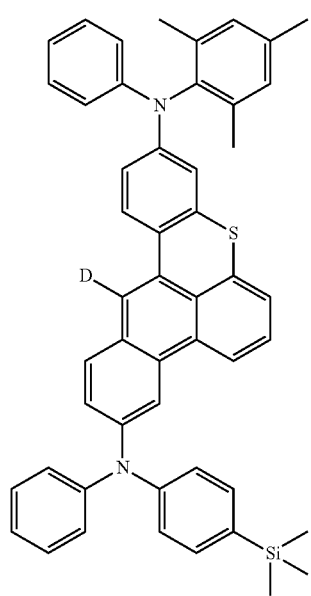
110A
112A 473
-continued
474
-continued
113A
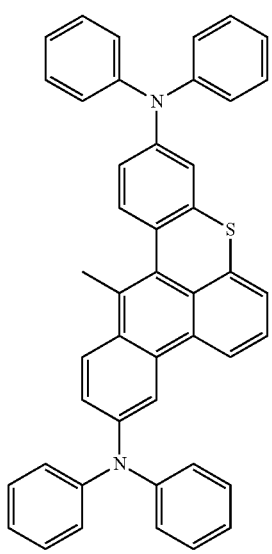
115A
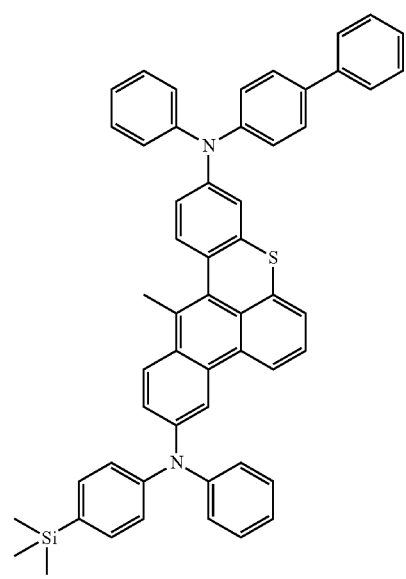
114A
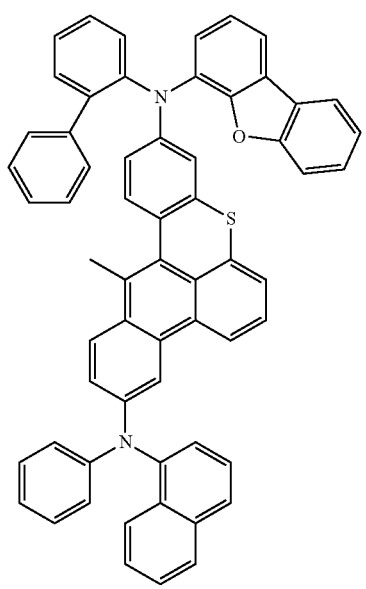
116A
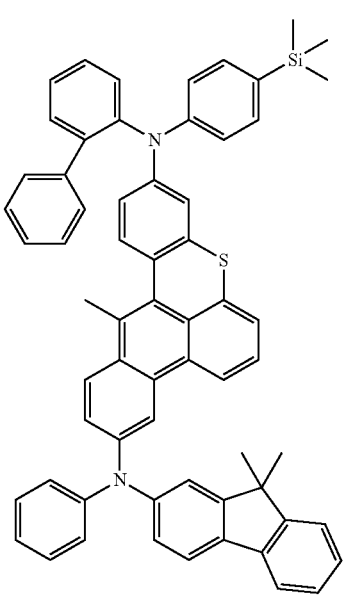

475
-continued
476
-continued
117A
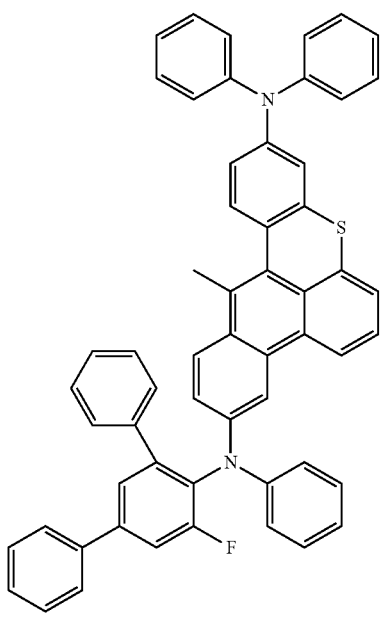
119A
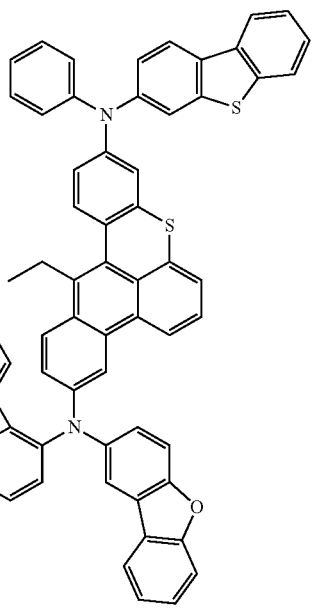
118A
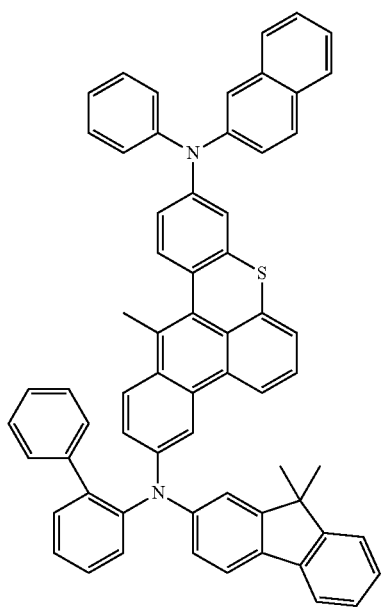
120A
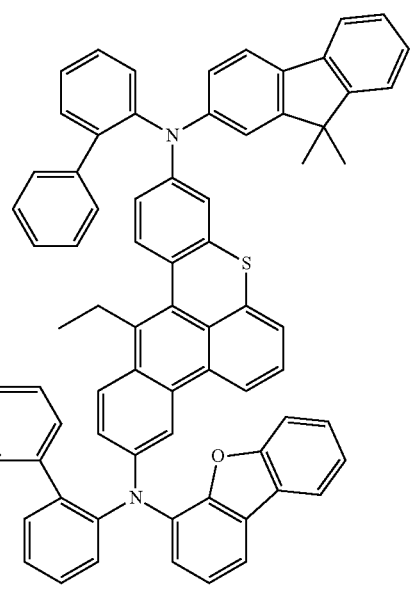

477
-continued
478
-continued
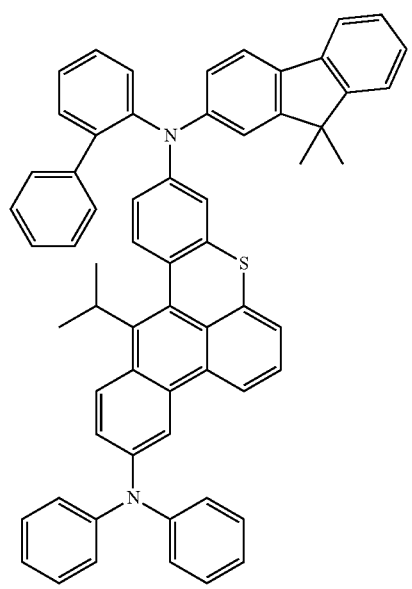
121A
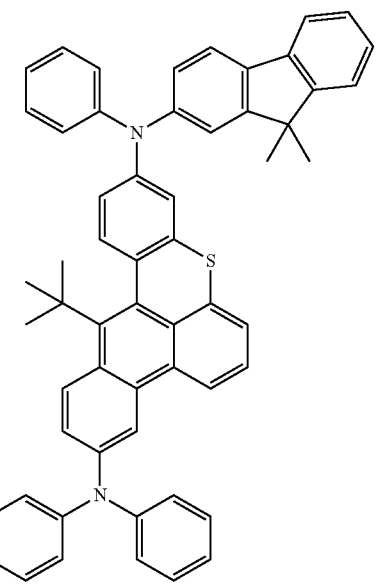
123A
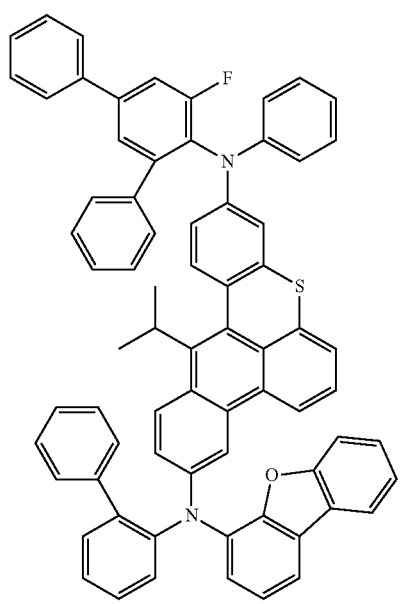
122A
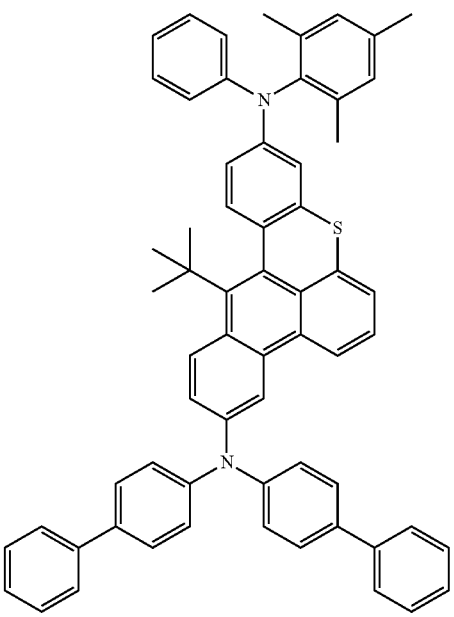
124A 479
-continued
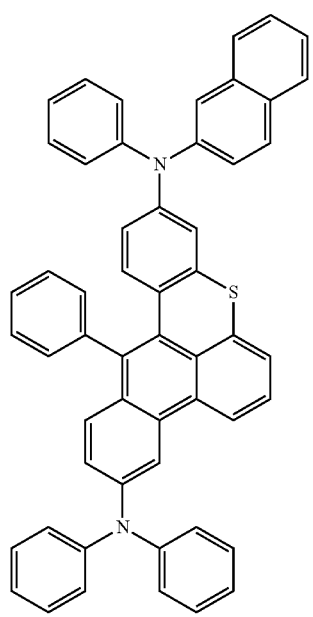
125A
480
-continued
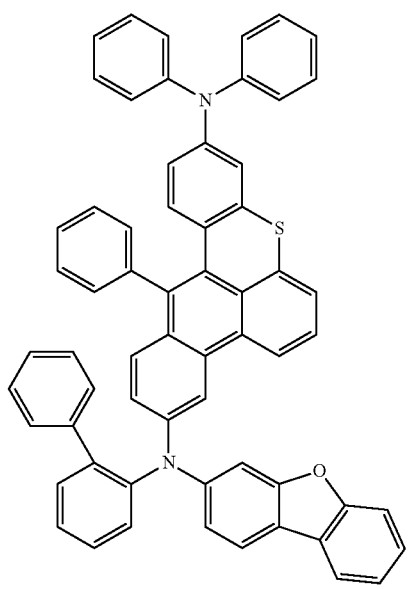
127A
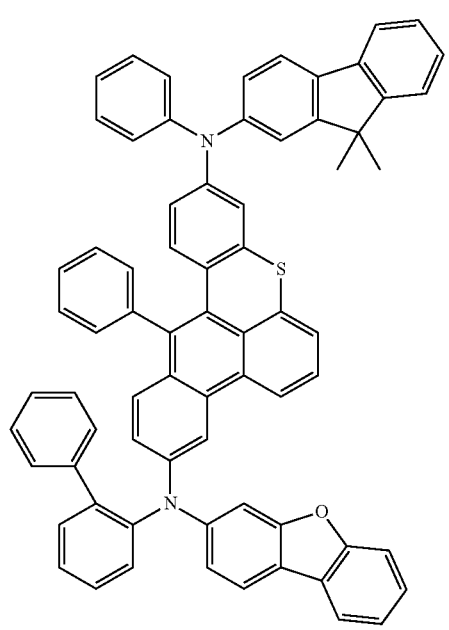
126A
128A 481
-continued
482
-continued
129A
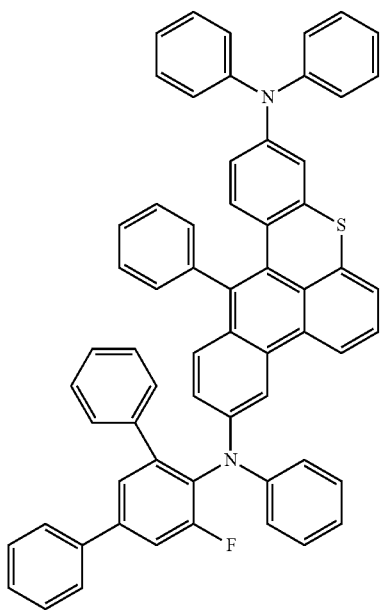
131A
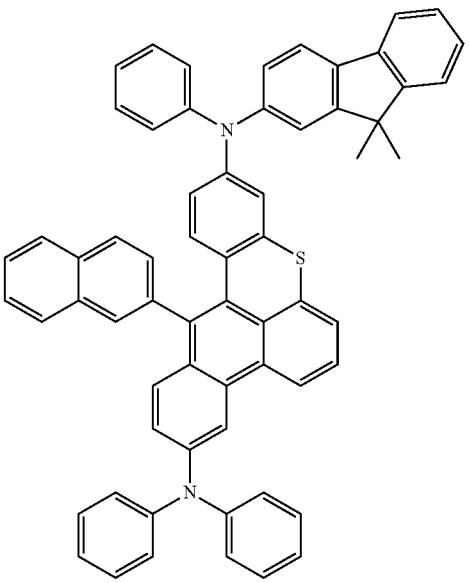
130A
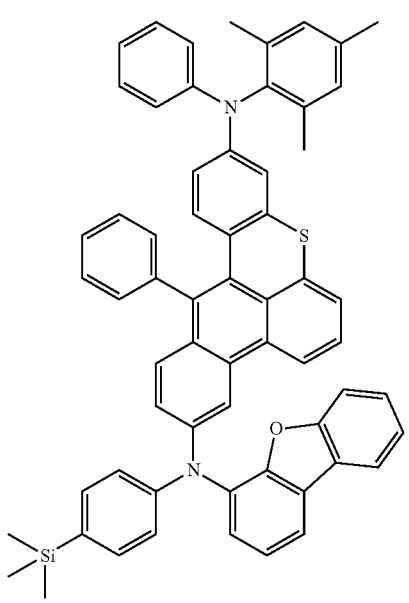
132A
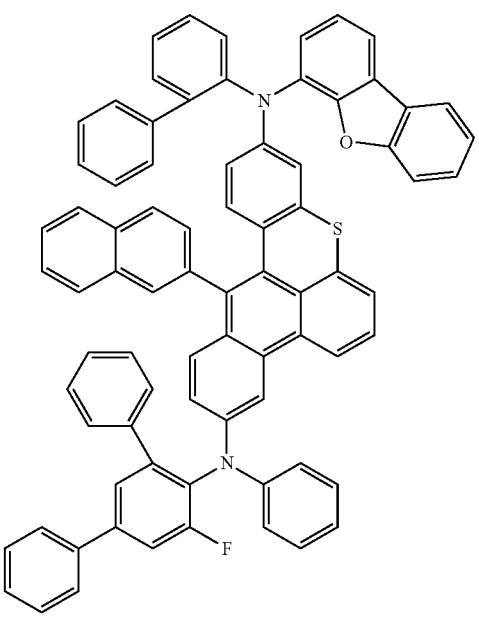

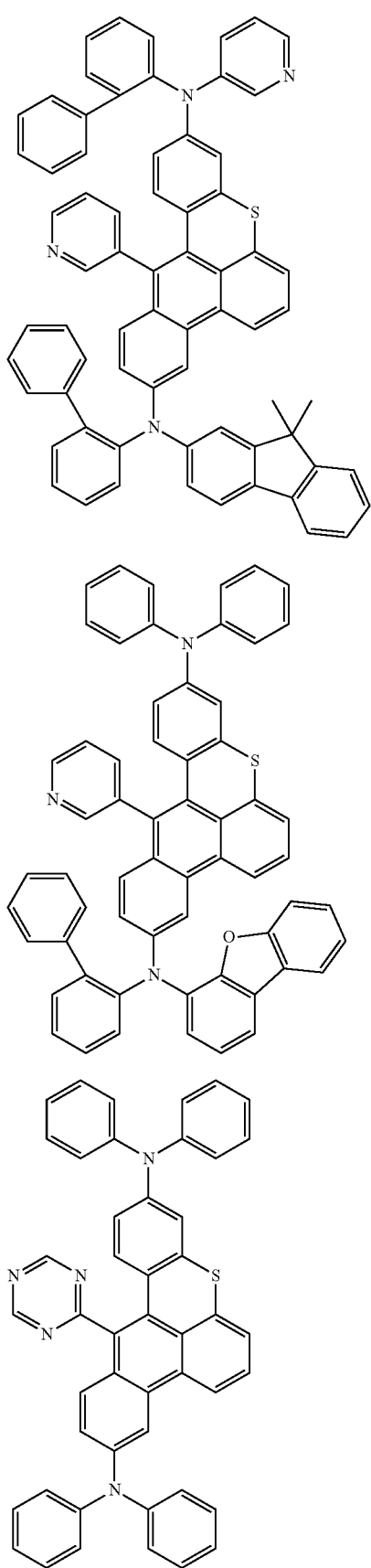
133A
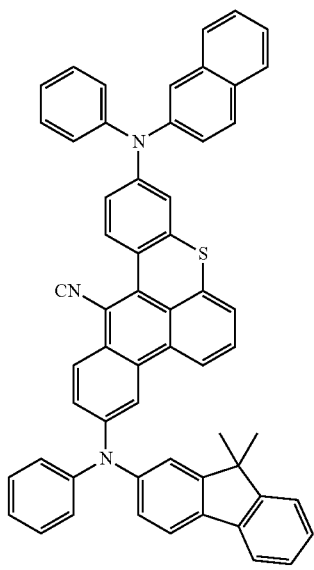
134A
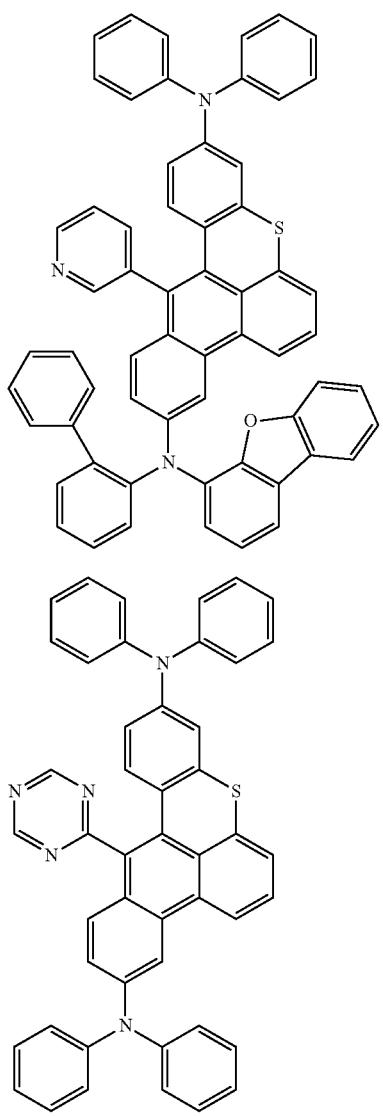
135A
136A
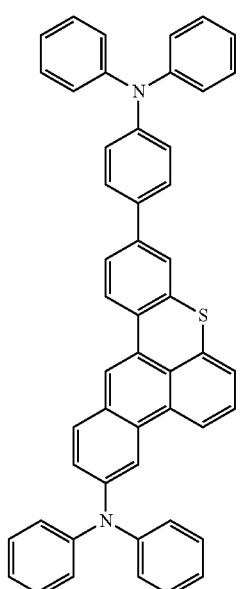
137A

485
-continued
138A
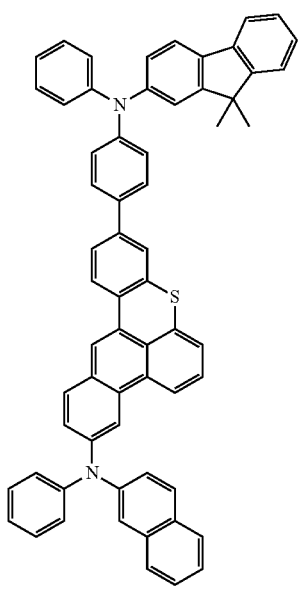
139A
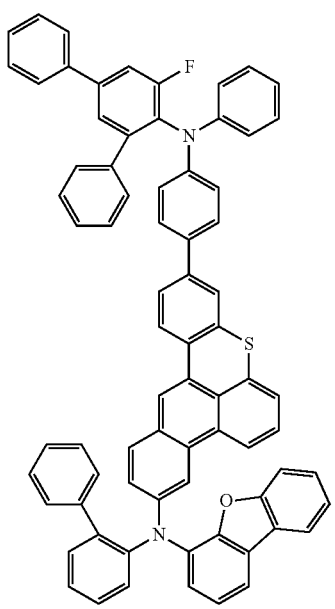
486
-continued
140A
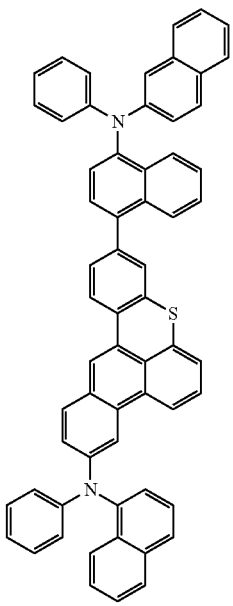
141A
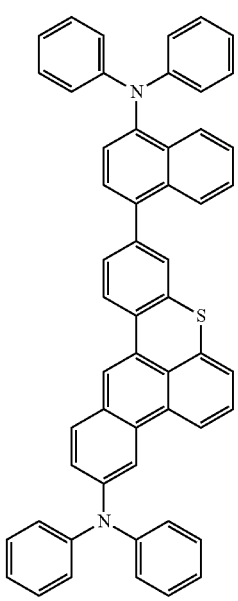

487
-continued
142A
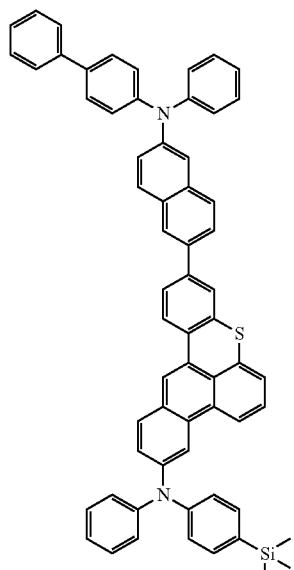
488
-continued
144A
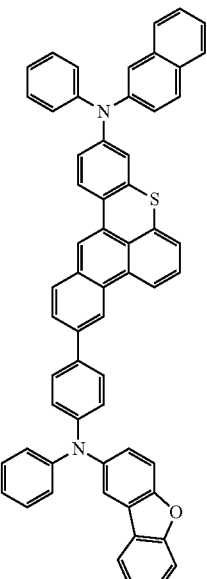
143A
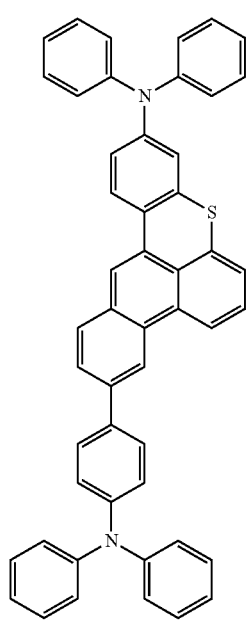
145A
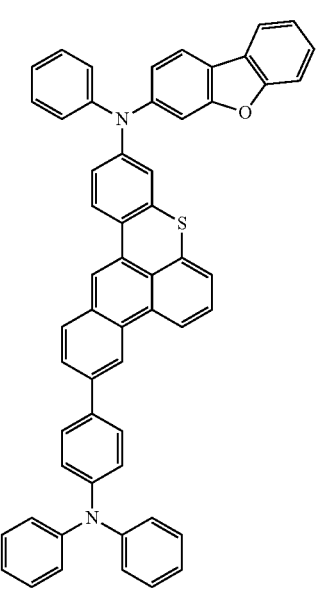

-continued
489
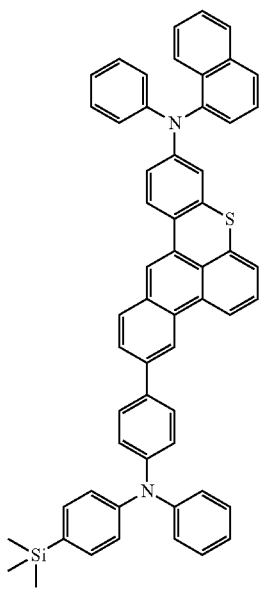
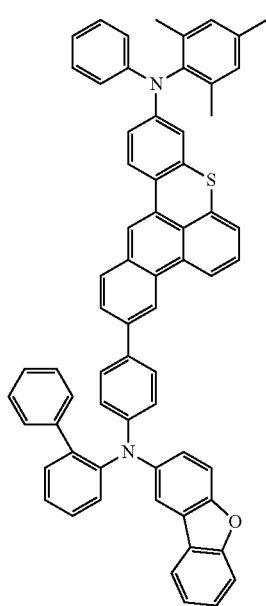
-continued
146A
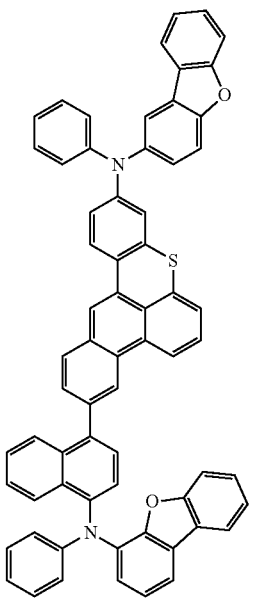
147A
490
148A
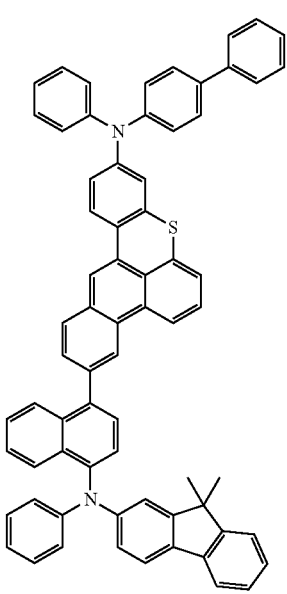
149A 491
-continued
492
-continued
150A
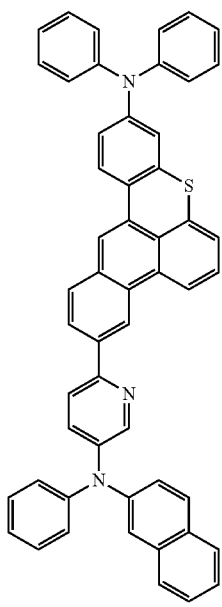
152A
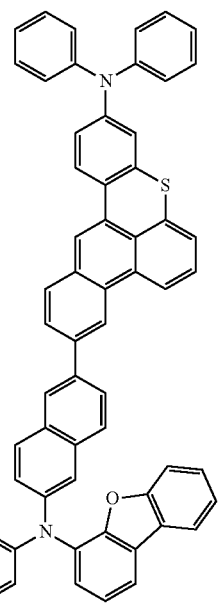
151A
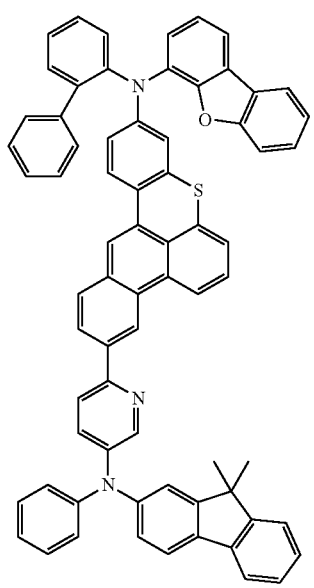
153A
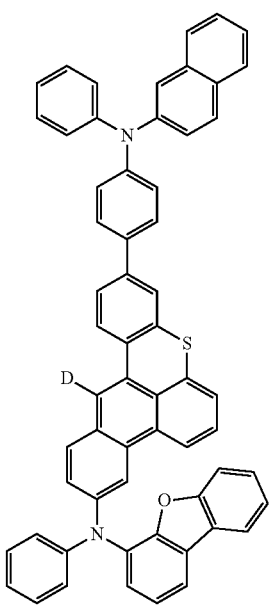

493
-continued
494
-continued
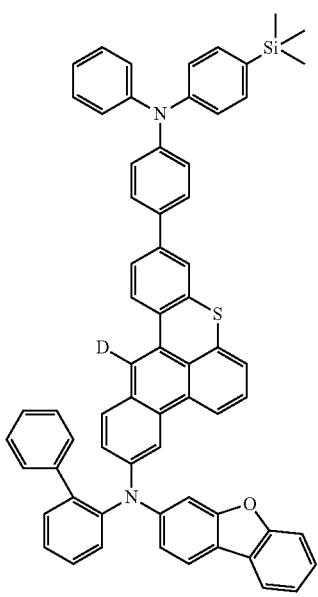
154A
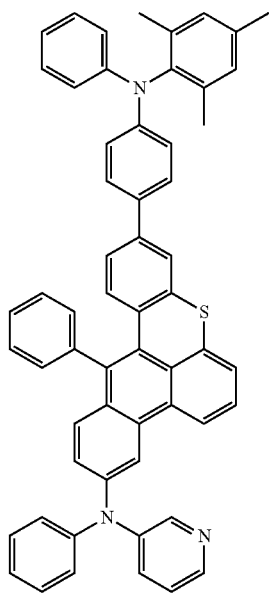
156A
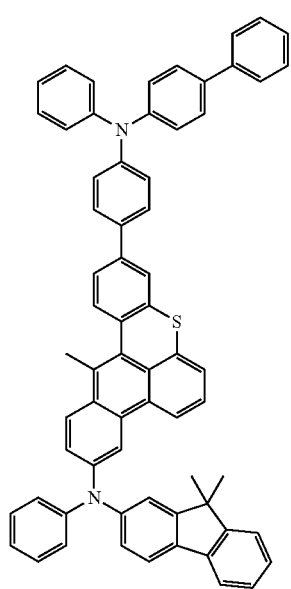
155A
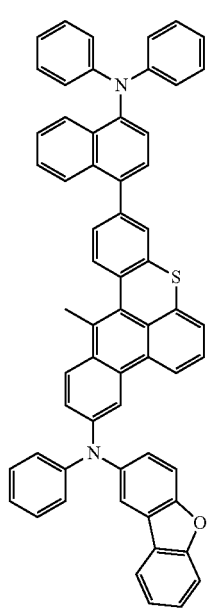
157A 495
-continued
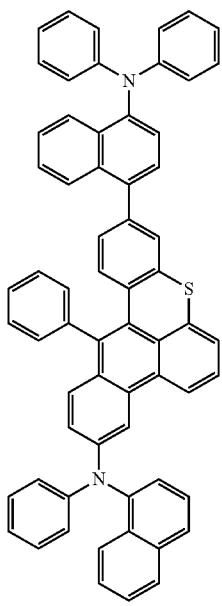
158A
159A
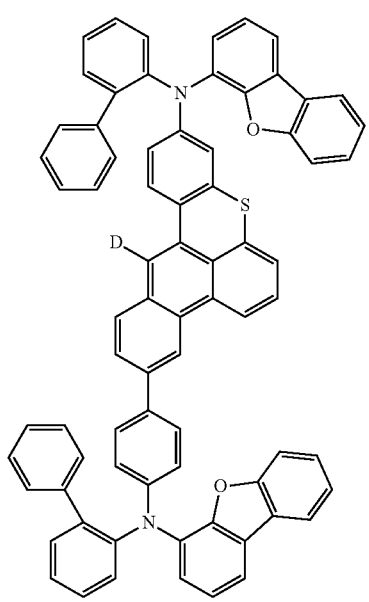
496
-continued
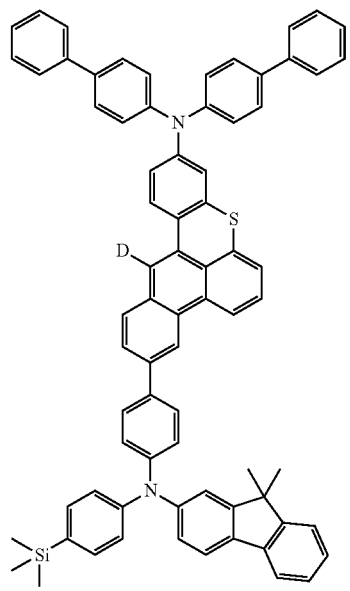
160A
161A
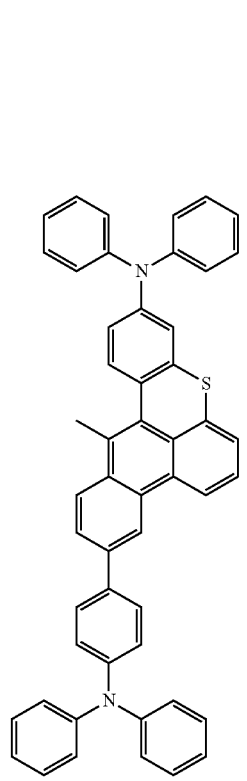

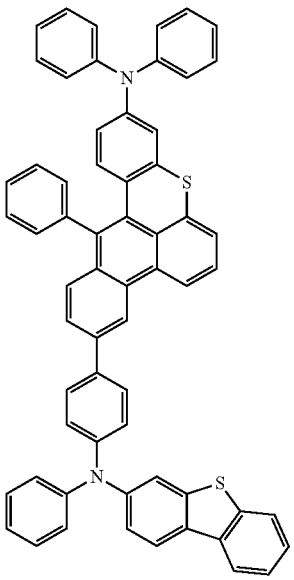

162A

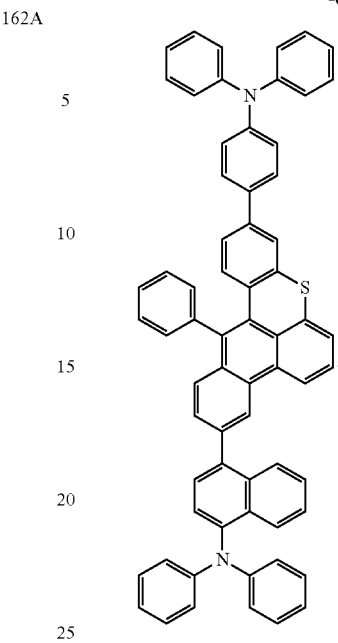

164A

17. An organic light-emitting device comprising:
a first electrode;
a second electrode facing the first electrode; and
an organic layer between the first electrode and the second electrode, the organic layer comprising an emission layer, and further comprising at least one of the condensed cyclic compounds of claim 1.

18. The organic light-emitting device of claim 17, wherein
the first electrode is an anode,
the second electrode is a cathode, and
the organic layer comprises:
   a hole transport region between the first electrode and the emission layer, the hole transport region comprising at least one selected from a hole injection layer, a hole transport layer, a buffer layer, and an electron blocking layer, and
   an electron transport region between the emission layer and the second electrode, the electron transport region comprising at least one selected from a hole blocking layer, an electron transport layer, and an electron injection layer,
wherein at least one selected from the hole transport region and the emission layer comprises the condensed cyclic compound.

19. The organic light-emitting device of claim 17, wherein the condensed cyclic compound is in the emission layer and the emission layer further comprises a host.

20. The organic light-emitting device of claim 18, wherein the hole transport region comprises the hole transport layer, and each of the hole transport layer and the emission layer comprises the condensed cyclic compound,
wherein the condensed cyclic compound in the hole transport layer is different from the condensed cyclic compound in the emission layer.

* * * * *